US012503459B2

(12) United States Patent
Uno

(10) Patent No.: US 12,503,459 B2
(45) Date of Patent: Dec. 23, 2025

(54) LIGHT EMITTING DEVICE AND AMINE COMPOUND FOR THE SAME

(71) Applicant: Samsung Display Co., Ltd., Yongin-si (KR)

(72) Inventor: Takuya Uno, Yokohama (JP)

(73) Assignee: Samsung Display Co., Ltd., Yongin-si (KR)

(*) Notice: Subject to any disclaimer, the term of this patent is extended or adjusted under 35 U.S.C. 154(b) by 1073 days.

(21) Appl. No.: 17/527,177

(22) Filed: Nov. 16, 2021

(65) Prior Publication Data

US 2022/0320441 A1 Oct. 6, 2022

(30) Foreign Application Priority Data

Mar. 26, 2021 (KR) ........................ 10-2021-0039929

(51) Int. Cl.
*C07D 405/14* (2006.01)
*C07D 405/04* (2006.01)
(Continued)

(52) U.S. Cl.
CPC ......... *C07D 405/14* (2013.01); *C07D 405/04* (2013.01); *C07D 409/14* (2013.01);
(Continued)

(58) Field of Classification Search
CPC .. C07D 405/04; C07D 307/91; C07D 209/82; H10K 85/636
See application file for complete search history.

(56) References Cited

U.S. PATENT DOCUMENTS

| | | | |
|---|---|---|---|
| 2019/0288220 A1 | 9/2019 | Kim et al. |
| 2020/0181165 A1 | 6/2020 | Koo et al. |
| 2021/0340103 A1 | 11/2021 | Mun et al. |

FOREIGN PATENT DOCUMENTS

| | | |
|---|---|---|
| CN | 108101896 A | 6/2018 |
| CN | 110577545 A | 12/2019 |

(Continued)

OTHER PUBLICATIONS

Machine-generated English-language translation of WO-2014129764-A1.*

(Continued)

*Primary Examiner* — Vu A Nguyen
(74) *Attorney, Agent, or Firm* — Lerner David LLP

(57) ABSTRACT

A light emitting device, includes: a first electrode; a second electrode disposed on the first electrode; and at least one functional layer disposed between the first electrode and the second electrode and including an amine compound of Formula 1:

Formula 1

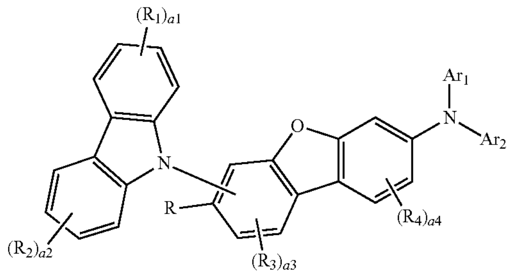

in Formula 1, the variables are described herein.

21 Claims, 6 Drawing Sheets

(51) Int. Cl.

| | |
|---|---|
| ***C07D 409/14*** | (2006.01) |
| ***H10K 50/15*** | (2023.01) |
| ***H10K 50/18*** | (2023.01) |
| ***H10K 59/122*** | (2023.01) |
| ***H10K 85/60*** | (2023.01) |

(52) U.S. Cl.

CPC ......... *H10K 85/633* (2023.02); *H10K 85/636* (2023.02); *H10K 50/15* (2023.02); *H10K 50/181* (2023.02); *H10K 59/122* (2023.02); *H10K 85/6572* (2023.02); *H10K 85/6574* (2023.02); *H10K 85/6576* (2023.02)

(56) References Cited

FOREIGN PATENT DOCUMENTS

| | | | | | |
|---|---|---|---|---|---|
| CN | 111533678 | A | | 8/2020 | |
| CN | 113135903 | A | * | 7/2021 | ........... C07D 405/04 |
| JP | 6007467 | B2 | | 3/2012 | |
| KR | 10-2014-0145370 | A | | 12/2014 | |
| KR | 10-2018-0137315 | | | 12/2018 | |
| KR | 20180137315 | A | * | 12/2018 | ........... H10K 85/636 |
| KR | 10-2019-0108222 | | | 9/2019 | |
| KR | 10-2019-0134301 | | | 12/2019 | |
| KR | 10-2019-0135707 | A | | 12/2019 | |
| KR | 10-2073322 | | | 2/2020 | |
| KR | 102187984 | | | 12/2020 | |
| KR | 102188832 | B1 | | 12/2020 | |
| WO | WO-2014129764 | A1 | * | 8/2014 | ........... C07D 409/04 |

OTHER PUBLICATIONS

Machine-generated English-language translation of KR-20180137315-A.*

Machine-generated English-language translation of CN-113135903-A.*

* cited by examiner

LIGHT EMITTING DEVICE AND AMINE COMPOUND FOR THE SAME

CROSS-REFERENCE TO RELATED APPLICATIONS

This application claims priority from and the benefit of Korean Patent Application No. 10-2021-0039929, filed on Mar. 26, 2021, which is hereby incorporated by reference for all purposes as if fully set forth herein.

BACKGROUND

Field

Embodiments of the invention relate generally to light emitting devices and an amine compound incorporated therein, and, more particularly, to an amine compound used as a hole transport material and a light emitting device including the same.

Discussion of the Background

Recently use of an organic electroluminescence display device an image display device is being actively developed. The organic electroluminescence display device is a display device including so-called a self-luminescent light emitting device in which holes and electrons injected from a first electrode and a second electrode recombine in an emission layer so that a light emitting material in an emission layer emits light to achieve display.

The above information disclosed in this Background section is only for understanding of the background of the inventive concepts, and, therefore, it may contain information that does not constitute prior art.

SUMMARY

Applicant realized that an increase in the emission efficiency and the lifespan of light emitting devices used as display devices is desirable, as is the development of materials for light emitting devices to stably achieve the desired characteristics. Light-emitting devices constructed according to the principles and illustrative implementations of the invention exhibit excellent emission efficiency and a long-lifespan. When amine compounds made according to principles and illustrative implementations of the invention are included in a light emitting device, the light emitting device has high efficiency and long-lifespan.

Additional features of the inventive concepts will be set forth in the description which follows, and in part will be apparent from the description, or may be learned by practice of the inventive concepts.

According to one aspect of the invention, a light emitting device includes: a first electrode; a second electrode disposed on the first electrode; and at least one functional layer disposed between the first electrode and the second electrode and including an amine compound of Formula 1:

Formula 1

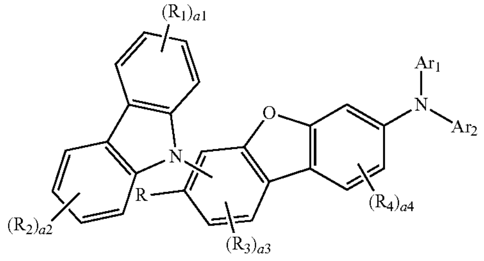

in Formula 1, the variables are described herein.

The Formula 1 may be one of Formula 1-1 to Formula 1-3, as described herein.

The Formula 1 may be of Formula 2-1, as described herein.

The Formula 1 may be of Formula 2-2, as described herein.

The groups $Ar_1$ and $Ar_2$ may be each, independently from one another, a substituted or unsubstituted phenyl group, a substituted or unsubstituted naphthyl group, a substituted or unsubstituted phenanthryl group, a substituted or unsubstituted triphenylenyl group, a substituted or unsubstituted fluorenyl group, a substituted or unsubstituted dibenzofuran group, a substituted or unsubstituted dibenzothiophene group, a substituted carbazole group, an unsubstituted naphthobenzofuran group, or an unsubstituted benzonaphthothiophene group.

The groups $Ar_1$ and $Ar_2$ may be each, independently from one another, one of A-1 to A-7, as described herein.

At least one of $Ar_1$ and $Ar_2$ may be a substituted or unsubstituted phenyl group.

The variables $R_1$ and $R_2$ may each be, independently from one another, a deuterium atom, a fluorine atom, a methyl group, or a t-butyl group.

At least one of $R_1$ to $R_4$ may be a deuterium atom, or at least one of $R_1$ to $R_4$, $Ar_1$ and $Ar_2$ may be a deuterium atom as a substituent.

The at least one functional layer may include an emission layer, a hole transport region disposed between the first electrode and the emission layer, and an electron transport region disposed between the emission layer and the second electrode, and the hole transport region may include the amine compound.

The hole transport region may include a hole injection layer disposed on the first electrode, a hole transport layer disposed on the hole injection layer, and an electron blocking layer disposed on the hole transport layer, and at least one of the hole injection layer, the hole transport layer, and the electron blocking layer may include the amine compound.

The electron blocking layer may include the amine compound, and the hole transport layer may include a compound of Formula H-1, as described herein.

The amine compound may include one compound of Compound Group 1, as described herein.

According to another aspect of the invention, an amine compound is of Formula 1:

Formula 1

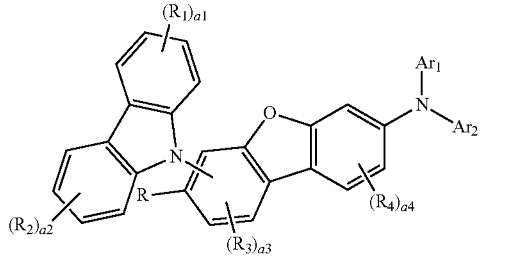

in Formula 1, the variables are described herein.

Formula 1 may be one of Formula 1-1 to Formula 1-3, as described herein.

Formula 1 may be of Formula 2-1, as described herein.

Formula 1 may be of Formula 2-2, as described herein.

The groups $Ar_1$ and $Ar_2$ may each be, independently from one another, a substituted or unsubstituted phenyl group, a substituted or unsubstituted naphthyl group, a substituted or unsubstituted phenanthryl group, a substituted or unsubstituted triphenylenyl group, a substituted or unsubstituted fluorenyl group, a substituted or unsubstituted dibenzofuran group, a substituted or unsubstituted dibenzothiophene group, a substituted carbazole group, an unsubstituted naphthobenzofuran group, or an unsubstituted benzonaphthothiophene group.

The groups $Ar_1$ and $Ar_2$ may each be, independently from one another, one of A-1 to A-7, as described herein.

At least one of $Ar_1$ and $Ar_2$ may be a substituted or unsubstituted phenyl group.

The variables $R_1$ and $R_2$ may each be, independently from one another, a deuterium atom, a fluorine atom, a methyl group, or a t-butyl group.

At least one of $R_1$ to $R_4$ may be a deuterium atom, or at least one of $R_1$ to $R_4$, $Ar_1$ and $Ar_2$ may be a deuterium atom as a substituent.

Formula 1 may be one compound of Compound Group 1, as described herein.

It is to be understood that both the foregoing general description and the following detailed description are illustrative and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate illustrative embodiments of the invention, and together with the description serve to explain the inventive concepts.

DETAILED DESCRIPTION

Figure 1:
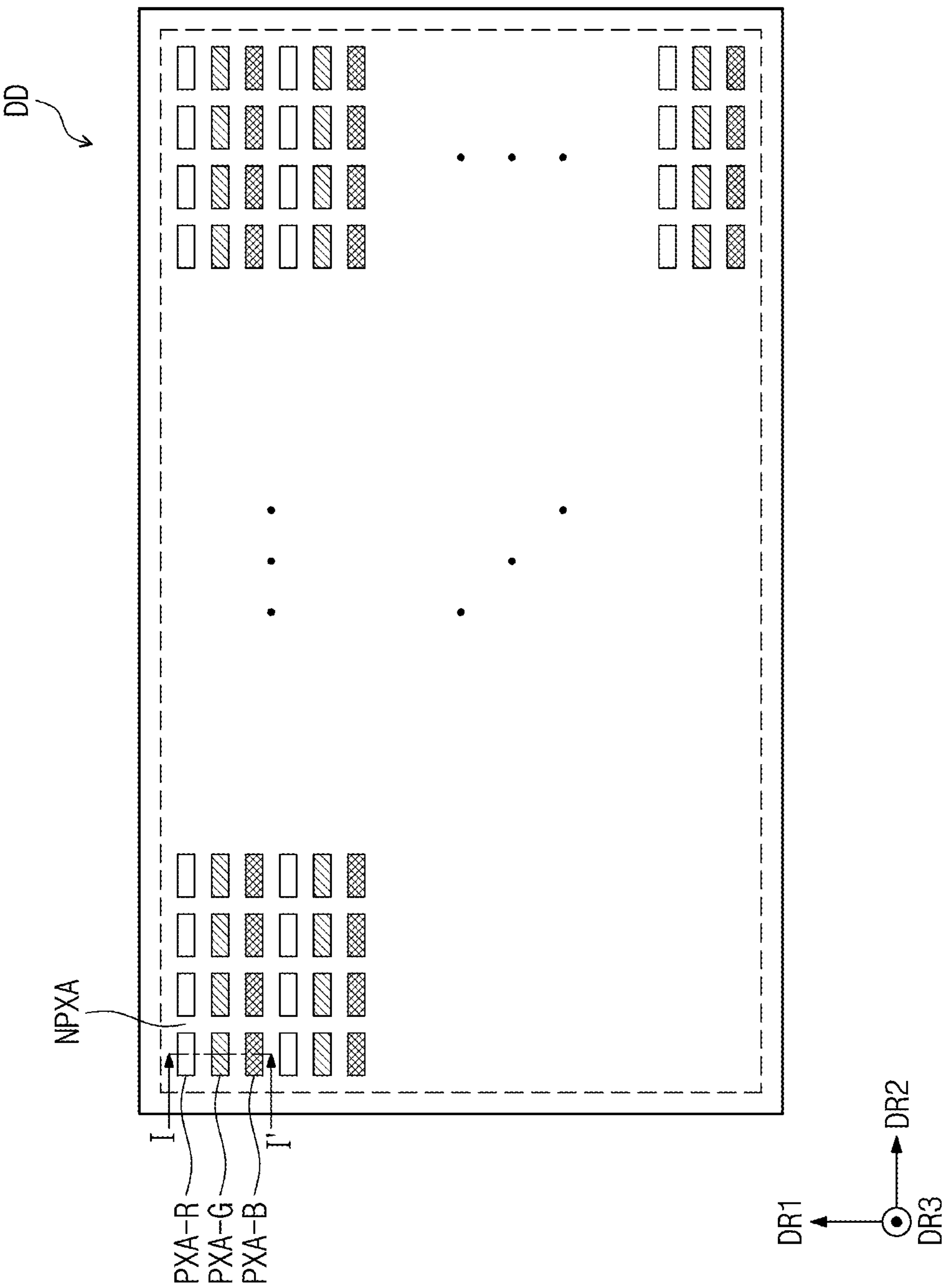
FIG. 1 is a plan view illustrating an embodiment of a display apparatus constructed according to the principles of the invention.

In the following description, for the purposes of explanation, numerous specific details are set forth in order to provide a thorough understanding of various embodiments or implementations of the invention. As used herein "embodiments" and "implementations" are interchangeable words that are non-limiting examples of devices or methods employing one or more of the inventive concepts disclosed herein. It is apparent, however, that various embodiments may be practiced without these specific details or with one or more equivalent arrangements. In other instances, well-known structures and devices are shown in block diagram form in order to avoid unnecessarily obscuring various embodiments. Further, various embodiments may be different, but do not have to be exclusive. For example, specific shapes, configurations, and characteristics of an embodiment may be used or implemented in another embodiment without departing from the inventive concepts.

Unless otherwise specified, the illustrated embodiments are to be understood as providing illustrative features of varying detail of some ways in which the inventive concepts may be implemented in practice. Therefore, unless otherwise specified, the features, components, parts, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an embodiment may be implemented differently, a specific process order may be performed differently from the described order. For example, two consecutively described processes may be performed substantially at the same time or performed in an order opposite to the described order. Also, like reference numerals denote like elements, and duplicative explanations are omitted to avoid redundancy.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, numerals, integers, steps, operations, elements, parts, components, and/or groups thereof, but do not preclude the presence or addition of one or more other features, numerals, integers, steps, operations, elements, parts, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various embodiments are described herein with reference to sectional and/or exploded illustrations that are schematic illustrations of idealized embodiments and/or intermediate structures. As such, variations from the shapes of the illustrations as a result, for example, of manufacturing techniques and/or tolerances, are to be expected. Thus, embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

Figure 2:
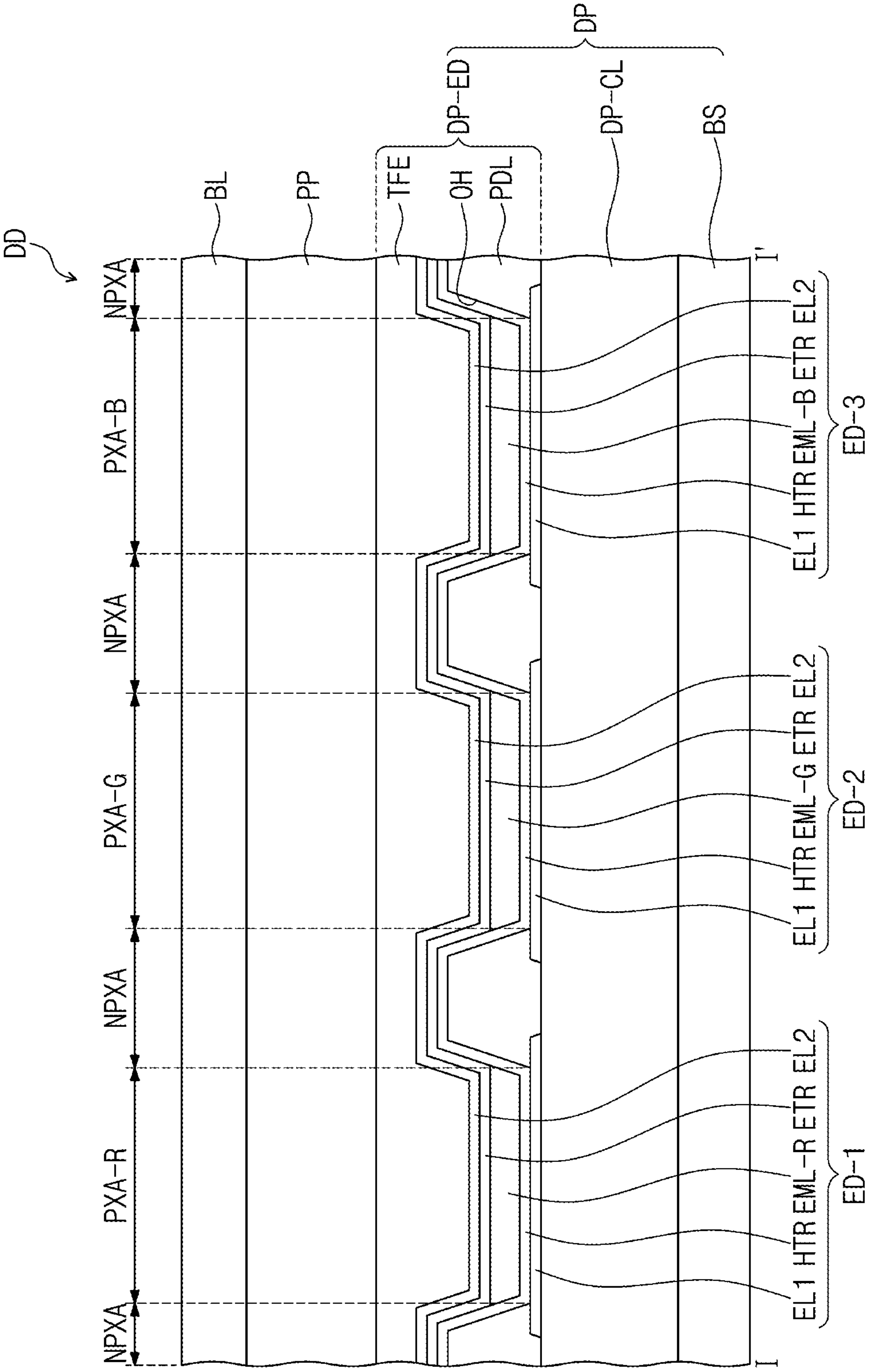
FIG. 2 is a cross-sectional view of the display apparatus taken along line I-I' of FIG. 1.

FIG. 1 is a plan view illustrating an embodiment of a display apparatus constructed according to the principles of the invention. FIG. 2 is a cross-sectional view of the display apparatus taken along line I-I' of FIG. 1. Particularly, FIG. 2 is a cross-sectional view showing a part corresponding to line I-I'.

The display apparatus DD may include a display panel DP and an optical layer PP disposed on the display panel DP. The display panel DP includes light emitting devices ED-1, ED-2 and ED-3. The display apparatus DD may include multiple light emitting devices ED-1, ED-2 and ED-3. The optical layer PP may be disposed on the display panel DP and control external light reflected by the display panel DP. The optical layer PP may include, for example, a polarization layer or a color filter layer. In some embodiments, the optical layer PP may be omitted from the display apparatus DD.

On the optical layer PP, a base substrate BL may be disposed. The base substrate BL may be a member providing a base surface where the optical layer PP is disposed. The base substrate BL may be a glass substrate, a metal substrate, a plastic substrate, etc. However, embodiments are not limited thereto, and the base substrate BL may be an inorganic layer, an organic layer or a composite material layer. In addition, different from the drawings, the base substrate BL may be omitted in an embodiment.

The display apparatus DD may further include a filling layer. The filling layer may be disposed between a display device layer DP-ED and a base substrate BL. The filling layer may be an organic layer. The filling layer may include at least one of an acrylic resin, a silicon-based resin and an epoxy-based resin.

The display panel DP may include a base layer BS, a circuit layer DP-CL provided on the base layer BS and a display device layer DP-ED. The display device layer DP-ED may include a pixel definition layer PDL, light emitting devices ED-1, ED-2 and ED-3 disposed in the pixel definition layer PDL, and an encapsulation layer TFE disposed on the light emitting devices ED-1, ED-2 and ED-3.

The base layer BS may be a member providing a base surface where the display device layer DP-ED is disposed. The base layer BS may be a glass substrate, a metal substrate, a plastic substrate, etc. However, embodiments are not limited thereto, and the base layer BS may be an inorganic layer, an organic layer, or a composite material layer.

In an embodiment, the circuit layer DP-CL is disposed on the base layer BS, and the circuit layer DP-CL may include multiple transistors. Each of the transistors may include a control electrode, an input electrode, and an output electrode. For example, the circuit layer DP-CL may include switching transistors and driving transistors for driving the light emitting devices ED-1, ED-2 and ED-3 of the display device layer DP-ED.

Each of the light emitting devices ED-1, ED-2 and ED-3 may have the structures of light emitting devices ED of embodiments made according to FIG. 3 to FIG. 6, which are described further below. Each of the light emitting devices ED-1, ED-2 and ED-3 may include a first electrode EL1, a hole transport region HTR, emission layers EML-R, EML-G and EML-B, an electron transport region ETR, and a second electrode EL2.

FIG. 2 shows an embodiment where the emission layers EML-R, EML-G and EML-B of light emitting devices ED-1, ED-2 and ED-3, which are in opening portions OH defined in a pixel definition layer PDL, are disposed, and a hole transport region HTR, an electron transport region ETR and a second electrode EL2 are provided as common layers in all light emitting devices ED-1, ED-2 and ED-3. However, embodiments are not limited thereto. Unlike FIG. 2, in another embodiment, the hole transport region HTR and the electron transport region ETR may be patterned and provided in the opening portions OH defined in the pixel definition layer PDL. For example, in an embodiment, the hole transport region HTR, the emission layers EML-R, EML-G and EML-B, and the electron transport region ETR of the light emitting devices ED-1, ED-2 and ED-3 may be patterned by an ink jet printing method.

An encapsulation layer TFE may cover the light emitting devices ED-1, ED-2 and ED-3. The encapsulation layer TFE may encapsulate the display device layer DP-ED. The encapsulation layer TFE may be a thin film encapsulation layer. The encapsulation layer TFE may be one layer or a stacked layer of multiple layers. The encapsulation layer TFE includes at least one insulating layer. The encapsulation layer TFE may include at least one inorganic layer (hereinafter, encapsulating inorganic layer). In addition, the encapsulation layer TFE may include at least one organic layer (hereinafter, encapsulating organic layer) and at least one encapsulating inorganic layer.

The encapsulating inorganic layer protects the display device layer DP-ED from at least one of moisture and oxygen, and the encapsulating organic layer protects the display device layer DP-ED from foreign materials such as dust particles. The encapsulating inorganic layer may include a silicon nitride, a silicon oxynitride, silicon oxide, a titanium oxide, or an aluminum oxide, without specific limitation. The encapsulating organic layer may include an acrylic compound, an epoxy-based compound, etc. The encapsulating organic layer may include a photopolymerizable organic material, without specific limitation. The encapsulation layer TFE may be disposed on the second electrode EL2 and may be disposed while filling the opening portion OH.

Referring to FIG. 1 and FIG. 2, the display apparatus DD may include a non-luminous area NPXA and luminous areas PXA-R, PXA-G and PXA-B. The luminous areas PXA-R, PXA-G and PXA-B may be areas emitting light produced from the light emitting devices ED-1, ED-2 and ED-3, respectively. The luminous areas PXA-R, PXA-G and PXA-B may be separated from each other on a plane.

The luminous areas PXA-R, PXA-G and PXA-B may be areas separated by the pixel definition layer PDL. The non-luminous areas NPXA may be areas between neighboring luminous areas PXA-R, PXA-G and PXA-B and may be areas corresponding to the pixel definition layer PDL. Each of the luminous areas PXA-R, PXA-G and PXA-B may overlap one of the pixels. The pixel definition layer PDL may divide the light emitting devices ED-1, ED-2 and ED-3. The emission layers EML-R, EML-G and EML-B of the light emitting devices ED-1, ED-2 and ED-3 may be disposed and divided in the opening portions OH defined in the pixel definition layer PDL.

The luminous areas PXA-R, PXA-G and PXA-B may be divided into multiple groups according to the color of light produced from the light emitting devices ED-1, ED-2 and ED-3. In the display apparatus DD shown in FIG. 1 and FIG. 2, three luminous areas PXA-R, PXA-G and PXA-B capable of emitting red light, green light and blue light are illustrated as an embodiment. For example, the display apparatus DD may include a red luminous area PXA-R, a green luminous area PXA-G and a blue luminous area PXA-B, which are separated from each other.

In the display apparatus DD, multiple light emitting devices ED-1, ED-2 and ED-3 may emit light having different wavelength regions. For example, in an embodiment, the display apparatus DD may include a first light emitting device ED-1 emitting red light, a second light emitting device ED-2 emitting green light, and a third light emitting device ED-3 emitting blue light. That is, each of the red luminous area PXA-R, the green luminous area PXA-G, and the blue luminous area PXA-B of the display apparatus DD may correspond to the first light emitting device ED-1, the second light emitting device ED-2, and the third light emitting device ED-3.

However, embodiments are not limited thereto, and the first to third light emitting devices ED-1, ED-2 and ED-3 may emit light in the same wavelength region, or at least one thereof may emit light in a different wavelength region. For example, all the first to third light emitting devices ED-1, ED-2 and ED-3 may emit blue light.

The luminous areas PXA-R, PXA-G and PXA-B in the display apparatus DD may be arranged in a generally elongated (stripe) shape. Referring to FIG. 1, multiple red luminous areas PXA-R, multiple green luminous areas PXA-G and multiple blue luminous areas PXA-B may be arranged along a second directional axis DR2. In addition, the red luminous area PXA-R, the green luminous area PXA-G and the blue luminous area PXA-B may be arranged in columns along a first directional axis DR1.

In FIG. 1 and FIG. 2, the size of the areas of the luminous areas PXA-R, PXA-G and PXA-B are shown similar, but embodiments are not limited thereto. The areas of the luminous areas PXA-R, PXA-G and PXA-B may have different sizes from each other according to the wavelength region of light emitted. The areas of the luminous areas PXA-R, PXA-G and PXA-B may mean planar areas defined by the first directional axis DR1 and the second directional axis DR2.

The type of the luminous areas PXA-R, PXA-G and PXA-B is not limited to the configuration shown in FIG. 1, and the order of the red luminous areas PXA-R, the green luminous areas PXA-G and the blue luminous areas PXA-B may be provided in various combinations according to the properties of display quality required for the display apparatus DD. For example, the luminous areas PXA-R, PXA-G and PXA-B may be arranged in a configuration sold under the trade designation PenTile matrix by Samsung Display Co., Ltd. of Gyeonggi-do, Republic of Korea, or a in diamond configuration.

In addition, the size of areas of the luminous areas PXA-R, PXA-G and PXA-B may be different from each other. For example, in an embodiment, the area of the green luminous area PXA-G may be smaller than the area of the blue luminous area PXA-B, but embodiments are not limited thereto.

Figure 3:
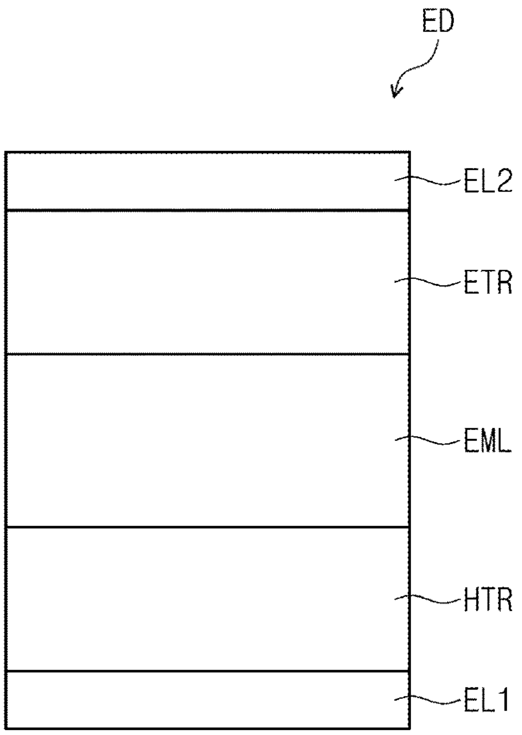
FIG. 3 is a cross-sectional view schematically illustrating an embodiment of a light emitting device constructed according to the principles of the invention.
Figure 4:
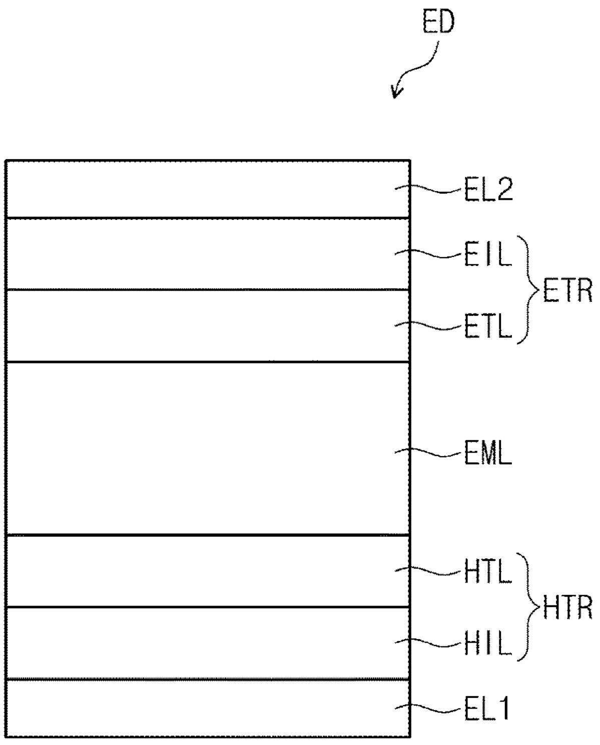
FIG. 4 is a cross-sectional view schematically illustrating another embodiment of a light emitting device constructed according to the principles of the invention.
Figure 5:
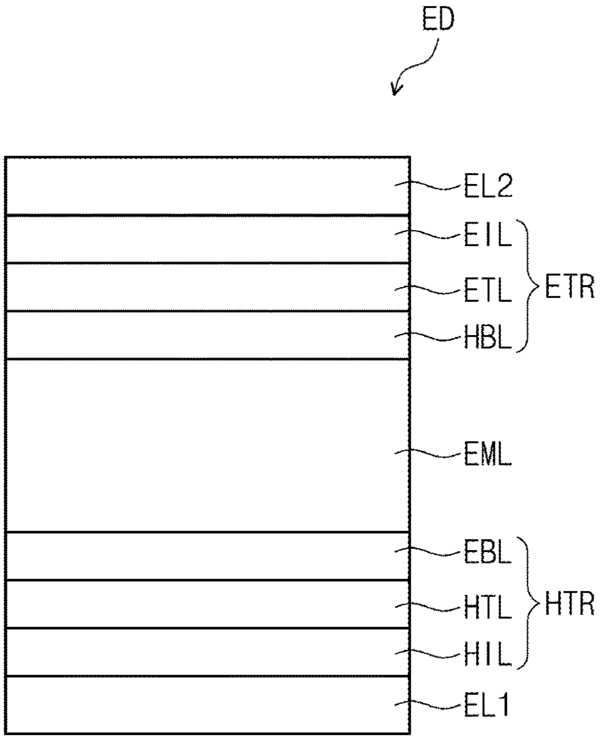
FIG. 5 is a cross-sectional view schematically illustrating a further embodiment of a light emitting device constructed according to the principles of the invention.
Figure 6:
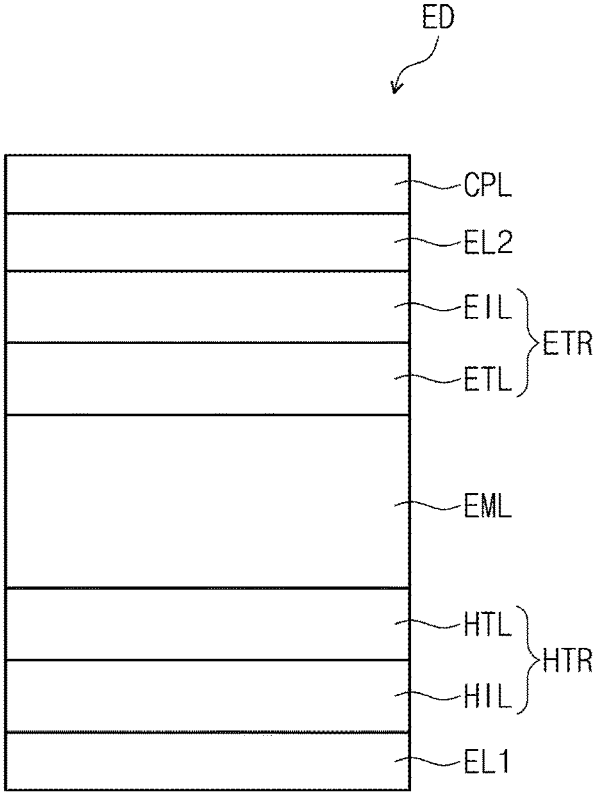
FIG. 6 is a cross-sectional view schematically illustrating yet another embodiment of a light emitting device constructed according to the principles of the invention.

FIG. 3 is a cross-sectional view schematically illustrating an embodiment of a light emitting device constructed according to the principles of the invention. FIG. 4 is a cross-sectional view schematically illustrating another embodiment of a light emitting device constructed according to the principles of the invention. FIG. 5 is a cross-sectional view schematically illustrating a further embodiment of a light emitting device constructed according to the principles of the invention. FIG. 6 is a cross-sectional view schematically illustrating yet another embodiment of a light emitting device constructed according to the principles of the invention.

The light emitting device ED may include a first electrode EL1, a hole transport region HTR, an emission layer EML, an electron transport region ETR, and a second electrode EL2 stacked in order. When compared with FIG. 3, FIG. 4 shows the cross-sectional view of a light emitting device ED, wherein a hole transport region HTR includes a hole injection layer HIL and a hole transport layer HTL, and an electron transport region ETR includes an electron injection layer EIL and an electron transport layer ETL. In addition, when compared with FIG. 3, FIG. 5 shows the cross-sectional view of a light emitting device ED, wherein a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. When compared with FIG. 4, FIG. 6 shows the cross-sectional view of a light emitting device ED, including a capping layer CPL disposed on the second electrode EL2.

The first electrode EL1 has conductivity. The first electrode EL1 may be formed using a metal material, a metal alloy or a conductive compound. The first electrode EL1 may be an anode or a cathode. However, embodiments are not limited thereto, not limited thereto. In addition, the first electrode EL1 may be a pixel electrode. The first electrode EL1 may be a transmissive electrode, a transflective electrode, or a reflective electrode. If the first electrode EL1 is the transmissive electrode, the first electrode EL1 may include a transparent metal oxide such as an indium tin oxide (ITO), an indium zinc oxide (IZO), a zinc oxide (ZnO), and an indium tin zinc oxide (ITZO). If the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, W, compounds thereof, or mixtures thereof (for example, a mixture of Ag and Mg). Also, the first electrode EL1 may have a structure including multiple layers including a reflective layer or a transflective layer formed using the above materials, and a transmissive conductive layer formed using ITO, IZO, ZnO, or ITZO. For example, the first electrode EL1 may include a three-layer structure of an ITO/Ag/ITO. However, embodiments are not limited thereto, not limited thereto. The first electrode EL1 may include the above-described metal materials, combinations of two or more metal materials selected from the above-described metal materials, or oxides of the above-described metal materials. The thickness of the first electrode EL1 may be from about 700 Å to about 10,000 Å. For example, the thickness of the first electrode EL1 may be from about 1,000 Å to about 3,000 Å.

The hole transport region HTR is provided on the first electrode EL1. In the light emitting device ED, the hole transport region HTR may include the amine compound.

Definitions

As used herein, the term "substituted or unsubstituted" corresponds to substituted or unsubstituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkynyl group, an alkoxy group, a hydrocarbon ring group, an aryl group, and a heterocyclic group. In addition, each of the exemplified substituents may be substituted or unsubstituted. For example, a biphenyl group may be interpreted as an aryl group or a phenyl group substituted with a phenyl group.

As used herein, the term "forming a ring via the combination with an adjacent group" may mean forming a substituted or unsubstituted hydrocarbon ring, or a substituted or unsubstituted heterocycle via the combination with an adjacent group. The hydrocarbon ring includes an aliphatic hydrocarbon ring and an aromatic hydrocarbon ring. The heterocycle includes an aliphatic heterocycle and an aromatic heterocycle. The hydrocarbon ring and the heterocycle may be monocycles or polycycles. In addition, the ring formed via the combination with an adjacent group may be combined with another ring to form a spiro structure.

As used herein, the term "adjacent group" may mean a substituent substituted for an atom which is directly combined with an atom substituted with a corresponding substituent, another substituent substituted for an atom which is substituted with a corresponding substituent, or a substituent sterically positioned at the nearest position to a corresponding substituent. For example, in 1,2-dimethylbenzene, two methyl groups may be interpreted as "adjacent groups" to each other, and in 1,1-diethylcyclopentene, two ethyl groups may be interpreted as "adjacent groups" to each other. In addition, in 4,5-dimethylphenanthrene, two methyl groups may be interpreted as "adjacent groups" to each other.

As used herein, the halogen atom may be a fluorine atom, a chlorine atom, a bromine atom or an iodine atom.

As used herein, the term "atom" may mean an element or its corresponding radical bonded to one or more other atoms.

The terms "hydrogen" and "deuterium" refer to their respective atoms and corresponding radicals with the deuterium radical abbreviated "-D", and the terms "—F, —Cl, —Br, and —I" are radicals of, respectively, fluorine, chlorine, bromine, and iodine.

As used herein, the term room temperature may mean about 20-about 24° C.

As used herein, the term "equivalent" means mole equivalent and may be abbreviated "equiv".

As used herein, the alkyl group may be a linear, branched or cyclic type. The carbon number of the alkyl group may be 1 to 50, 1 to 30, 1 to 20, 1 to 10, or 1 to 6. Examples of the alkyl group may include methyl, ethyl, n-propyl, isopropyl, n-butyl, s-butyl, t-butyl, butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

As used herein, the alkenyl group may be a linear chain or a branched chain. The carbon number is not specifically limited but may be 2 to 30, 2 to 20, or 2 to 10. Examples of the alkenyl group may include a vinyl group, a 1-butenyl group, a 1-pentenyl group, a 1,3-butadienyl aryl group, a styrenyl group, a styrylvinyl group, etc., without limitation.

As used herein, the aryl group means an optional functional group or substituent derived from an aromatic hydrocarbon ring. The aryl group may be a monocyclic aryl group or a polycyclic aryl group. The carbon number for forming rings in the aryl group may be 6 to 30, 6 to 20, or 6 to 15. Examples of the aryl group may include a phenyl, a naphthyl, a fluorenyl, an anthracenyl, a phenanthryl, a biphenyl, a terphenyl, a quaterphenyl, a quinqphenyl, a sexiphenyl, a triphenylenyl, a pyrenyl, a benzofluoranthenyl, a chrysenyl, etc., without limitation.

As used herein, the fluorenyl group may be substituted, and two substituents may be combined with each other to form a spiro structure. Examples of a substituted fluorenyl group are as follows, but embodiments are not limited thereto:

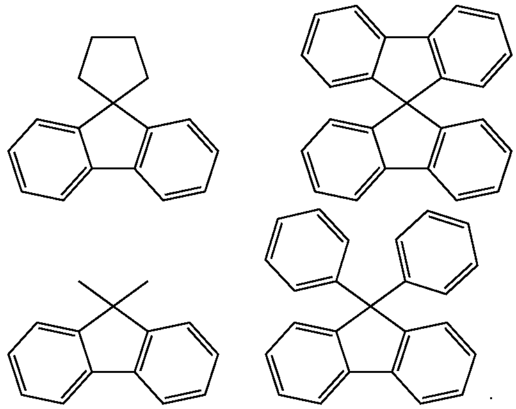

As used herein, the heteroaryl group may include one or more of B, O, N, P, Si, and S as heteroatoms. If the heteroaryl group includes two or more heteroatoms, two or more heteroatoms may be the same or different. The heteroaryl group may be a monocyclic heterocyclic group or a polycyclic heterocyclic group. The carbon number for forming rings of the heteroaryl group may be 2 to 30, 2 to 20, or 2 to 10. Examples of the heteroaryl group may include a thiophene, a furan, a pyrrole, an imidazole, a triazole, a pyridine, a bipyridine, a pyrimidine, a triazine, an acridyl, a pyridazine, a pyrazinyl, a quinoline, a quinazoline, a quinoxaline, a phenoxazine, a phthalazine, a pyrido pyrimidine, a pyrido pyrazine, a pyrazino, a pyrazine, an isoquinoline, an indole, a carbazole, an N-arylcarbazole, an N-heteroarylcarbazole, an N-alkylcarbazole, a benzoxazole, a benzoimidazole, a benzothiazole, a benzocarbazole, a benzothiophene, a dibenzothiophene, a thienothiophene, a benzofurane, a phenanthroline, a thiazole, an isooxazole, an oxazole, an oxadiazole, a thiadiazole, a phenothiazine, a dibenzosilole, a dibenzofuran, etc., without limitation.

As used herein, the silyl group includes an alkyl silyl group and an aryl silyl group. Examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, etc., without limitation.

As used herein, the thio group may include an alkyl thio group and an aryl thio group. The thio group may mean the above-defined alkyl group or aryl group combined with a sulfur atom. Examples of the thio group include a methylthio group, an ethylthio group, a propylthio group, a pentylthio group, a hexylthio group, an octylthio group, a dodecylthio group, a cyclopentylthio group, a cyclohexylthio group, a phenylthio group, a naphthylthio group, etc., without limitation.

As used herein, the oxy group may mean the above-defined alkyl group or aryl group which is combined with an oxygen atom. The oxy group may include an alkoxy group and an aryl oxy group. The alkoxy group may be a linear, a branched or a cyclic chain. The carbon number of the alkoxy group is not specifically limited but may be, for example, 1 to 20 or 1 to 10. Examples of the oxy group may include a methoxy, an ethoxy, an n-propoxy, an isopropoxy, a butoxy, a pentyloxy, a hexyloxy, an octyloxy, a nonyloxy, a decyloxy, a benzyloxy, etc. However, embodiments are not limited thereto.

As used herein, the carbon number of the amine group is not specifically limited, but may be 1 to 30. The amine group may include an alkyl amine group and an aryl amine group. Examples of the amine group include a methylamine group, a dimethylamine group, a phenylamine group, a diphenylamine group, a naphthylamine group, a 9-methyl-anthracenylamine group, a triphenylamine group, etc., without limitation.

As used herein, an alkyl group in the alkylthio group, alkyl oxy group, alkyl silyl group, and alkyl amine group may be the same as the examples of the above-described alkyl group. In addition, as used herein, the aryl group in the aryl thio group, aryl oxy group, aryl silyl group, and aryl amine group may be the same as the examples of the above-described aryl group.

As used herein, a direct linkage may mean a single bond.

As used herein,

“”

and “——*” mean positions to be connected.

In the light emitting device ED, the hole transport region HTR may include an amine compound represented by Formula 1 below. The amine compound may be dibenzofuran of which one benzene ring of both benzene rings is combined with an amine group, and the other benzene ring is combined with a carbazole group.

Formula 1

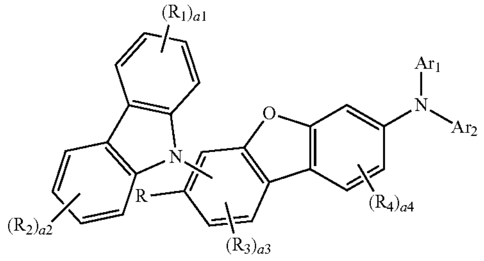

In Formula 1, R may be a hydrogen atom or a deuterium atom. The variables a1 and a2 may be each independently an integer of 0 to 4. The variables $R_1$ and $R_2$ may be each independently a hydrogen atom, a deuterium atom, a halogen atom, or a substituted or unsubstituted alkyl group of 1 to 20 carbon atoms. If a1 is an integer of 2 or more, multiple $R_1$ groups may be the same, or at least one thereof may be different. If a2 is an integer of 2 or more, multiple $R_2$ groups may be the same, or at least one thereof may be different.

In an embodiment, $R_1$ and $R_2$ may be each independently a deuterium atom, a fluorine atom, a methyl group, or a t-butyl group. For example, a1 and a2 may be 1, and $R_1$ and $R_2$ may be the same. $R_1$ and $R_2$ may be the same and may be a fluorine atom, a methyl group, or a t-butyl group. If a1 and a2 are 1, in a carbazole group including $R_1$ and $R_2$, $R_1$ and $R_2$ may be combined with carbon atoms at symmetric positions with respect to the nitrogen atom of the carbazole, respectively. However, this is only an illustration, and embodiments are not limited thereto.

In Formula 1, a3 may be an integer of 0 to 2, and a4 may be an integer of 0 to 3. $R_3$ and $R_4$ may be each independently a hydrogen atom, a deuterium atom, a halogen atom, a substituted or unsubstituted alkyl group of 1 to 20 carbon atoms, or a substituted or unsubstituted aryl group of 6 to 40 ring-forming carbon atoms. If a3 is an integer of 2 or more, multiple $R_3$ groups may be the same, or at least one thereof may be different. If a4 is an integer of 2 or more, multiple $R_4$ groups may be the same, or at least one thereof may be different. For example, at least one of a3 and a4 may be 0. Differently, at least one of a3 and a4 may be 1. If a3 is 1, $R_3$ may be a fluorine atom, a methyl group, or an unsubstituted phenyl group.

In Formula 1, $Ar_1$ and $Ar_2$ may be each independently a substituted or unsubstituted aryl group of 6 to 40 ring-forming carbon atoms, or a substituted or unsubstituted heteroaryl group of 2 to 40 ring-forming carbon atoms. At least one of $Ar_1$ and $Ar_2$ may be a substituted or unsubstituted phenyl group.

At least one of $R_1$ to $R_4$, $Ar_1$ and $Ar_2$ may include a deuterium atom as a substituent. In addition, at least one of $R_1$ to $R_4$ may be a deuterium atom. The amine compound may include a deuterium atom. For example, a1 may be an integer of 2 or more, and multiple $R_1$ groups may be deuterium atoms. The variable a2 may be an integer of 2 or more, and multiple $R_2$ groups may be deuterium atoms. The variables $Ar_1$ and $Ar_2$ may be substituted biphenyl groups, and the substituent of the biphenyl group may include a deuterium atom.

In an embodiment, the amine compound does not include a substituted or unsubstituted thiophene group. In addition, in Formula 1, $R_1$ to $R_4$, $Ar_1$ and $Ar_2$ may not include an amine group as a substituent. The amine compound does not include another tertiary amine in addition to the nitrogen atom with which $Ar_1$ and $Ar_2$ are combined. The amine compound includes one tertiary amine and does not include two or more tertiary amines.

If at least one of $R_1$ and $R_2$ is a substituted alkyl group, a substituted or unsubstituted thiophene group and an amine group are not included in the substituent of the alkyl group. If at least one of $R_3$ and $R_4$ is a substituted alkyl group or a substituted aryl group, a substituted or unsubstituted thiophene group and an amine group are not included in the substituent of the alkyl group and the aryl group. If at least one of $Ar_1$ and $Ar_2$ is a substituted aryl group, a substituted or unsubstituted thiophene group and an amine group are not included in the substituent of the aryl group. In addition, if at least one of $Ar_1$ and $Ar_2$ is a substituted or unsubstituted heteroaryl group, a thiophene group is not included in the heteroaryl group. If at least one of $Ar_1$ and $Ar_2$ is a substituted heteroaryl group, a substituted or unsubstituted thiophene group and an amine group are not included in the substituent of the heteroaryl group.

In an embodiment, $Ar_1$ and $Ar_2$ may be each independently a substituted or unsubstituted phenyl group, a substituted or unsubstituted naphthyl group, a substituted or unsubstituted phenanthryl group, a substituted or unsubstituted triphenylenyl group, or a substituted or unsubstituted fluorenyl group. In addition, $Ar_1$ and $Ar_2$ may be each independently a substituted or unsubstituted dibenzofuran group, a substituted or unsubstituted dibenzothiophene group, a substituted carbazole group, an unsubstituted naphthobenzofuran group, or an unsubstituted benzonaphthothiophene group.

$Ar_1$ and $Ar_2$ may be each independently represented by any one of A-1 to A-7 below.

A-1

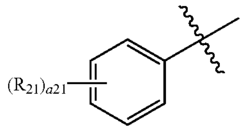

A-2

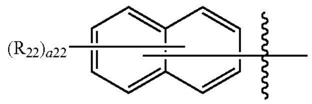

A-3

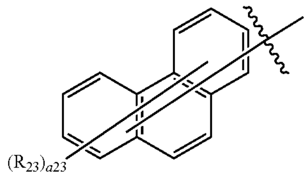

A-4

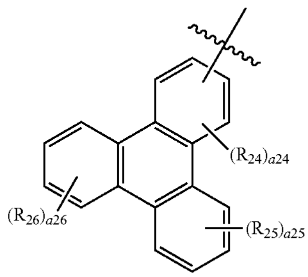

A-5

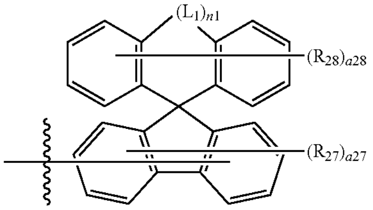

A-6

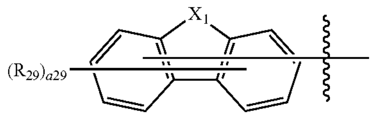

-continued

A-7

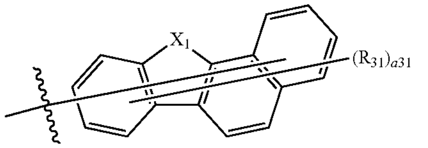

In A-1, a21 may be an integer of 0 to 5, and $R_{21}$ may be a hydrogen atom, a deuterium atom, a substituted or unsubstituted aryl group of 6 to 40 ring-forming carbon atoms, or a substituted or unsubstituted heteroaryl group of 2 to 40 ring-forming carbon atoms. If a21 is an integer of 2 or more, multiple $R_{21}$ groups may be the same, or at least one thereof may be different. For example, $R_{21}$ may be a substituted or unsubstituted phenyl group, a substituted or unsubstituted biphenyl group, a substituted or unsubstituted naphthyl group, a substituted or unsubstituted phenanthryl group, an unsubstituted adamantyl group, a substituted carbazole group, a substituted or unsubstituted dibenzofuran group, or an unsubstituted dibenzothiophene group.

In A-2, a22 may be an integer of 0 to 7, and $R_{22}$ may be a hydrogen atom, a deuterium atom, or a substituted or unsubstituted aryl group of 6 to 40 ring-forming carbon atoms. If a22 is an integer of 2 or more, multiple $R_{22}$ groups may be the same, or at least one thereof may be different. For example, $R_{22}$ may be an unsubstituted phenyl group.

In A-3, a23 may be an integer of 0 to 9, and $R_{23}$ may be a hydrogen atom, a deuterium atom, a substituted or unsubstituted aryl group of 6 to 40 ring-forming carbon atoms, or a substituted or unsubstituted heteroaryl group of 2 to 40 ring-forming carbon atoms. If a23 is an integer of 2 or more, multiple $R_{23}$ groups may be the same, or at least one thereof may be different.

In A-4, a24 may be an integer of 0 to 3, and a25 and a26 may be each independently an integer of 0 to 4. The variables $R_{24}$ and $R_{26}$ may be each independently a hydrogen atom, a deuterium atom, a substituted or unsubstituted aryl group of 6 to 40 ring-forming carbon atoms, or a substituted or unsubstituted heteroaryl group of 2 to 40 ring-forming carbon atoms. If a24 is an integer of 2 or more, multiple $R_{24}$ groups may be the same, or at least one thereof may be different. If a25 is an integer of 2 or more, multiple $R_{25}$ groups may be the same, or at least one thereof may be different. If a26 is an integer of 2 or more, multiple $R_{26}$ groups may be the same, or at least one thereof may be different.

In A-5, n1 may be 0 or 1, and $L_1$ may be a direct linkage. If n1 is 0, A-5 may be a fluorenyl group substituted with two phenyl groups. If n1 is 1, A-5 may be a fluorenyl group in which two phenyl groups form a spiro structure. In A-5, a27 may be an integer of 0 to 7, and a28 may be an integer of 0 to 10. The variables $R_{27}$ and $R_{28}$ may be each independently a hydrogen atom, a deuterium atom, a substituted or unsubstituted aryl group of 6 to 40 ring-forming carbon atoms, or a substituted or unsubstituted heteroaryl group of 2 to 40 ring-forming carbon atoms. If a27 is an integer of 2 or more, multiple $R_{27}$ groups may be the same, or at least one thereof may be different. If a28 is an integer of 2 or more, multiple $R_{26}$ groups may be the same, or at least one thereof may be different.

In A-6, $X_1$ may be $NR_{30}$, O, or S. If $X_1$ is $NR_{30}$, A-6 may be a substituted or unsubstituted carbazole group. If $X_1$ is O, A-6 may be a substituted or unsubstituted dibenzofuran group. If $X_1$ is S, A-6 may be a substituted or unsubstituted dibenzothiophene group. The variable a29 may be an integer of 0 to 7, and $R_{29}$ and $R_{30}$ may be each independently a hydrogen atom, a deuterium atom, a substituted or unsubstituted aryl group of 6 to 40 ring-forming carbon atoms, or a substituted or unsubstituted heteroaryl group of 2 to 40 ring-forming carbon atoms. If a29 is an integer of 2 or more, multiple $R_{29}$ groups may be the same, or at least one thereof may be different. For example, $R_{29}$ may be an unsubstituted phenyl group or an unsubstituted carbazole group. In addition, $R_{30}$ may be an unsubstituted phenyl group. However, these are only illustrations, and embodiments are not limited thereto.

In A-7, $X_2$ may be O, or S. If $X_2$ is 0, A-7 may be an unsubstituted naphthobenzofuran. Differently, if $X_2$ is S, A-7 may be an unsubstituted benzonaphthothiophene group. In A-7, a31 may be an integer of 0 to 9. The variable $R_{31}$ may be a hydrogen atom, a deuterium atom, a substituted or unsubstituted aryl group of 6 to 40 ring-forming carbon atoms, or a substituted or unsubstituted heteroaryl group of 2 to 40 ring-forming carbon atoms. If a31 is an integer of 2 or more, multiple $R_{31}$ groups may be the same, or at least one thereof may be different.

According to an embodiment, Formula 1 may be represented by any one of Formula 1-1 to Formula 1-3.

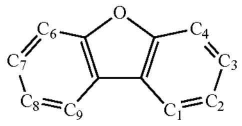

Dibenzofuran

Formula 1-1 may be a compound in which an amine group is bonded to the carbon at position 3 ($C_3$) of dibenzofuran, and a carbazole group is bonded to the carbon at position 6 ($C_6$). Formula 1-2 may be a compound in which an amine group is bonded to the carbon at position 3 ($C_3$) of dibenzofuran, and a carbazole group is bonded to the carbon at position 8 ($C_8$). Formula 1-3 may be a compound in which an amine group is bonded to the carbon at position 3 ($C_3$) of dibenzofuran, and a carbazole group is bonded to the carbon at position 9 ($C_9$).

Formula 1-1

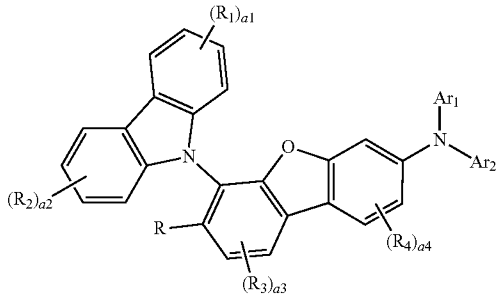

-continued

Formula 1-2

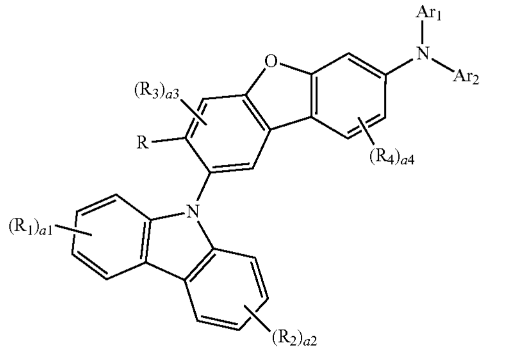

Formula 1-3

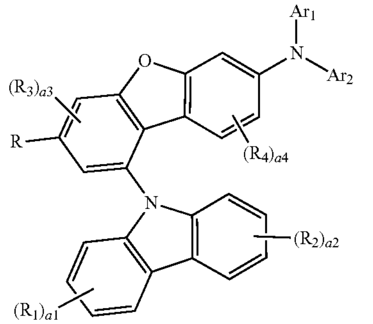

In Formula 1-1 to Formula 1-3, the same explanation as that on $Ar_1$, $Ar_2$, a1 to a4, R, and $R_1$ to $R_4$ referring to Formula 1 may be applied.

In addition, Formula 1 may be represented by Formula 2-1 below. Formula 2-1 represents a case where any one of $Ar_1$ and $Ar_2$ is a substituted or unsubstituted biphenyl group.

In Formula 2-1, the same explanation as that on a1 to a4, R, and $R_1$ to $R_4$ referring to Formula 1 may be applied.

In Formula 2-1, a11 may be an integer of 0 to 4, $Ar_{11}$ may be a hydrogen atom, a deuterium atom, or a substituted or unsubstituted aryl group of 6 to 40 ring-forming carbon atoms. If a11 is an integer of 2 or more, multiple $Ar_{11}$ groups may be the same, or at least one thereof may be different.

$R_{11}$ to $R_{15}$ may be each independently a hydrogen atom, a deuterium atom, a halogen atom, a substituted or unsubstituted silyl group, a substituted or unsubstituted alkenyl group of 2 to 10 carbon atoms, a substituted or unsubstituted aryl group of 6 to 40 ring-forming carbon atoms, or a substituted or unsubstituted heteroaryl group of 2 to 40 ring-forming carbon atoms, or combined with an adjacent group to form a ring.

If at least one of $R_{11}$ to $R_{15}$ is a substituted or unsubstituted alkenyl group of 2 to 10 carbon atoms, adjacent groups may be combined to form a ring. For example, $R_{12}$ and $R_{13}$ may be propenyl groups, and $R_{12}$ and $R_{13}$ may be combined to form a naphthyl group. In addition, $R_{12}$ to $R_{15}$ are propenyl groups, $R_{12}$ and $R_{13}$ may be combined, and $R_{14}$ and $R_{15}$ may be combined to form a phenanthryl group. However, there are only illustrations, and embodiments are not limited thereto.

In Formula 2-1, $Ar_{13}$ may be a substituted or unsubstituted aryl group of 6 to 40 ring-forming carbon atoms, or a substituted or unsubstituted heteroaryl group of 2 to 40 ring-forming carbon atoms. For example, $Ar_{13}$ may be a substituted aryl group or a substituted heteroaryl group. The group $Ar_{13}$ may include a phenyl group, a naphthyl group, a phenanthryl group, a fluorenyl group, a carbazole group, a dibenzofuran group, or a dibenzothiophene group as a substituent.

Formula 1 may be represented by Formula 2-2 below. Formula 2-2 represents a case where any one of $Ar_1$ and $Ar_2$ includes a substituted or unsubstituted carbazole group, a substituted or unsubstituted dibenzofuran group, or a substituted or unsubstituted dibenzothiophene group.

Formula 2-1

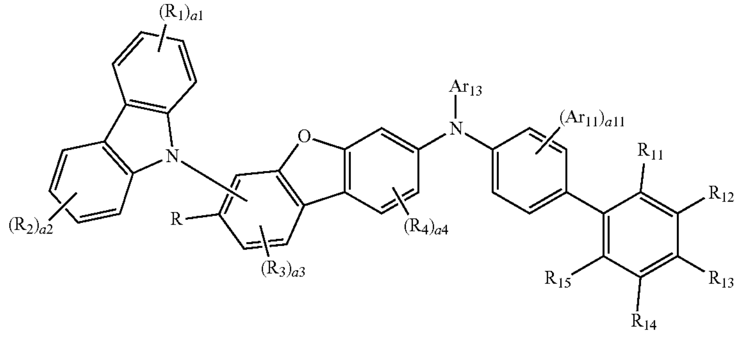

Formula 2-2

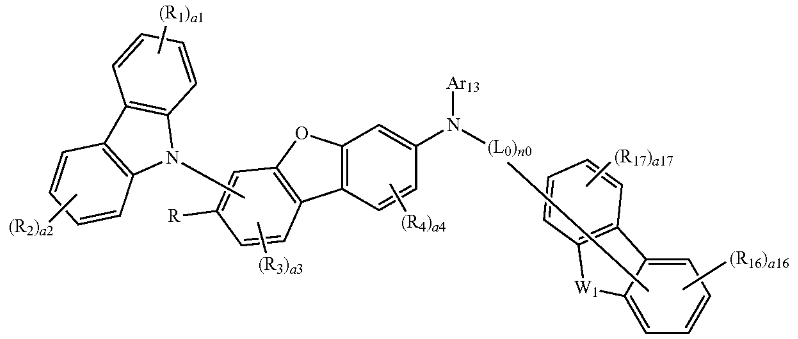

In Formula 2-2, $Ar_{13}$ may have the same meaning as in Formula 2-1. In Formula 2-2, a1 to a4, R, and $R_1$ to $R_4$ may have the same meaning as in Formula 1.

The variable n0 may be an integer of 0 to 3, and $L_0$ may be a direct linkage, a substituted or unsubstituted aryl group of 6 to 40 ring-forming carbon atoms, or a substituted or unsubstituted heteroaryl group of 2 to 40 ring-forming carbon atoms. For example, $L_0$ may be a substituted or unsubstituted phenyl group or a substituted or unsubstituted dibenzofuran group. $W_1$ may be $CR_{18}R_{19}$, $NR_{20}$, O, or S. A fused ring of three rings, including $W_1$ as a ring-forming atom may be a substituted or unsubstituted fluorene, a substituted or unsubstituted carbazole, a substituted or unsubstituted dibenzofuran, or a substituted or unsubstituted dibenzothiophene.

In Formula 2-2, a16 may be an integer of 0 to 4, and a17 may be an integer of 0 to 4. If a16 is an integer of 2 or more, multiple $R_{16}$ groups may be the same, or at least one thereof may be different. If a17 is an integer of 2 or more, multiple $R_{17}$ groups may be the same, or at least one thereof may be different.

The variables $R_{16}$ to $R_{20}$ may be each independently a hydrogen atom, a deuterium atom, a substituted or unsubstituted alkenyl group of 2 to 10 carbon atoms, a substituted or unsubstituted aryl group of 6 to 40 ring-forming carbon atoms, or a substituted or unsubstituted heteroaryl group of 2 to 40 ring-forming carbon atoms, or combined with an adjacent group to form a ring. For example, $W_1$ may be $CR_{18}R_{19}$, $R_{18}$ and $R_{19}$ may be combined, and a fluorene of a Spiro structure including $W_1$ as a ring-forming atom may be formed. The variable $W_1$ may be O, two $R_{17}$ groups may be combined, and a naphthobenzofuran group including $W_1$ as a ring-forming atom may be formed. The variable $W_1$ may be S, two $R_{17}$ groups may be combined, and a benzonaphthothiophene group including $W_1$ as a ring-forming atom may be formed.

The amine compound, represented by Formula 1 may be represented by any one of the compounds in Compound Group 1 below. The hole transport region HTR of a light emitting device ED may include at least one of the amine compounds shown in Compound Group 1 below.

Compound Group 1

A1

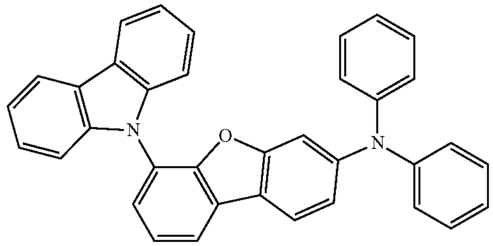

A2

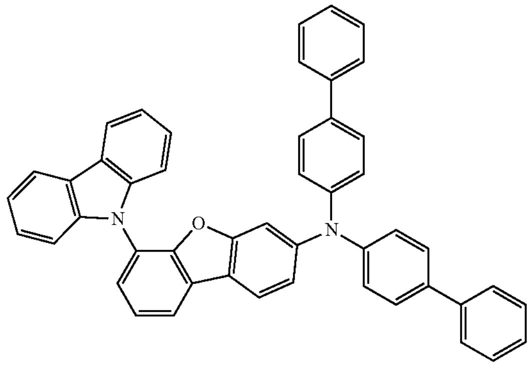

A3

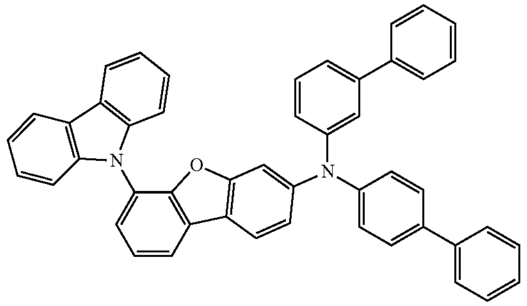

-continued
A4
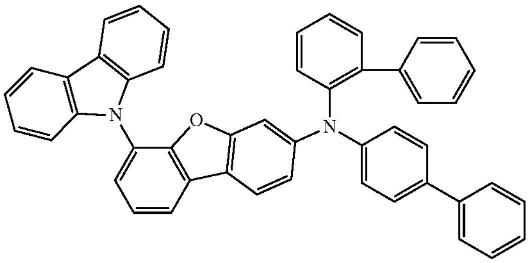
A5
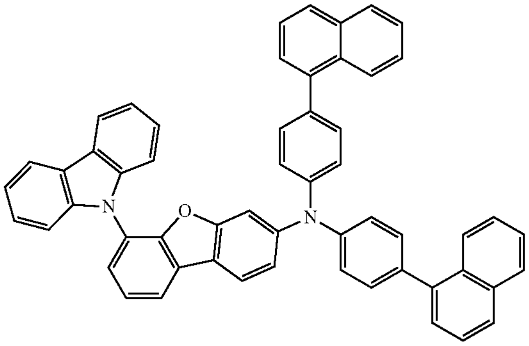
A6
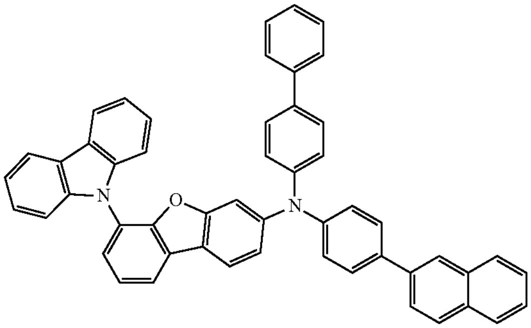
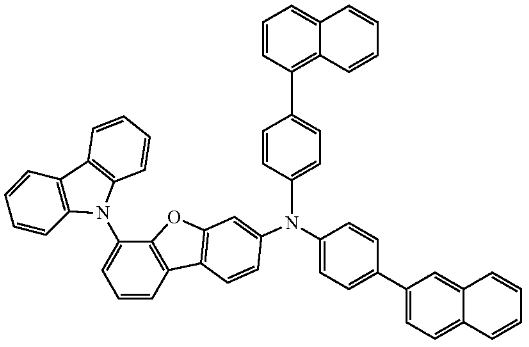
A8
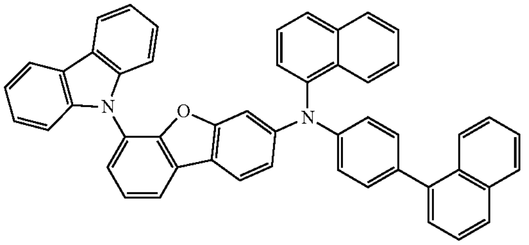
-continued
A9
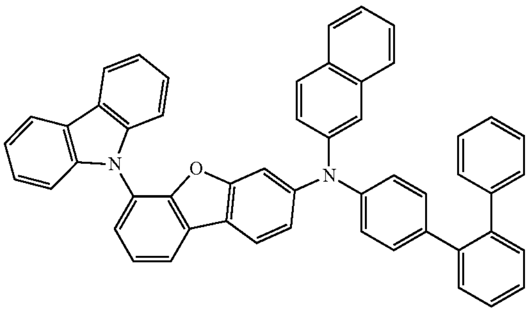
A10
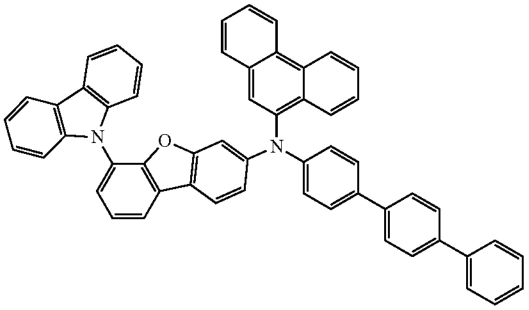
A11
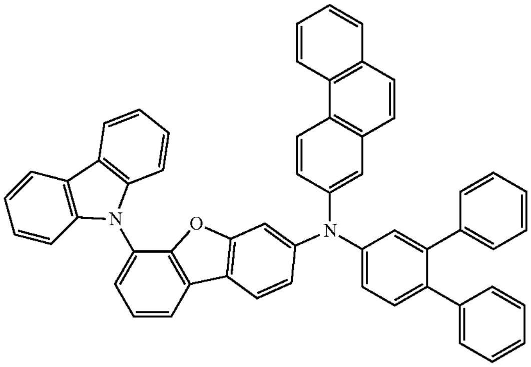
A12
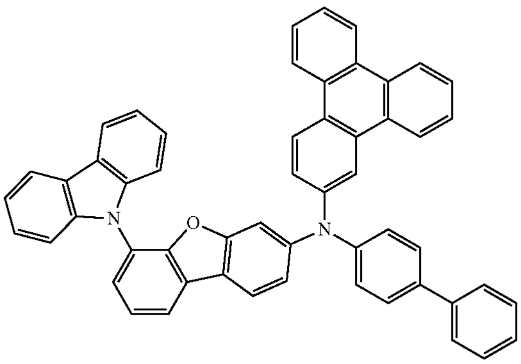

-continued
A13
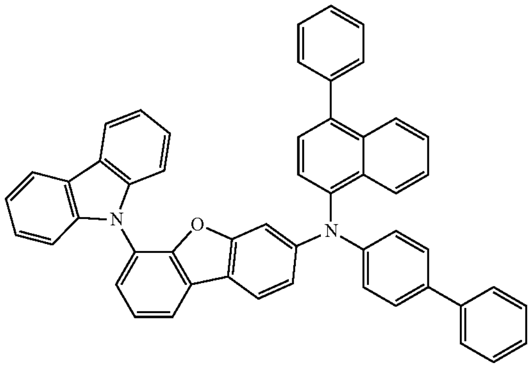
A14
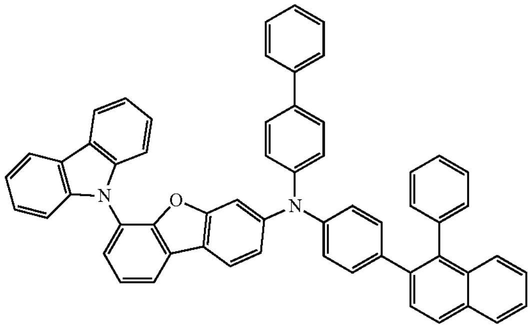
A15
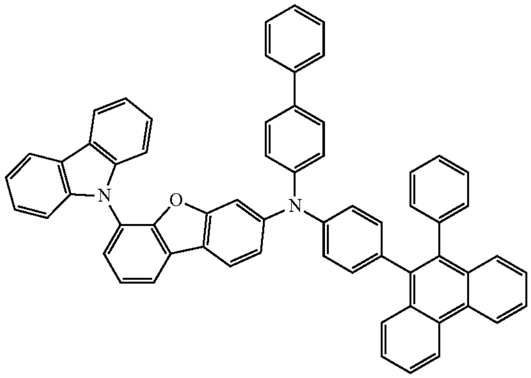
A16
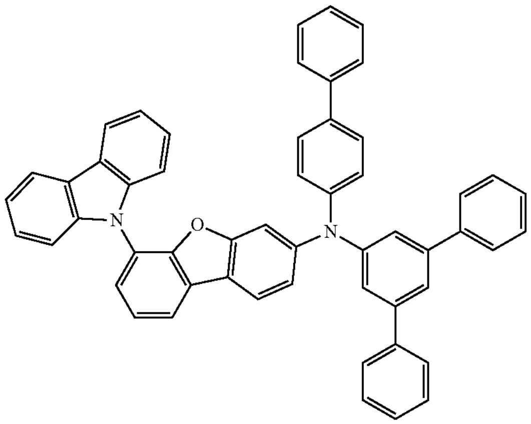
-continued
A17
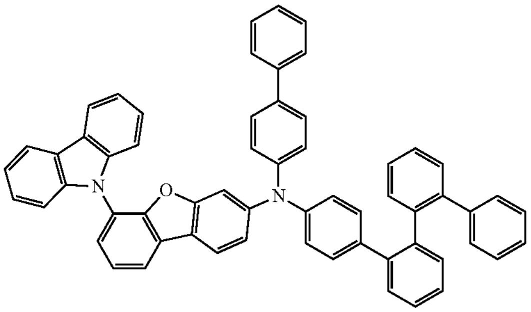
A18
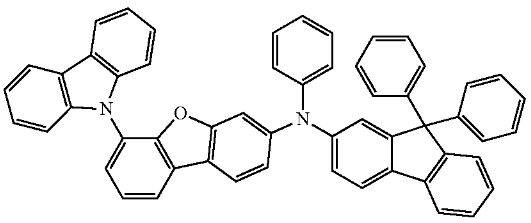
A19
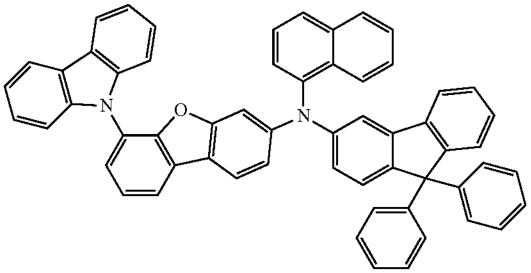
A20
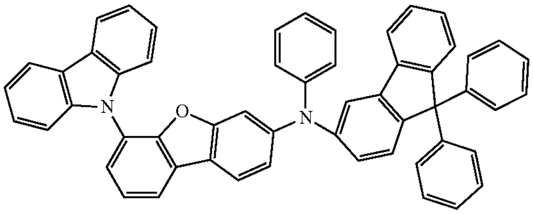
A21
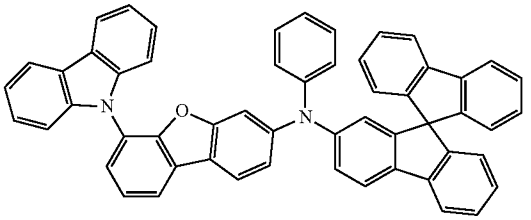

-continued
A22
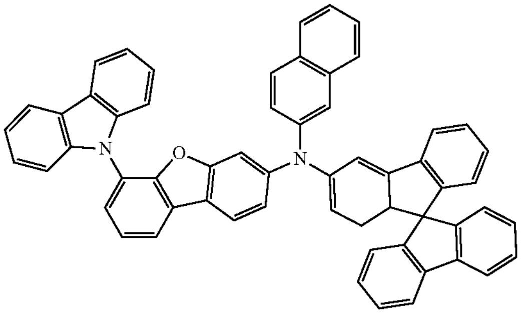
A23
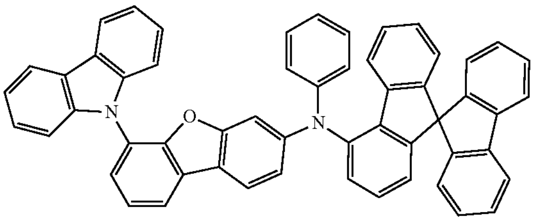
A24
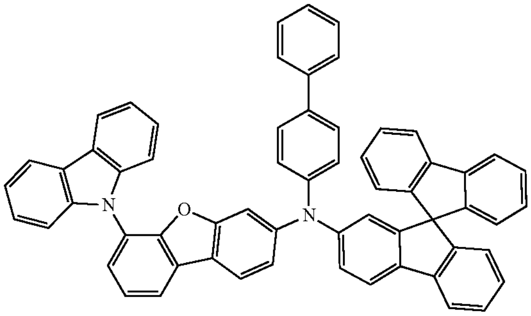
A25
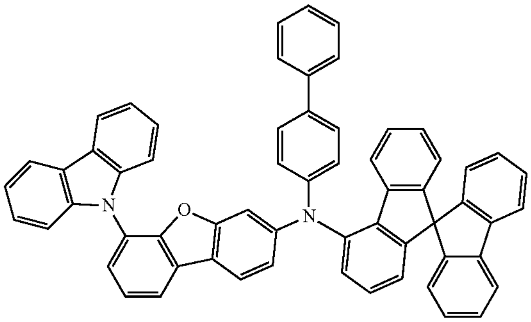
A26
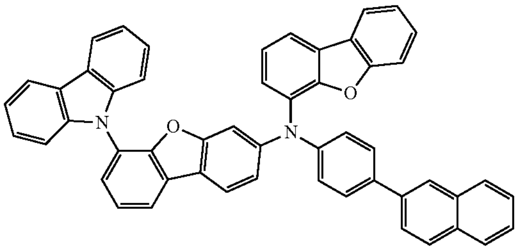
-continued
A27
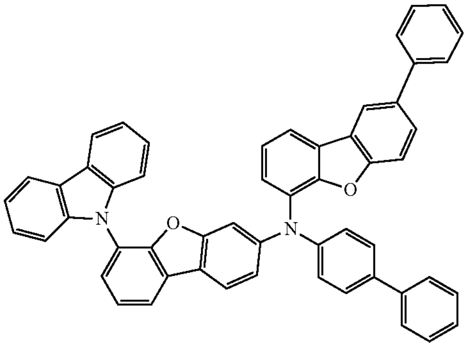
A28
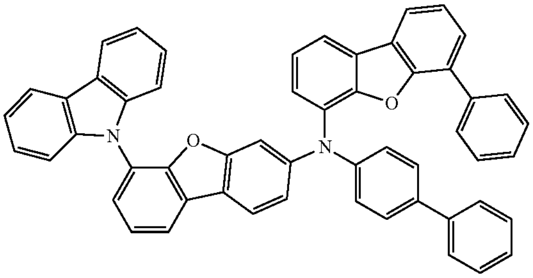
A29
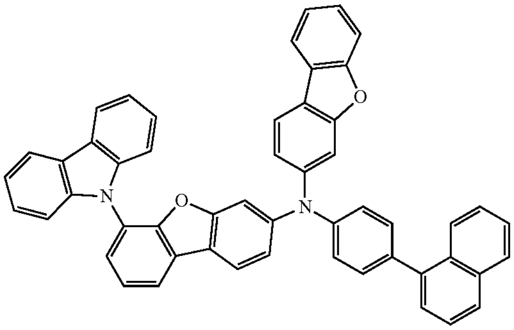
A30
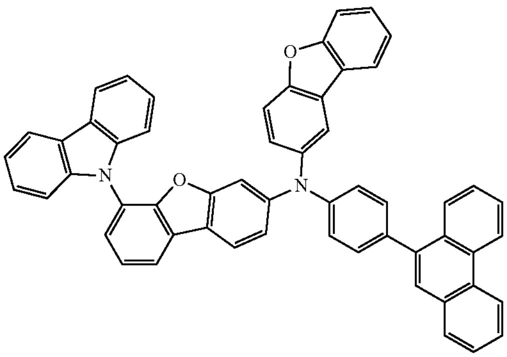

-continued
A31
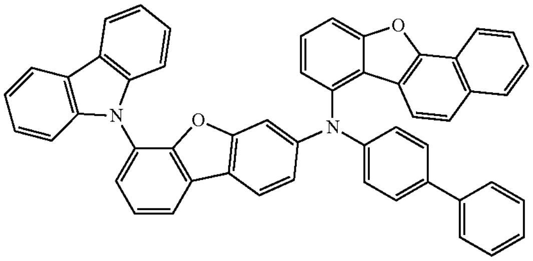
A32
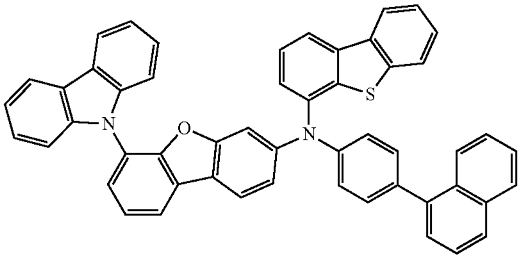
A33
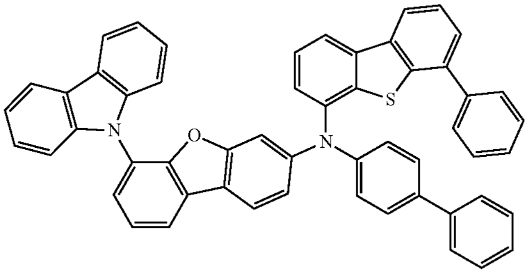
A34
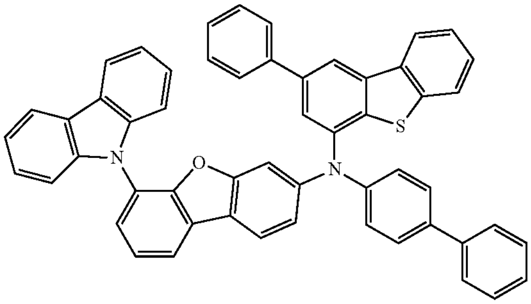
A35
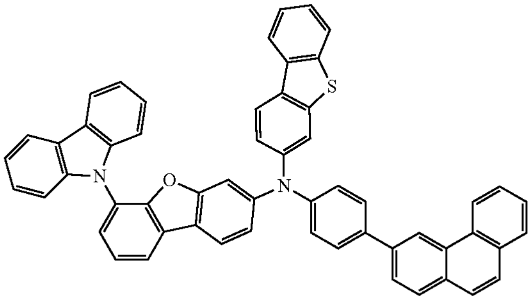
-continued
A36
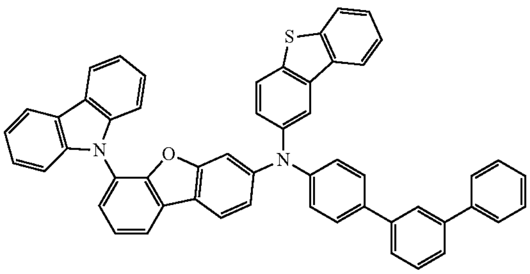
A36
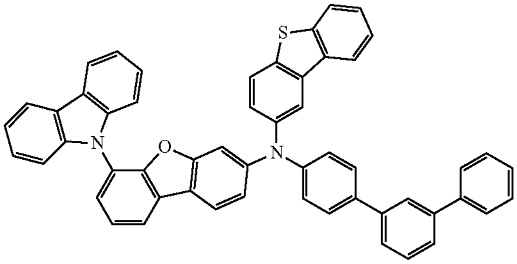
A37
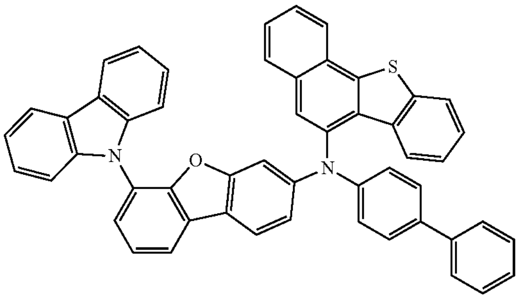
A38
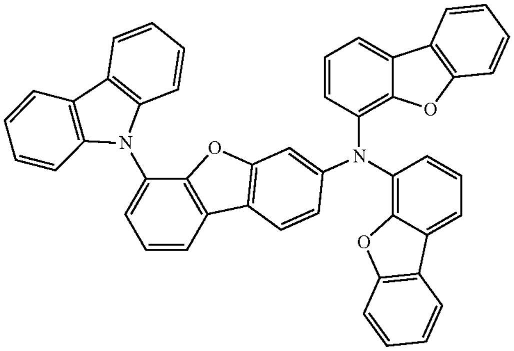
A39
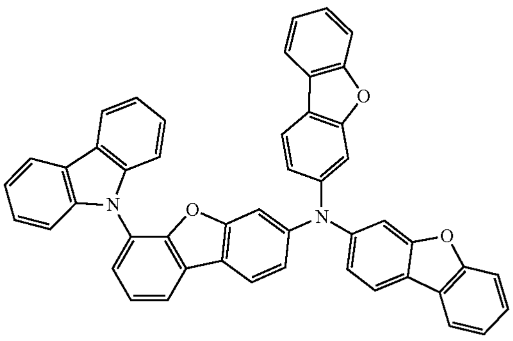

-continued
A40
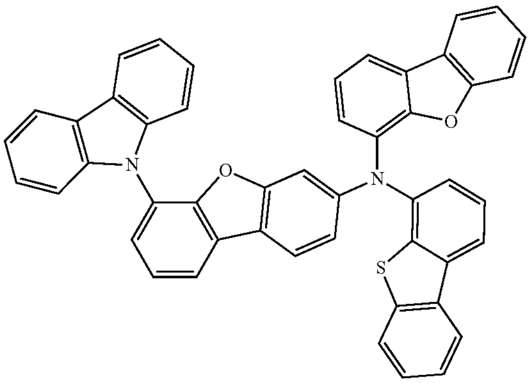
A41
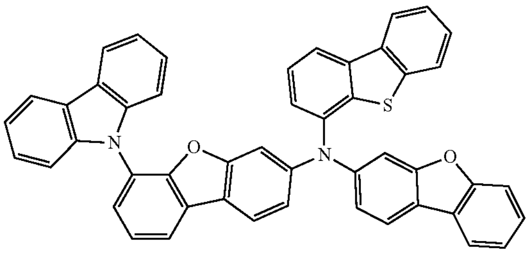
A42
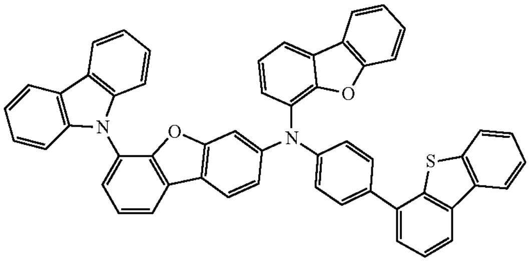
A43
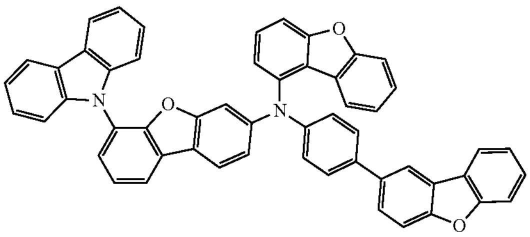
A44
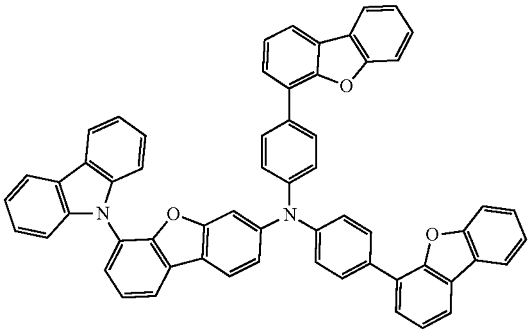
-continued
A45
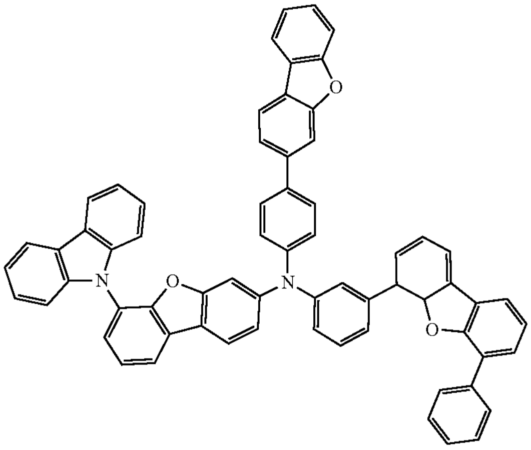
A46
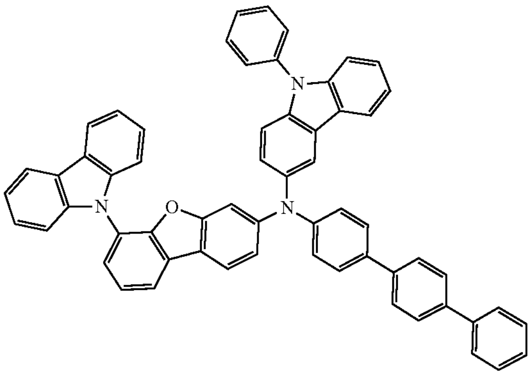
A47
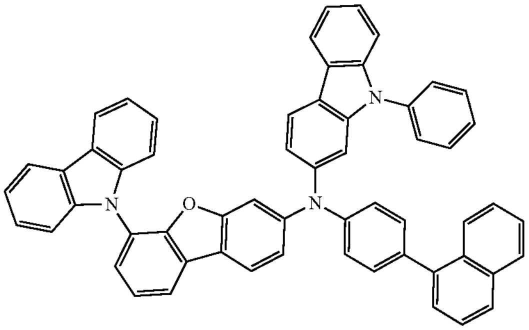
A48
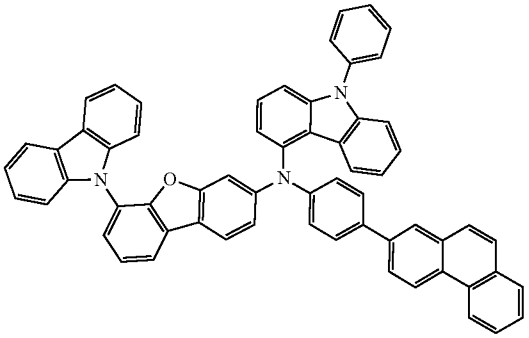

-continued
A49
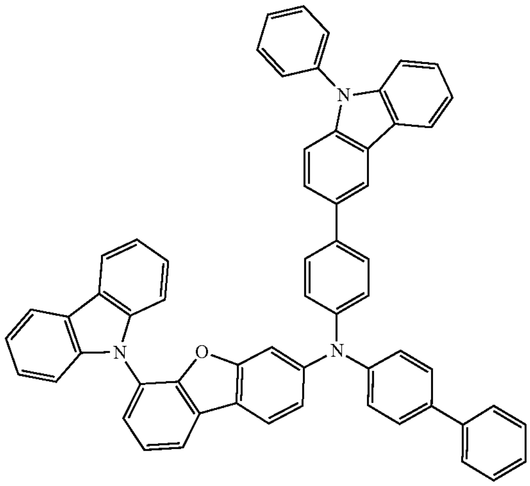
A50
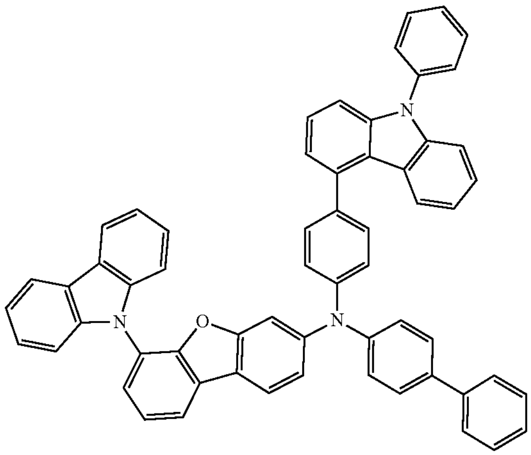
A51
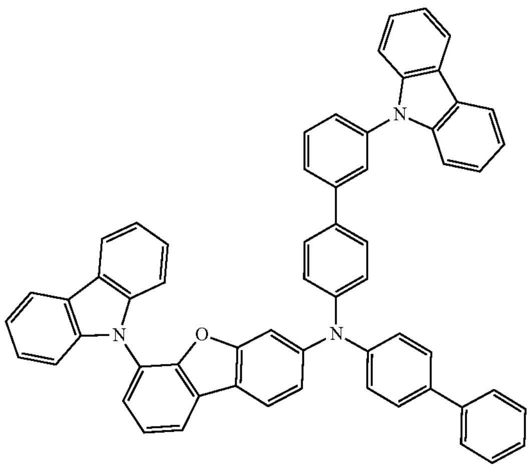
-continued
A52
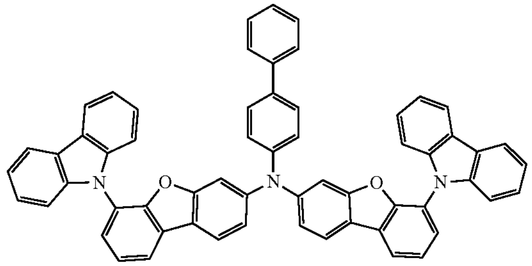
A53
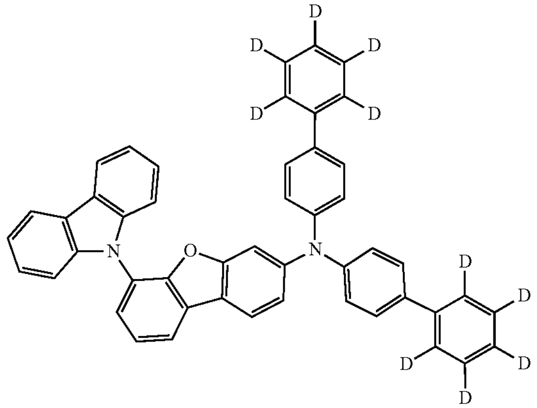
A54
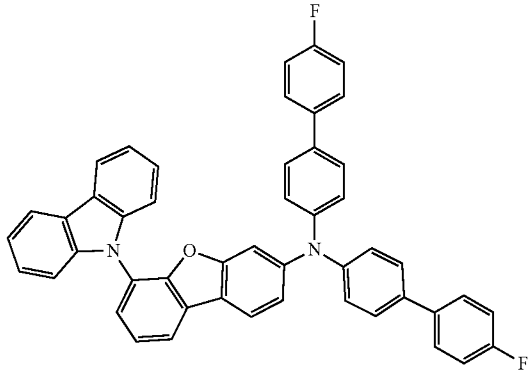
A55
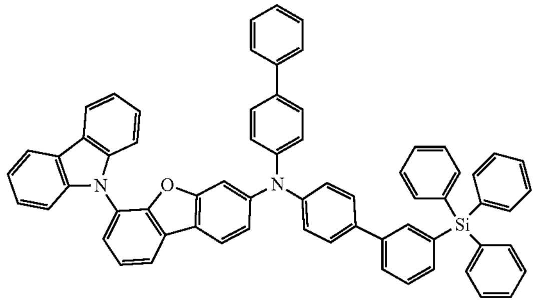

-continued
A56
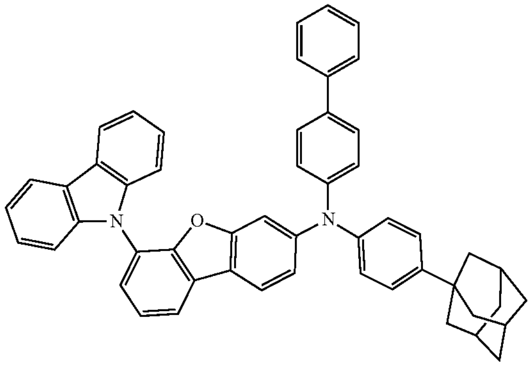
A57
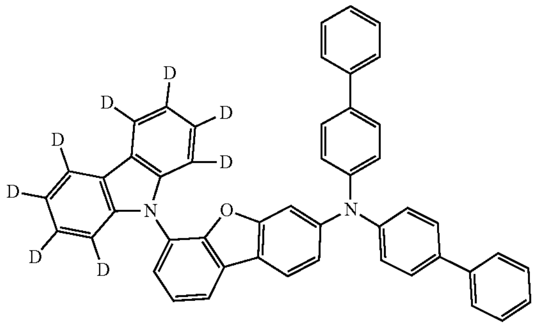
A58
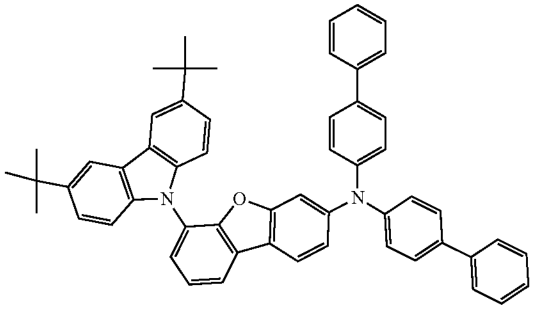
A59
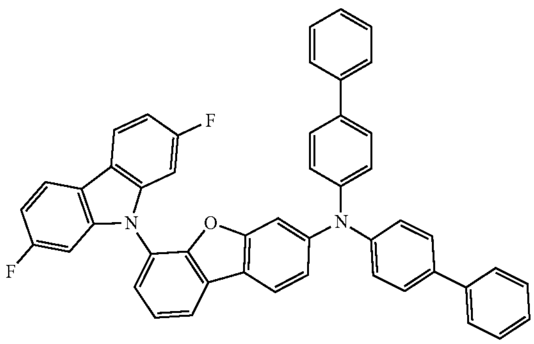
-continued
A60
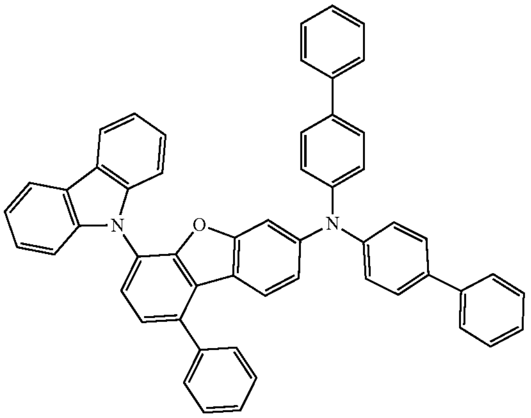
A61
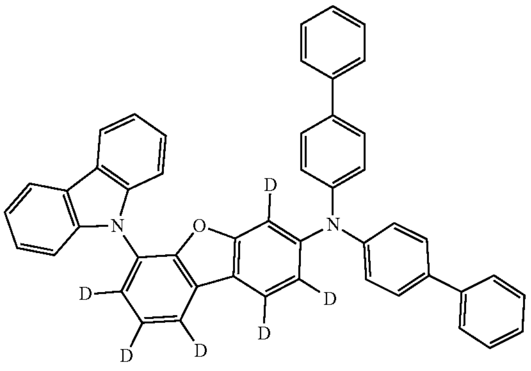
A62
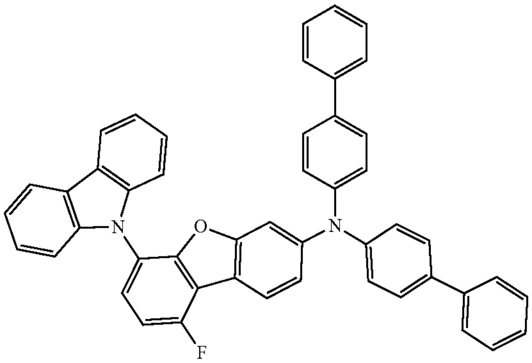
A63
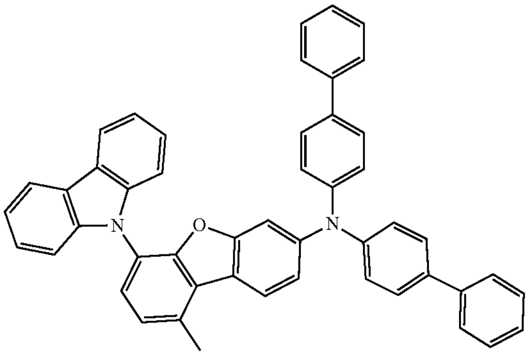

-continued
A64
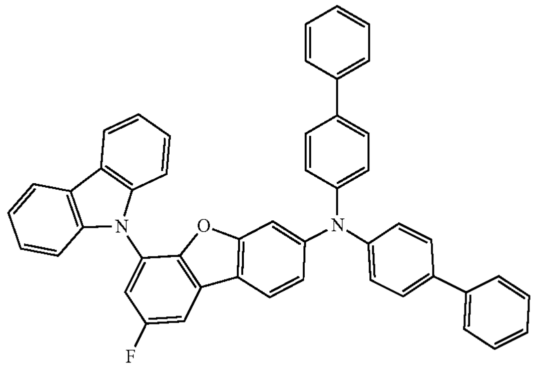
A65
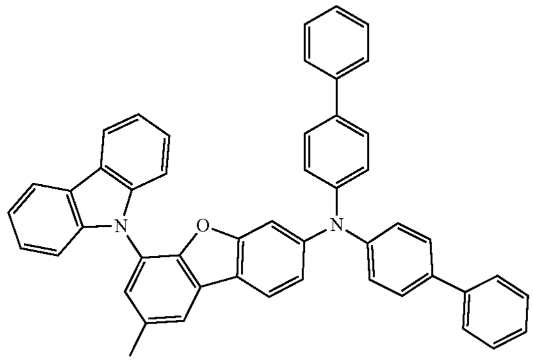
B1
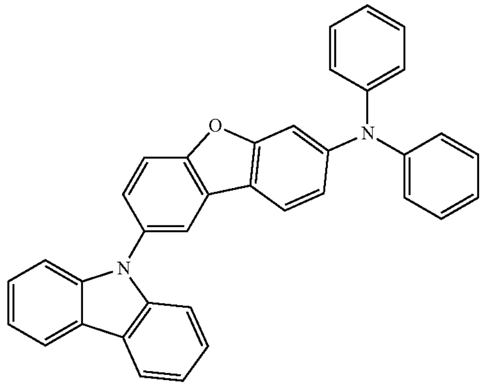
B2
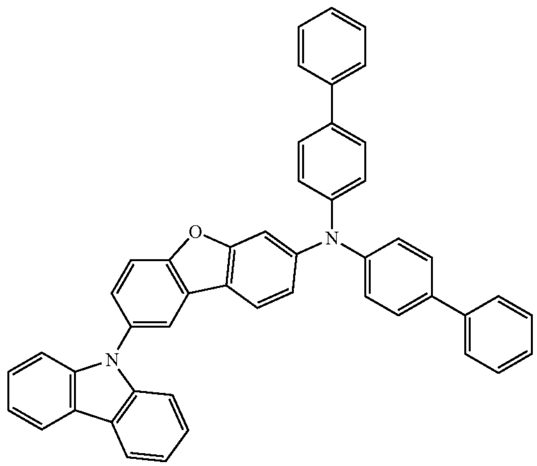
-continued
B3
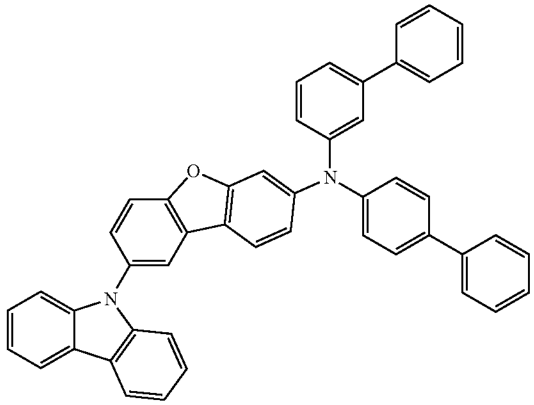
B4
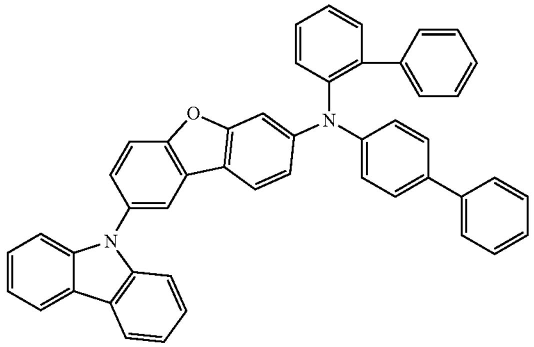
B5
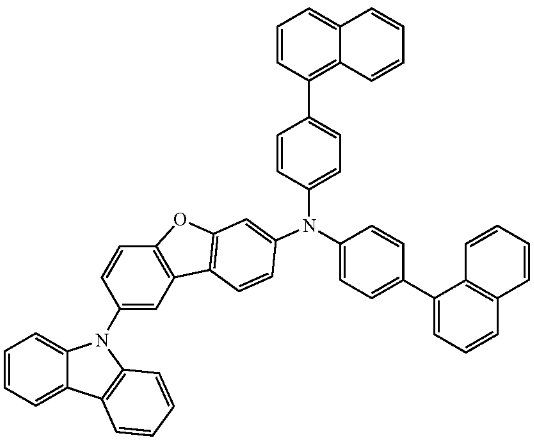

-continued
B6
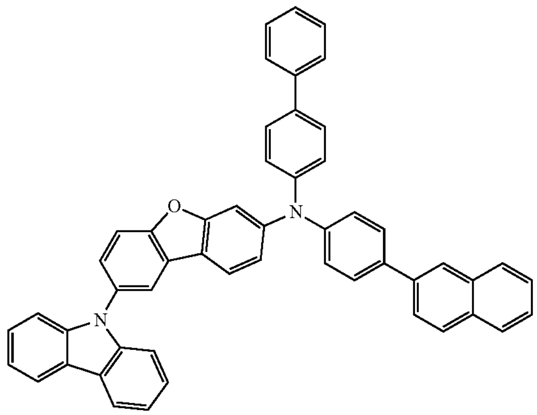
B7
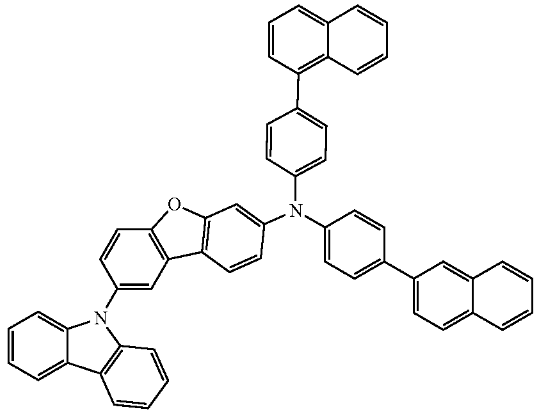
B8
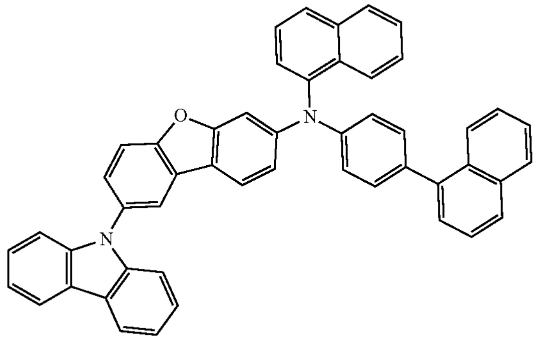
B9
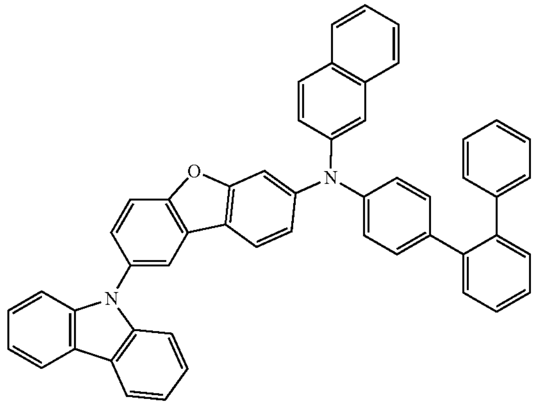
-continued
B10
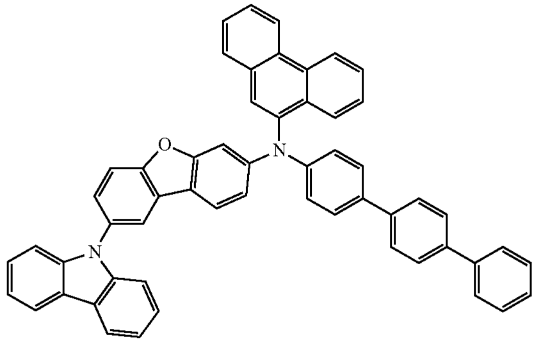
B11
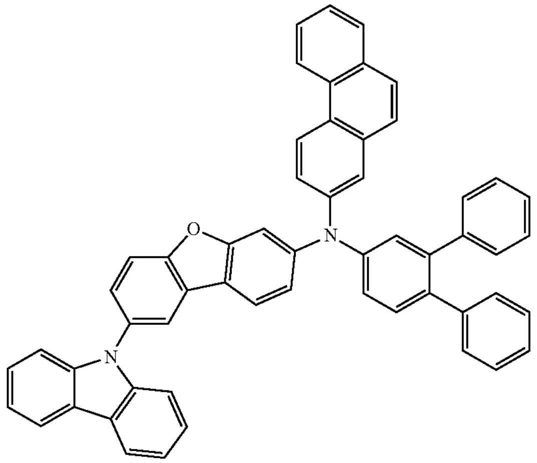
B12
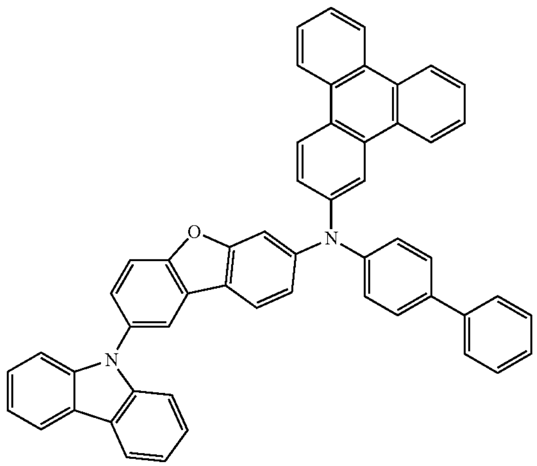

-continued
B13
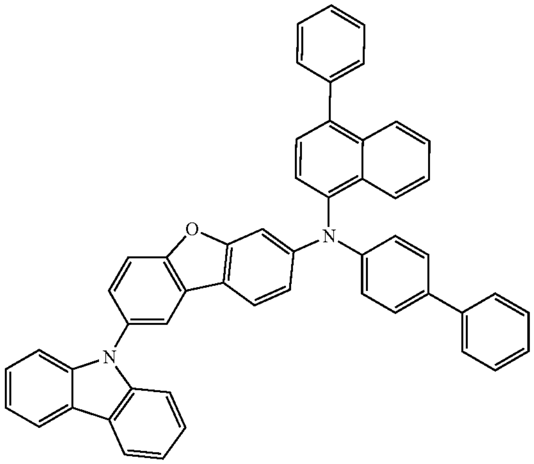
B14
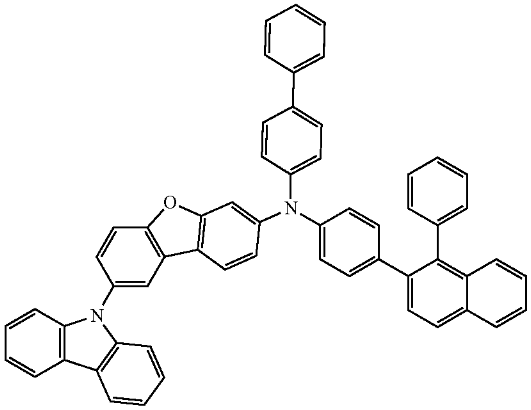
B15
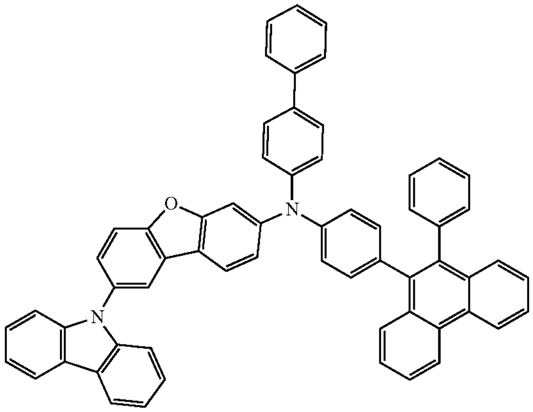
-continued
B16
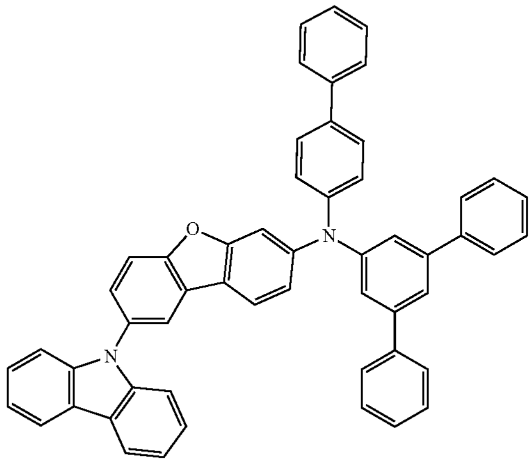
B17
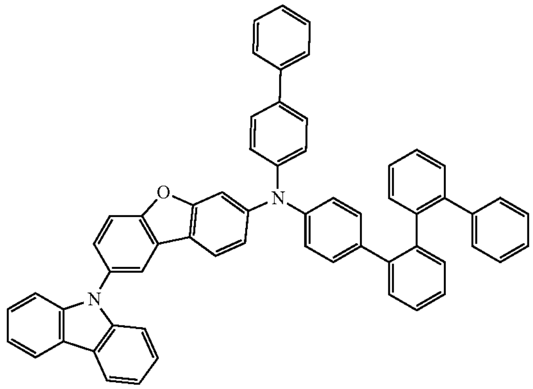
B18
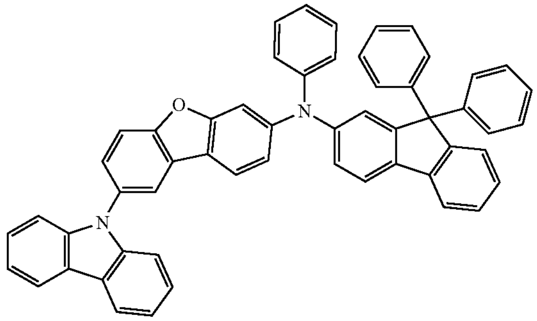
B19
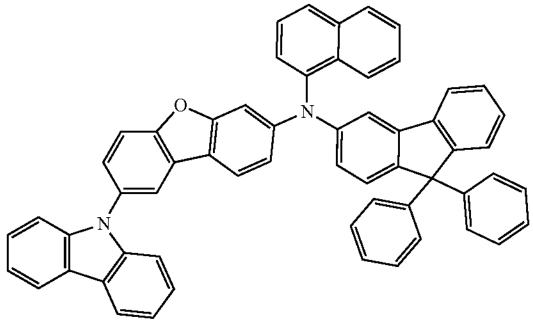

-continued
B20
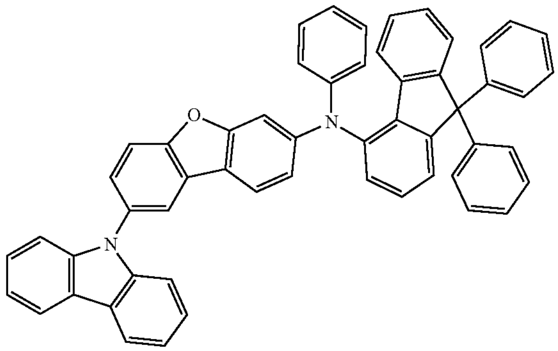
B21
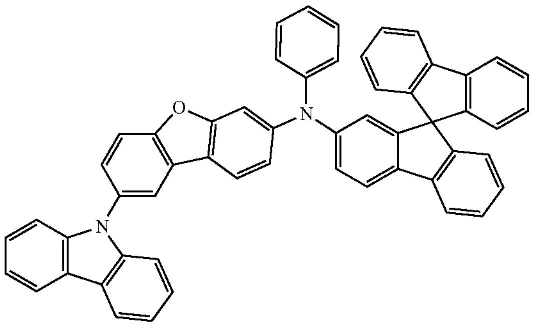
B22
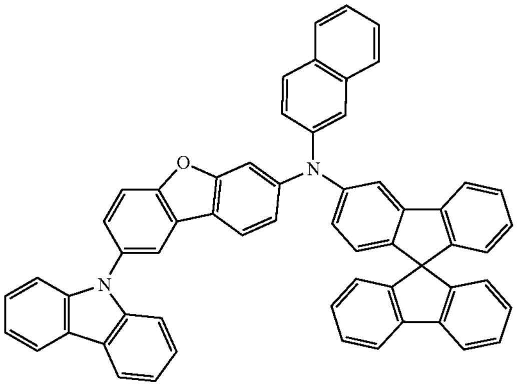
B23
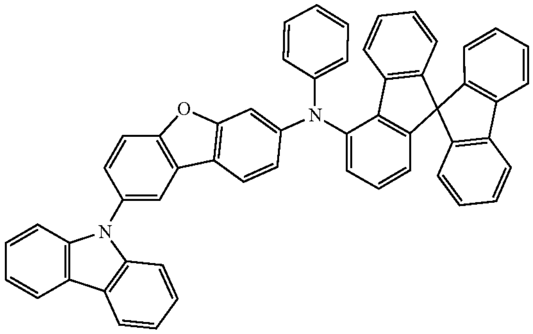
-continued
B24
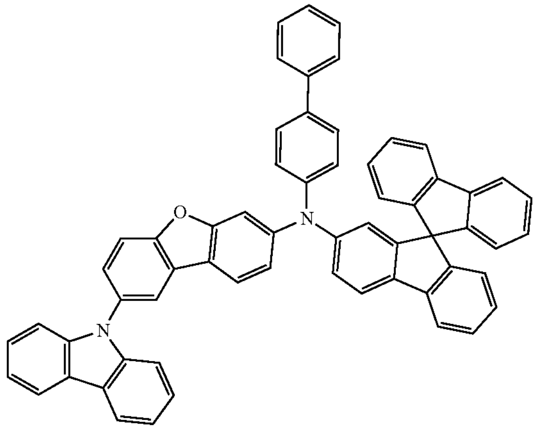
B25
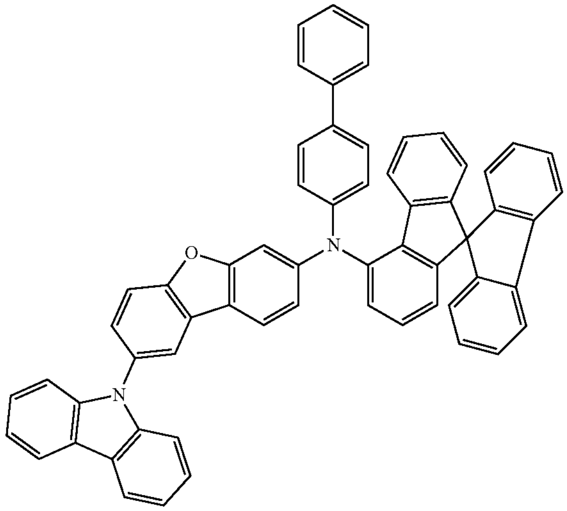
B26
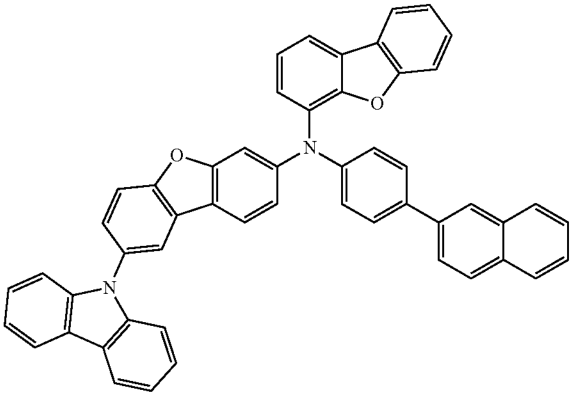

-continued
B27
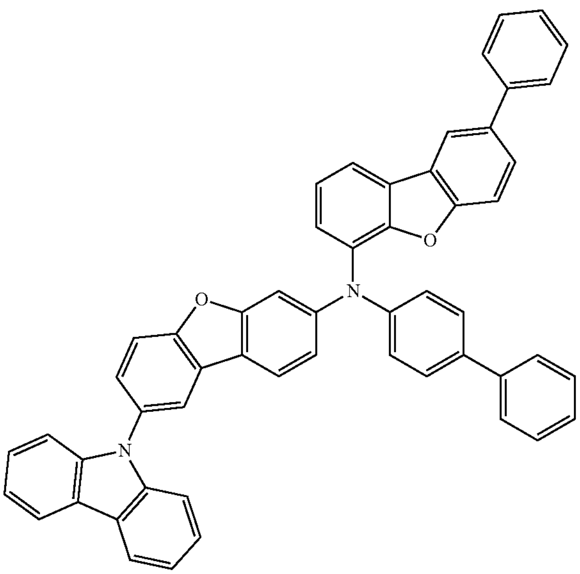
B28
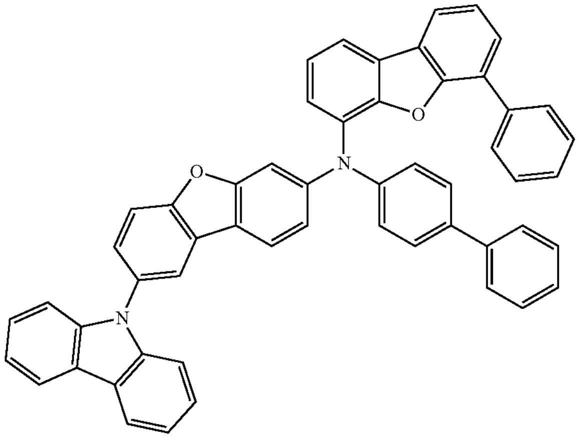
B29
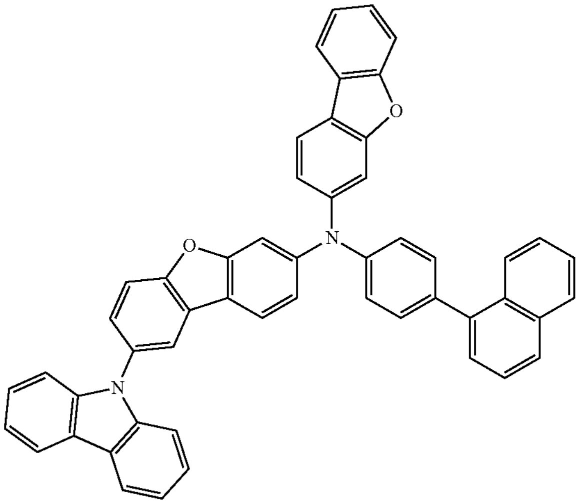
-continued
B30
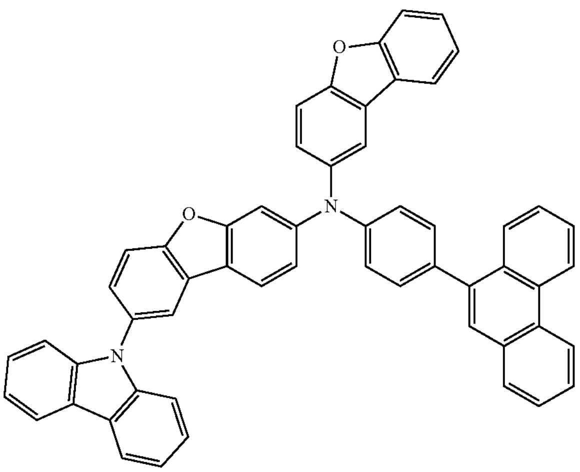
B31
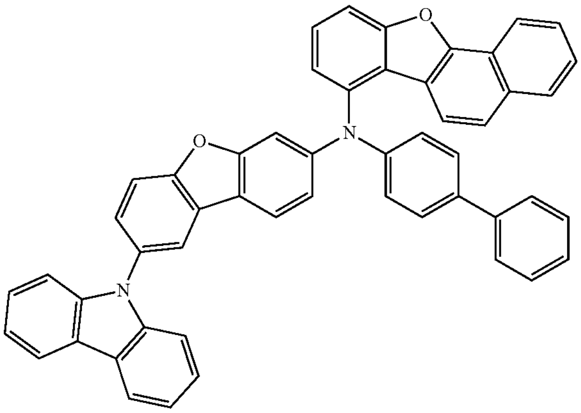
B32
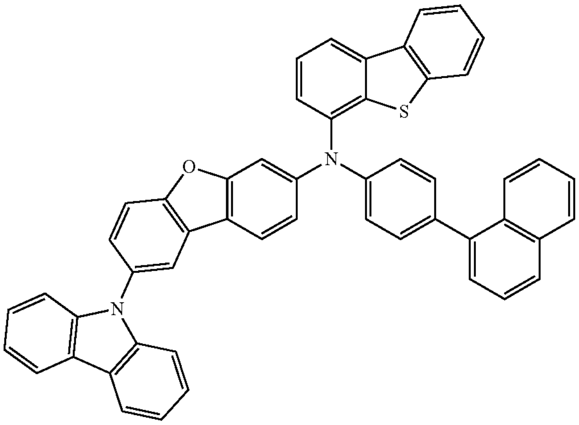

-continued
B33
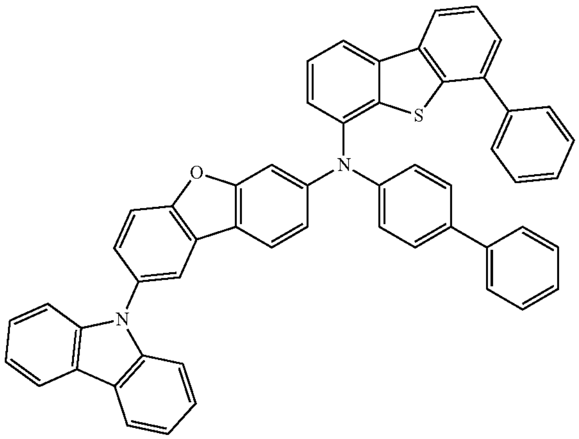
B34
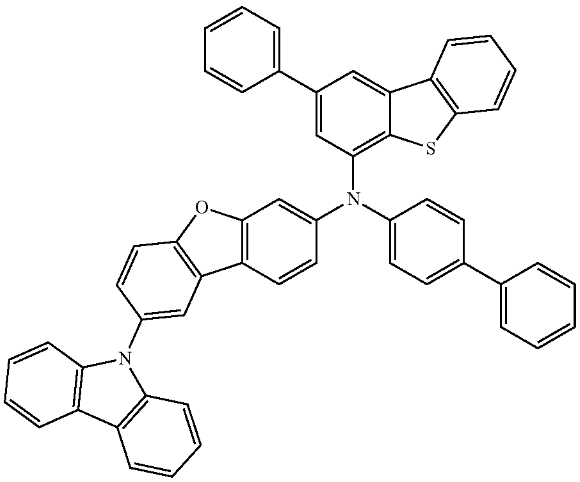
B35
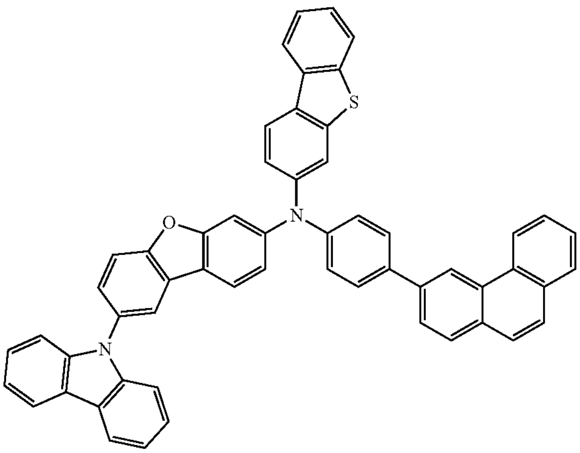
-continued
B36
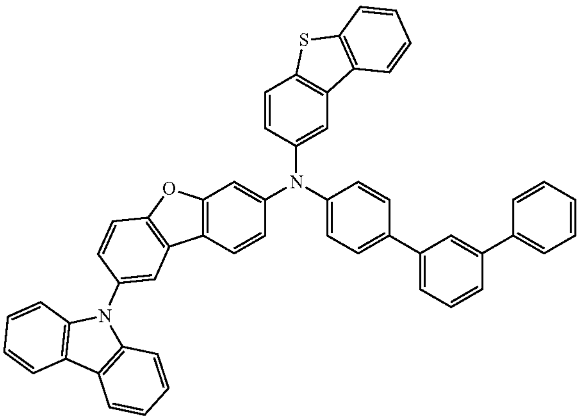
B37
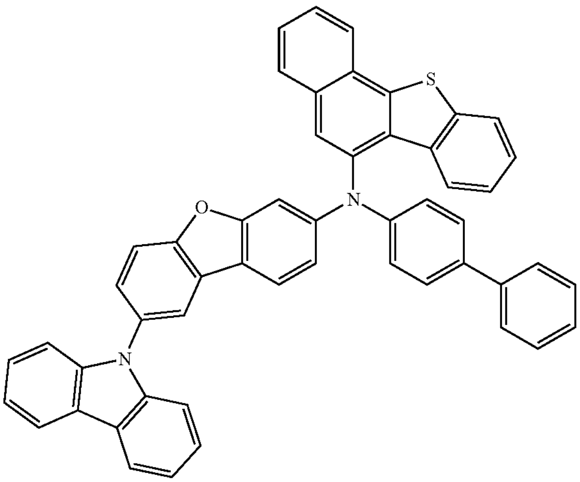
B38
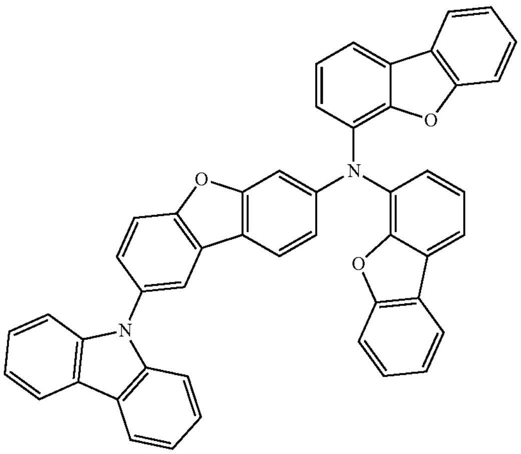

-continued
B39
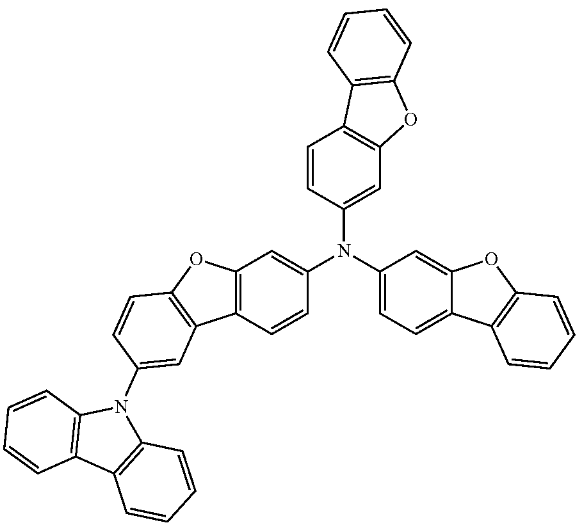
B40
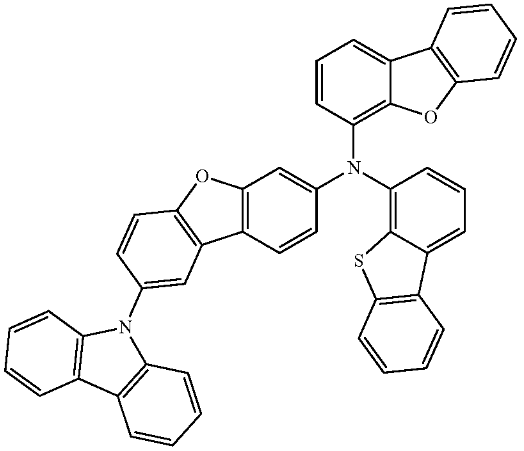
B41
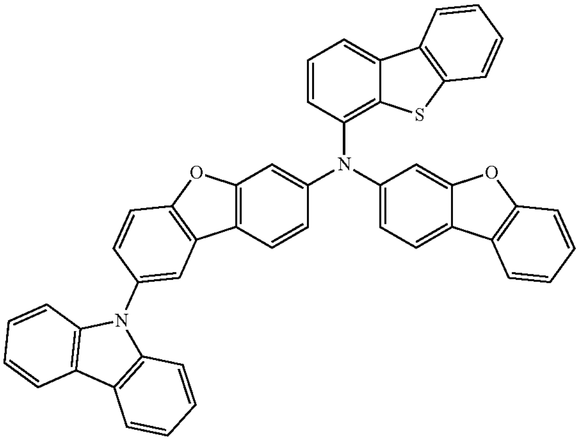
-continued
B42
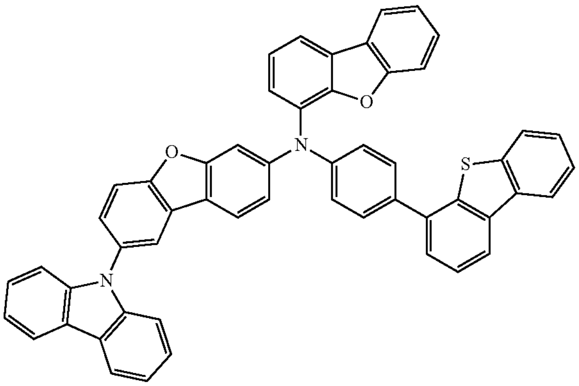
B43
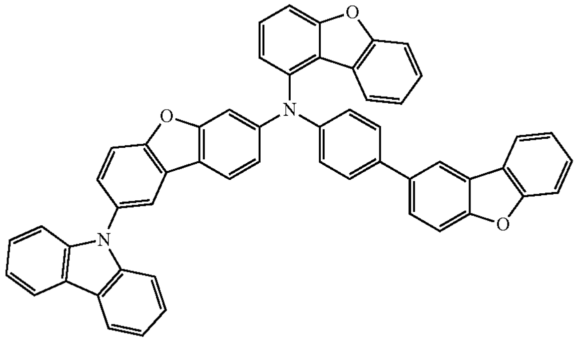
B44
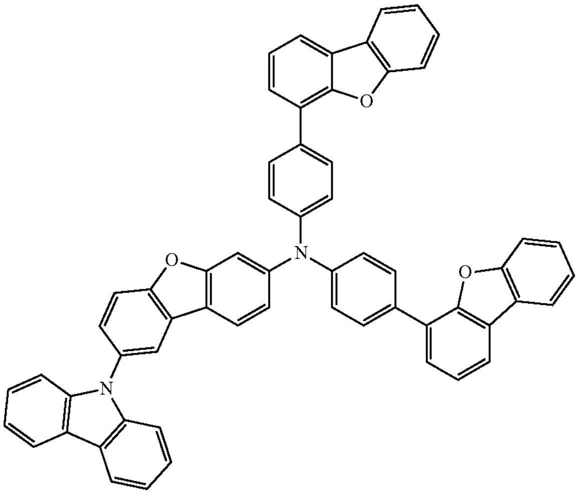

-continued
B45
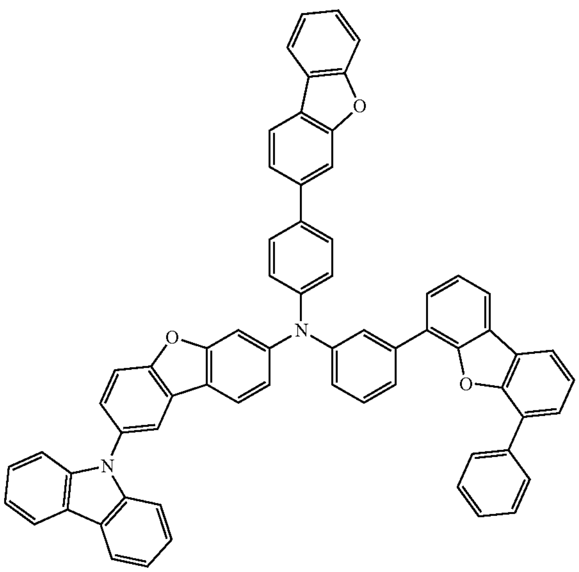
B46
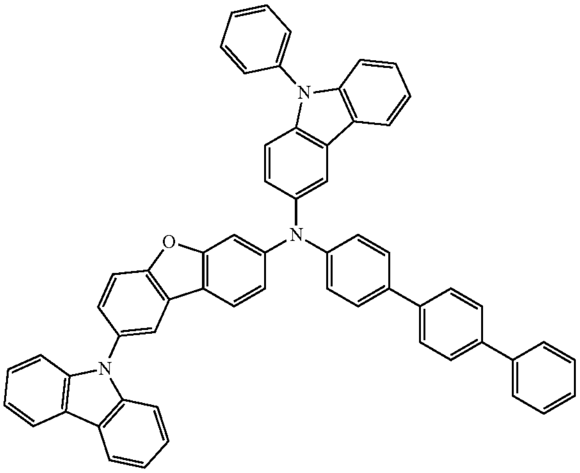
B47
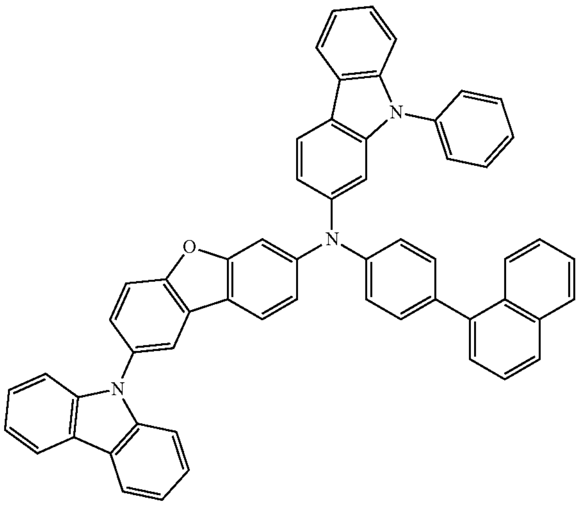
-continued
B48
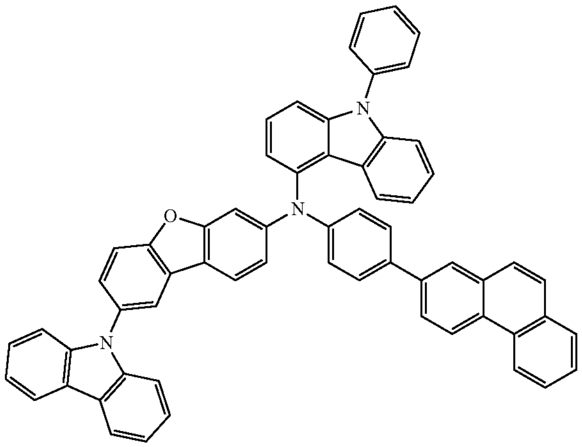
B49
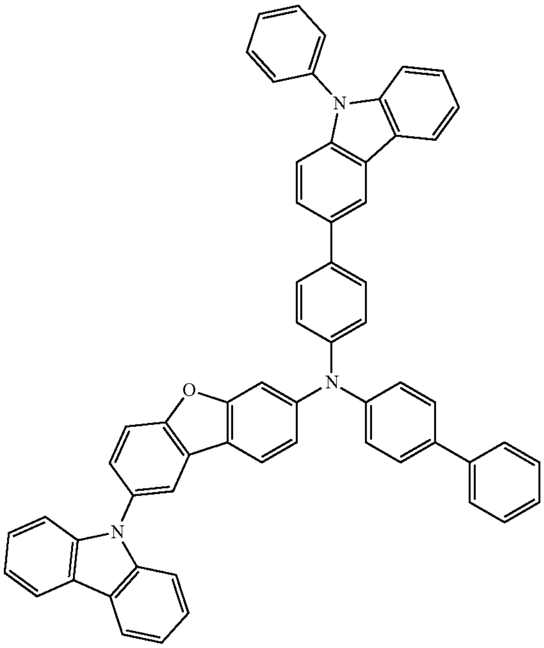

-continued
B50
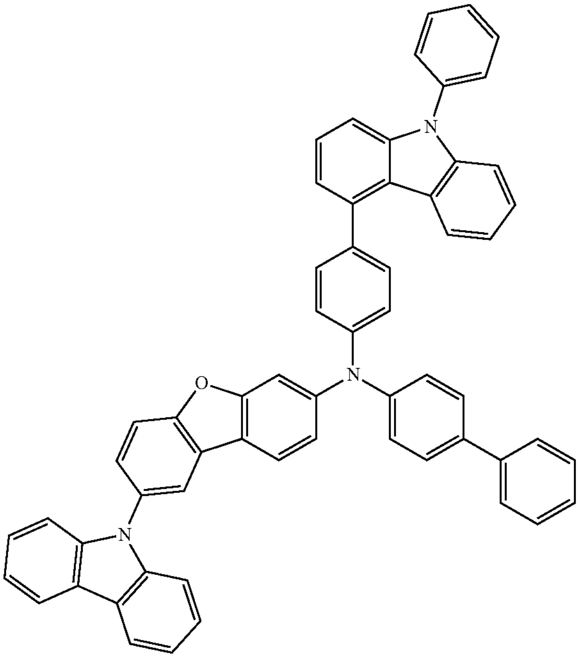
B51
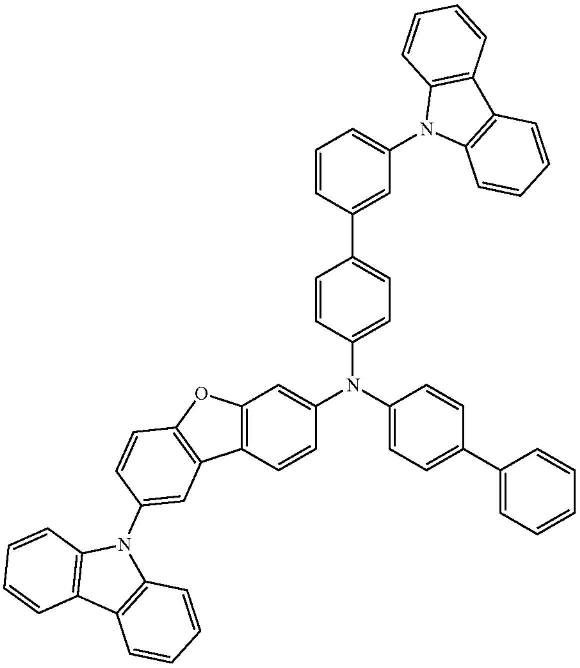
-continued
B52
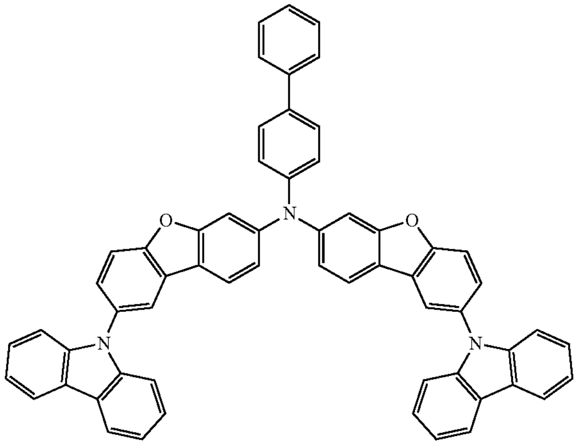
B53
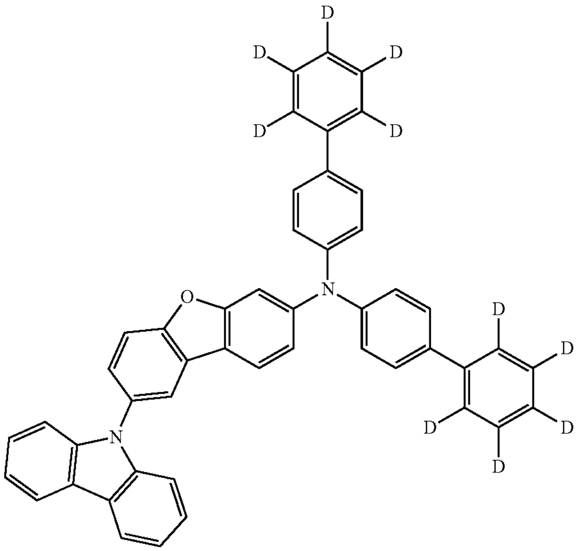
B54
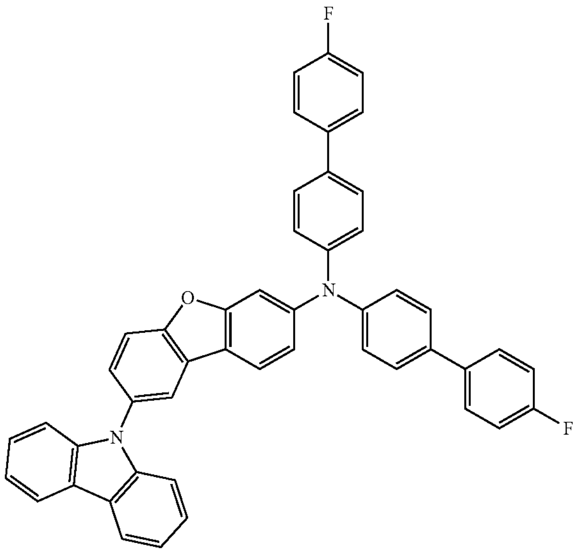

B55
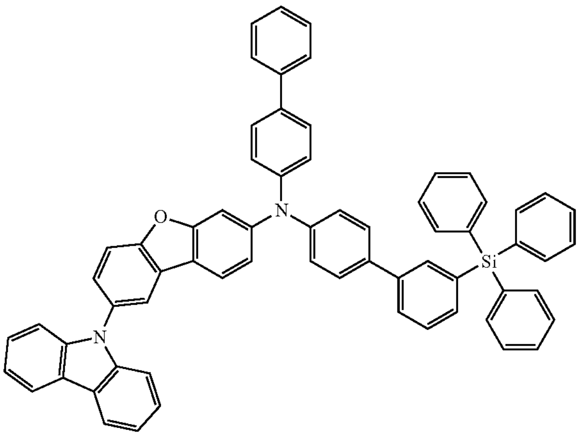
B56
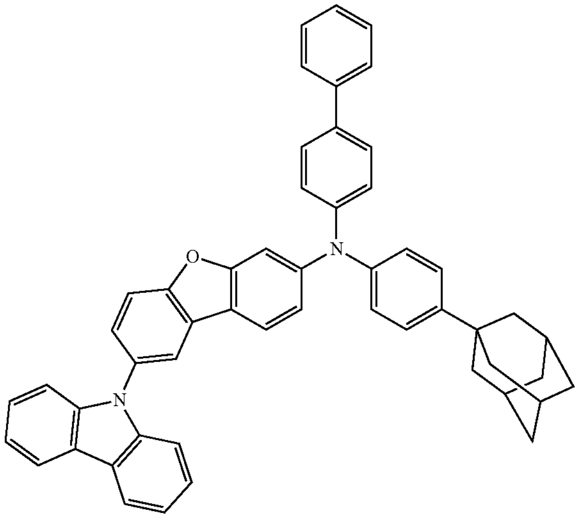
B57
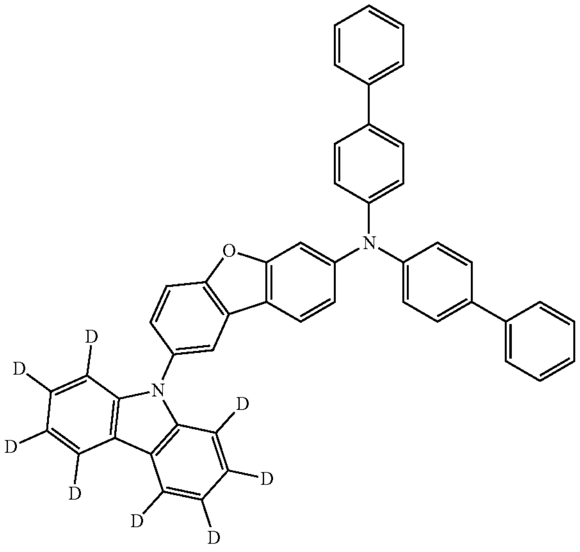
B58
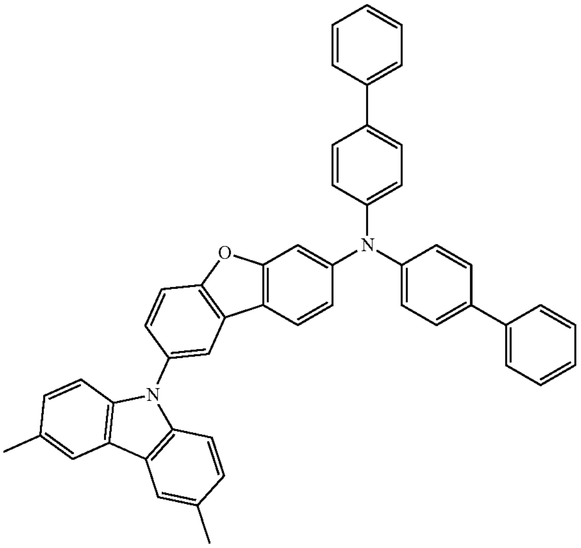
B59
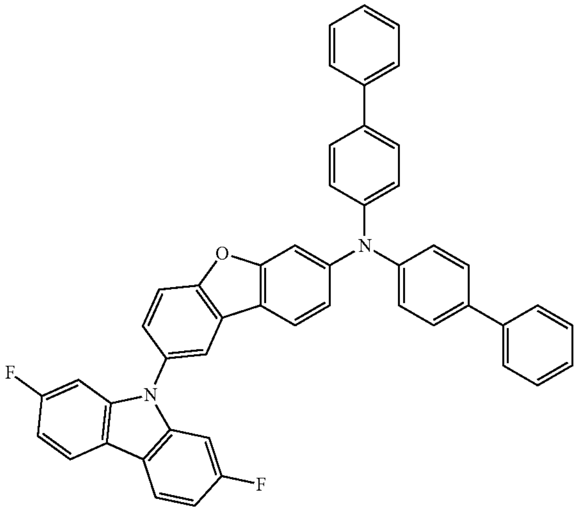
B60
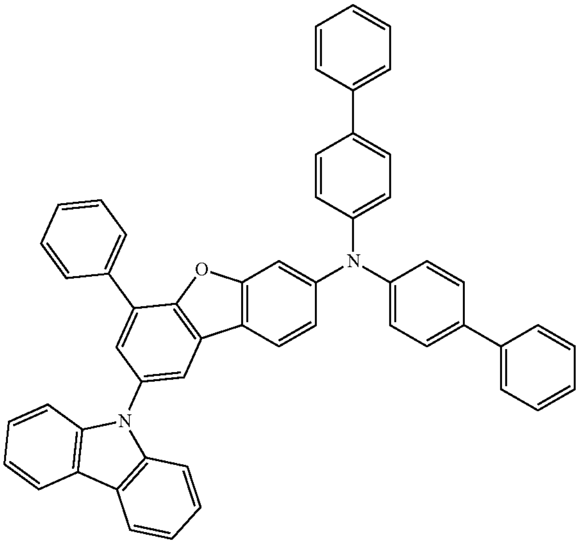

-continued
B61
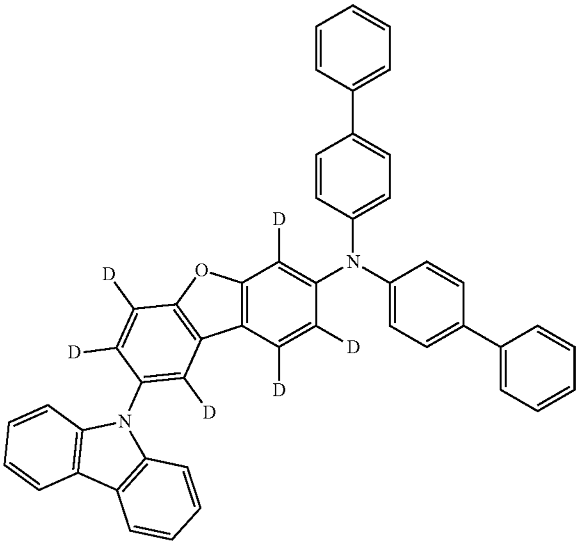
B62
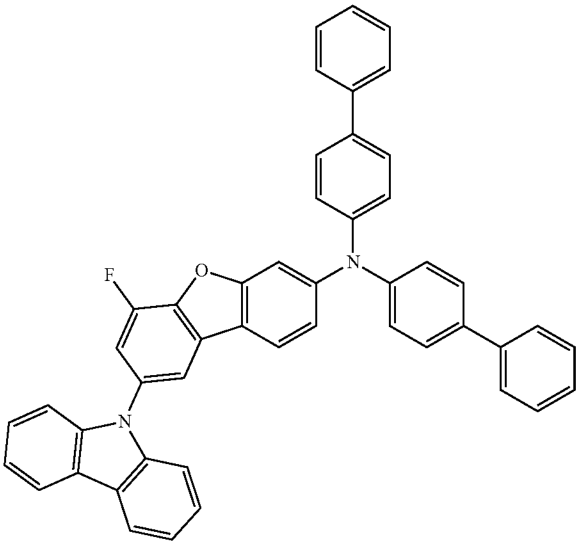
-continued
B63
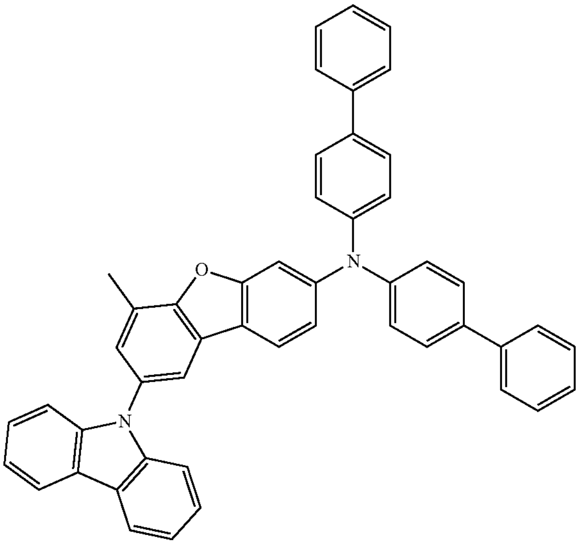
C1
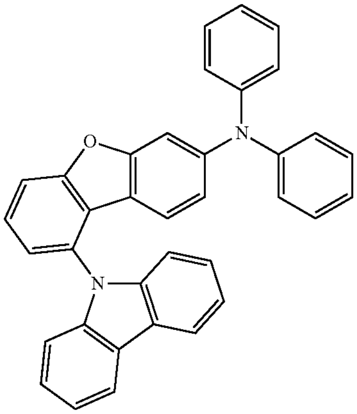
C2
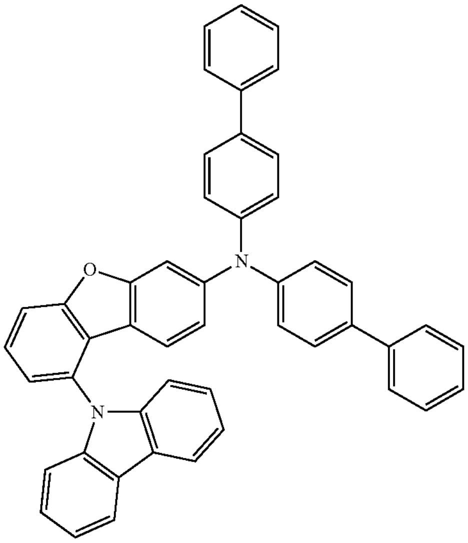

-continued
C3
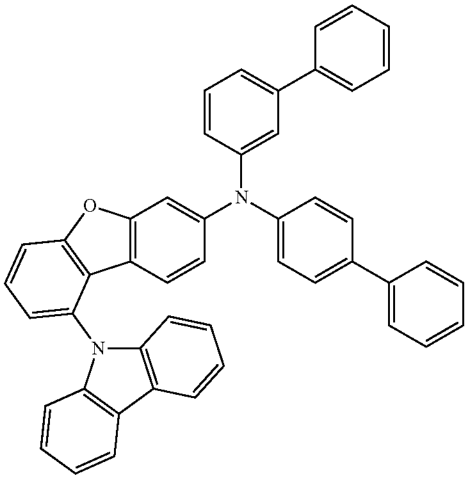
C4
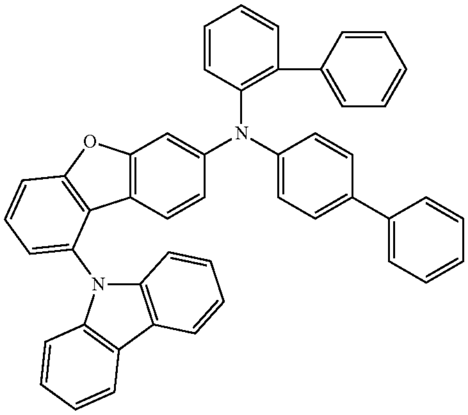
C5
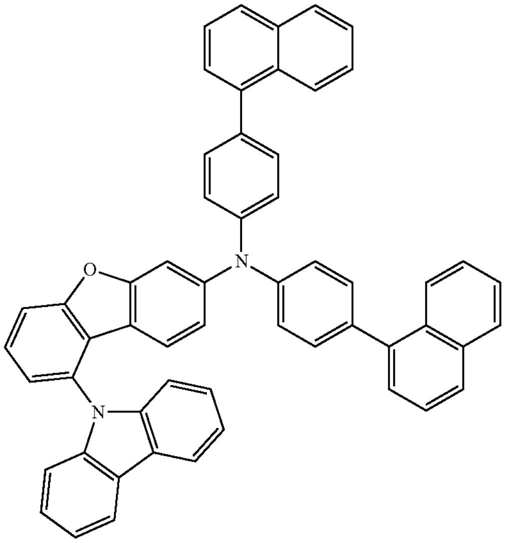
-continued
C6
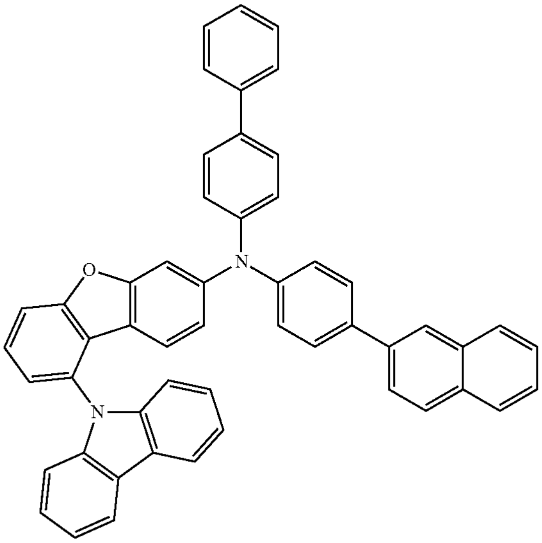
C7
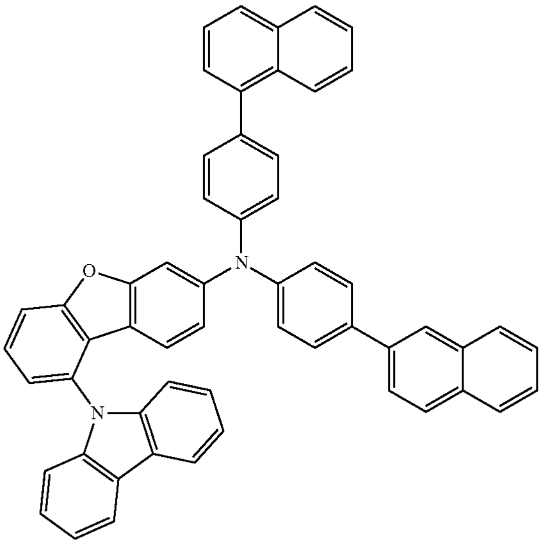
C8
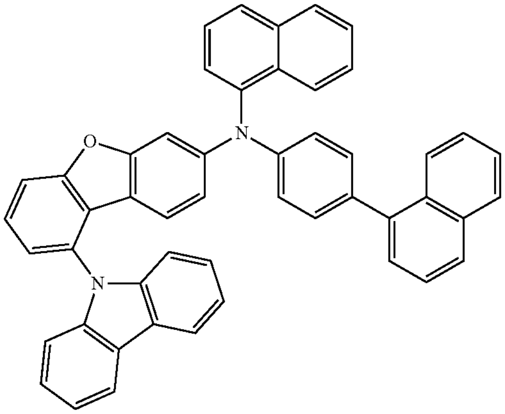

-continued
C9
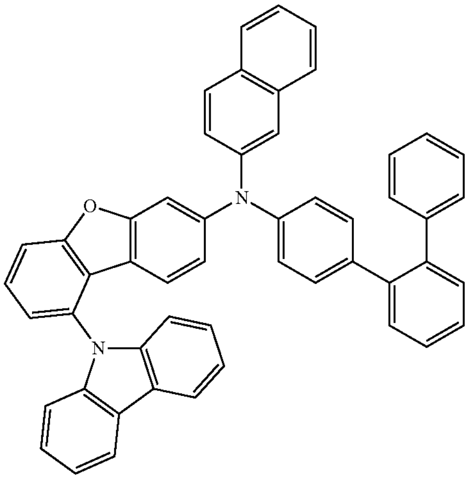
C10
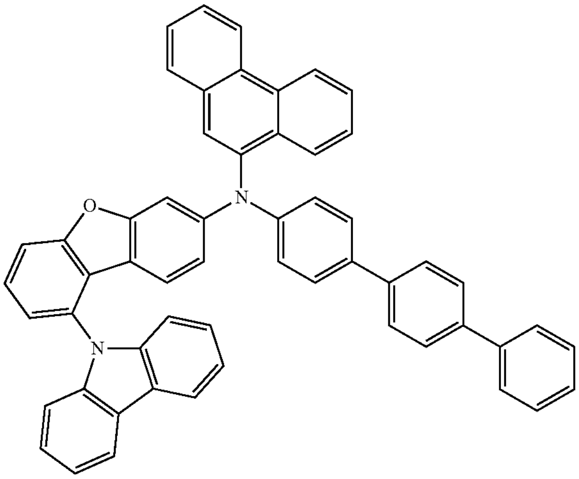
C11
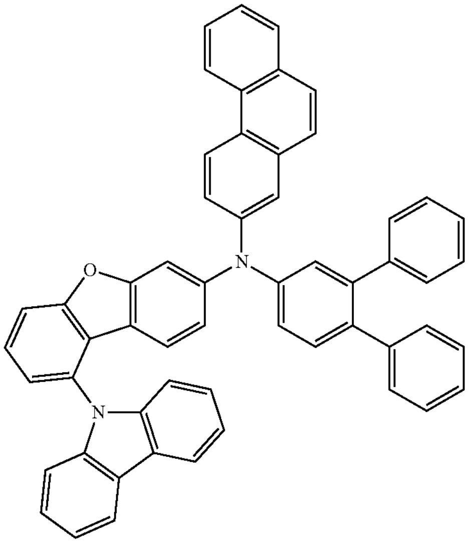
-continued
C12
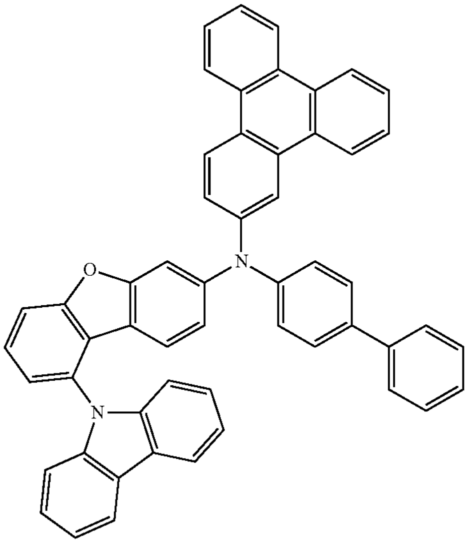
C13
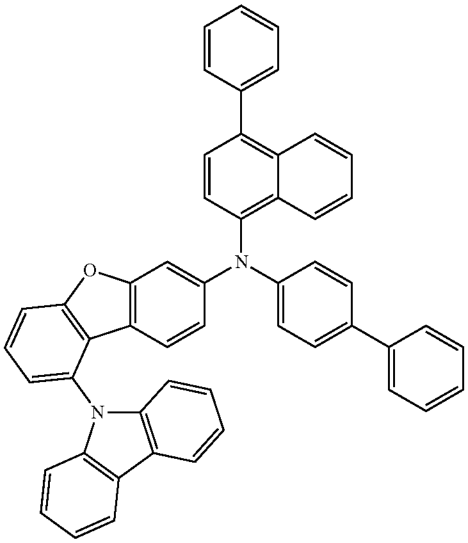
C14
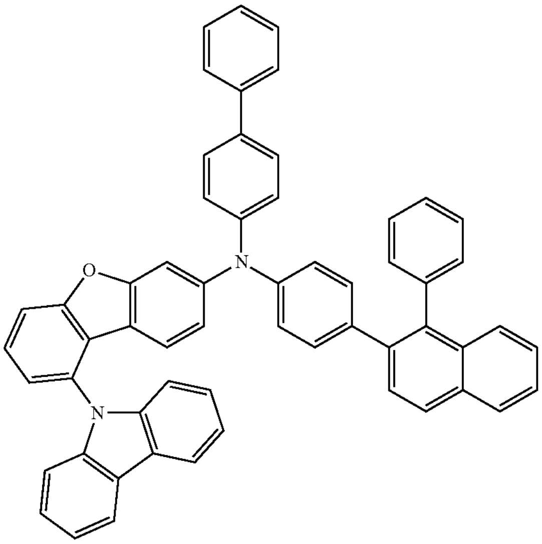

-continued
C15
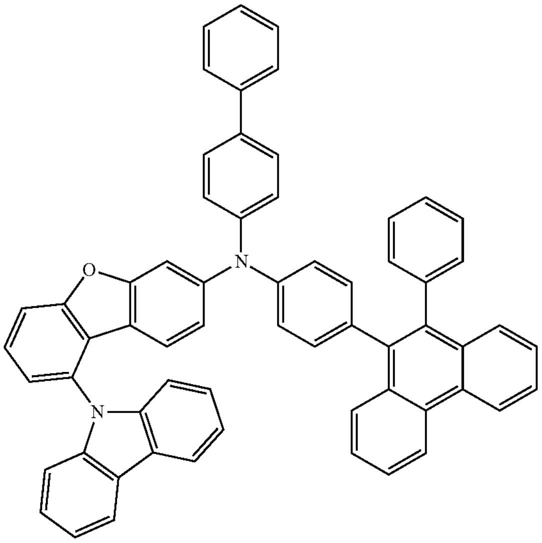
C16
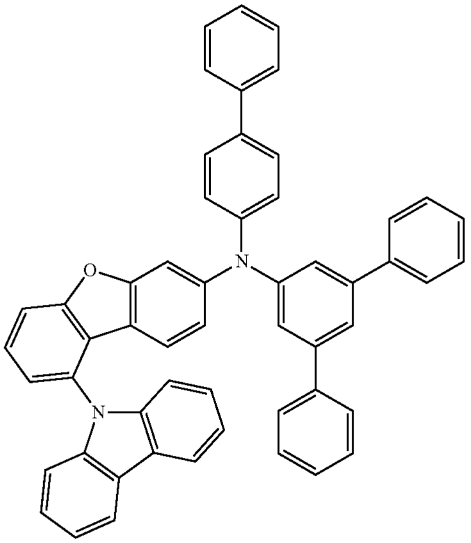
C17
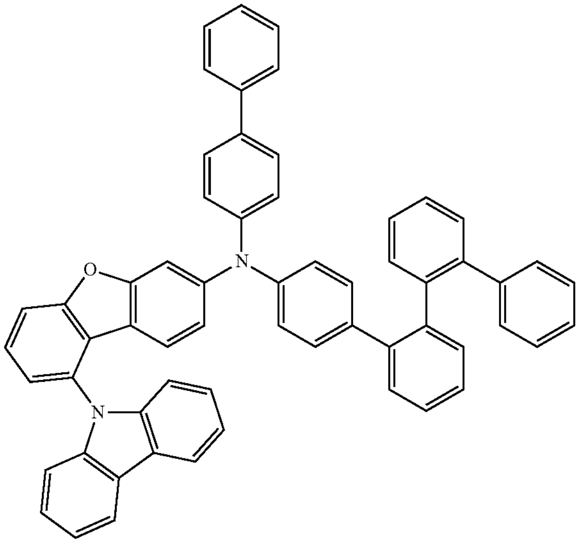
-continued
C18
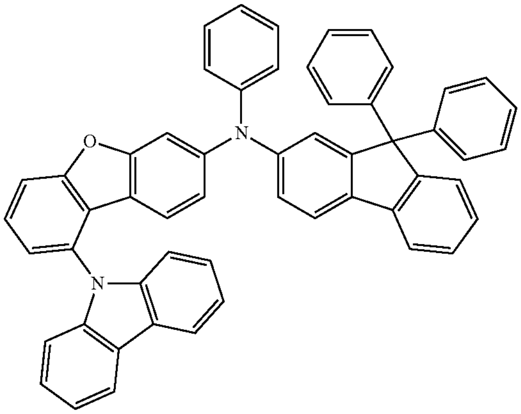
C19
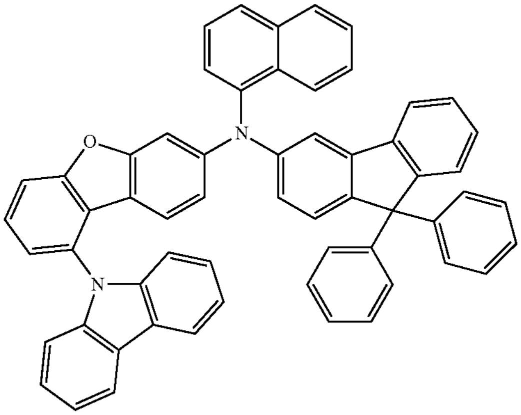
C20
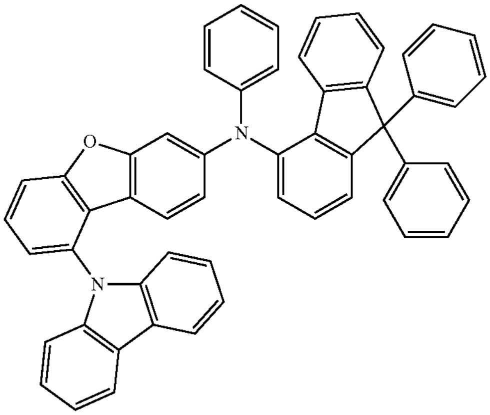

-continued
C21
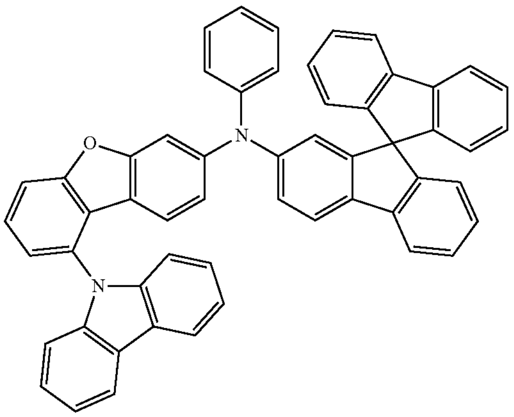
C22
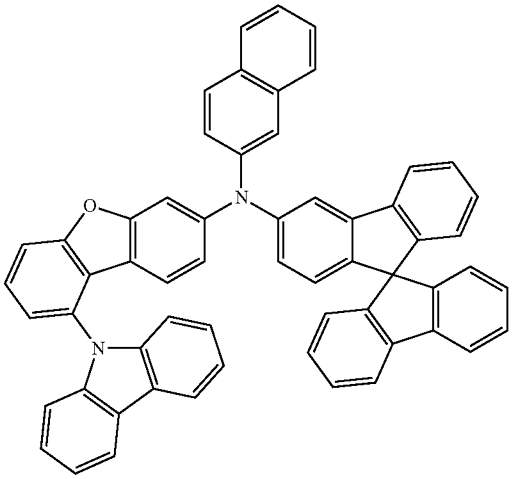
C23
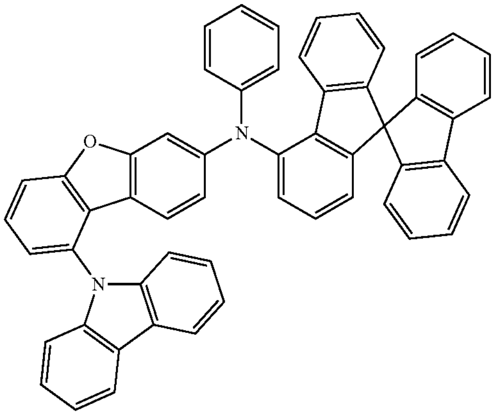
-continued
C24
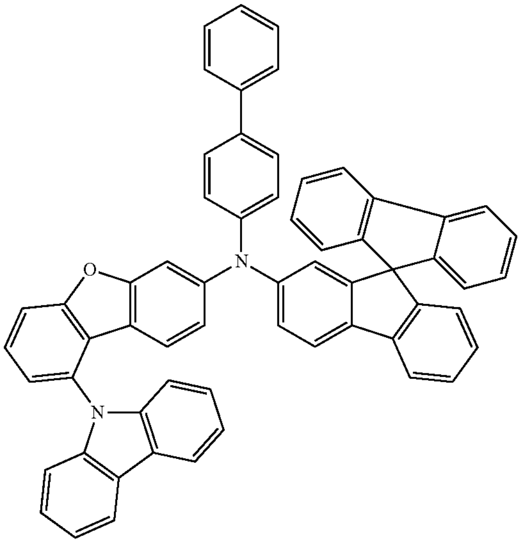
C25
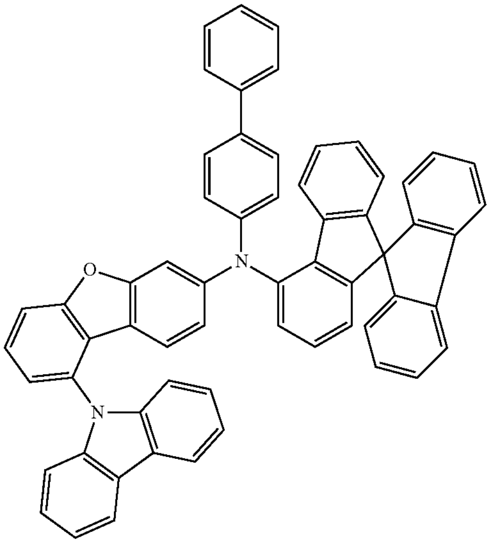
C26
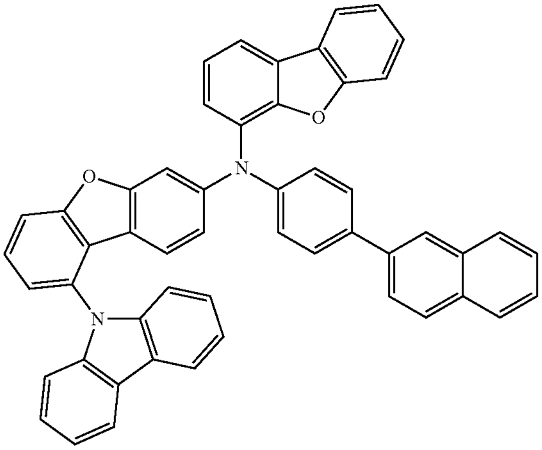

-continued
C27
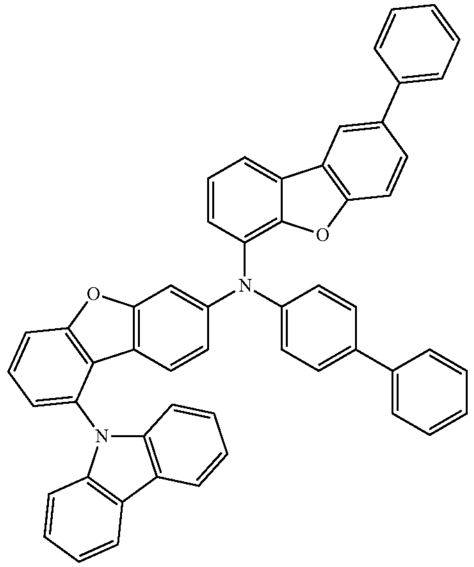
C28
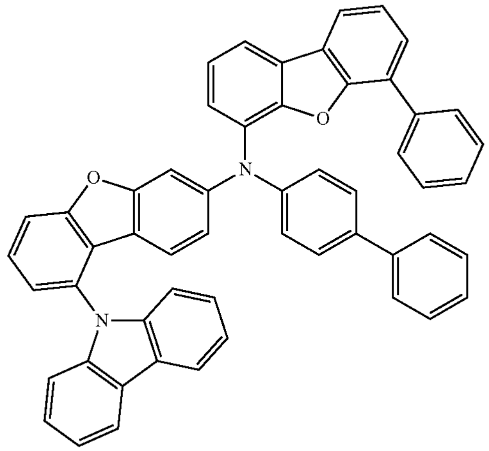
C29
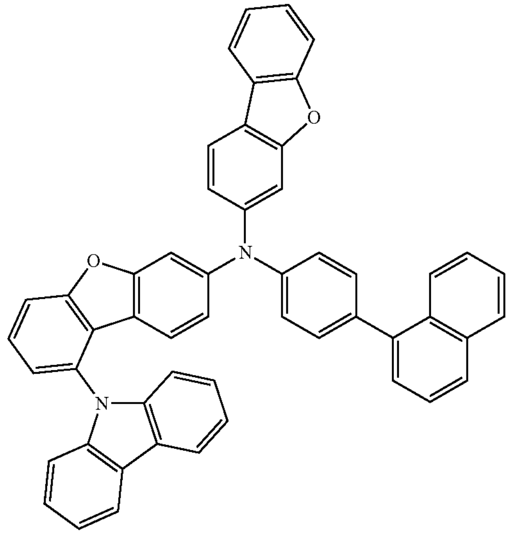
-continued
C30
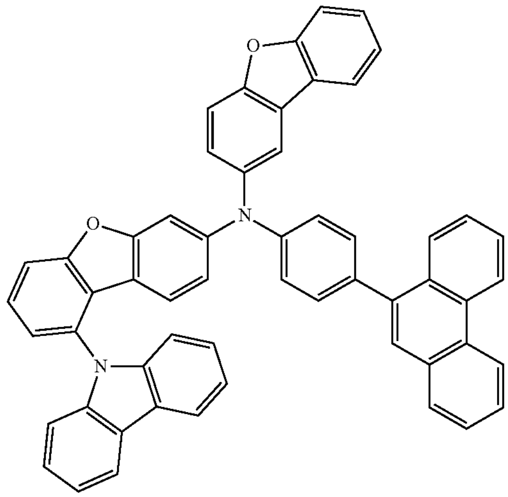
C31
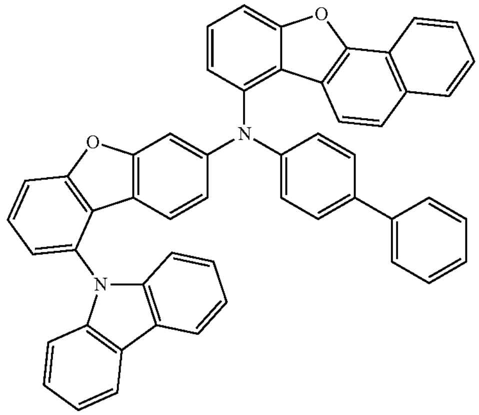
C32
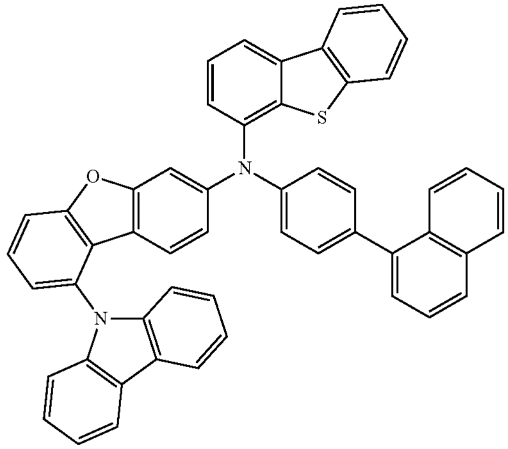

-continued
C33
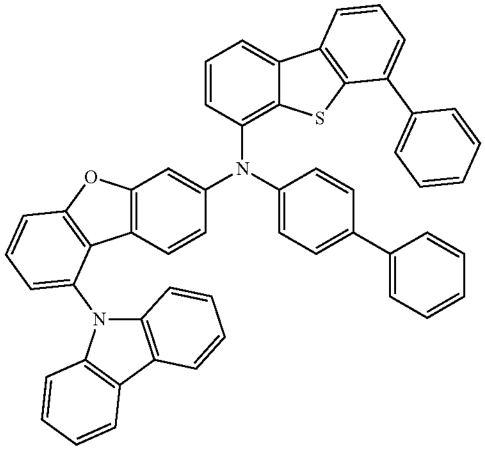
C34
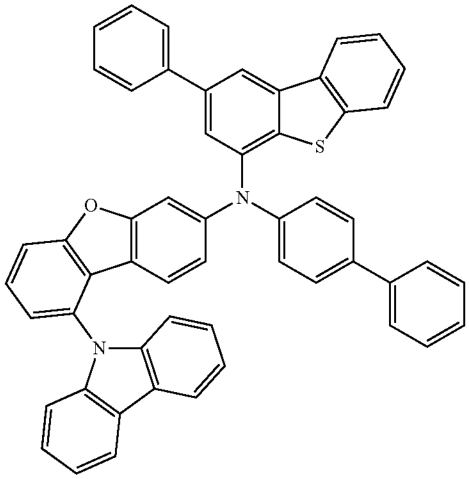
C35
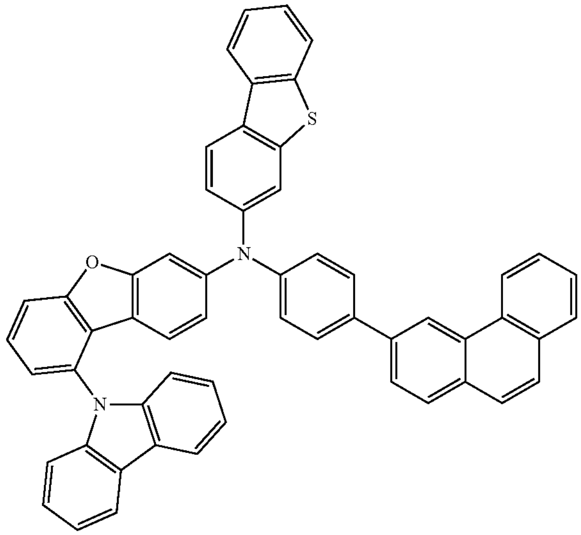
-continued
C36
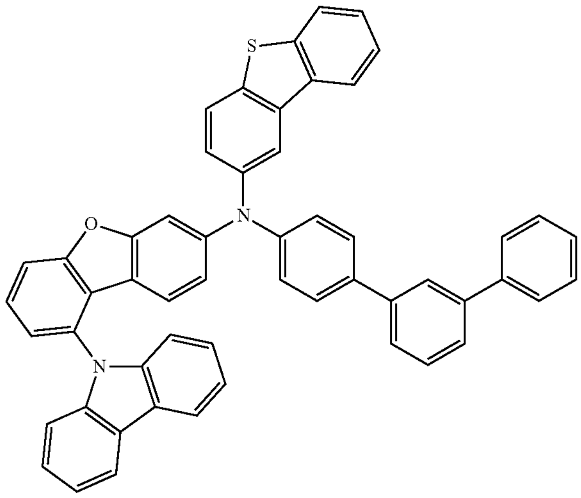
C37
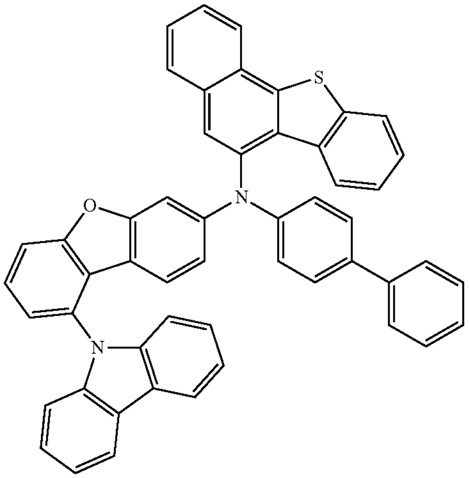
C38
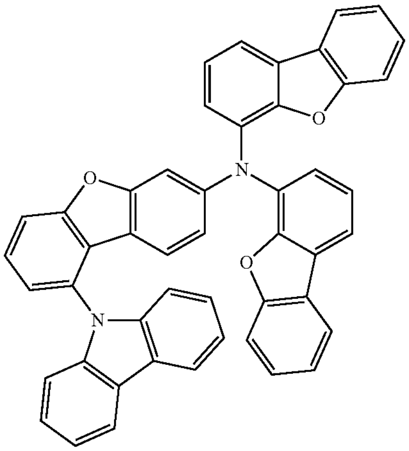

-continued
C39
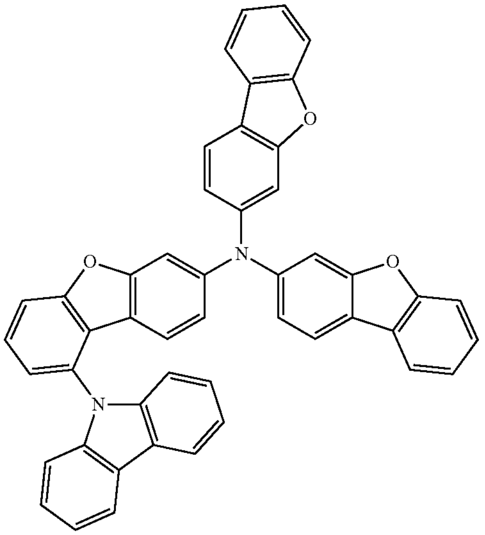
C40
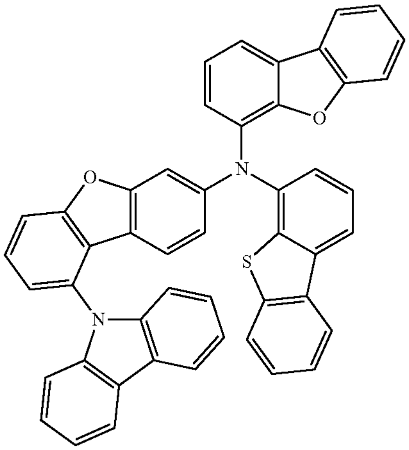
C41
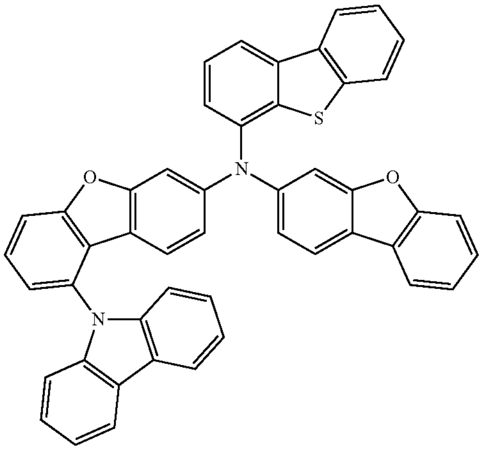
-continued
C42
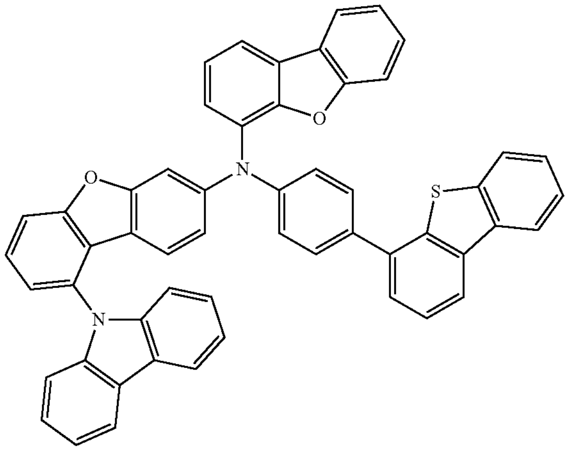
C43
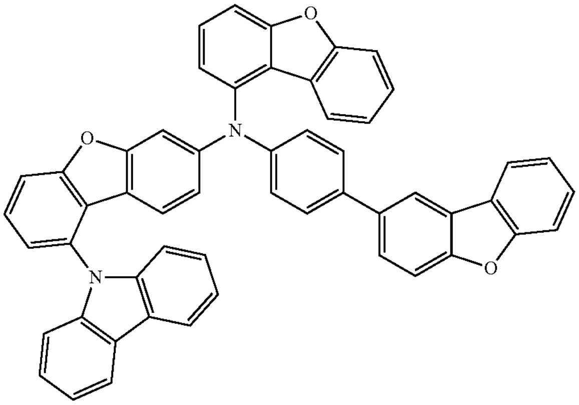
C44
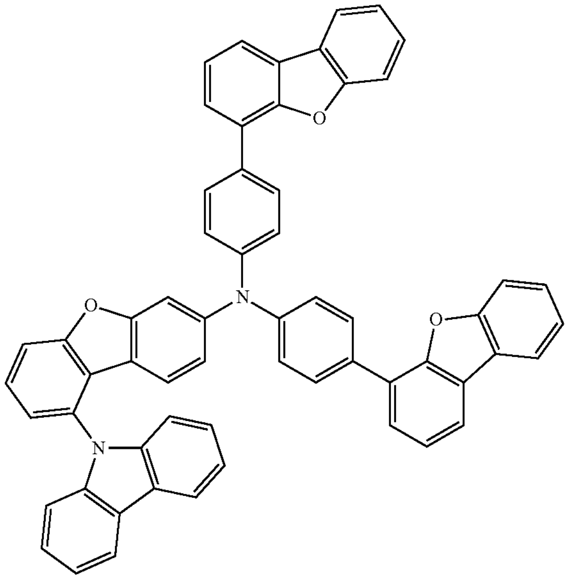

-continued
C45
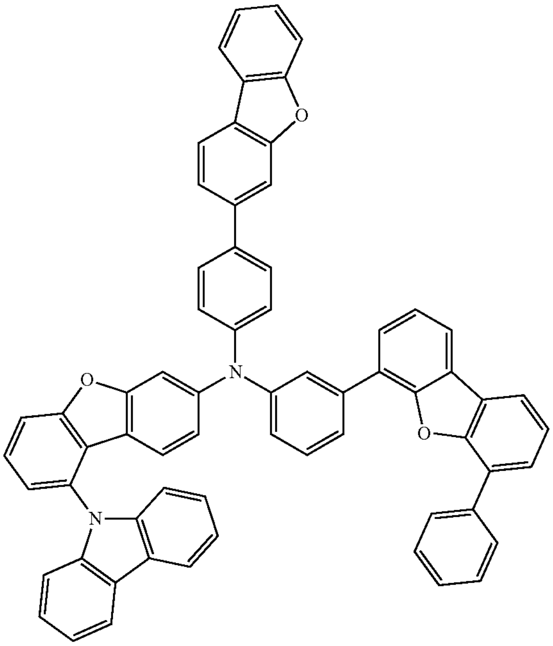
C46
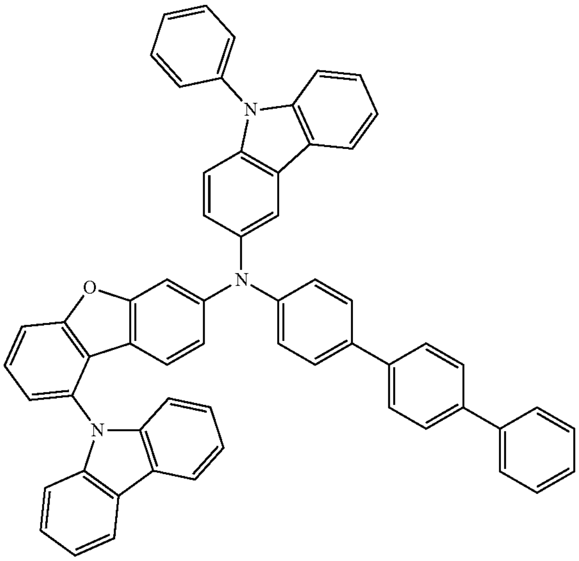
-continued
C47
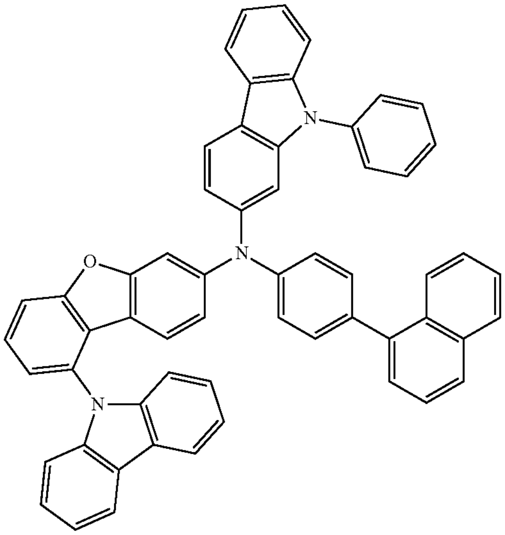
C48
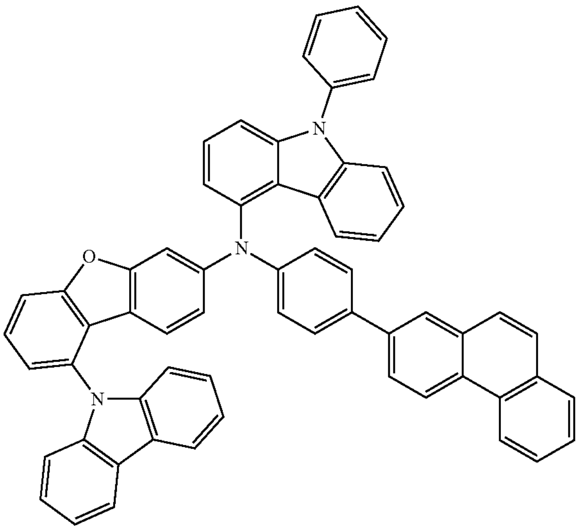

-continued
C49
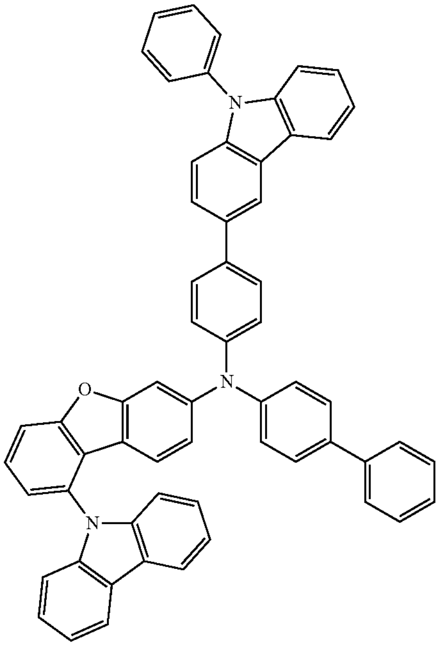
C50
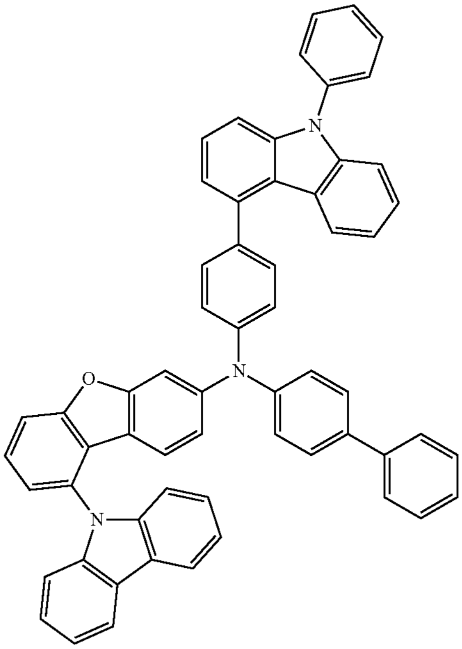
-continued
C51
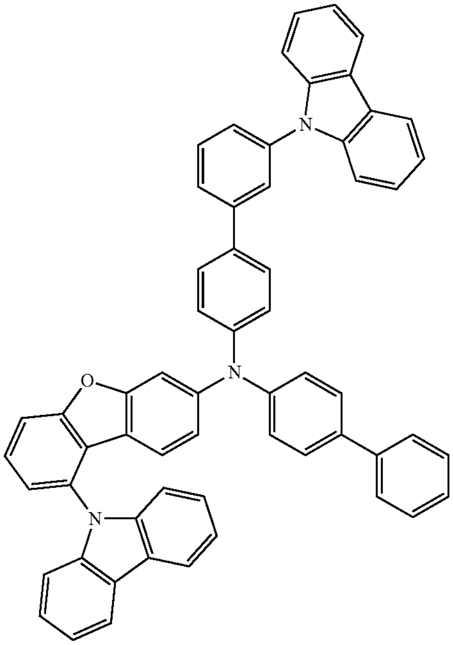
C52
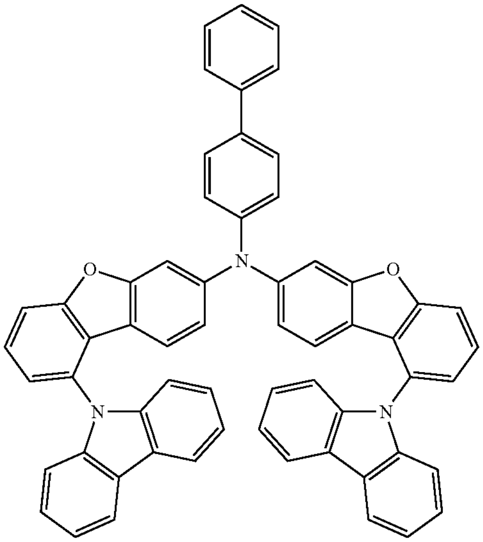

-continued
C53
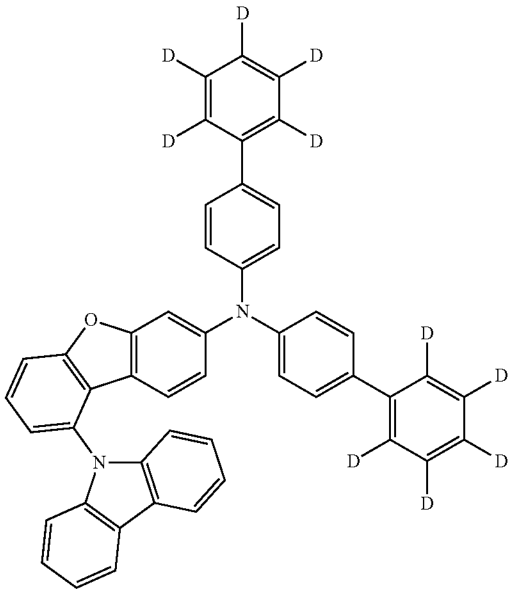
C54
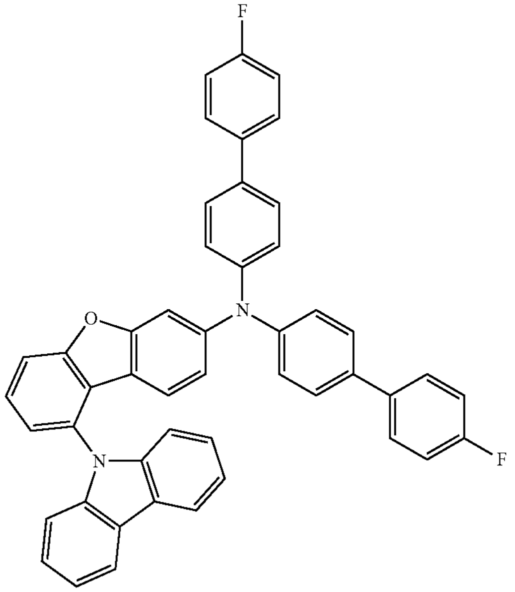
-continued
C55
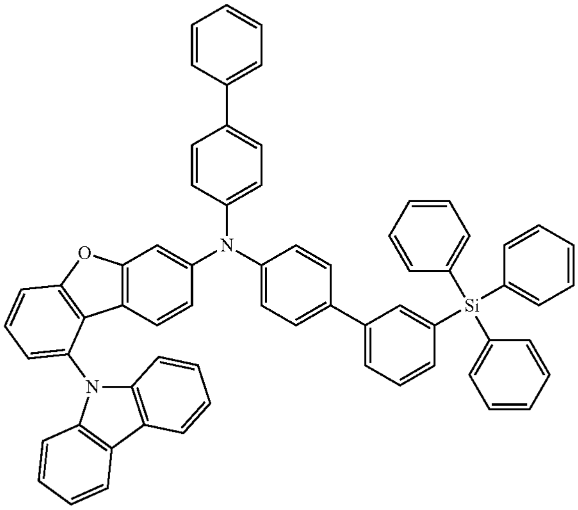
C56
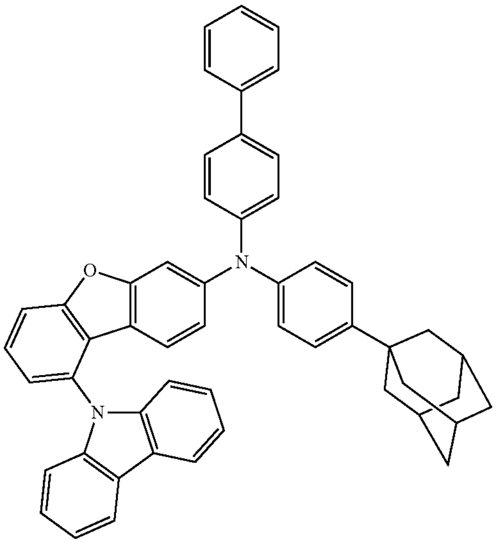

-continued
C57
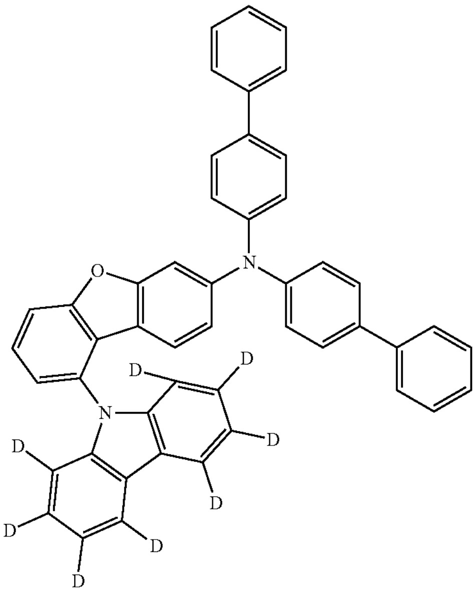
C58
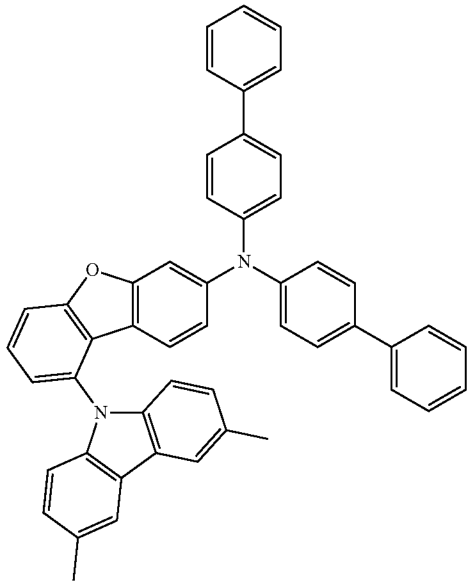
-continued
C59
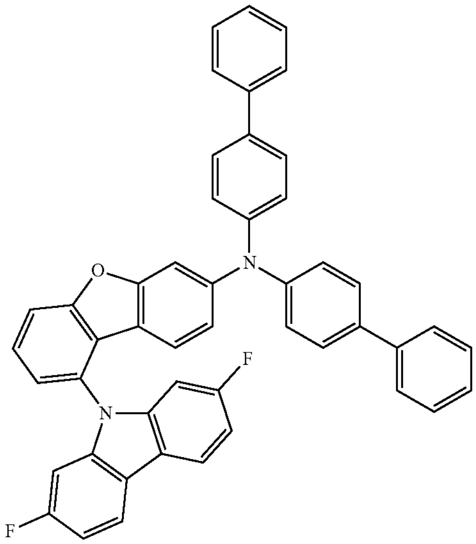
C60
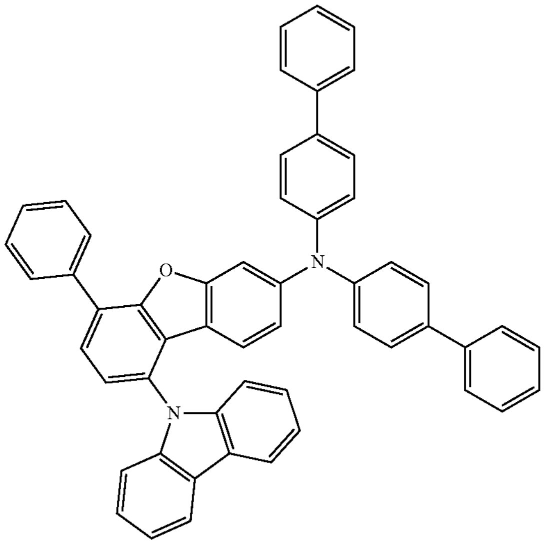
C61
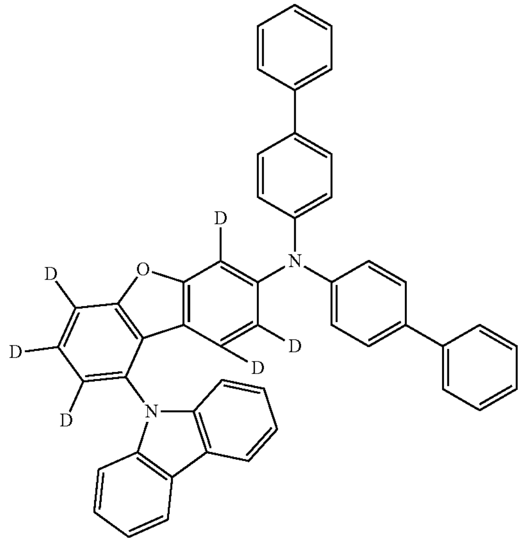

-continued

C62

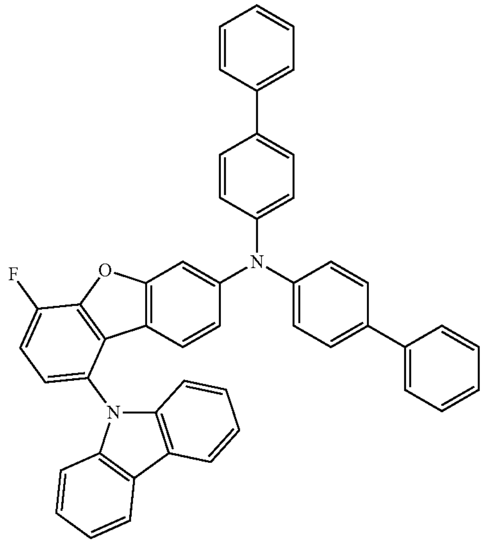

C63

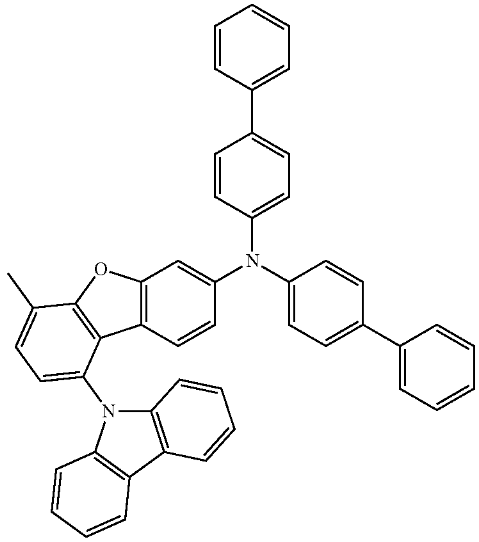

In A53, A57, A61, B53, B57, B61, C53, C57, and C61, "D" is a deuterium atom.

The amine compound represented by Formula 1 may be a dibenzofuran in which an amine group and a carbazole group are bonded to both benzene rings, respectively. In the dibenzofuran, one benzene ring may include carbon at position 1 ($C_1$) to carbon at position 4 ($C_4$), and the other benzene ring may include carbon at position 6 ($C_6$) to carbon at position 9 ($C_9$). The amine compound may be dibenzofuran in which an amine group is bonded to one benzene ring, and a carbazole group is bonded to the other benzene ring.

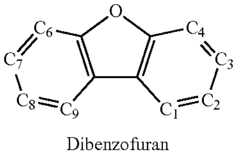

Dibenzofuran

The amine group and the carbazole group may be bonded to carbon atoms at asymmetric positions with the oxygen atom of the dibenzofuran as a center. The amine group may be bonded to the carbon at position 3 ($C_3$) of the dibenzofuran, and to the carbon at position 7 ($C_7$) which is symmetric to the carbon at position 3 ($C_3$) of the dibenzofuran, an amine group may not be bonded. The amine group may be bonded to the carbon at position 6 ($C_6$), carbon at position 8 ($C_8$) or carbon at position 9 ($C_9$) of the dibenzofuran. An embodiment of the amine compound, in which an amine group and a carbazole group are bonded to carbon atoms at asymmetric positions of the dibenzofuran, may show three-dimensional properties of a molecular structure. Due to the three-dimensional structure of the amine compound, layer properties may be improved, and excellent tolerance to electrons and thermal stability may be shown. The amine compound may be used as a material for a hole transport region of a light emitting device, and may contribute to the improvement of the emission efficiency and lifespan of the light emitting device.

The hole transport region HTR may include at least one of a hole injection layer HIL, a hole transport layer HTL, a buffer layer, an emission auxiliary layer, or an electron blocking layer EBL. At least one of the hole injection layer HIL, the hole transport layer HTL or the electron blocking layer EBL may include the amine compound.

The thickness of the hole transport region HTR may be, for example, from about 50 Å to about 15,000 Å. The hole transport region HTR may have a single layer formed using a single material, a single layer formed using multiple different materials, or a multilayer structure including multiple layers formed using multiple different materials.

For example, the hole transport region HTR may have the structure of a single layer of a hole injection layer HIL or a hole transport layer HTL, and may have a structure of a single layer formed using a hole injection material and a hole transport material. Otherwise, the hole transport region HTR may have a structure of a single layer formed using multiple different materials, or a structure stacked from the first electrode EL1 of hole injection layer HIL/hole transport layer HTL, hole injection layer HIL/hole transport layer HTL/buffer layer, hole injection layer HIL/buffer layer, hole transport layer HTL/buffer layer, or hole injection layer HIL/hole transport layer HTL/electron blocking layer EBL, without limitation.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

In the light emitting device ED, the hole transport region HTR may further include the compounds of a hole transport region HTR, which will be explained below. At least one of the hole injection layer HIL, hole transport layer HTL, or electron blocking layer EBL may include the compounds of the hole transport region HTR, which will be explained below.

The hole transport region HTR may include a compound represented by Formula H-1 below. For example, the hole transport layer HTL may include the compound represented by Formula H-1, and the electron blocking layer EBL may include the amine compound.

Formula H-1

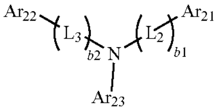

In Formula H-1 above, $L_2$ and $L_3$ may be each independently a direct linkage, a substituted or unsubstituted arylene group of 6 to 30 ring-forming carbon atoms, or a substituted or unsubstituted heteroarylene group of 2 to 30 ring-forming carbon atoms. The variables b 1 and b2 may be each independently an integer of 0 to 10. If b1 or b2 is an integer of 2 or more, multiple $L_2$ and $L_3$ may be each independently a substituted or unsubstituted arylene group of 6 to 30 ring-forming carbon atoms, or a substituted or unsubstituted heteroarylene group of 2 to 30 ring-forming carbon atoms.

In Formula H-1, $Ar_{21}$ and $Ar_{22}$ may be each independently a substituted or unsubstituted aryl group of 6 to 30 ring-forming carbon atoms, or a substituted or unsubstituted heteroaryl group of 2 to 30 ring-forming carbon atoms. In addition, in Formula H-1, $Ar_{23}$ may be a substituted or unsubstituted aryl group of 6 to 30 ring-forming carbon atoms, or a substituted or unsubstituted heteroaryl group of 2 to 30 ring-forming carbon atoms.

The compound represented by Formula H-1 may be a monoamine compound. Otherwise, the compound represented by Formula H-1 may be a diamine compound in which at least one of $Ar_{21}$ to $Ar_{23}$ includes an amine group as a substituent. In addition, the compound represented by Formula H-1 may be a carbazole-based compound in which at least one of $Ar_{21}$ and $Ar_{22}$ includes a substituted or unsubstituted carbazole group, or a fluorene-based compound in which at least one of $Ar_{21}$ and $Ar_{22}$ includes a substituted or unsubstituted fluorene group.

The compound represented by Formula H-1 may be represented by any one of the compounds in Compound Group H below. However, the compounds shown in Compound Group H are only illustrations, and the compound represented by Formula H-1 is not limited to the compounds represented in Compound Group H below.

Compound Group H

H-1-1

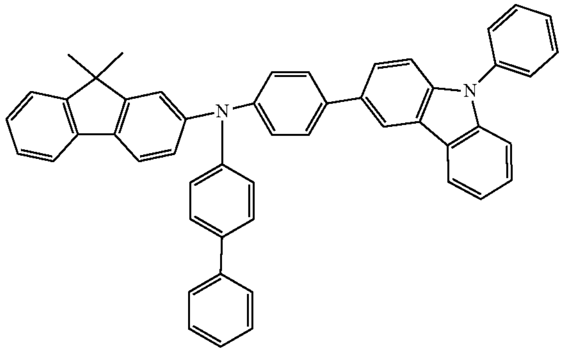

-continued

H-1-2

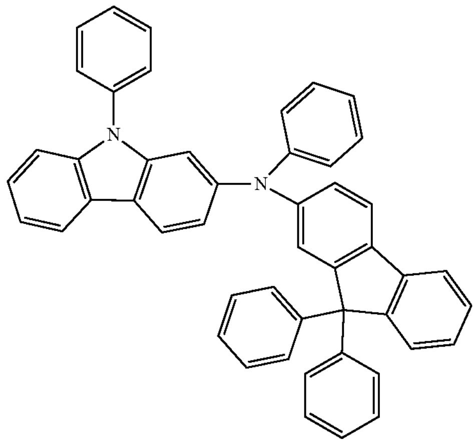

H-1-3

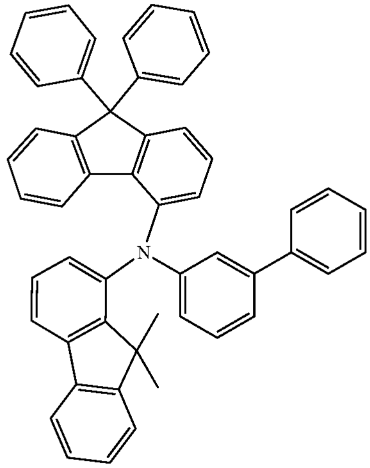

H-1-4

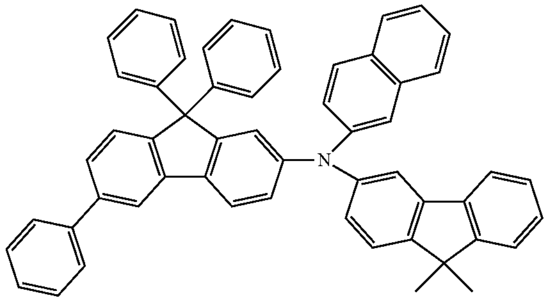

H-1-5

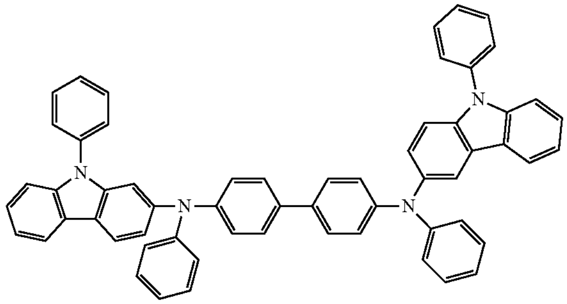

H-1-6
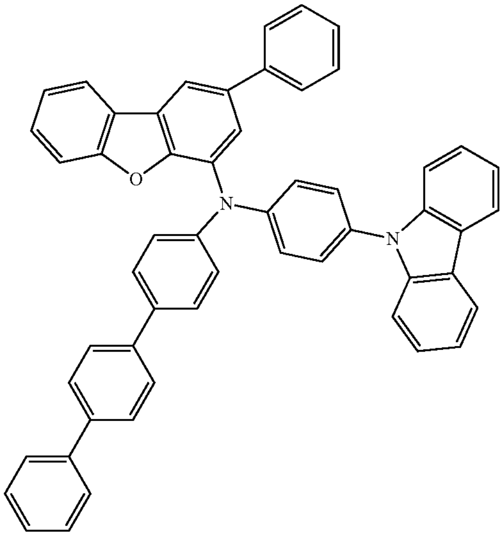
H-1-7
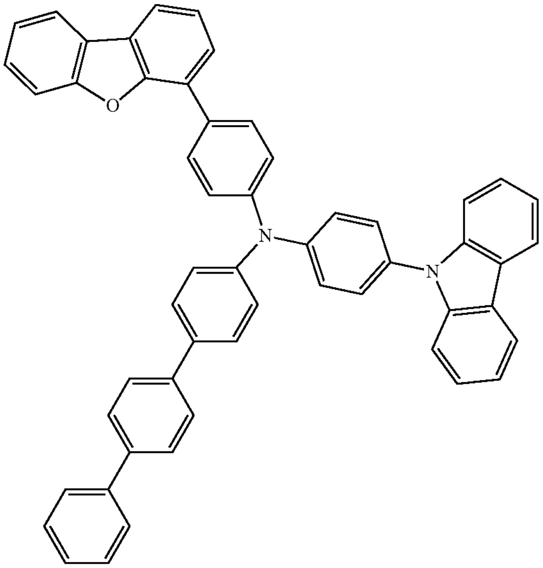
H-1-8
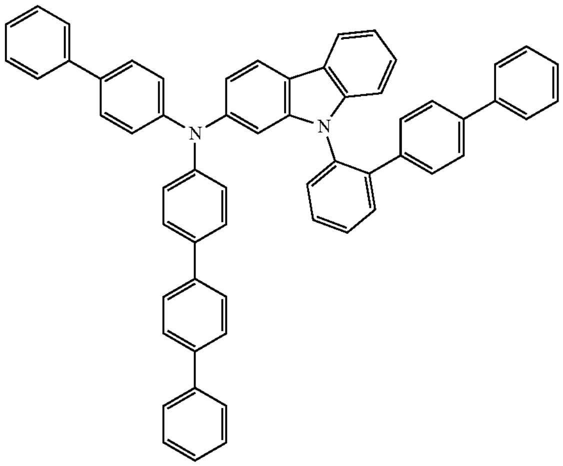
H-1-9
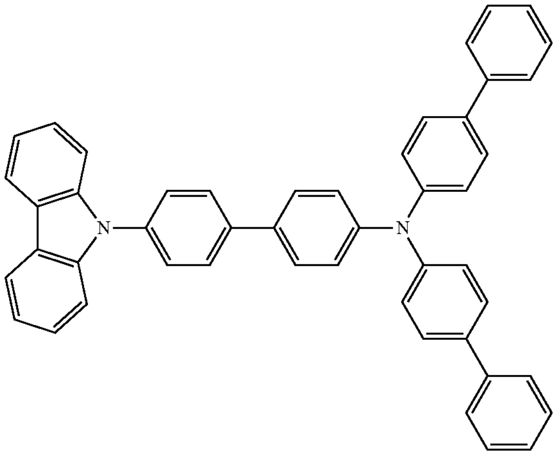
H-1-10
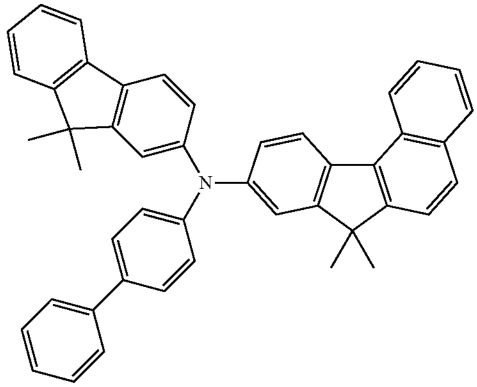
H-1-11
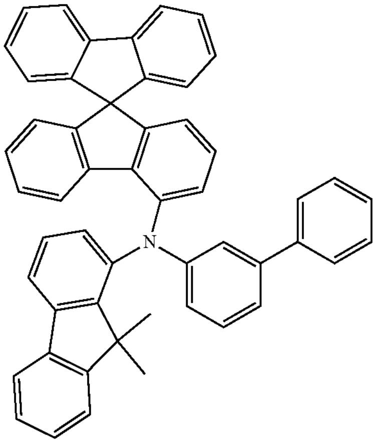

-continued
H-1-12
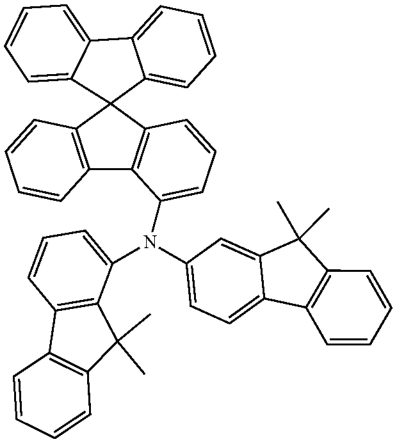
H-1-13
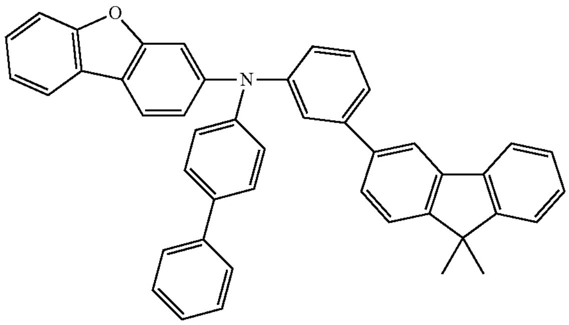
H-1-14
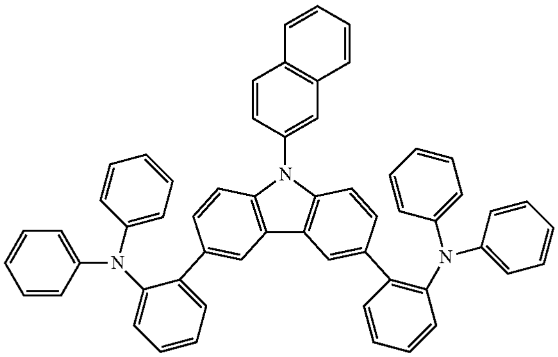
-continued
H-1-15
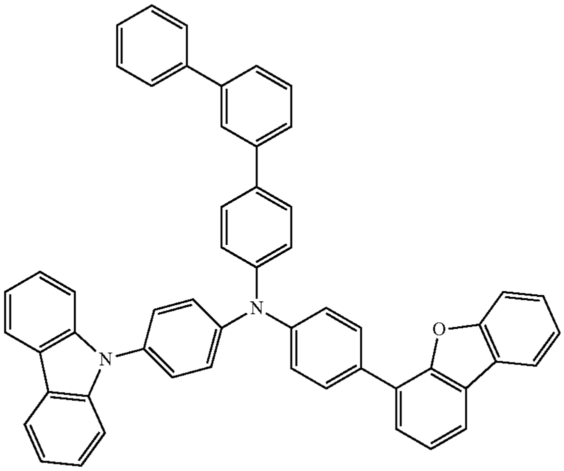
H-1-16
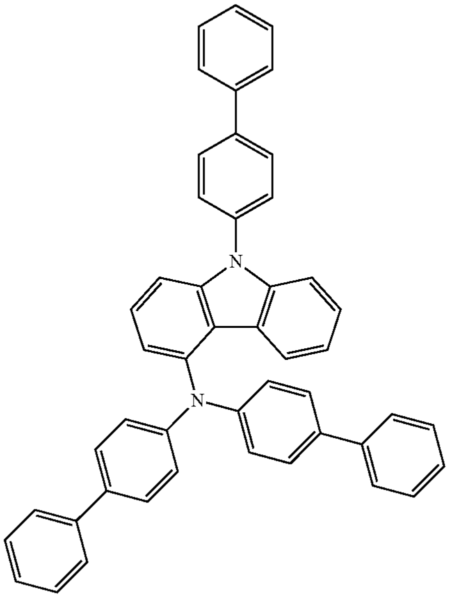
H-1-17
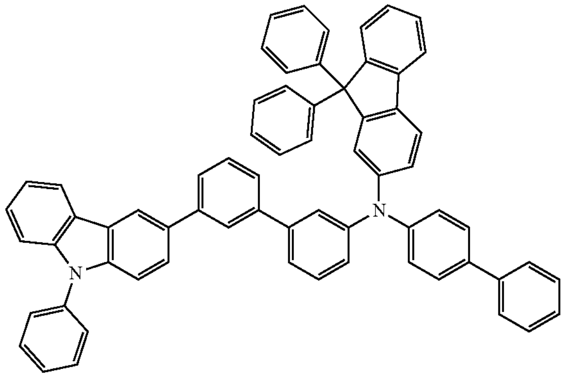

-continued

H-1-18

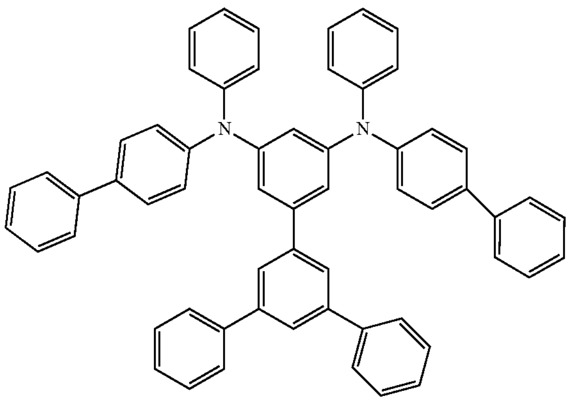

H-1-19

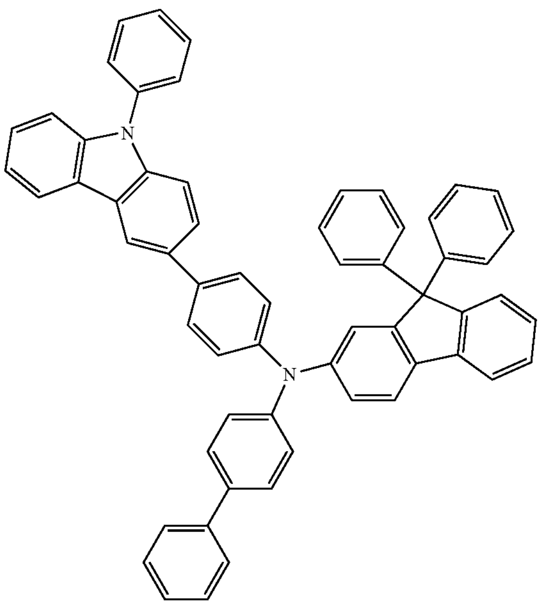

The hole transport region HTR may include a phthalocyanine compound such as copper phthalocyanine, $N^1$,$N^{1'}$-([1,1'-biphenyl]-4,4'-diyl)bis($N^1$-phenyl-$N^4$,$N^4$-di-m-tolylbenzene-1,4-diamine) (DNTPD), 4,4',4"-[tris(3-methylphenyl)phenylamino]triphenylamine (m-MTDATA), 4,4',4"-tris(N,N-diphenylamino)triphenylamine (TDATA), 4,4',4"-tris[N(2-naphthyl)-N-phenylamino]-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(1-naphthalene-1-yl)-N,N'-diphenylbenzidine (NPB), triphenylamine-containing polyetherketone (TPAPEK), 4-isopropyl-4'-methyldiphenyliodonium [tetrakis(pentafluorophenyl)borate], and dipyrazino[2,3-f:2',3'-h] quinoxaline-2,3,6,7,10,11-hexacarbonitrile (HATCN).

In addition, The hole transport region HTR may include carbazole derivatives such as N-phenyl carbazole and polyvinyl carbazole, fluorene-based derivatives, N,N'-bis(3-methylphenyl)-N,N'-diphenyl-[1,1'-biphenyl]-4,4'-diamine (TPD), triphenylamine-based derivatives such as 4,4',4"-tris(N-carbazolyl)triphenylamine (TCTA), N,N'-di(1-naphthalene-1-yl)-N,N'-diphenyl-benzidine (NPB), 4,4'-cyclohexylidene bis[N,N-bis(4-methylphenyl)benzeneamine] (TAPC), 4,4'-bis[N,N'-(3-tolyl)amino]-3,3'-dimethylbiphenyl (HMTPD), 9-(4-tert-butylphenyl)-3,6-bis(triphenylsilyl)-9H-carbazole (CzSi), 9-phenyl-9H-3,9'-bicarbazole (CCP), 1,3-bis(N-carbazolyl)benzene (mCP), 1,3-bis(1,8-dimethyl-9H-carbazol-9-yl)benzene (mDCP), etc.

The thickness of the hole transport region HTR may be from about 100 Å to about 10,000 Å, for example, from about 100 Å to about 5,000 Å. In case where the hole transport region HTR includes a hole injection layer HIL, the thickness of the hole injection layer HIL may be, for example, from about 30 Å to about 1,000 Å. In case where the hole transport region HTR includes a hole transport layer HTL, the thickness of the hole transport layer HTL may be from about 30 Å to about 1,000 Å. For example, in case where the hole transport region HTR includes an electron blocking layer, the thickness of the electron blocking layer EBL may be from about 10 Å to about 1,000 Å. If the thicknesses of the hole transport region HTR, the hole injection layer HIL, the hole transport layer HTL and the electron blocking layer EBL satisfy the above-described ranges, satisfactory hole transport properties may be achieved without substantial increase of a driving voltage.

The hole transport region HTR may further include a charge generating material to increase conductivity in addition to the above-described materials. The charge generating material may be dispersed uniformly or non-uniformly in the hole transport region HTR. The charge generating material may be, for example, a p-dopant. The p-dopant may include at least one of metal halide compounds, quinone derivatives, metal oxides, and cyano group-containing compounds, without limitation. For example, the p-dopant may include metal halide compounds such as CuI and RbI, quinone derivatives such as tetracyanoquinodimethane (TCNQ) and 2,3,5,6-tetrafluoro-7,7',8,8-tetracyanoquinodimethane (F4-TCNQ), metal oxides such as a tungsten oxide and a molybdenum oxide, cyano group-containing compounds such as dipyrazino[2,3-f: 2',3'-h] quinoxaline-2,3,6,7,10,11-hexacarbonitrile (HATCN) and 4-[[2,3-bis[cyano-(4-cyano-2,3,5,6-tetrafluorophenyl)methylidene]cyclopropylidene]-cyanomethyl]-2,3,5,6-tetrafluorobenzonitrile (NDP9), etc., without limitation.

As described above, the hole transport region HTR may further include at least one of a buffer layer or an electron blocking layer EBL in addition to the hole injection layer HIL and the hole transport layer HTL. The buffer layer may compensate resonance distance according to the wavelength of light emitted from an emission layer EML and may increase light emitting efficiency. The materials included in the buffer layer may be the same materials included in the hole transport region HTR. The electron blocking layer EBL is a layer playing the role of blocking the injection of electrons from an electron transport region ETR to a hole transport region HTR.

The emission layer EML is provided on the hole transport region HTR. The emission layer EML may have a thickness of, for example, about 100 Å to about 1,000 Å or about 100 Å to about 300 Å. The emission layer EML may have a single layer formed using a single material, a single layer formed using multiple different materials, or a multilayer structure having multiple layers formed using multiple different materials.

In the light emitting device ED, the emission layer EML may include anthracene derivatives, pyrene derivatives, fluoranthene derivatives, chrysene derivatives, dihydrobenzanthracene derivatives, or triphenylene derivatives. Particularly, the emission layer EML may include anthracene derivatives or pyrene derivatives.

In the light emitting devices ED shown in FIG. 3 to FIG. 6, the emission layer EML may include a host and a dopant, and the emission layer EML may include a compound represented by Formula E-1 below. The compound represented by Formula E-1 below may be used as a fluorescence host material.

Formula E-1

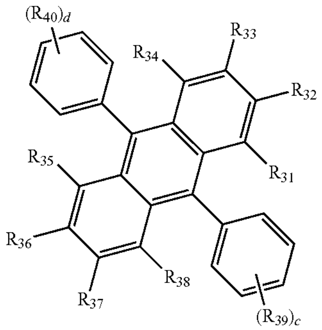

In Formula E-1, $R_{31}$ to $R_{40}$ may be each independently a hydrogen atom, a deuterium atom, a halogen atom, a substituted or unsubstituted silyl group, a substituted or unsubstituted thio group, a substituted or unsubstituted oxy group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or combined with an adjacent group to form a ring. The variables $R_{31}$ to $R_{40}$ may be combined with an adjacent group to form a saturated hydrocarbon ring, an unsaturated hydrocarbon ring, a saturated heterocycle or an unsaturated heterocycle. The variables $R_{31}$ to $R_{40}$ may be combined with an adjacent group or an adjacent benzene ring to form a fused ring.

In Formula E-1, "c" and "d" may be each independently an integer of 0 to 5.

Formula E-1 may be represented by any one of Compound E1 to Compound E19 below.

E1

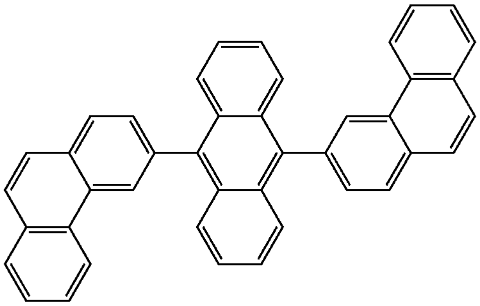

E2

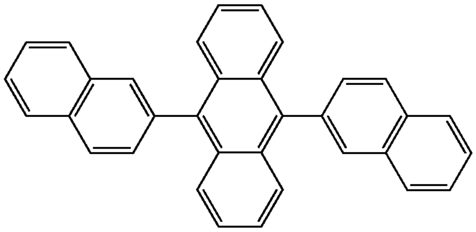

-continued

E3

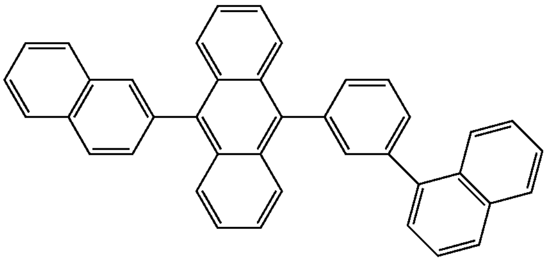

E4

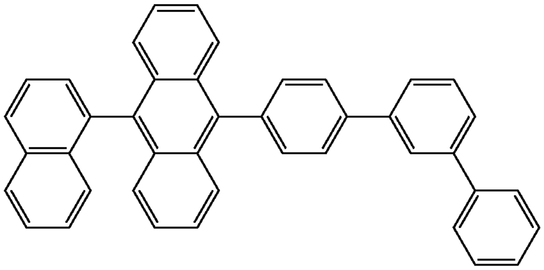

E5

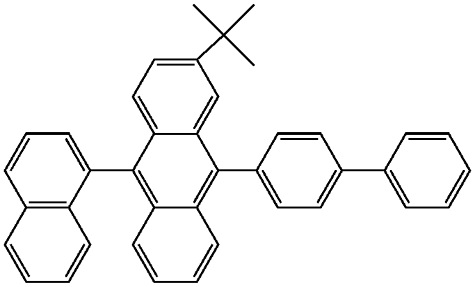

E6

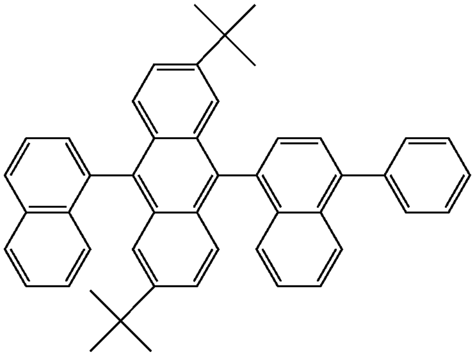

E7

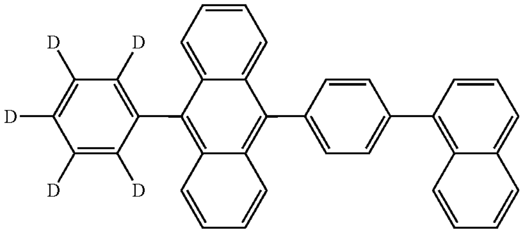

-continued
E8
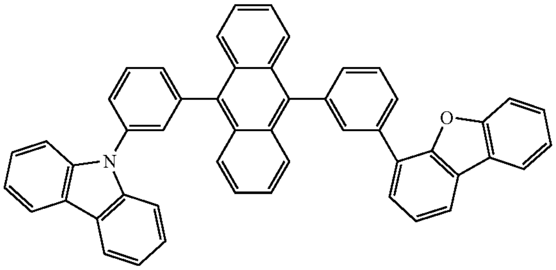
E9
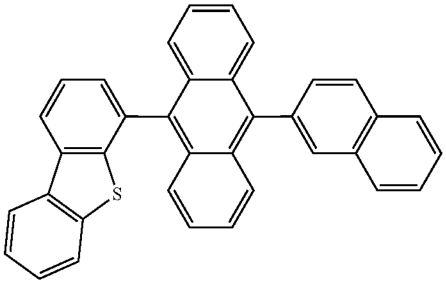
E10
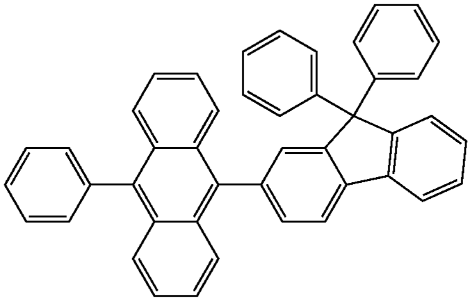
E11
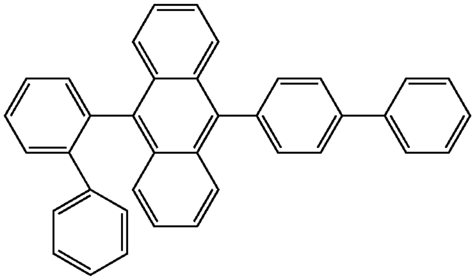
E12
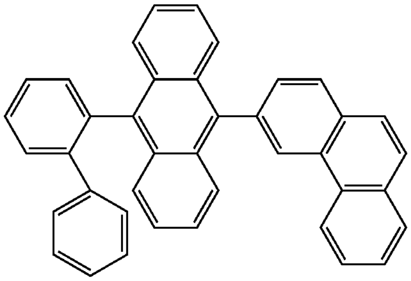
-continued
E13
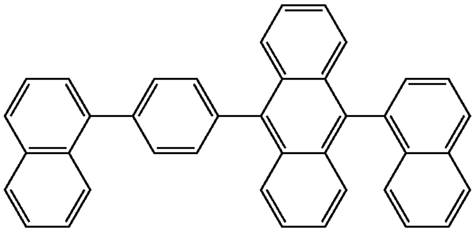
E14
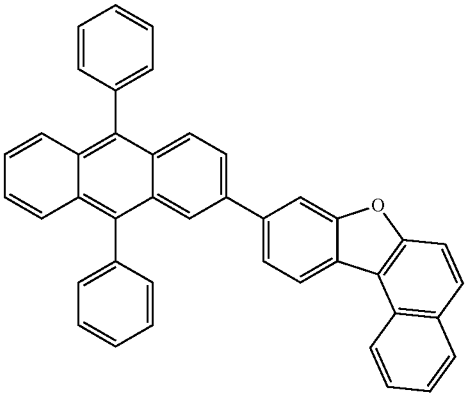
E15
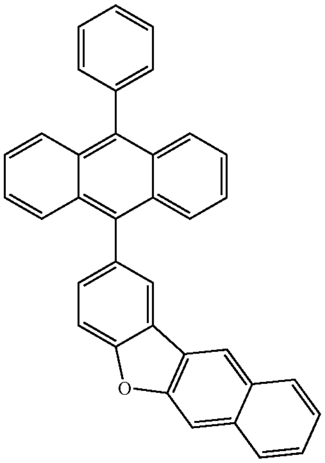
E16
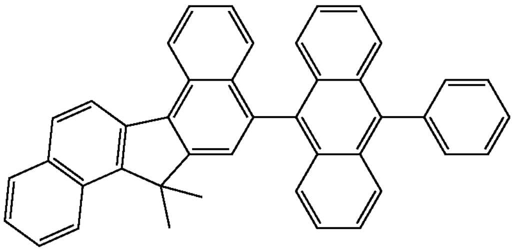

-continued

E17

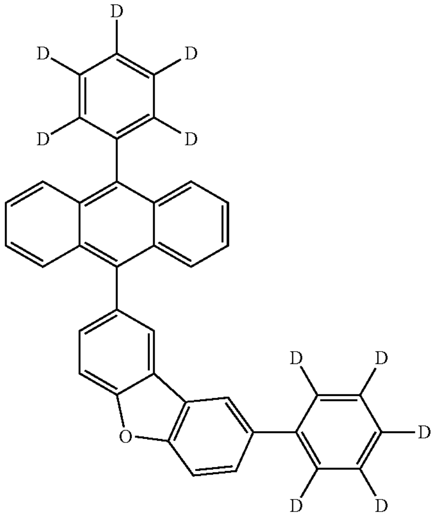

E18

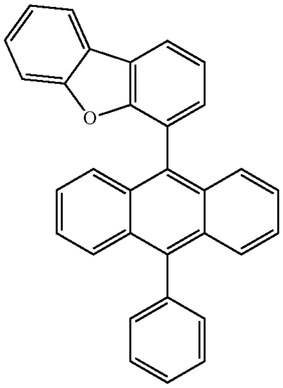

E19

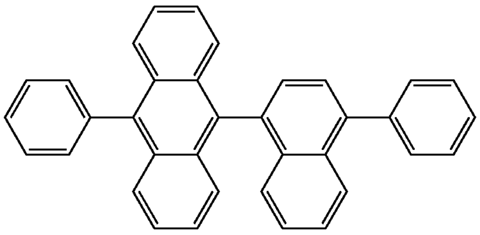

In an embodiment, the emission layer EML may include a compound represented by Formula E-2a or Formula E-2b below. The compound represented by Formula E-2a or Formula E-2b below may be used as a phosphorescence host material.

Formula E-2a

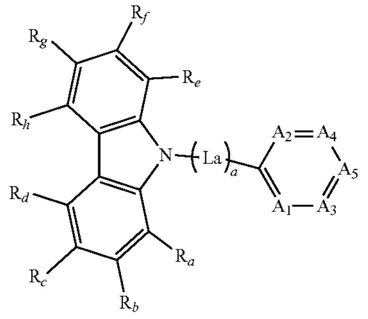

In Formula E-2b, "a" may be an integer of 0 to 10, $L_a$ may be a direct linkage, a substituted or unsubstituted arylene group of 6 to 30 ring-forming carbon atoms, or a substituted or unsubstituted heteroarylene group of 2 to 30 ring-forming carbon atoms. If "a" is an integer of 2 or more, multiple $L_a$ may be each independently a substituted or unsubstituted arylene group of 6 to 30 ring-forming carbon atoms, or a substituted or unsubstituted heteroarylene group of 2 to 30 ring-forming carbon atoms.

In addition, in Formula E-2a, $A_1$ to $A_5$ may be each independently N or $CR_i$. $R_a$ to $R_i$ may be each independently a hydrogen atom, a deuterium atom, a substituted or unsubstituted amine group, a substituted or unsubstituted thio group, a substituted or unsubstituted oxy group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. The variables $R_a$ to $R_i$ may be combined with an adjacent group to form a hydrocarbon ring or a heterocycle including N, O, S, etc. as a ring-forming atom.

In Formula E-2a, two or three selected from $A_1$ to $A_5$ may be N, and the remainder may be $CR_i$.

Formula E-2b

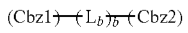

In Formula E-2b, Cbz1 and Cbz2 may be each independently an unsubstituted carbazole group, or a carbazole group substituted with an aryl group of 6 to 30 ring-forming carbon atoms. The variable $L_b$ may be a direct linkage, a substituted or unsubstituted arylene group of 6 to 30 ring-forming carbon atoms, or a substituted or unsubstituted heteroarylene group of 2 to 30 ring-forming carbon atoms. "b" is an integer of 0 to 10, and if "b" is an integer of 2 or more, multiple $L_b$ may be each independently a substituted or unsubstituted arylene group of 6 to 30 ring-forming carbon atoms, or a substituted or unsubstituted heteroarylene group of 2 to 30 ring-forming carbon atoms.

The compound represented by Formula E-2a or Formula E-2b may be represented by any one of the compounds in Compound Group E-2 below. However, the compounds shown in Compound Group E-2 below are only illustrations, and the compound represented by Formula E-2a or Formula E-2b is not limited to the compounds represented in Compound Group E-2 below.

Compound Group E-2
E-2-1
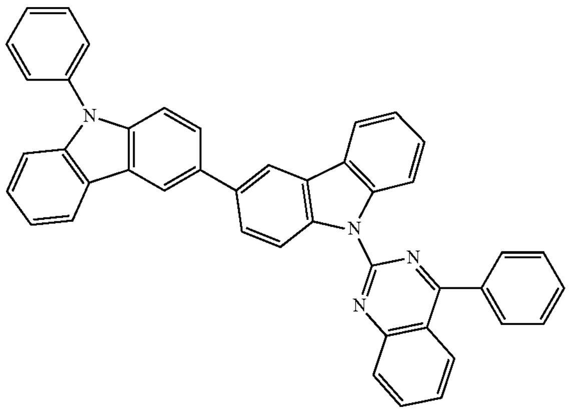
E-2-2
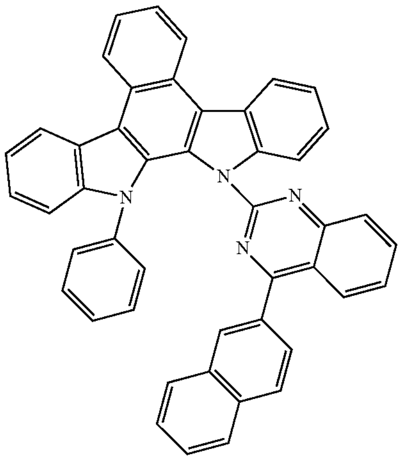
E-2-3
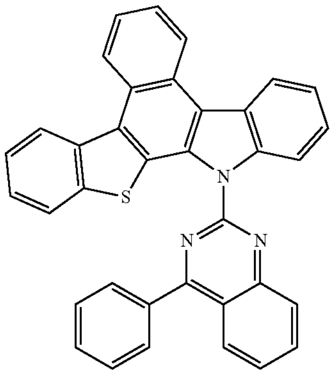
-continued
E-2-4
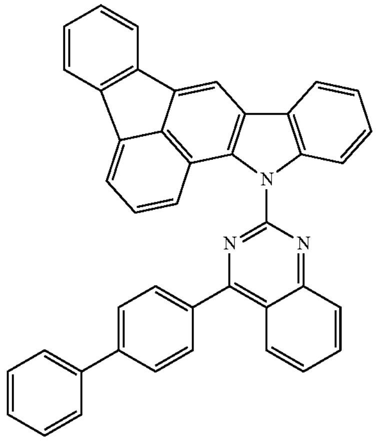
E-2-5
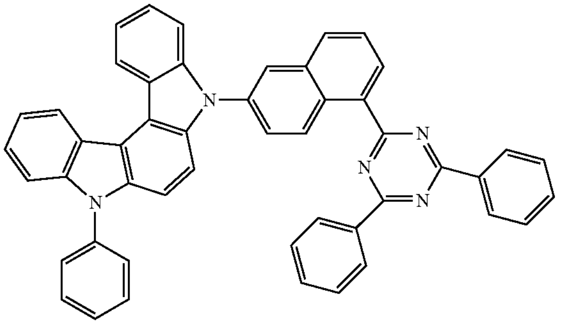
E-2-6
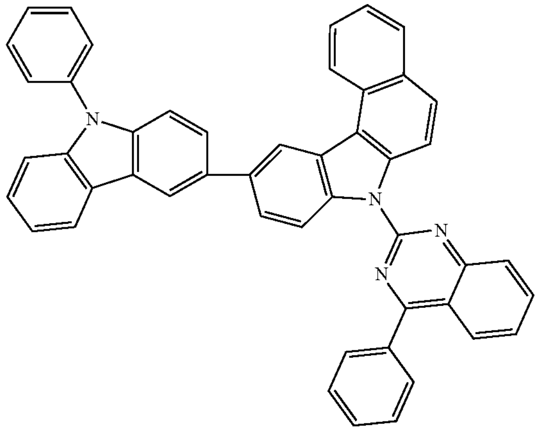

-continued
E-2-7
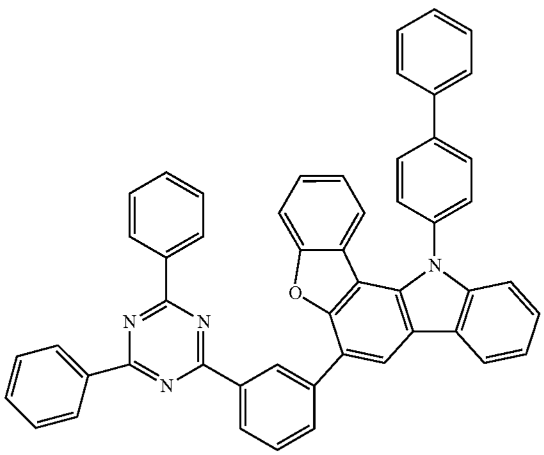
E-2-8
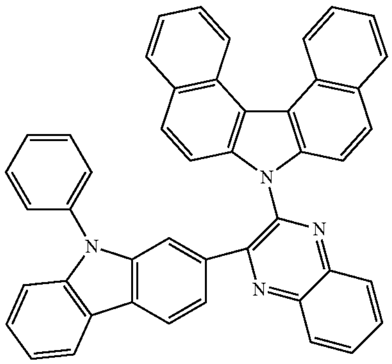
E-2-9
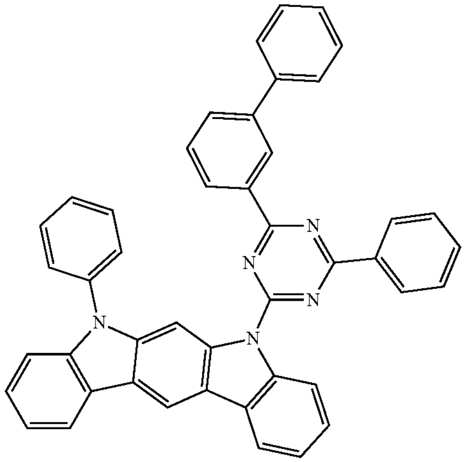
-continued
E-2-10
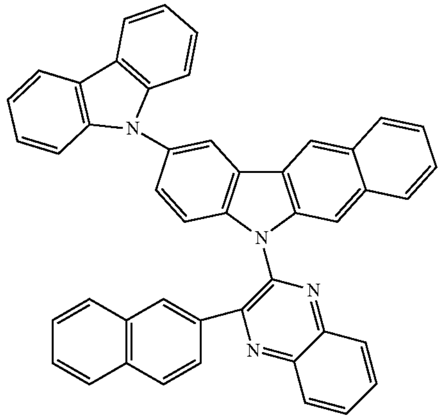
E-2-11
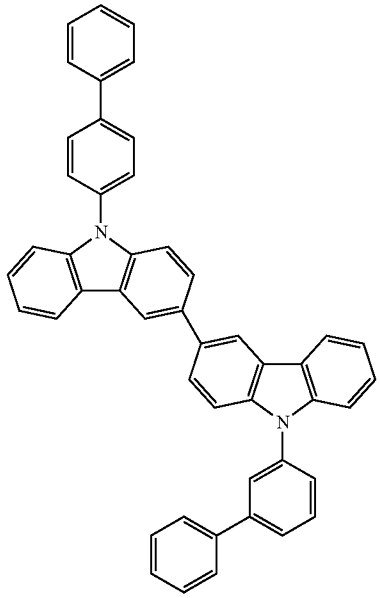
E-2-12
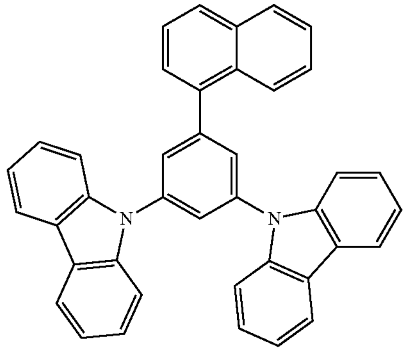

-continued
E-2-13
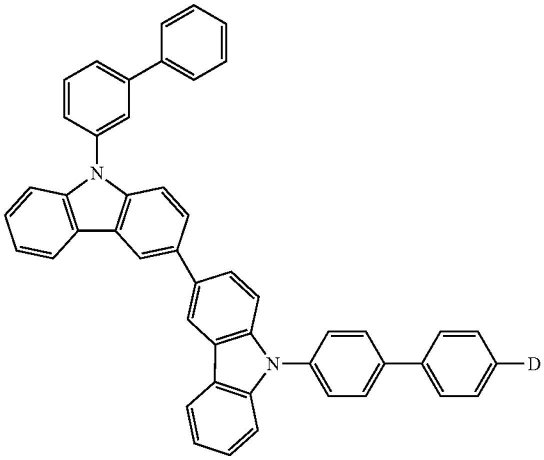
E-2-14
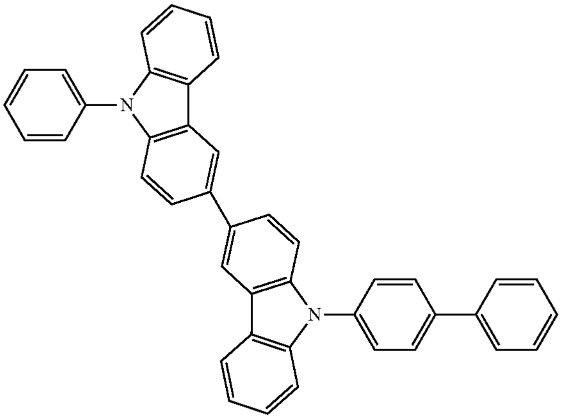
E-2-15
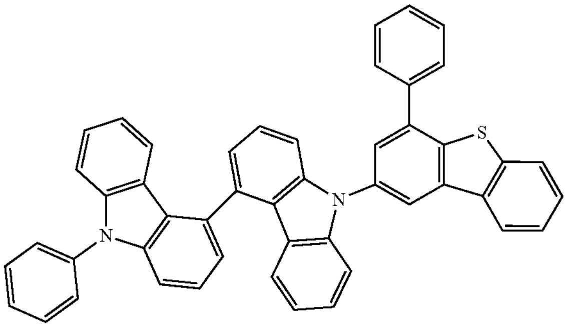
-continued
E-2-16
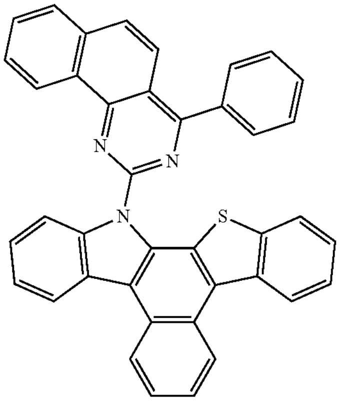
E-2-17
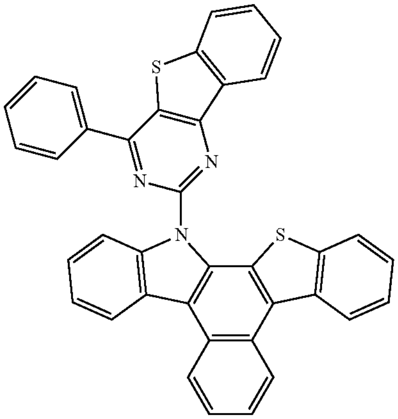
E-2-18
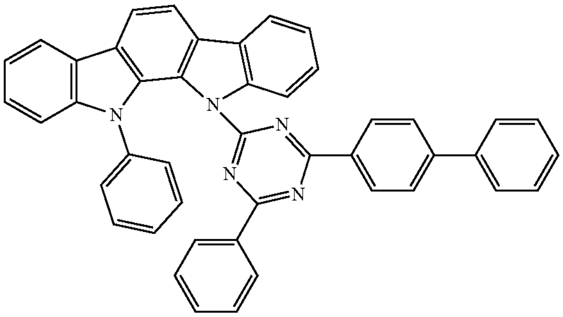
E-2-19
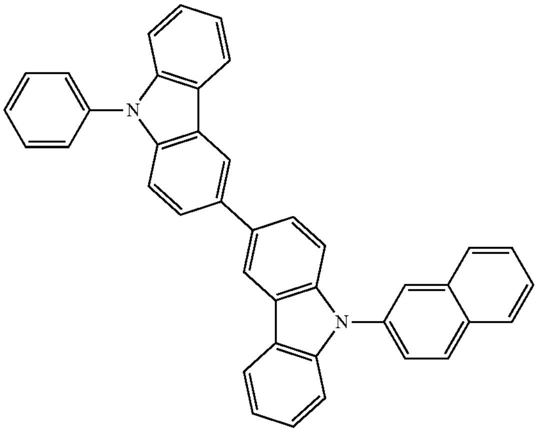

-continued

E-2-20

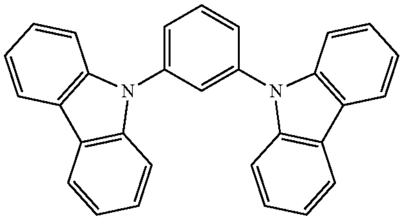

E-2-21

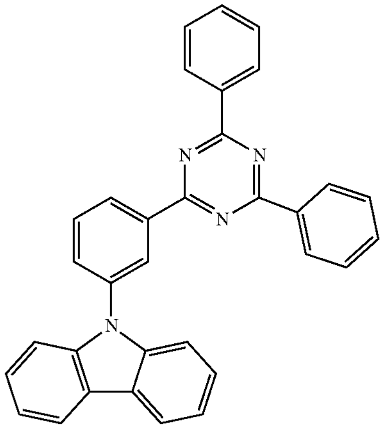

E-2-22

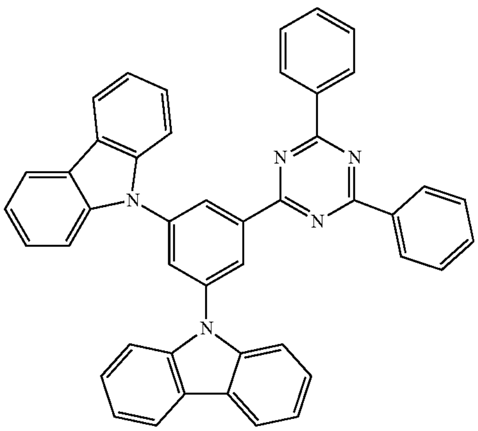

E-2-23

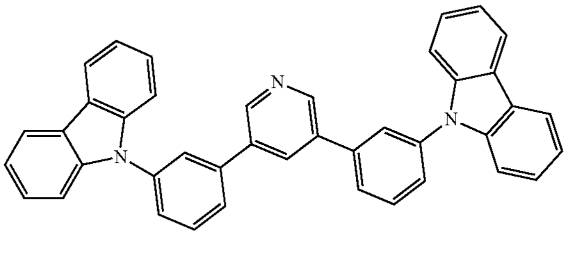

-continued

E-2-24

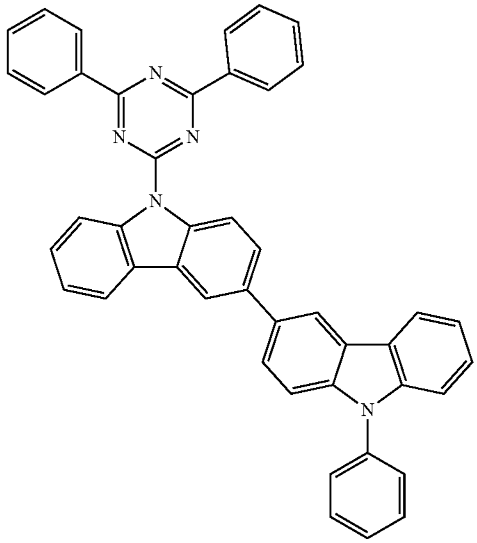

The emission layer EML may further include a common material well-known in the art as a host material. For example, the emission layer EML may include as a host material, at least one of bis[2-(diphenylphosphino)phenyl] ether oxide (DPEPO), 4,4'-bis(N-carbazolyl)-1,1'-biphenyl (CBP), 1,3-bis(carbazol-9-yl)benzene (mCP), 2,8-bis(diphenylphosphoryl)dibenzo[b,d]furan (PPF), 4,4',4"-tris(carbazol-9-yl)-triphenylamine (TCTA), or 1,3,5-tris(1-phenyl-1H-benzo[d]imidazole-2-yl)benzene (TPBi). However, embodiments are not limited thereto. For example, tris(8-hydroxyquinolino)aluminum ($Alq_3$), poly(N-vinylcarbazole) (PVK), 9,10-di(naphthalene-2-yl)anthracene (ADN), 2-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), hexaphenylcyclotriphosphazene (CP1), 1,4-bis(triphenylsilyl)benzene (UGH2), hexaphenylcyclotrisiloxane ($DPSiO_3$), octaphenylcyclotetrasiloxane ($DPSiO_4$), etc. may be used as the host material.

The emission layer EML may include a compound represented by Formula M-a or Formula M-b below. The compound represented by Formula M-a or Formula M-b may be used as a phosphorescence dopant material.

Formula M-a

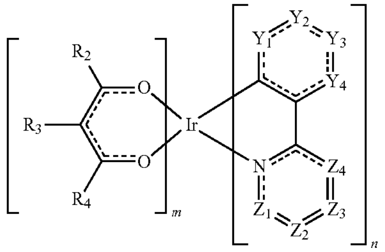

In Formula M-a, $Y_1$ to $Y_4$, and $Z_1$ to $Z_4$ may be each independently $CR_1$ or N, and $R_1$ to $R_4$ may be each independently a hydrogen atom, a deuterium atom, a substituted or unsubstituted amine group, a substituted or unsubstituted thio group, a substituted or unsubstituted oxy group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. In Formula M-a, "m" is 0 or 1, and "n" is 2 or 3. In Formula M-a, if "m" is 0, "n" is 3, and if "m" is 1, "n" is 2.

The compound represented by Formula M-a may be used as a phosphorescence dopant. The compound represented by Formula M-a may be represented by any one of Compounds M-a1 to M-a25 below. However, Compounds M-a1 to M-a25 below are illustrations, and the compound represented by Formula M-a is not limited to the compounds represented by Compounds M-a1 to M-a25 below.

M-a1

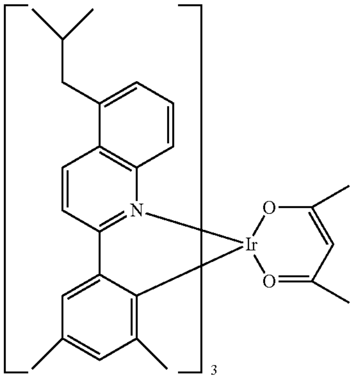

M-a2

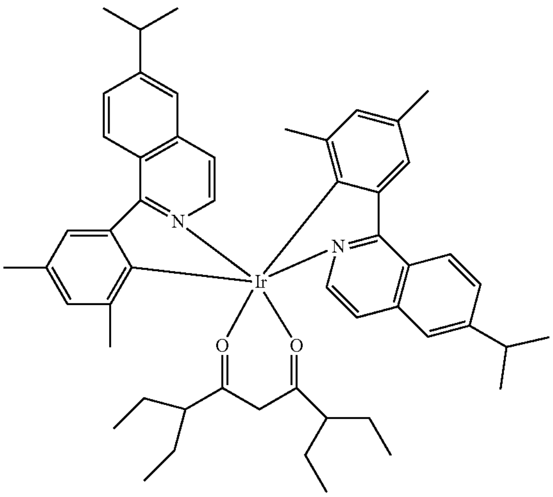

M-a3

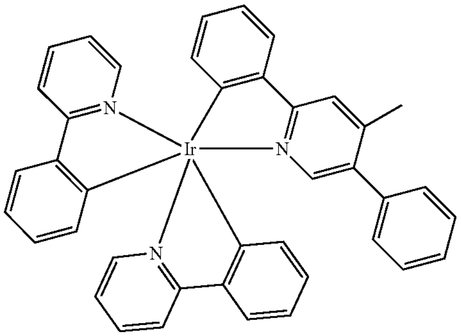

-continued

M-a4

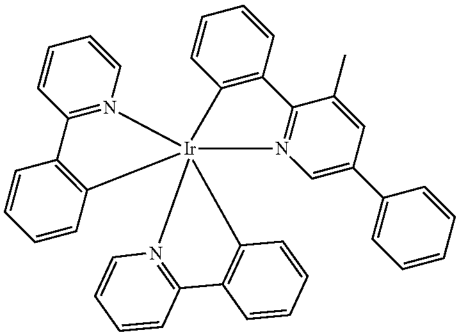

M-a5

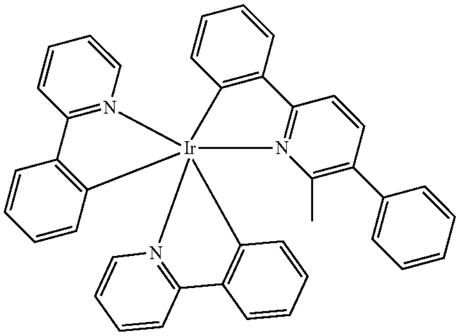

M-a6

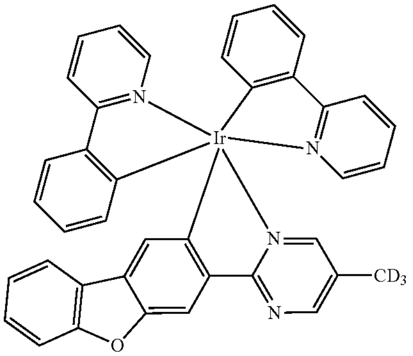

M-a7

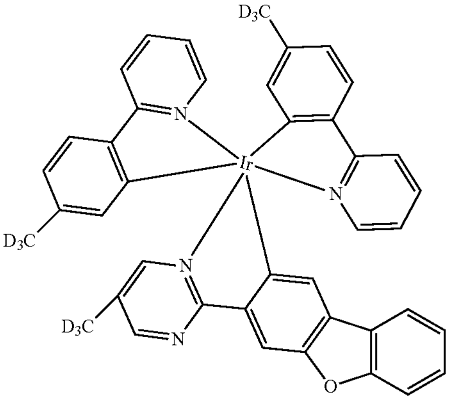

-continued
M-a8
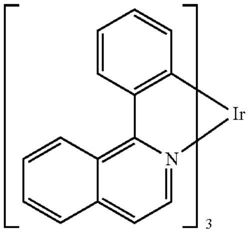
M-a9
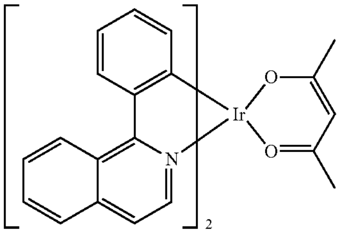
M-a10
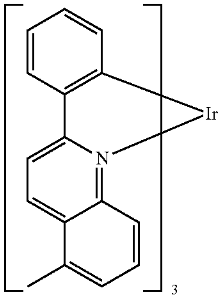
M-a11
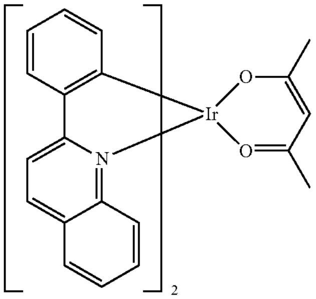
M-a12
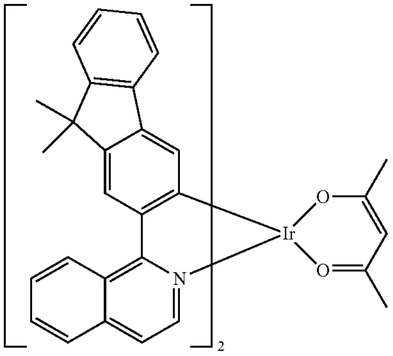
-continued
M-a13
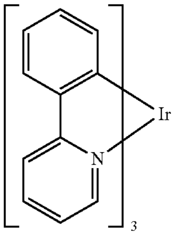
M-a14
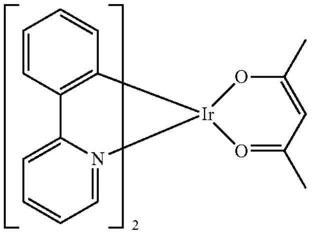
M-a15
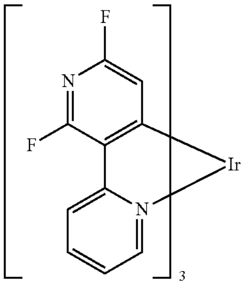
M-a16
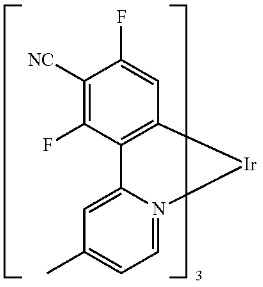
M-a17
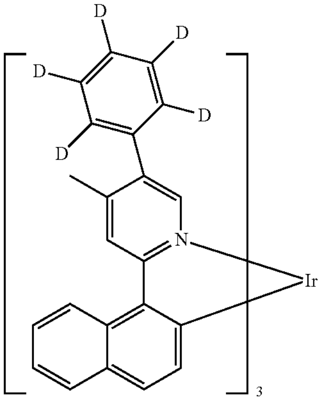

-continued
M-a18
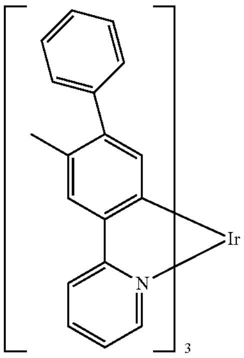
M-a19
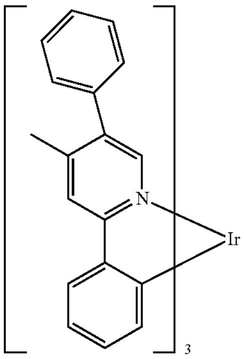
M-a20
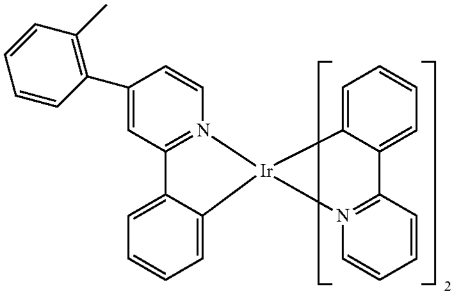
M-a21
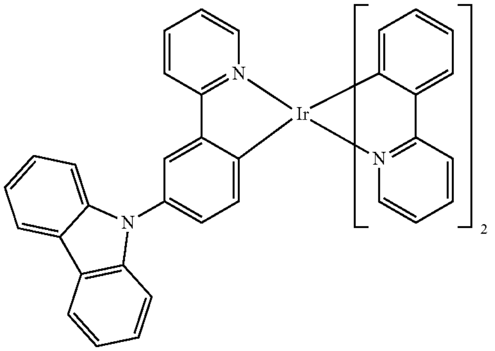
-continued
M-a22
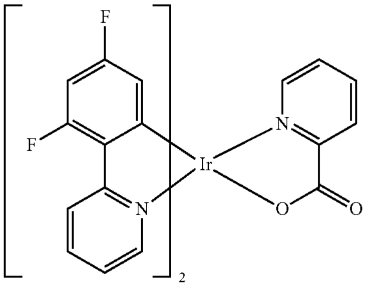
M-a23
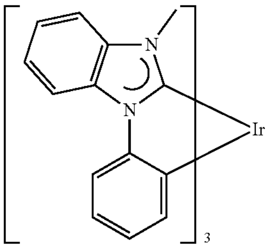
M-a24
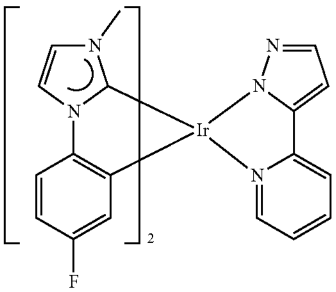
M-a25
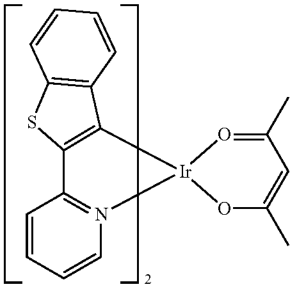
Compound M-a1 and Compound M-a2 may be used as red dopant materials, and Compound M-a3 to Compound M-a7 may be used as green dopant materials.
Formula M-b
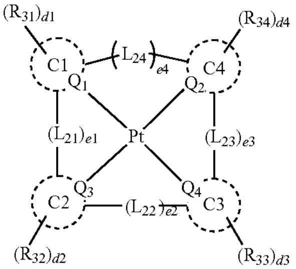

In Formula M-b, $Q_1$ to $Q_4$ are each independently C or N, $C_1$ to $C_4$ are each independently a substituted or unsubstituted hydrocarbon ring of 5 to 30 ring-forming carbon atoms, or a substituted or unsubstituted heterocycle of 2 to 30 ring-forming carbon atoms. $L_{21}$ to $L_{24}$ are each independently a direct linkage,

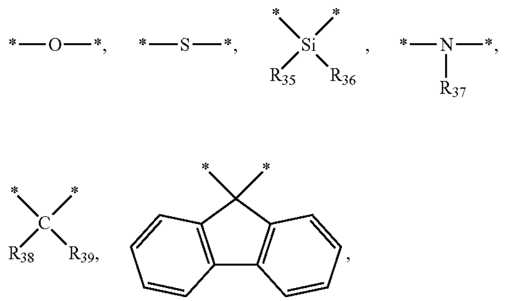

a substituted or unsubstituted divalent alkyl group of 1 to 20 carbon atoms, a substituted or unsubstituted arylene group of 6 to 30 ring-forming carbon atoms, or a substituted or unsubstituted heteroarylene group of 2 to 30 ring-forming carbon atoms, and e1 to e4 are each independently 0 or 1. The variables $R_{31}$ to $R_{39}$ are each independently a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or combined with an adjacent group to form a ring, and d1 to d4 are each independently an integer of 0 to 4.

The compound represented by Formula M-b may be used as a blue phosphorescence dopant or a green phosphorescence dopant. The compound represented by Formula M-b may be represented by any one of the compounds below. However, the compounds below are illustrations, and the compound represented by Formula M-b is not limited to the compounds represented below.

M-b-1

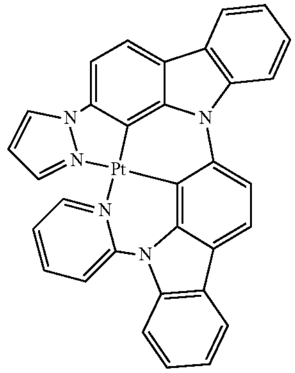

-continued

M-b-2

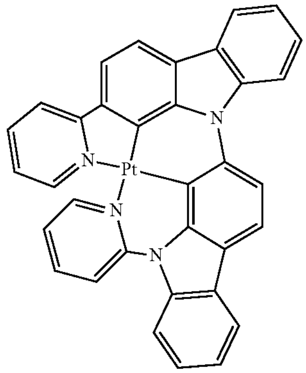

M-b-3

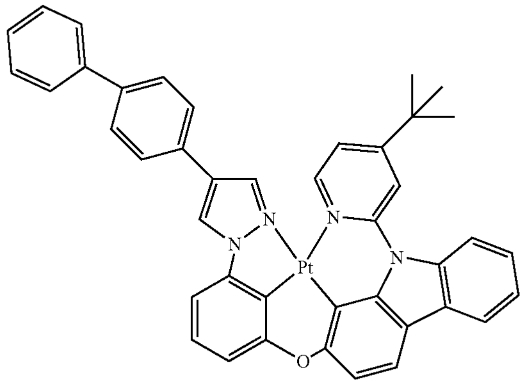

M-b-4

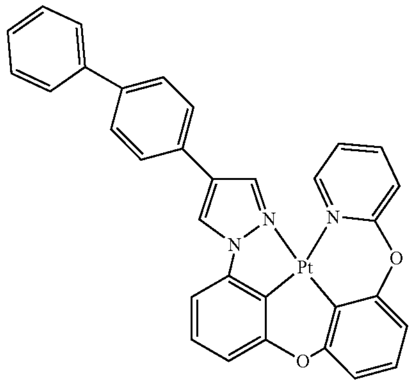

M-b-5

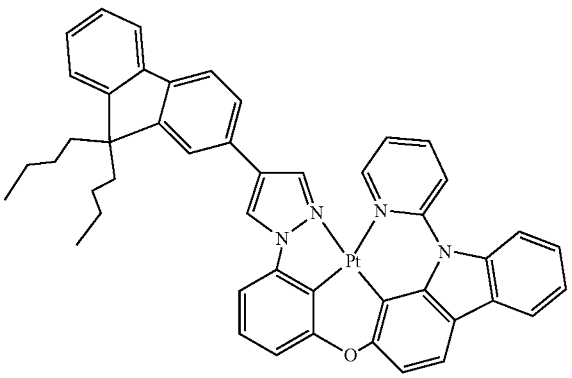

-continued

M-b-6

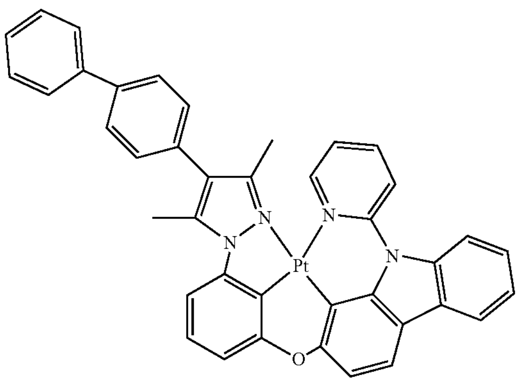

M-b-7

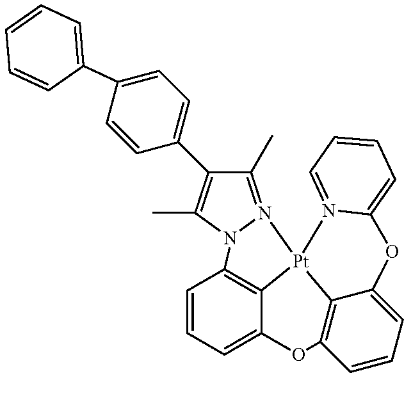

M-b-8

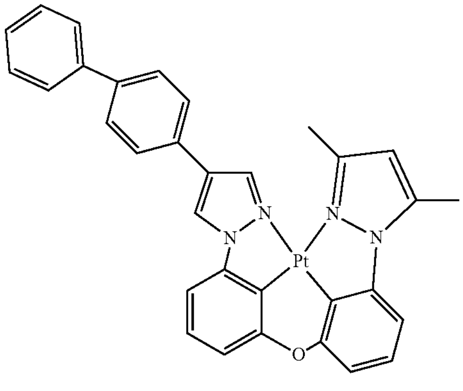

M-b-9

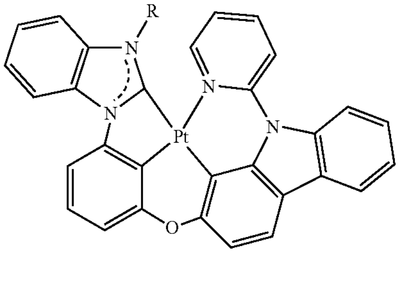

-continued

M-b-10

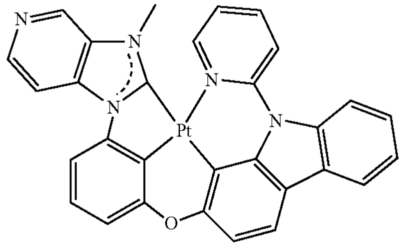

M-b-11

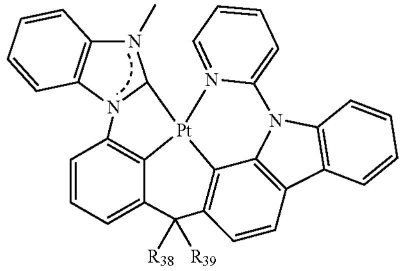

In the compounds above, R, $R_{38}$, and $R_{39}$ may be each independently a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms. The emission layer EML may include any one of Formula F-a to Formula F-c below. The compounds represented by Formula F-a to Formula F-c below may be used as fluorescence dopant materials.

Formula F-a

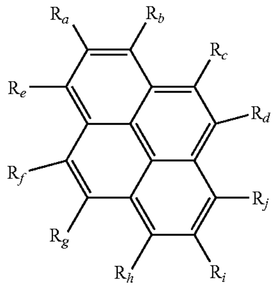

In Formula F-a, two selected from $R_a$ to $R_j$ may be each independently substituted with $*-NAr_1Ar_2$. The remainder not substituted with $*-NAr_1Ar_2$ of $R_a$ to $R_j$ may be each independently a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms. In $*-NAr_1Ar_2$, $Ar_1$ and $Ar_2$ may be each independently a substituted or unsubstituted aryl group of 6 to 30 ring-forming carbon atoms, or a substituted or unsubstituted heteroaryl group of 2 to 30 ring-forming carbon atoms. For example, at least one of $Ar_1$ and $Ar_2$ may be a heteroaryl group including O or S as a ring-forming atom.

Formula F-b

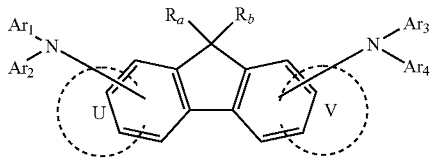

In Formula F-b, $R_a$ and $R_b$ may be each independently a hydrogen atom, a deuterium atom, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. $Ar_1$ to $Ar_4$ may be each independently a substituted or unsubstituted aryl group of 6 to 30 ring-forming carbon atoms, or a substituted or unsubstituted heteroaryl group of 2 to 30 ring-forming carbon atoms. In Formula F-b, U and V may be each independently a substituted or unsubstituted hydrocarbon ring of 5 to 30 ring-forming carbon atoms, or a substituted or unsubstituted heterocycle of 2 to 30 ring-forming carbon atoms. In Formula F-b, the number of rings represented by U and V may be each independently 0 or 1. For example, in Formula F-b, if the number of U or V is 1, one ring forms a fused ring at the designated part by U or V, and if the number of U or V is 0, a ring is not present at the designated part by U or V. Particularly, if the number of U is 0, and the number of V is 1, or if the number of U is 1, and the number of V is 0, a fused ring having the fluorene core of Formula F-b may be a ring compound with four rings. In addition, if the number of both U and V is 0, the fused ring of Formula F-b may be a ring compound with three rings. In addition, if the number of both U and V is 1, a fused ring having the fluorene core of Formula F-b may be a ring compound with five rings.

Formula F-c

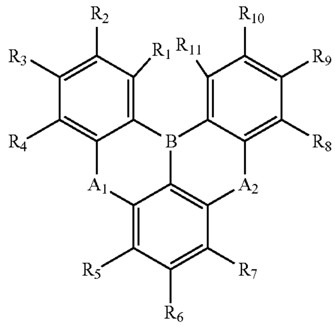

In Formula F-c, $A_1$ and A2 may be each independently O, S, Se, or $NR_m$, and $R_m$ may be a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms. The variables $R_1$ to $R_{11}$ are each independently a hydrogen atom, a deuterium atom, a halogen atom, a cyano group, a substituted or unsubstituted amine group, a substituted or unsubstituted boryl group, a substituted or unsubstituted oxy group, a substituted or unsubstituted thio group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or combined with an adjacent group to form a ring.

In Formula F-c, $A_1$ and $A_2$ may be each independently combined with the substituents of an adjacent ring to form a fused ring. For example, if $A_1$ and $A_2$ may be each independently $NR_m$, $Ar_1$ may be combined with $R_4$ or $R_5$ to form a ring. In addition, $A_2$ may be combined with $R_7$ or $R_8$ to form a ring.

In an embodiment, the emission layer EML may include as a known dopant material, styryl derivatives (for example, 1,4-bis[2-(3-N-ethylcarbazoryl)vinyl]benzene (BCzVB), 4-(di-p-tolylamino)-4'-[(di-p-tolylamino)styryl]stilbene (DPAVB), N-(4-((E)-2-(6-((E)-4-(diphenylamino)styryl) naphthalen-2-yl)vinyl)phenyl)-N-phenylbenzenamine (N-BDAVBi), and 4,4'-bis[2-(4-(N,N-diphenylamino)phenyl)vinyl]biphenyl (DPAVBi)), perylene and the derivatives thereof (for example, 2,5,8,11-tetra-t-butylperylene (TBP)), pyrene and the derivatives thereof (for example, 1,1-dipyrene, 1,4-dipyrenylbenzene, and 1,4-bis(N,N-diphenylamino)pyrene), etc.

The emission layer EML may include a known phosphorescence dopant material. For example, the phosphorescence dopant may use a metal complex including iridium (Ir), platinum (Pt), osmium (Os), gold (Au), titanium (Ti), zirconium (Zr), hafnium (Hf), europium (Eu), terbium (Tb) or thulium (Tm). Particularly, iridium(III) bis(4,6-difluorophenylpyridinato-N,C2')picolinate (FIrpic), bis(2,4-difluorophenylpyridinato)-tetrakis(1-pyrazolyl)borate iridium(III) (Fir6), or platinum octaethyl porphyrin (PtOEP) may be used as the phosphorescence dopant. However, embodiments are not limited thereto.

In the case where the emission layer EML emits green light, the emission layer EML may further include, for example, a fluorescence material including tris(dibenzoylmethanato)phenanthoroline europium (PBD:Eu(DBM)$_3$(Phen)) or perylene. In the case where the emission layer EML emits red light, the dopant included in the emission layer EML may be selected from, for example, a metal complex or an organometallic complex such as bis(1-phenylisoquinoline)acetylacetonate iridium (PIQIr(acac)), bis(1-phenylquinoline)acetylacetonate iridium (PQIr(acac)), tris(1-phenylquinoline)iridium (PQIr) and octaethylporphyrin platinum (PtOEP), rubrene and the derivatives thereof, and 4-dicyanomethylene-2-(p-dimethylaminostyryl)-6-methyl-4H-pyrane (DCM) and the derivatives thereof.

In the case where the emission layer EML emits green light, the emission layer EML may further include, for example, a fluorescence material including tris(8-hydroxyquinolino)aluminum ($Alq_3$). In the case where the emission layer EML emits green light, the dopant included in the emission layer EML may be selected from, for example, a metal complex or an organometallic complex such as fac-tris(2-phenylpyridine)iridium ($Ir(ppy)_3$), and coumarin and the derivatives thereof.

In the case where the emission layer EML emits blue light, the emission layer EML may further include a fluorescence material including any one selected from the group consisting of spiro-4,4"-bis(2,2"diphenylvinil)-1,1"-biphenyl(spiro-DPVBi), 2,2",7,7"-tetrakis(biphenyl-4-yl)-9,9"-spirobifluorene (spiro-6P), distyryl-benzene (DSB), distyryl-arylene (DSA), a polyfluorene (PFO)-based polymer and a poly(p-phenylene vinylene) (PPV)-based polymer. In the case where the emission layer EML emits blue light, the dopant included in the emission layer EML may be selected from a metal complex or an organometallic complex such as Bis[2-(4,6-difluorophenyl)pyridinato-C2,N](picolinato)iridium(III) ((4,6-F2ppy)2Irpic), and perylene and the derivatives thereof.

The emission layer EML may include a quantum dot material. The core of the quantum dot may be selected from a compound of Groups II-VI, a compound of Groups a compound of Groups I, III, and VI, a compound of Groups III-V, a compound of Groups III, II, and V group compound, a compound of Groups IV-VI, a Group of IV element, a Group of IV compound, and combinations thereof.

The compound of Groups II-VI may be selected from the group consisting of: a binary compound selected from the group consisting of CdSe, CdTe, CdS, ZnS, ZnSe, ZnTe, ZnO, HgS, HgSe, HgTe, MgSe, MgS, and mixtures thereof; a ternary compound selected from the group consisting of CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and mixtures thereof; and a quaternary compound selected from the group consisting of HgZnTeS, CdZnSeS, CdZnSeTe, CdZnSTe, CdHgSeS, CdHgSeTe, CdHgSTe, HgZnSeS, HgZnSeTe, HgZnSTe, and mixtures thereof.

The compound of Groups III-VI may include a binary compound such as $In_2S_3$, and $In_2Se_3$, a ternary compound such as $InGaS_3$, and $InGaSe_3$, or optional combinations thereof. The compound of Groups I, III, and VI may be selected from a ternary compound selected from the group consisting of AgInS, $AgInS_2$, CuInS, $CuInS_2$, $AgGaS_2$, $CuGaS_2$, $CuGaO_2$, $AgGaO_2$, $AgAlO_2$ and mixtures thereof, or a quaternary compound such as $AgInGaS_2$, and $CuInGaS_2$.

The compound of Groups III-V may be selected from the group consisting of a binary compound selected from the group consisting of GaN, GaP, GaAs, GaSb, AlN, AlP, AlAs, AlSb, InN, InP, InAs, InSb, and mixtures thereof, a ternary compound selected from the group consisting of GaNP, GaNAs, GaNSb, GaPAs, GaPSb, AlNP, AlNAs, AlNSb, AlPAs, AlPSb, InGaP, InAlP, InNP, InNAs, InNSb, InPAs, InPSb, and mixtures thereof, and a quaternary compound selected from the group consisting of GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and mixtures thereof. The compound of Groups III-V may further include a metal of Group II. For example, InZnP, etc. may be selected as a compound of Groups III, II, and V.

The compound of Groups IV-VI may be selected from the group consisting of a binary compound selected from the group consisting of SnS, SnSe, SnTe, PbS, PbSe, PbTe, and mixtures thereof, a ternary compound selected from the group consisting of SnSeS, SnSeTe, SnSTe, PbSeS, PbSeTe, PbSTe, SnPbS, SnPbSe, SnPbTe, and mixtures thereof, and a quaternary compound selected from the group consisting of SnPbSSe, SnPbSeTe, SnPbSTe, and mixtures thereof. The element of Group IV may be selected from the group consisting of Si, Ge, and a mixture thereof. The compound of Group IV may be a binary compound selected from the group consisting of SiC, SiGe, and a mixture thereof.

In this case, the binary compound, the ternary compound or the quaternary compound may be present at uniform concentration in a particle or may be present at a partially different concentration distribution state in the same particle. In addition, a core/shell structure in which one quantum dot wraps another quantum dot may be possible. The interface of the core and the shell may have a concentration gradient in which the concentration of an element present in the shell is decreased toward the center.

In some embodiments, the quantum dot may have the above-described core-shell structure including a core including a nanocrystal and a shell wrapping the core. The shell of the quantum dot may play the role of a protection layer for preventing the chemical deformation of the core to maintain semiconductor properties and/or a charging layer for imparting the quantum dot with electrophoretic properties. The shell may have a single layer or a multilayer. Examples of the shell of the quantum dot may include a metal or a non-metal oxide, a semiconductor compound, or combinations thereof.

For example, the metal or non-metal oxide may include a binary compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$ and NiO, or a ternary compound such as $MgAl_2O_4$, $CoFe_2O_4$, $NiFe_2O_4$ and $CoMn_2O_4$, but embodiments are not limited thereto.

Also, the semiconductor compound may include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, etc., but embodiments are not limited thereto.

The quantum dot may have a full width of half maximum (FWHM) of emission wavelength spectrum of about 45 nm or less, preferably, about 40 nm or less, more preferably, about 30 nm or less. Within this range, color purity or color reproducibility may be improved. In addition, light emitted via such a quantum dot is emitted in all directions, and light view angle properties may be improved. In addition, the shape of the quantum dot may be generally used shapes in the art, without specific limitation. More particularly, the shape of a generally spherical, a generally pyramidal, a generally multi-armed, or a generally cubic nanoparticle, or a generally nanotube-shaped, a generally nanowire-shaped, a generally nanofiber-shaped, a generally nanoplate-shaped particle, etc. may be used. The quantum dot may control the color of light emitted according to the particle size, and accordingly, the quantum dot may have various emission colors such as blue, red and green.

In the light emitting device ED, as shown in FIG. 3 to FIG. 6, the electron transport region ETR is provided on the emission layer EML. The electron transport region ETR may include at least one of an hole blocking layer HBL, an electron transport layer ETL or an electron injection layer EIL. However, embodiments are not limited thereto.

The electron transport region ETR may have a single layer formed using a single material, a single layer formed using multiple different materials, or a multilayer structure having multiple layers formed using multiple different materials. For example, the electron transport region ETR may have a single layer structure of an electron injection layer EIL or an electron transport layer ETL, or a single layer structure formed using an electron injection material and an electron transport material. Further, the electron transport region ETR may have a single layer structure formed using multiple different materials, or a structure stacked from the emission layer EML of electron transport layer ETL/electron injection layer EIL, or hole blocking layer HBL/electron transport layer ETL/electron injection layer EIL, without limitation. The thickness of the electron transport region ETR may be, for example, from about 1,000 Å to about 1,500 Å.

The electron transport region ETR may be formed using various methods such as a vacuum deposition method, a spin coating method, a cast method, a Langmuir-Blodgett (LB)

method, an inkjet printing method, a laser printing method, and a laser induced thermal imaging (LITI) method.

The electron transport region ETR may include a compound represented by Formula ET-1 below.

Formula ET-1

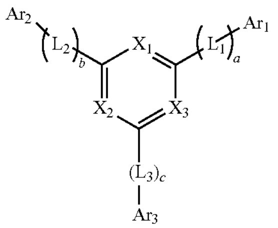

In Formula ET-1, at least one of $X_1$ to $X_3$ is N, and the remainder are $CR_a$. The variable $R_a$ may be a hydrogen atom, a deuterium atom, a substituted or unsubstituted alkyl of 1 to 20 carbon atoms, a substituted or unsubstituted aryl group of 6 to 30 ring-forming carbon atoms, or a substituted or unsubstituted heteroaryl group of 2 to 30 ring-forming carbon atoms. The variables $Ar_1$ to $Ar_3$ may be each independently a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

In Formula ET-1, "a" to "c" may be each independently an integer of 0 to 10. In Formula ET-1, $L_1$ to $L_3$ may be each independently a direct linkage, a substituted or unsubstituted arylene group of 6 to 30 ring-forming carbon atoms, or a substituted or unsubstituted heteroarylene group of 2 to 30 ring-forming carbon atoms. If "a" to "c" are integers of 2 or more, $L_1$ to $L_3$ may be each independently a substituted or unsubstituted arylene group of 6 to 30 ring-forming carbon atoms, or a substituted or unsubstituted heteroarylene group of 2 to 30 ring-forming carbon atoms.

The electron transport region ETR may include an anthracene-based compound. However, embodiments are not limited thereto, and the electron transport region ETR may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate ($Bebq_2$), 9,10-di(naphthalene-2-yl)anthracene (ADN), 1,3-bis[3,5-di(pyridin-3-yl)phenyl]benzene (BmPyPhB), and mixtures thereof, without limitation.

The electron transport region ETR may include at least one of Compounds ET1 to ET36 below.

ET1

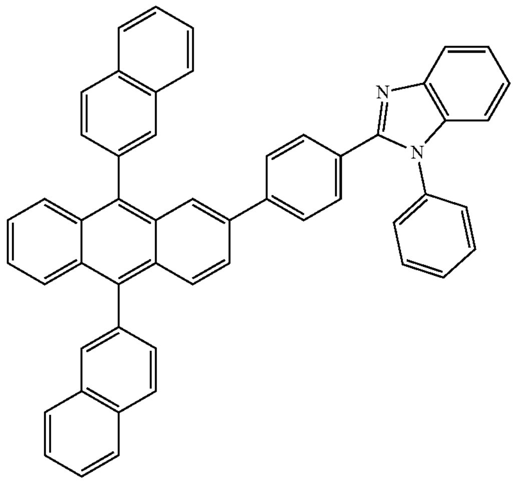

ET2

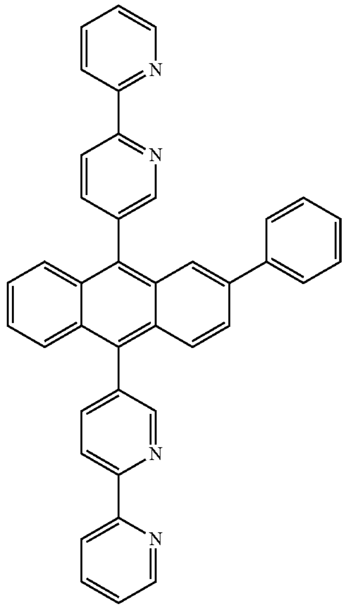

ET3

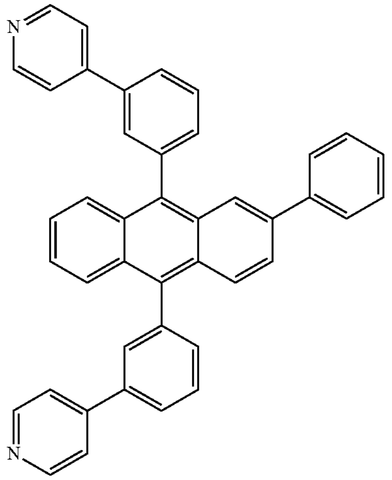

-continued
ET4
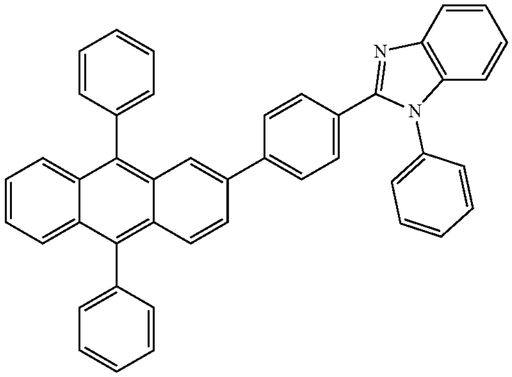
ET5
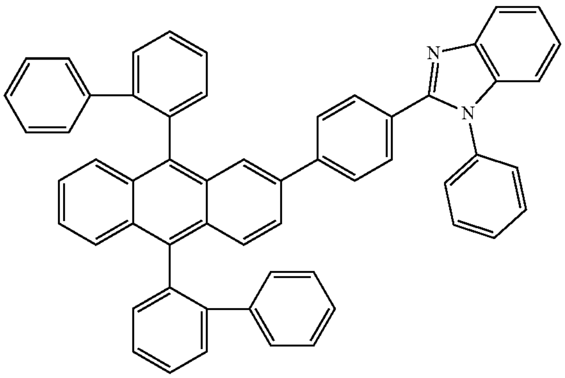
ET6
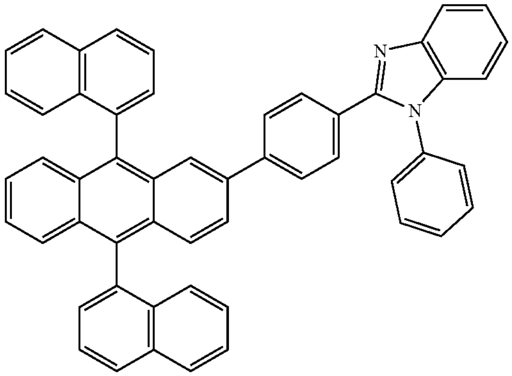
-continued
ET7
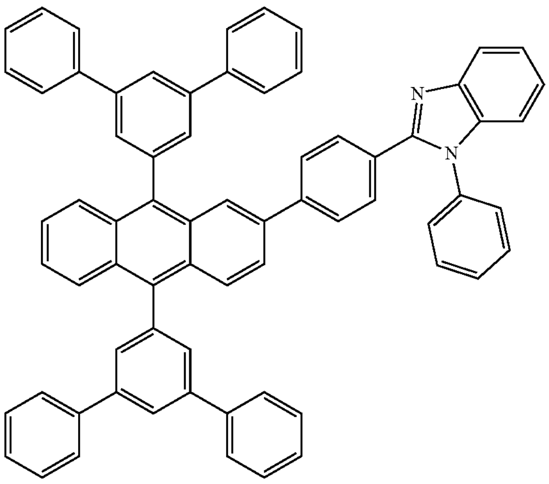
ET8
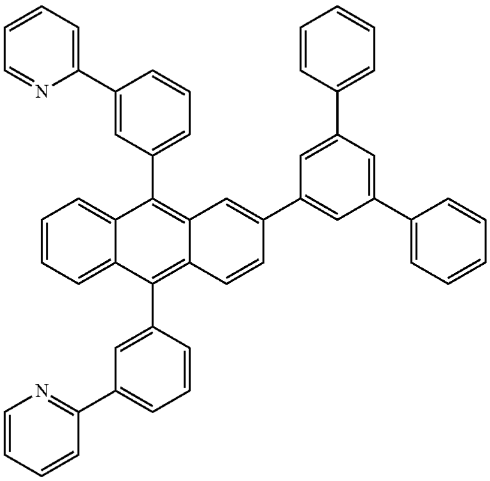
ET9
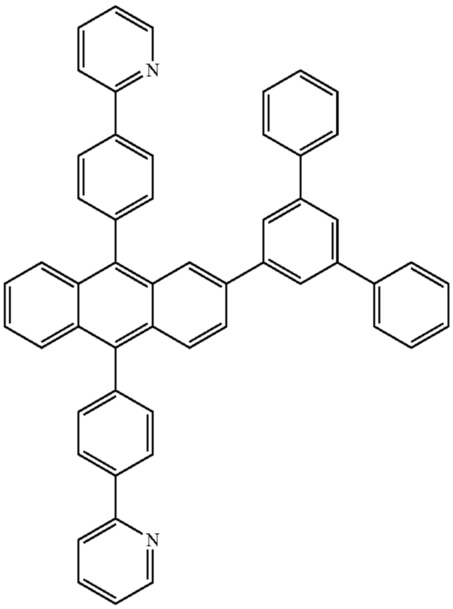

-continued
ET10
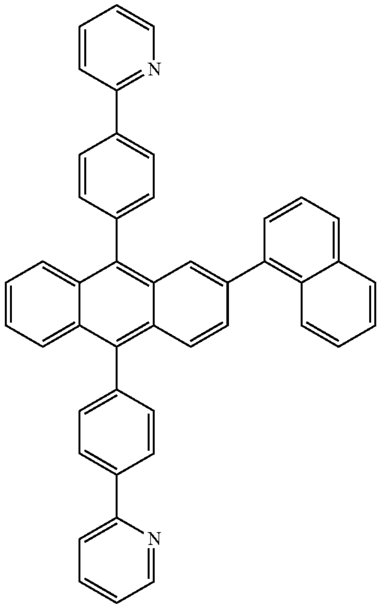
ET11
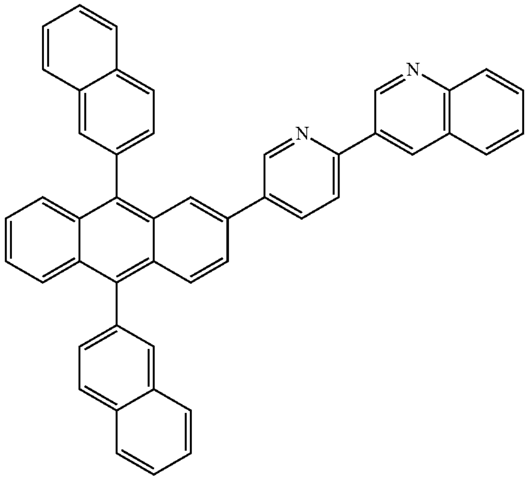
ET12
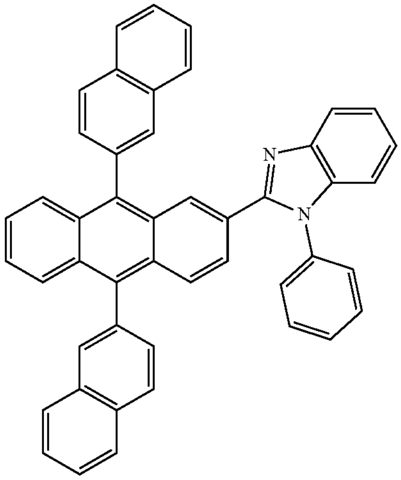
-continued
ET13
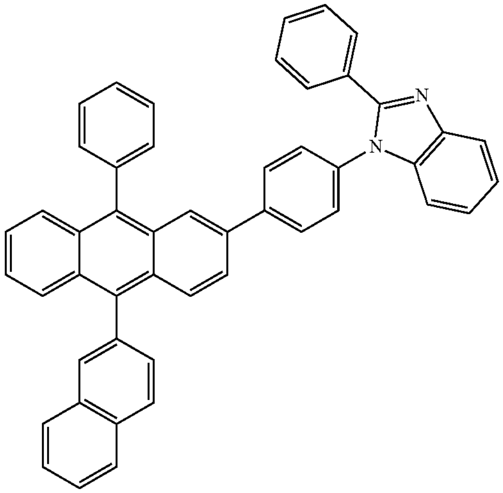
ET14
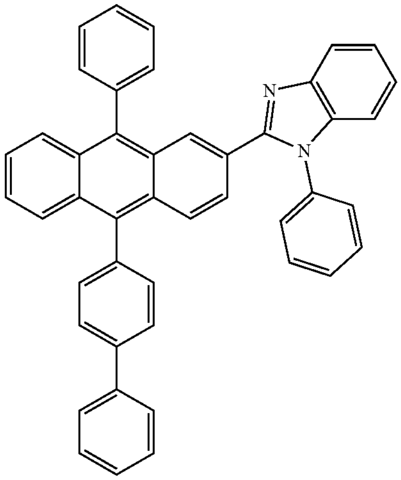
ET15
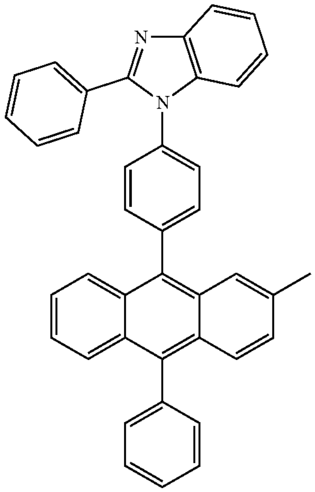

-continued
ET16
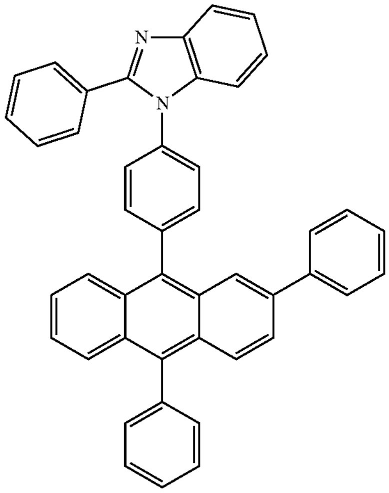
ET17
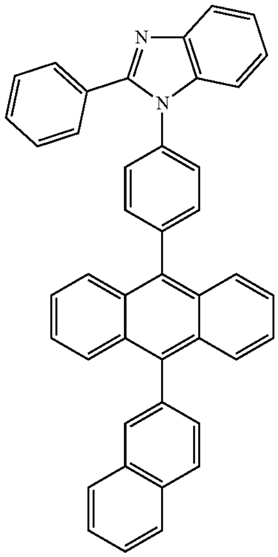
ET18
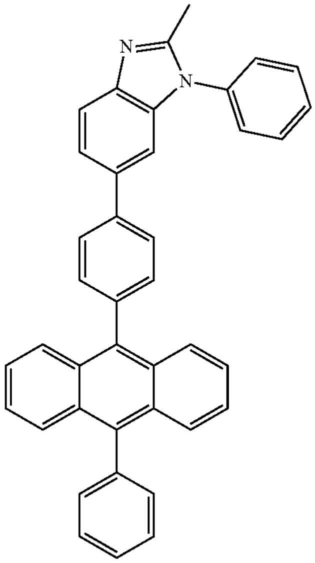
-continued
ET19
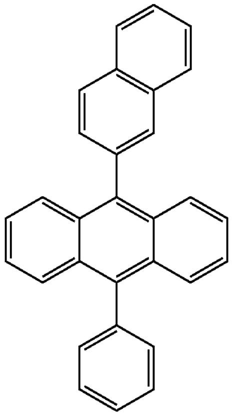
ET20
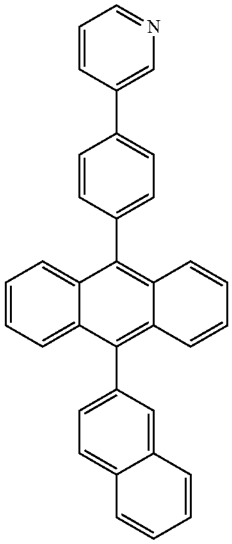
ET21
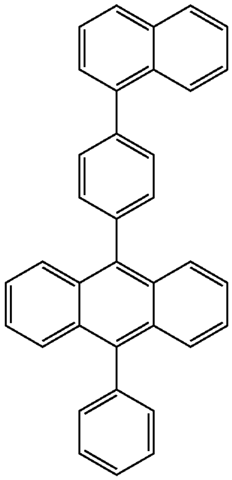

-continued
ET22
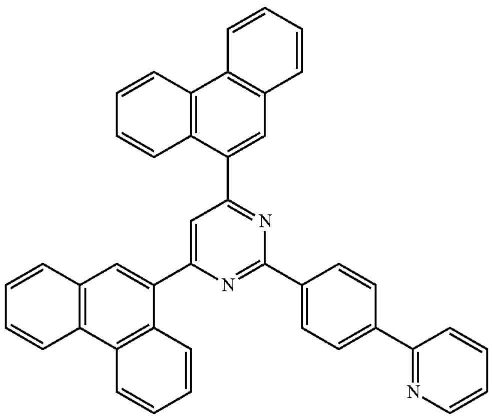
ET23
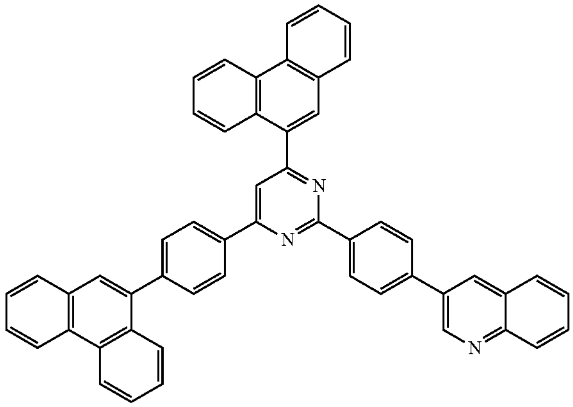
ET24
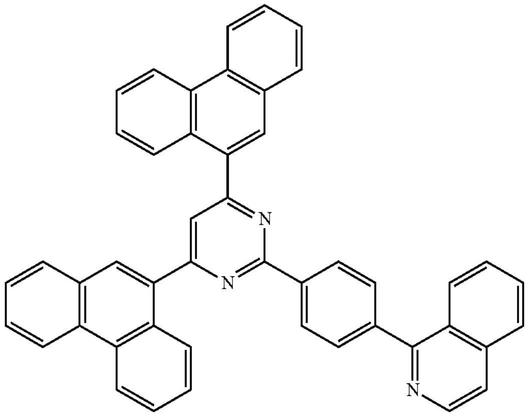
-continued
ET25
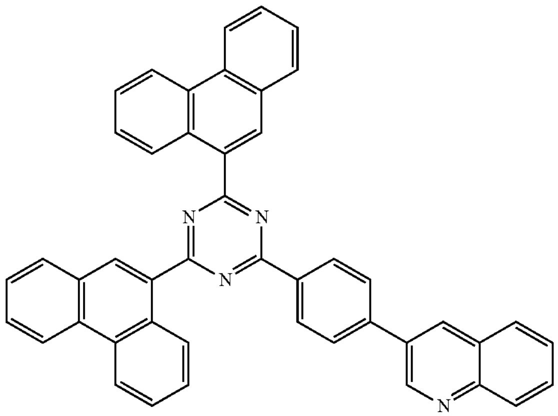
ET26
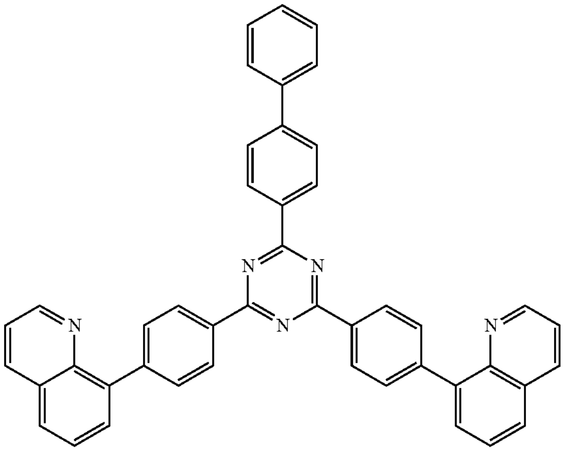
ET27
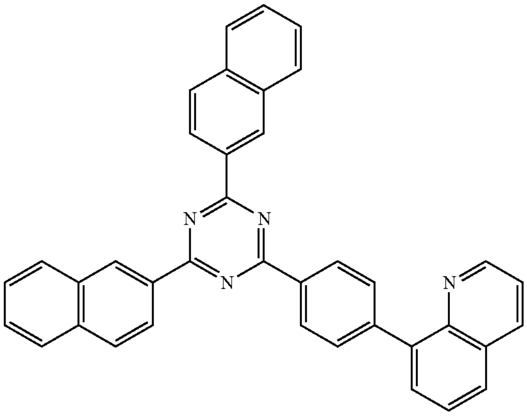

-continued
ET28
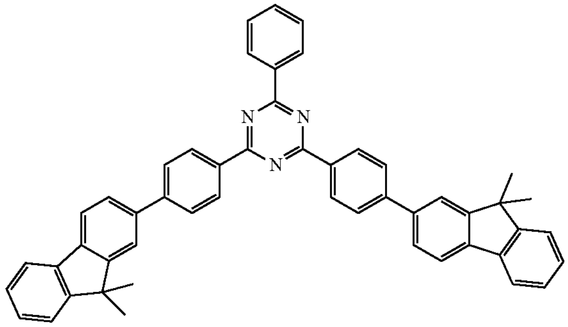
ET29
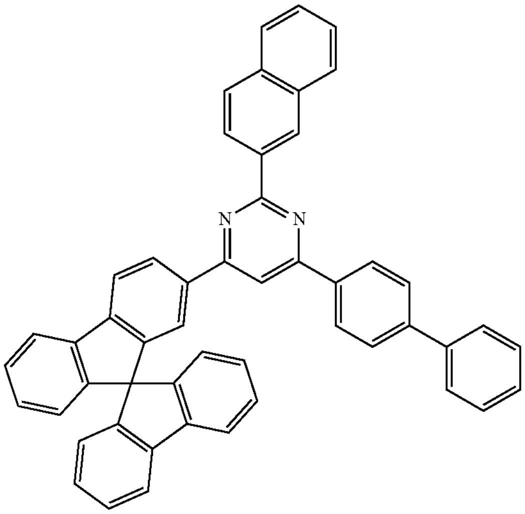
ET30
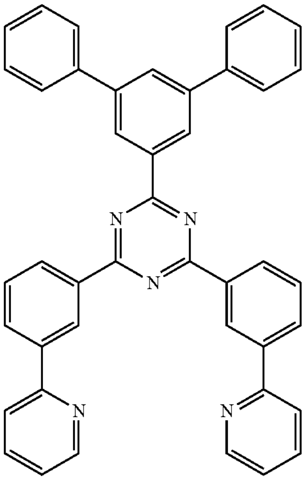
-continued
ET31
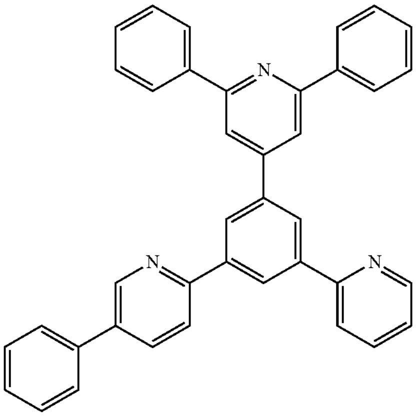
ET32
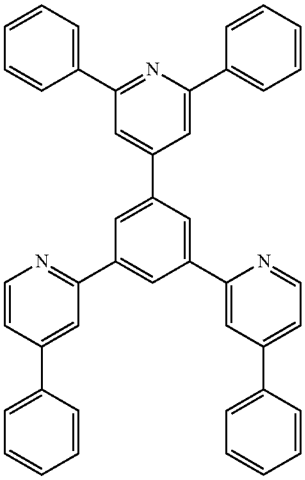
ET33
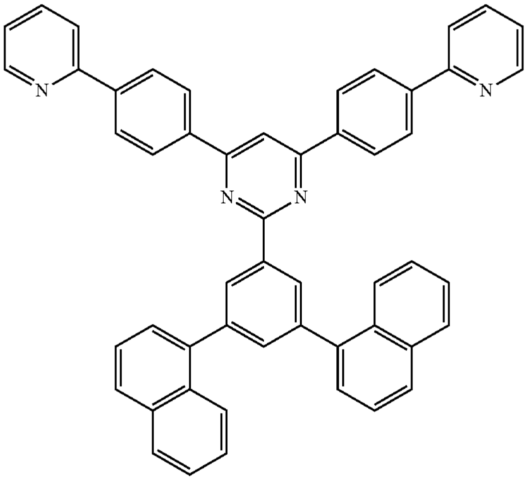

-continued

ET34

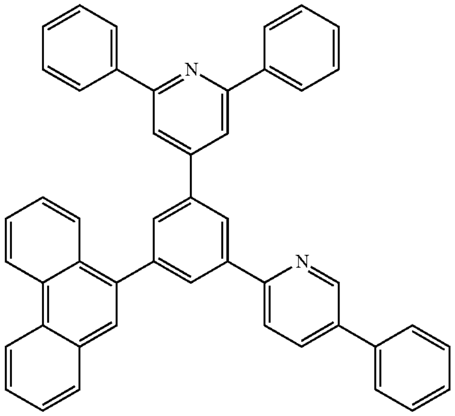

ET35

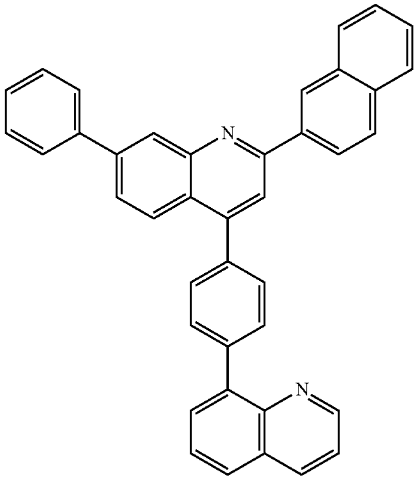

ET36

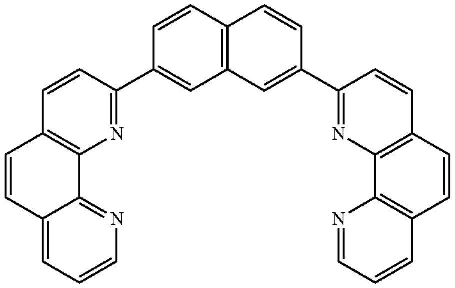

In addition, the electron transport region ETR may include a metal halide such as LiF, NaCl, CsF, RbCl, RbI, CuI and KI, a metal in lanthanoides such as Yb, or a co-depositing material of the metal halide and the metal in lanthanoides. For example, the electron transport region ETR may include KI:Yb, RbI:Yb, etc., as the co-depositing material. The electron transport region ETR may use a metal oxide such as $Li_2O$ and BaO, or 8-hydroxy-lithium quinolate (Liq). However, embodiments are not limited thereto. The electron transport region ETR also may be formed using a mixture material of an electron transport material and an insulating organometal salt. The organometal salt may be a material having an energy band gap of about 4 eV or more. Particularly, the organometal salt may include, for example, metal acetates, metal benzoates, metal acetoacetates, metal acetylacetonates, or metal stearates.

The electron transport region ETR may include at least one of 2,9-dimethyl-4,7-diphenyl-1,10-phenanthroline (BCP), or 4,7-diphenyl-1,10-phenanthroline (Bphen) in addition to the aforementioned materials. However, embodiments are not limited thereto. The electron transport region ETR may include the compounds of the electron transport region in at least one of an electron injection layer EIL, an electron transport layer ETL, and a hole blocking layer HBL.

If the electron transport region ETR includes the electron transport layer ETL, the thickness of the electron transport layer ETL may be from about 100 Å to about 1,000 Å, for example, from about 150 Å to about 500 Å. If the thickness of the electron transport layer ETL satisfies the above-described range, satisfactory electron transport properties may be obtained without substantial increase of a driving voltage. If the electron transport region ETR includes the electron injection layer EIL, the thickness of the electron injection layer EIL may be from about 1 Å to about 100 Å, and from about 3 Å to about 90 Å. If the thickness of the electron injection layer EIL satisfies the above described range, satisfactory electron injection properties may be obtained without inducing substantial increase of a driving voltage.

The second electrode EL2 is provided on the electron transport region ETR. The second electrode EL2 may be a common electrode. The second electrode EL2 may be a cathode or an anode, but embodiments are not limited thereto. For example, if the first electrode EL1 is an anode, the second electrode EL2 may be a cathode, and if the first electrode EL1 is a cathode, the second electrode EL2 may be an anode.

The second electrode EL2 may be a transmissive electrode, a transflective electrode or a reflective electrode. If the second electrode EL2 is the transmissive electrode, the second electrode EL2 may include a transparent metal oxide, for example, an ITO, an IZO, a ZnO, an ITZO, etc.

If the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, Yb, W, compounds including thereof, or mixtures thereof (for example, AgMg, AgYb, or MgYb). Otherwise, the second electrode EL2 may have a multilayered structure including a reflective layer or a transflective layer formed using the above-described materials and a transparent conductive layer formed using the ITO, IZO, ZnO, ITZO, etc. For example, the second electrode EL2 may include the aforementioned metal materials, combinations of two or more metal materials selected from the aforementioned metal materials, or oxides of the aforementioned metal materials.

The second electrode EL2 may be connected with an auxiliary electrode. If the second electrode EL2 is connected with the auxiliary electrode, the resistance of the second electrode EL2 may decrease. On the second electrode EL2 in the light emitting device ED, a capping layer CPL may be further disposed. The capping layer CPL may include a multilayer or a single layer. In an embodiment, the capping layer CPL may be an organic layer or an inorganic layer. For example, if the capping layer CPL includes an inorganic material, the inorganic material may include an alkali metal compound such as lithium fluoride (LiF), an alkaline earth metal compound such as $MgF_2$, SiON, $SiN_x$, $SiO_y$, etc.

For example, if the capping layer CPL includes an organic material, the organic material may include 2,2'-Dimethyl-N,N'-di-[(1-naphthyl)-N,N'-diphenyl]-1,1'-biphenyl-4,4'-diamine (α-NPD), N,N'-di(naphthalene-1-yl)-N,N'-diphenyl-benzidine (NPB), N,N'-bis(3-methylphenyl)-N,N'-diphenyl-[1,1-biphenyl]-4,4'-diamine (TPD), 4,4',4"-tris(3-methylphenylphenylamino) triphenylamine (m-MTDATA), tris(8-hydroxyquinolinato)aluminum ($Alq_3$), Copper(II) phthalocyanine (CuPc), N4,N4,N4',N4'-tetra(biphenyl-4-yl) biphenyl-4,4'-diamine (TPD15), 4,4',4"-tris(carbazol sol-9-yl) triphenylamine (TCTA), etc., or includes an epoxy resin, or an acrylate such as methacrylate. In addition, a capping layer CPL may include at least one of Compounds P1 to P5 below, but embodiments are not limited thereto.

P1

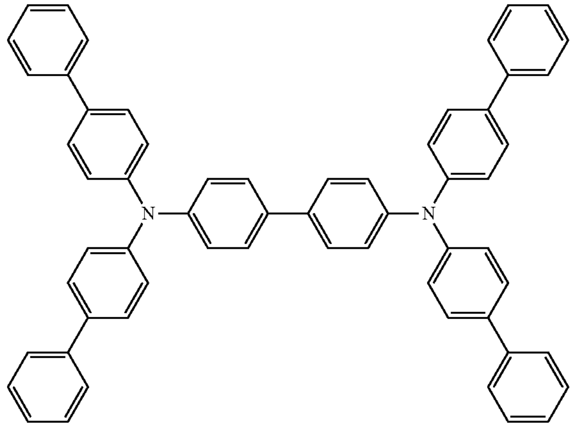

P2

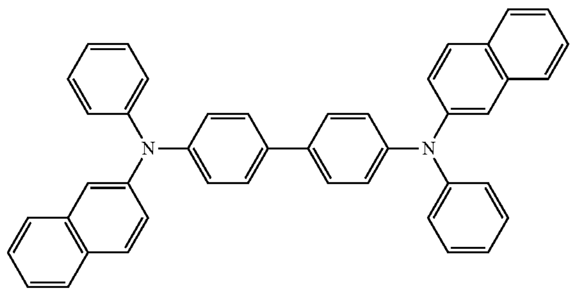

P3

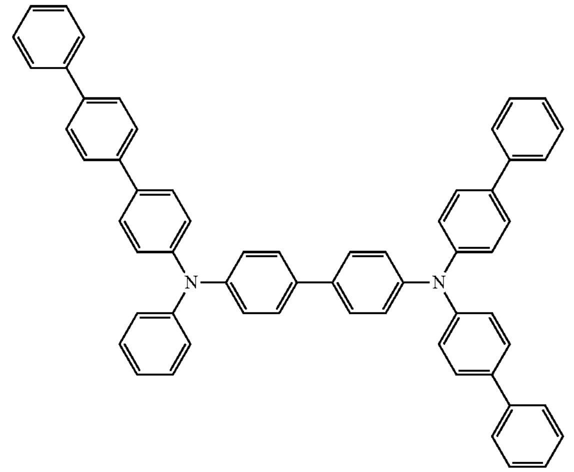

-continued

P4

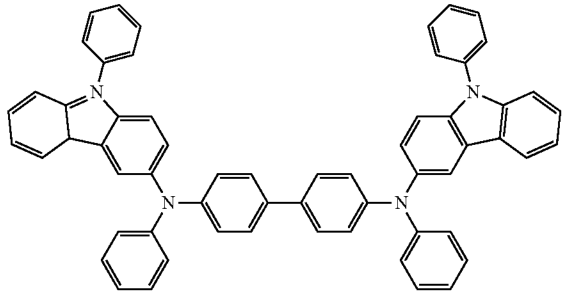

P5

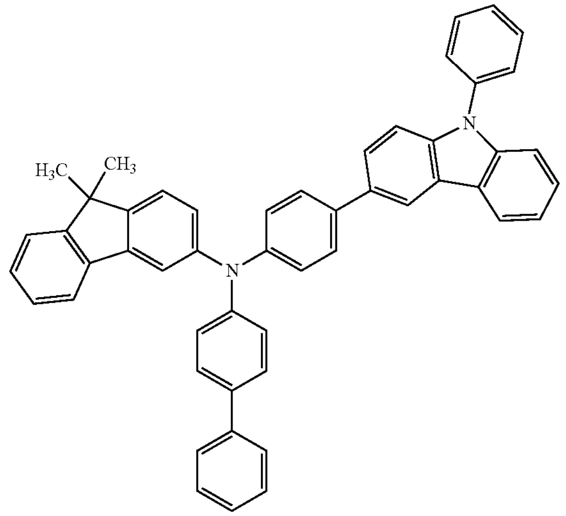

The refractive index of the capping layer CPL may be about 1.6 or more. Particularly, the refractive index of the capping layer CPL with respect to light in a wavelength range of about 550 nm to about 660 nm may be about 1.6 or more.

Figure 7:
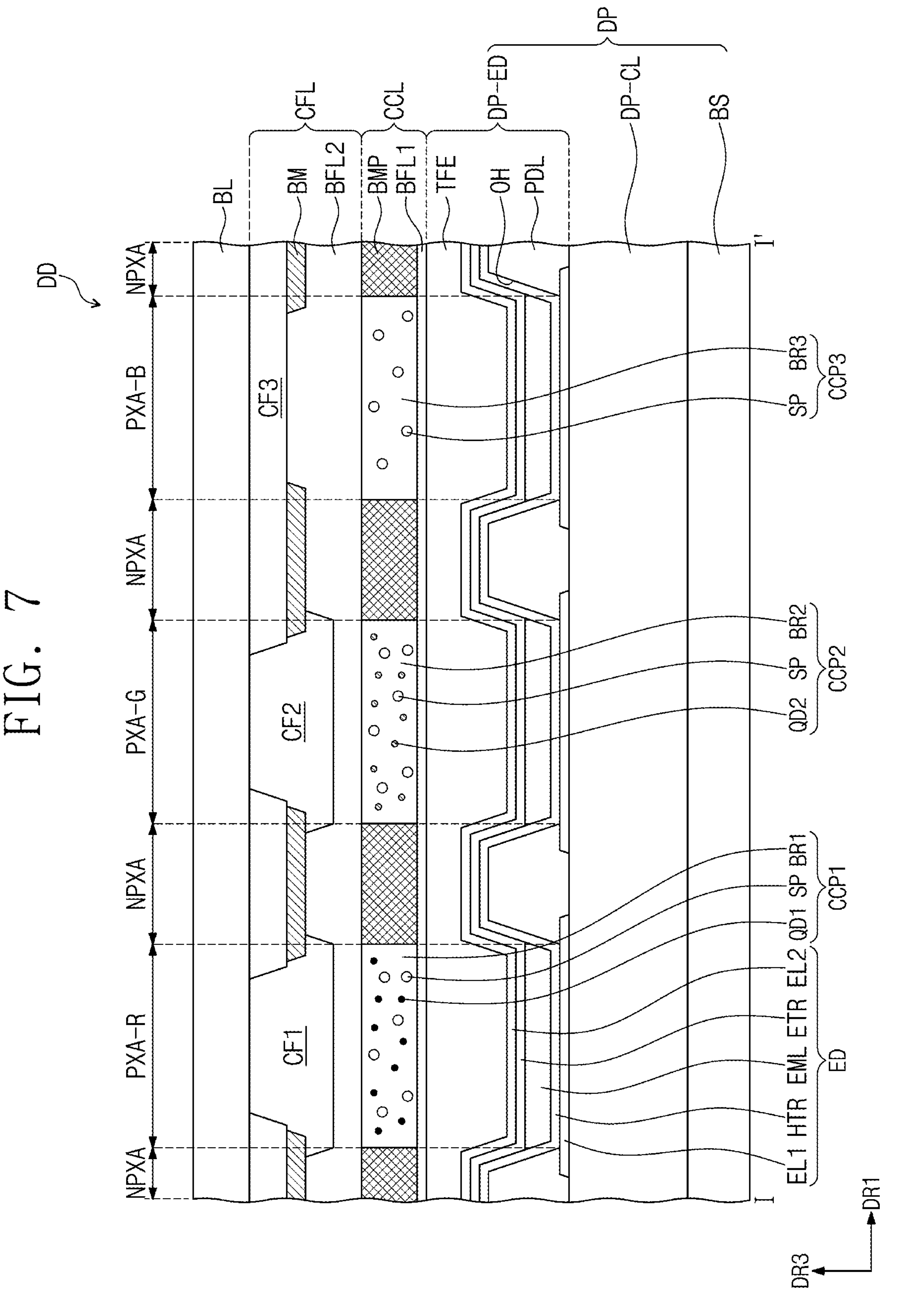
FIG. 7 is a cross-sectional view illustrating another embodiment of a display apparatus taken along line I-I' of FIG. 1.
Figure 8:
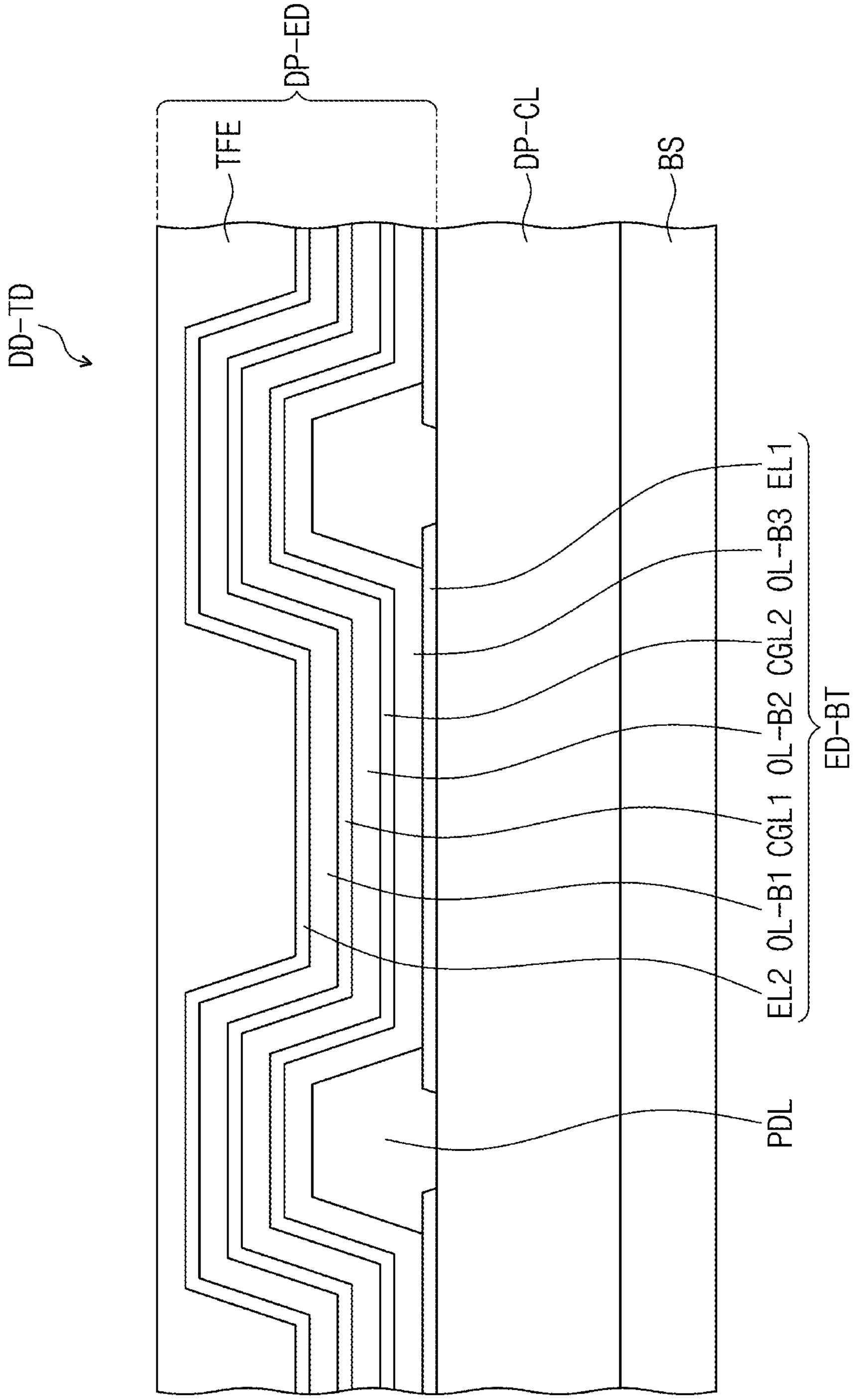
FIG. 8 is a cross-sectional view illustrating a portion of a further embodiment of a display apparatus taken along line I-I' of FIG. 1.

FIG. 7 is a cross-sectional view illustrating another embodiment of a display apparatus taken along line I-I' of FIG. 1. FIG. 8 is a cross-sectional view illustrating a portion of a further embodiment of a display apparatus taken along line I-I' of FIG. 1. In the explanation on the display apparatuses of embodiments, referring to FIG. 7 and FIG. 8, the repetitive explanations related to the same or similar elements described in connection with FIG. 1 to FIG. 6 will not be explained again, but instead only the different features will be primarily explained.

Referring to FIG. 7, the display apparatus DD may include a display panel DP including a display device layer DP-ED, a light controlling layer CCL disposed on the display panel DP and a color filter layer CFL. In the embodiment shown in FIG. 7, the display panel DP includes a base layer BS, a circuit layer DP-CL provided on the base layer BS and a display device layer DP-ED, and the display device layer DP-ED may include a light emitting device ED.

The light emitting device ED may include a first electrode EL1, a hole transport region HTR disposed on the first electrode EL1, an emission layer EML disposed on the hole transport region HTR, an electron transport region ETR disposed on the emission layer EML, and a second electrode EL2 disposed on the electron transport region ETR. The same structures of the light emitting devices of FIG. 3 to FIG. 6 may be applied to the structure of the light emitting device ED shown in FIG. 7.

Referring to FIG. 7, the emission layer EML may be disposed in an opening part OH defined in a pixel definition layer PDL. For example, the emission layer EML divided by the pixel definition layer PDL and correspondingly provided to each of luminous areas PXA-R, PXA-G and PXA-B may emit light in the same wavelength region. In the display apparatus DD, the emission layer EML may emit blue light. Unlike what is shown in FIG. 7, in another embodiment, the emission layer EML may be provided as a common layer for all luminous areas PXA-R, PXA-G and PXA-B.

The light controlling layer CCL may be disposed on the display panel DP. The light controlling layer CCL may include a light converter. The light converter may be a quantum dot or a phosphor. The light converter may transform the wavelength of light provided and then emit. That is, the light controlling layer CCL may be a layer including a quantum dot or a layer including a phosphor. The light controlling layer CCL may include multiple light controlling parts CCP1, CCP2 and CCP3. The light controlling parts CCP1, CCP2 and CCP3 may be separated from one another.

Referring to FIG. 7, a partition pattern BMP may be disposed between the separated light controlling parts CCP1, CCP2 and CCP3, but embodiments are not limited thereto. In FIG. 8, the partition pattern BMP is shown not to be overlapped with the light controlling parts CCP1, CCP2 and CCP3, but at least a portion of the edge of the light controlling parts CCP1, CCP2 and CCP3 may be overlapped with the partition pattern BMP.

The light controlling layer CCL may include a first light controlling part CCP1 including a first quantum dot QD1 converting first color light provided from the light emitting device ED into second color light, a second light controlling part CCP2 including a second quantum dot QD2 converting first color light into third color light, and a third light controlling part CCP3 transmitting first color light.

In an embodiment, the first light controlling part CCP1 may provide red light which is the second color light, and the second light controlling part CCP2 may provide green light which is the third color light. The third color controlling part CCP3 may transmit and provide blue light which is the first color light provided from the light emitting device ED. For example, the first quantum dot QD1 may be a red quantum dot, and the second quantum dot QD2 may be a green quantum dot. The quantum dots QD1 and QD2 may have the same contents as described above.

In addition, the light controlling layer CCL may further include a scatterer SP. The first light controlling part CCP1 may include the first quantum dot QD1 and the scatterer SP, the second light controlling part CCP2 may include the second quantum dot QD2 and the scatterer SP, and the third light controlling part CCP3 may not include a quantum dot but include the scatterer SP. The scatterer SP may be an inorganic particle. For example, the scatterer SP may include at least one of $TiO_2$, ZnO, $Al_2O_3$, $SiO_2$, and a hollow silica. The scatterer SP may include at least one of $TiO_2$, ZnO, $Al_2O_3$, $SiO_2$, and the hollow silica, or may be a mixture of two or more materials selected of $TiO_2$, ZnO, $Al_2O_3$, $SiO_2$, and the hollow silica.

Each of the first light controlling part CCP1, the second light controlling part CCP2, and the third light controlling part CCP3 may include base resins BR1, BR2 and BR3 dispersing the quantum dots QD1 and QD2 and the scatterer SP. In an embodiment, the first light controlling part CCP1 may include the first quantum dot QD1 and the scatterer SP dispersed in the first base resin BR1, the second light controlling part CCP2 may include the second quantum dot QD2 and the scatterer SP dispersed in the second base resin BR2, and the third light controlling part CCP3 may include the scatterer particle SP dispersed in the third base resin BR3. The base resins BR1, BR2 and BR3 are mediums in which the quantum dots QD1 and QD2 and the scatterer SP are dispersed, and may be composed of various resin compositions which may be generally referred to as a binder. For example, the base resins BR1, BR2 and BR3 may be acrylic resins, urethane-based resins, silicone-based resins, epoxy-based resins, etc. The base resins BR1, BR2 and BR3 may be transparent resins. In an embodiment, the first base resin BR1, the second base resin BR2 and the third base resin BR3 may be the same or different from each other.

The light controlling layer CCL may include a barrier layer BFL1. The barrier layer BFL1 may play the role of blocking the penetration of at least one of moisture and oxygen (hereinafter, will be referred to as "humidity/oxygen"). The barrier layer BFL1 may block the exposure of the light controlling parts CCP1, CCP2 and CCP3 to humidity/oxygen. The barrier layer BFL1 may cover the light controlling parts CCP1, CCP2 and CCP3. In addition, the barrier layer BFL2 may be provided between the light controlling parts CCP1, CCP2 and CCP3 and a color filter layer CFL.

The barrier layers BFL1 and BFL2 may include at least one inorganic layer. That is, the barrier layers BFL1 and BFL2 may be formed by including an inorganic material. For example, the barrier layers BFL1 and BFL2 may be formed by including a silicon nitride, an aluminum nitride, a zirconium nitride, a titanium nitride, a hafnium nitride, a tantalum nitride, a silicon oxide, an aluminum oxide, a titanium oxide, a tin oxide, a cerium oxide, a silicon oxynitride or a metal thin film securing light transmittance. The barrier layers BFL1 and BFL2 may further include an organic layer. The barrier layers BFL1 and BFL2 may be composed of a single layer of multiple layers.

In the display apparatus DD, the color filter layer CFL may be disposed on the light controlling layer CCL. For example, the color filter layer CFL may be disposed directly on the light controlling layer CCL. In this case, the barrier layer BFL2 may be omitted. The color filter layer CFL may include a light blocking part BM and filters CF1, CF2 and CF3. The color filter layer CFL may include a first filter CF1 transmitting second color light, a second filter CF2 transmitting third color light, and a third filter CF3 transmitting first color light. For example, the first filter CF1 may be a red filter, the second filter CF2 may be a green filter, and the third filter CF3 may be a blue filter. Each of the filters CF1, CF2 and CF3 may include a polymer photosensitive resin and a pigment or a dye. The first filter CF1 may include a red pigment or a dye, the second filter CF2 may include a green pigment or a dye, and the third filter CF3 may include a blue pigment or a dye. Embodiments are not limited thereto, and the third filter CF3 may not include the pigment or dye. The third filter CF3 may include a polymer photosensitive resin and not include a pigment or a dye. The third filter CF3 may be transparent. The third filter CF3 may be formed using a transparent photosensitive resin. In addition, in an embodiment, the first filter CF1 and the second filter CF2 may be yellow filters. The first filter CF1 and the second filter CF2 may be provided in one body without distinction.

The light blocking part BM may be a black matrix. The light blocking part BM may be formed by including an organic light blocking material or an inorganic light blocking material including a black pigment or a black dye. The light blocking part BM may prevent light leakage phenomenon and divide the boundaries of adjacent filters CF1, CF2 and CF3. In addition, in an embodiment, the light blocking part BM may be formed as a blue filter. Each of the first to third filters CF1, CF2 and CF3 may overlap one of a red luminous area PXA-R, green luminous area PXA-G, and blue luminous area PXA-B.

On the color filter layer CFL, a base substrate BL may be disposed. The base substrate BL may be a member providing a base surface on which the color filter layer CFL, the light controlling layer CCL, etc. are disposed. The base substrate BL may be a glass substrate, a metal substrate, a plastic substrate, etc. However, embodiments are not limited thereto, and the base substrate BL may be an inorganic layer, an organic layer or a composite material layer. In addition, different from the drawing, the base substrate BL may be omitted in an embodiment.

FIG. 8 is a cross-sectional view showing a portion of the display apparatus. In FIG. 8, the cross-sectional view of a portion corresponding to the display panel DP in FIG. 7 is shown. In a display apparatus DD-TD, the light emitting device ED-BT may include multiple light emitting structures OL-B1, OL-B2 and OL-B3. The light emitting device ED-BT may include oppositely disposed first electrode EL1 and second electrode EL2, and the multiple light emitting structures OL-B1, OL-B2 and OL-B3 stacked in order in a thickness direction and provided between the first electrode EL1 and the second electrode EL2. Each of the light emitting structures OL-B1, OL-B2 and OL-B3 may include an emission layer EML (FIG. 7), and a hole transport region HTR and an electron transport region ETR disposed with the emission layer EML (FIG. 7) therebetween. That is, the light emitting device ED-BT included in the display apparatus DD-TD may be a light emitting device of a tandem structure including multiple emission layers.

In an embodiment shown in FIG. 8, light emitted from the light emitting structures OL-B1, OL-B2 and OL-B3 may be all blue light. However, embodiments are not limited thereto, and the wavelength regions of light emitted from the light emitting structures OL-B1, OL-B2 and OL-B3 may be different from each other. For example, the light emitting device ED-BT including the multiple light emitting structures OL-B1, OL-B2 and OL-B3 emitting light in different wavelength regions may emit white light. Between neighboring light emitting structures OL-B1, OL-B2 and OL-B3, charge generating layers CGL1 and CGL2 may be disposed. The charge generating layers CGL1 and CGL2 may include a p-type charge generating layer and/or an n-type charge generating layer.

Hereinafter, embodiments of the amine compound and the light emitting device including same will be particularly explained referring to specific embodiments and comparative embodiments described below.

EXAMPLES

1. Synthesis of Amine Compound

First, the synthetic method of one embodiment of an amine compound made according to the principles of the invention will be explained in particular illustrating the synthetic methods of Compounds A2, A18, A29, A33, A46, B8, B23, B32, B47, B55, C5, C26, C41, C48, and C53. In addition, the synthetic methods of the amine compounds explained hereinafter are embodiments, and the synthetic method of the compounds are not limited to the embodiments below.

The molecular weights of the compounds synthesized by the methods below were checked through mass spectroscopy/fast atom bombardment (FAB-MS) measurement using a device sold under the trade designation JMS-700V of JEOL Ltd, of Tokyo, Japan, and the compounds were identified by measuring proton nuclear magnetic resonance ($^1$H-NMR) using a device sold under the trade designation AVAVCE300M of Bruker Biospin K.K. Co., of Japan.

In the synthesis method, the yield is shown by calculating the ratio of the yield (number of moles) of the obtained compound to the reaction amount (number of moles) of the reactant shown to the left of the arrow in the reaction. For example, when 1 mol of compound is obtained using 10 mol of reactant, the yield can be calculated as 10%. 10% is 10 mol divided by 1 mol and multiplied by 100.

(1) Synthesis of Compound A2

Amine Compound A2 may be synthesized, for example, by the steps of Reaction 1 below.

Reaction 1

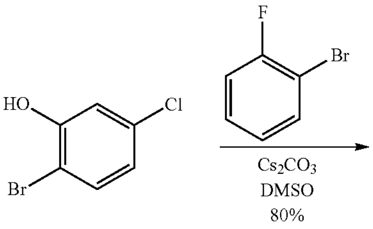

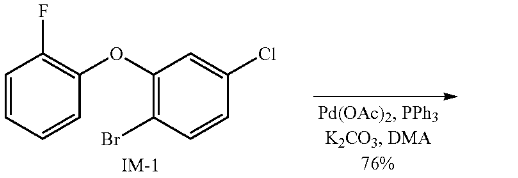

IM-2

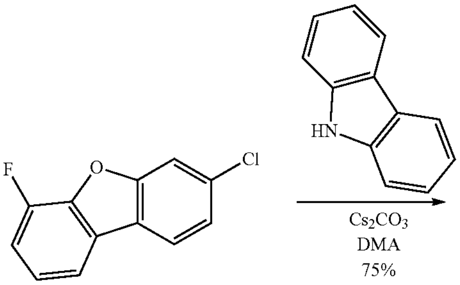

IM-2

-continued

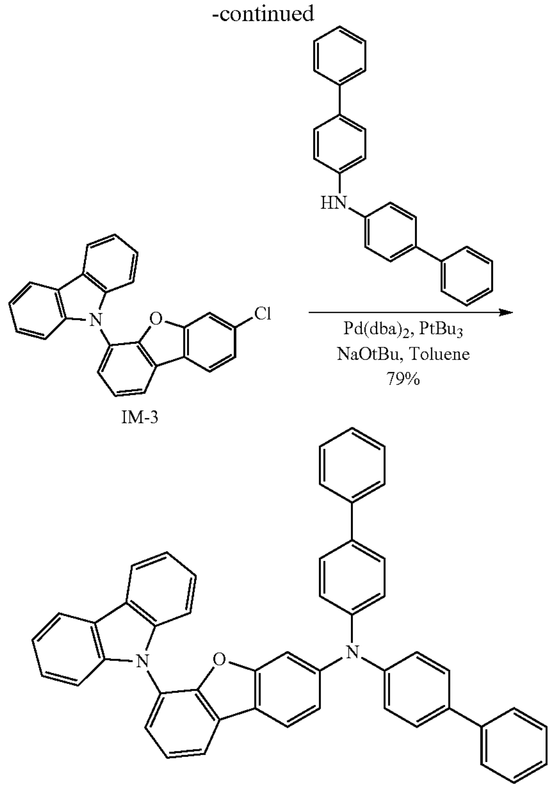

IM-3

A2

Synthesis of Intermediate Compound IM-1

Under argon (Ar) atmosphere, to a 500 milliliter (mL), three-neck flask, 25.00 gram (g); 120.5 millimole (mmol) of 2-bromo-5-chlorophenol, 31.63 g (1.5 equiv, 180.8 mmol) of 1-bromo-2-fluorobenzene, 196.32 g (5.0 equiv, 602.6 mmol) of cesium carbonate ($Cs_2CO_3$) and 241 mL (0.5 molar (M)) of dimethyl sulfoxide (DMSO) were added in order, followed by heating to about 140° C. and stirring. After cooling to room temperature, water ($H_2O$) was added to the reaction solution, and extraction with toluene was performed. Then, toluene was added to an aqueous layer, and an organic layer was extracted further. Organic layers were collected, washed with a saline solution and dried with magnesium sulfate ($MgSO_4$). The compound $MgSO_4$ was filtered, an organic layer was concentrated, and the crude product thus obtained was separated by silica gel column chromatography (using a mixture solvent of hexane and toluene as a developing layer) to obtain Intermediate Compound IM-1 (29.07 g, yield 80 percent (%)). By FAB-MS measurement, a molecular ion peak of m/z=301 was observed, and Intermediate Compound IM-1 was identified.

Synthesis of Intermediate Compound IM-2

Under Ar atmosphere, to a 1000 mL, three-neck flask, 25.00 g (82.9 mmol) of Intermediate Compound IM-1, 1.12 g (0.06 equiv, 5.0 mmol) of palladium(2+); diacetate (Pd $(OAc)_2$), 2.61 g (0.12 equiv, 9.9 mmol) of triphenylphosphine ($PPh_3$), 22.92 g (2.0 equiv, 165.8 mmol) of potassium carbonate ($K_2CO_3$) and 415 mL (0.2 M) of N,N-dimethylacetamide (DMA) were added in order, followed by heating to about 120° C. and stirring. After cooling to room temperature, water was added to the reaction solution, and extraction with toluene was performed. Toluene was added to an aqueous layer, and an organic layer was extracted further. Organic layers were collected, washed with a saline solution and dried with $MgSO_4$. The reaction solution was distilled off, and the crude product thus obtained was separated by silica gel column chromatography (using a mixture solvent of hexane and toluene as a developing layer) to obtain Intermediate Compound IM-2 (13.90 g, yield 76%). By FAB-MS measurement, a molecular ion peak of m/z=220 was observed, and Intermediate Compound IM-2 was identified.

Synthesis of Intermediate Compound IM-3

Under Ar atmosphere, to a 300 mL, three-neck flask, 10.00 g (45.3 mmol) of Intermediate Compound IM-2, 11.37 g (1.5 equiv, 68.0 mmol) of 9H-carbazole, 73.84 g (5.0 equiv, 226.6 mmol) of $Cs_2CO_3$ and 90 mL (0.5 M) of DMA were added in order, followed by heating to about 140° C. and stirring. After cooling to room temperature, water was added to the reaction solution, and extraction with toluene was performed. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Intermediate Compound IM-3 (12.50 g, yield 75%). By FAB-MS measurement, a molecular ion peak of m/z=367 was observed, and Intermediate Compound IM-3 was identified.

Synthesis of Compound A2

Under Ar atmosphere, to a 300 mL, three-neck flask, 10.00 g (27.2 mmol) of Intermediate Compound IM-3, 0.47 g (0.03 equiv, 0.8 mmol) of (1E,4E)-1,5-diphenylpenta-1,4-dien-3-one; palladium ($Pd(dba)_2$), 5.23 g (2.0 equiv, 54.4 mmol) of sodium; 2-methylpropan-2-olate (NaOtBu), 136 mL (0.2 M) of toluene, 9.61 g (1.1 equiv, 29.9 mmol) of bis(4-biphenylyl)amine and 0.55 g (0.1 equiv, 2.7 mmol) of tritert-butylphosphane ($PtBu_3$) were added in order, followed by heating, refluxing and stirring. After cooling to room temperature, water was added to the reaction solution, and an organic layer was separately taken. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Compound A2 (14.02 g, yield 79%) of a solid. By FAB-MS measurement, a molecular ion peak of m/z=652 was observed, and Compound A2 was identified.

(2) Synthesis of Compound A18

Amine Compound A1 8 may be synthesized, for example, by the steps of Reaction 2 below.

Reaction 2

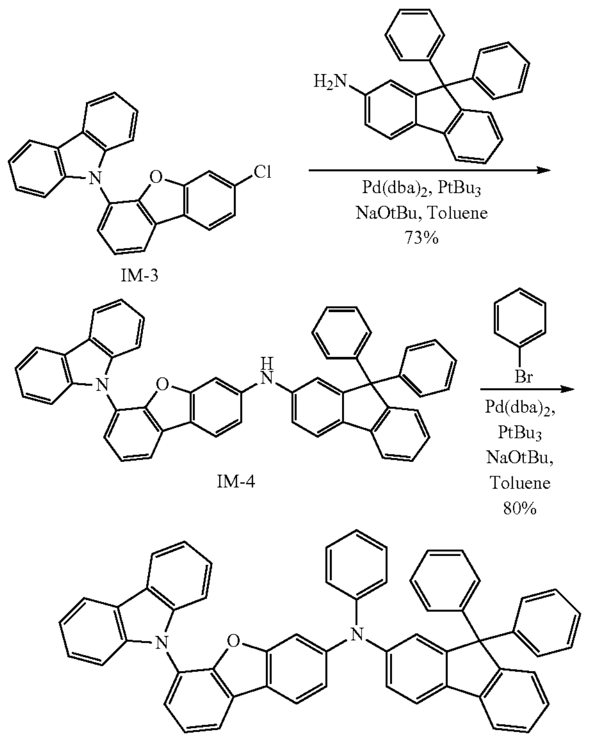

IM-3

IM-4

A18

Synthesis of Intermediate Compound IM-4

Under Ar atmosphere, to a 300 mL, three-neck flask, 10.00 g (27.2 mmol) of Intermediate Compound IM-3, 0.47 g (0.03 equiv, 0.8 mmol) of $Pd(dba)_2$, 2.61 g (1.0 equiv, 27.2 mmol) of NaOtBu, 136 mL (0.2 M) of toluene, 9.97 g (1.1 equiv, 29.9 mmol) of 9,9-diphenyl-9H-fluoren-1-amine and 0.55 g (0.1 equiv, 2.7 mmol) of $PtBu_3$ were added in order, followed by heating, refluxing and stirring. After cooling to room temperature, water was added to the reaction solution, and an organic layer was separately taken. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Intermediate Compound IM-4 (13.19 g, yield 73%). By FAB-MS measurement, a molecular ion peak of m/z=664 was observed, and Intermediate Compound IM-4 was identified.

Synthesis of Compound A18

Under Ar atmosphere, to a 300 mL, three-neck flask, 10.00 g (15.0 mmol) of Intermediate Compound IM-4, 0.26 g (0.03 equiv, 0.5 mmol) of $Pd(dba)_2$, 4.34 g (2.0 equiv, 45.1 mmol) of NaOtBu, 75 mL (0.2 M) of toluene, 2.60 g (1.1 equiv, 16.5 mmol) of bromobenzene and 0.30 g (0.1 equiv, 1.5 mmol) of $PtBu_3$ were added in order, followed by heating, refluxing and stirring. After cooling to room temperature, water was added to the reaction solution, and an organic layer was separately taken. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Compound A18 (8.92 g, yield 80%) of a solid. By FAB-MS measurement, a molecular ion peak of m/z=740 was observed, and Compound A18 was identified.

(3) Synthesis of Compound A29

Amine Compound A29 may be synthesized, for example, by the steps of Reaction 3 below.

Reaction 3

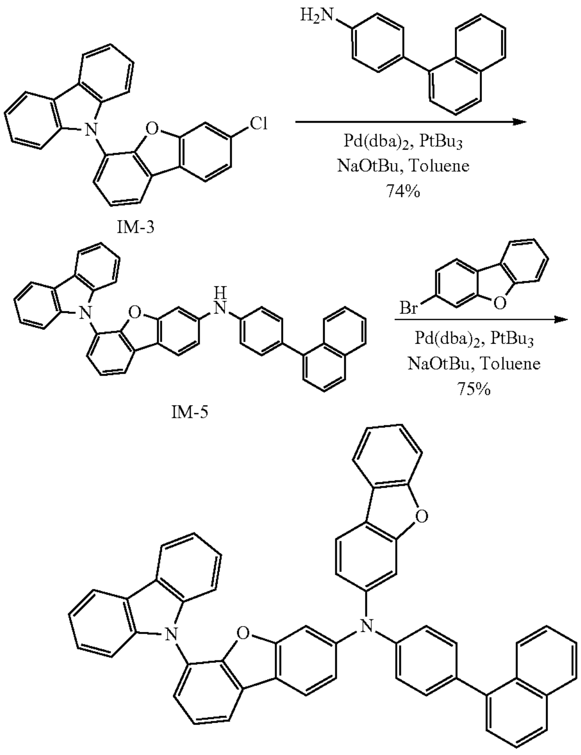

IM-3

IM-5

A29

Synthesis of Intermediate Compound IM-5

Under Ar atmosphere, to a 300 mL, three-neck flask, 10.00 g (27.2 mmol) of Intermediate Compound IM-3, 0.47 g (0.03 equiv, 0.8 mmol) of $Pd(dba)_2$, 2.61 g (1.0 equiv, 27.2 mmol) of NaOtBu, 136 mL (0.2 M) of toluene, 6.56 g (1.1 equiv, 29.9 mmol) of 4-(naphthalene-1-yl)aniline and 0.55 g (0.1 equiv, 2.7 mmol) of $PtBu_3$ were added in order, followed by heating, refluxing and stirring. After cooling to room temperature, water was added to the reaction solution, and an organic layer was separately taken. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Intermediate Compound IM-5 (11.08 g, yield 74%). By FAB-MS measurement, a molecular ion peak of m/z=550 was observed, and Intermediate Compound IM-5 was identified.

Synthesis of Compound A29

Under Ar atmosphere, to a 300 mL, three-neck flask, 10.00 g (18.2 mmol) of Intermediate Compound IM-5, 0.31 g (0.03 equiv, 0.5 mmol) of $Pd(dba)_2$, 5.24 g (2.0 equiv, 54.5 mmol) of NaOtBu, 90 mL (0.2 M) of toluene, 4.94 g (1.1 equiv, 20.0 mmol) of 3-bromodibenzofuran and 0.37 g (0.1 equiv, 1.8 mmol) of $PtBu_3$ were added in order, followed by heating, refluxing and stirring. After cooling to room temperature, water was added to the reaction solution, and an organic layer was separately taken. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Compound A29 (9.76 g, yield 75%) of a solid. By FAB-MS measurement, a molecular ion peak of m/z=716 was observed, and Compound A29 was identified.

(4) Synthesis of Compound A33

Amine Compound A33 may be synthesized, for example, by the steps of Reaction 4 below.

Reaction 4

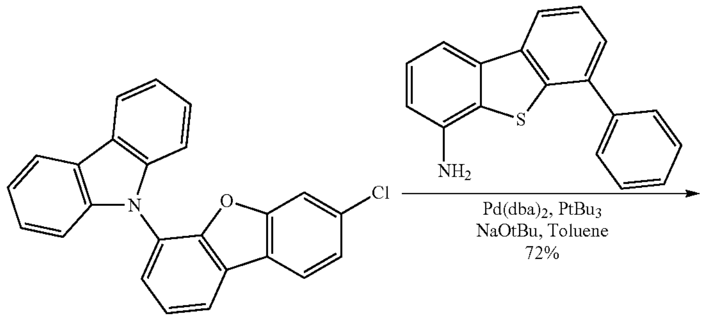

IM-3

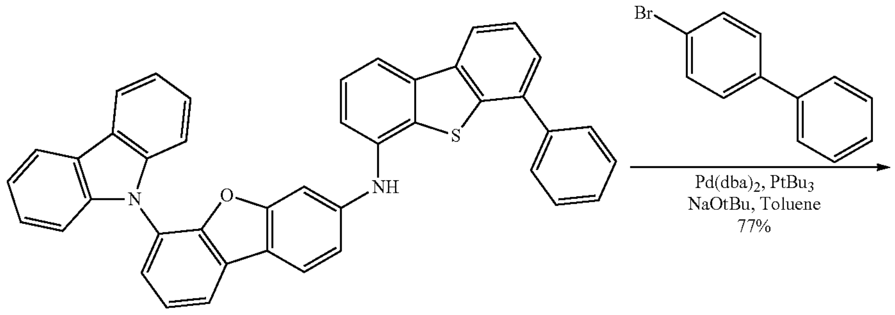

IM-6

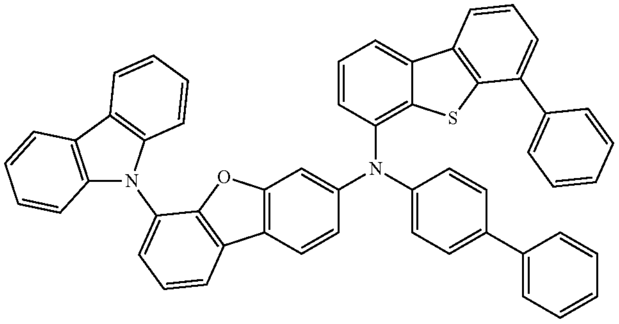

A33

Synthesis of Intermediate Compound IM-6

Under Ar atmosphere, to a 300 mL, three-neck flask, 10.00 g (27.2 mmol) of Intermediate Compound IM-3, 0.47 g (0.03 equiv, 0.8 mmol) of $Pd(dba)_2$, 2.61 g (1.0 equiv, 27.2 mmol) of NaOtBu, 136 mL (0.2 M) of toluene, 8.24 g (1.1 equiv, 29.9 mmol) of 6-phenyldibenzothiophen-4-amine and 0.55 g (0.1 equiv, 2.7 mmol) of $PtBu_3$ were added in order, followed by heating, refluxing and stirring. After cooling to room temperature, water was added to the reaction solution, and an organic layer was separately taken. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Intermediate Compound IM-6 (11.88 g, yield 72%). By FAB-MS measurement, a molecular ion peak of m/z=606 was observed, and Intermediate Compound IM-6 was identified.

Synthesis of Compound A33

Under Ar atmosphere, to a 300 mL, three-neck flask, 10.00 g (16.5 mmol) of Intermediate Compound IM-6, 0.28 g (0.03 equiv, 0.5 mmol) of $Pd(dba)_2$, 4.75 g (2.0 equiv, 49.4 mmol) of NaOtBu, 82 mL (0.2 M) of toluene, 4.23 g (1.1 equiv, 18.1 mmol) of 4-bromobiphenyl and 0.33 g (0.1 equiv, 1.6 mmol) of $PtBu_3$ were added in order, followed by heating, refluxing and stirring. After cooling to room temperature, water was added to the reaction solution, and an organic layer was separately taken. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Compound A33 (9.63 g, yield 77%) of a solid. By FAB-MS measurement, a molecular ion peak of m/z=758 was observed, and Compound A33 was identified.

(5) Synthesis of Compound A39

Amine Compound A39 may be synthesized, for example, by the step of Reaction 5 below.

Reaction 5

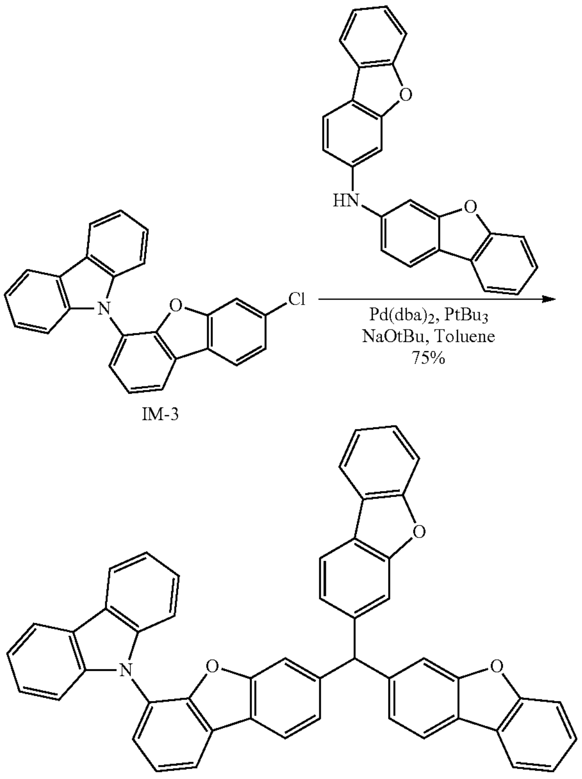

A39

Under Ar atmosphere, to a 300 mL, three-neck flask, 10.00 g (27.2 mmol) of Intermediate Compound IM-3, 0.47 g (0.03 equiv, 0.8 mmol) of $Pd(dba)_2$, 5.23 g (2.0 equiv, 54.4 mmol) of NaOtBu, 136 mL (0.2 M) of toluene, 10.45 g (1.1 equiv, 29.9 mmol) of bis(dibenzofuran-3-yl)amine and 0.55 g (0.1 equiv, 2.7 mmol) of $PtBu_3$ were added in order, followed by heating, refluxing and stirring. After cooling to room temperature, water was added to the reaction solution, and an organic layer was separately taken. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Compound A39 (13.88 g, yield 75%) of a solid. By FAB-MS measurement, a molecular ion peak of m/z=680 was observed, and Compound A39 was identified.

(6) Synthesis of Compound A46
Amine Compound A46 may be synthesized, for example, by the steps of Reaction 6 below.
Reaction 6
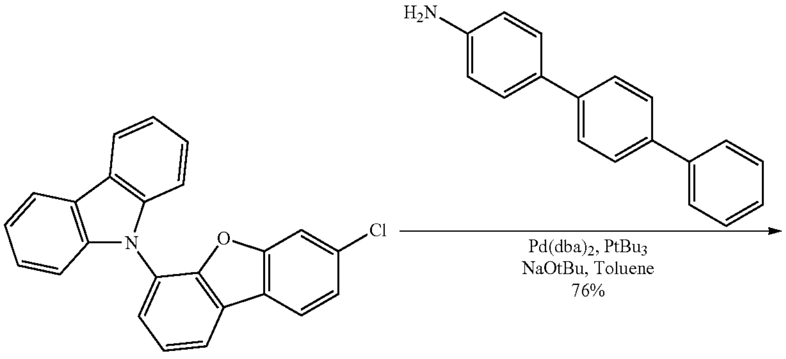
IM-3
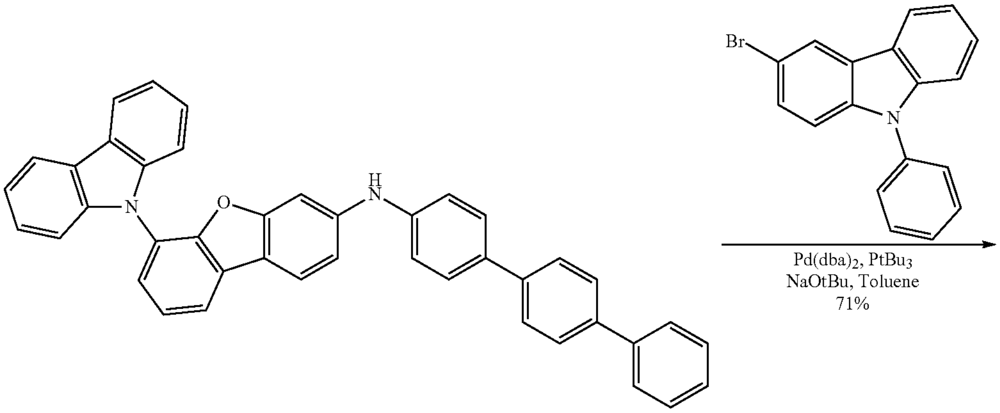
IM-7
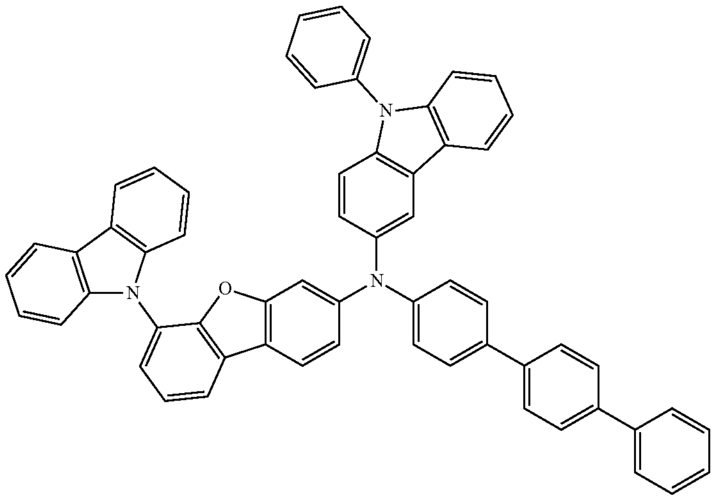
A46

Synthesis of Intermediate Compound IM-7

Under Ar atmosphere, to a 300 mL, three-neck flask, 10.00 g (27.2 mmol) of Intermediate Compound IM-3, 0.47 g (0.03 equiv, 0.8 mmol) of $Pd(dba)_2$, 2.61 g (1.0 equiv, 27.2 mmol) of NaOtBu, 136 mL (0.2 M) of toluene, 7.34 g (1.1 equiv, 29.9 mmol) of [1,1':4',1"-terphenyl]-4-amine and 0.55 g (0.1 equiv, 2.7 mmol) of $PtBu_3$ were added in order, followed by heating, refluxing and stirring. After cooling to room temperature, water was added to the reaction solution, and an organic layer was separately taken. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Intermediate Compound IM-7 (11.92 g, yield 76%). By FAB-MS measurement, a molecular ion peak of m/z=576 was observed, and Intermediate Compound IM-7 was identified.

Synthesis of Compound A46

Under Ar atmosphere, to a 300 mL, three-neck flask, 10.00 g (17.3 mmol) of Intermediate Compound IM-7, 0.30 g (0.03 equiv, 0.5 mmol) of $Pd(dba)_2$, 5.00 g (2.0 equiv, 52.0 mmol) of NaOtBu, 87 mL (0.2 molar (M)) of toluene, 6.15 g (1.1 equiv, 19.1 mmol) of 3-bromo-9-phenyl-9H-carbazole and 0.35 g (0.1 equiv, 1.7 mmol) of $PtBu_3$ were added in order, followed by heating, refluxing and stirring. After cooling to room temperature, water was added to the reaction solution, and an organic layer was separately taken. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Compound A46 (10.07 g, yield 71%) of a solid. By FAB-MS measurement, a molecular ion peak of m/z=817 was observed, and Compound A46 was identified.

(7) Synthesis of Compound B8

Amine Compound B8 may be synthesized, for example, by the steps of Reaction 7 below.

Reaction 7

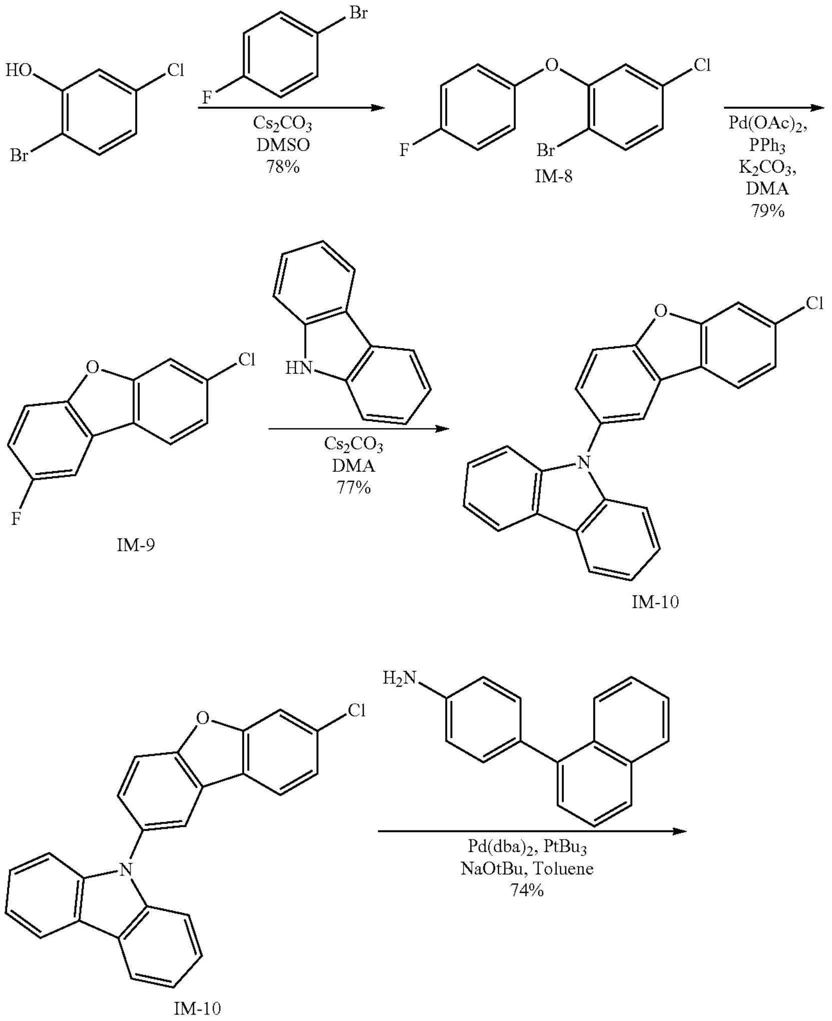

-continued

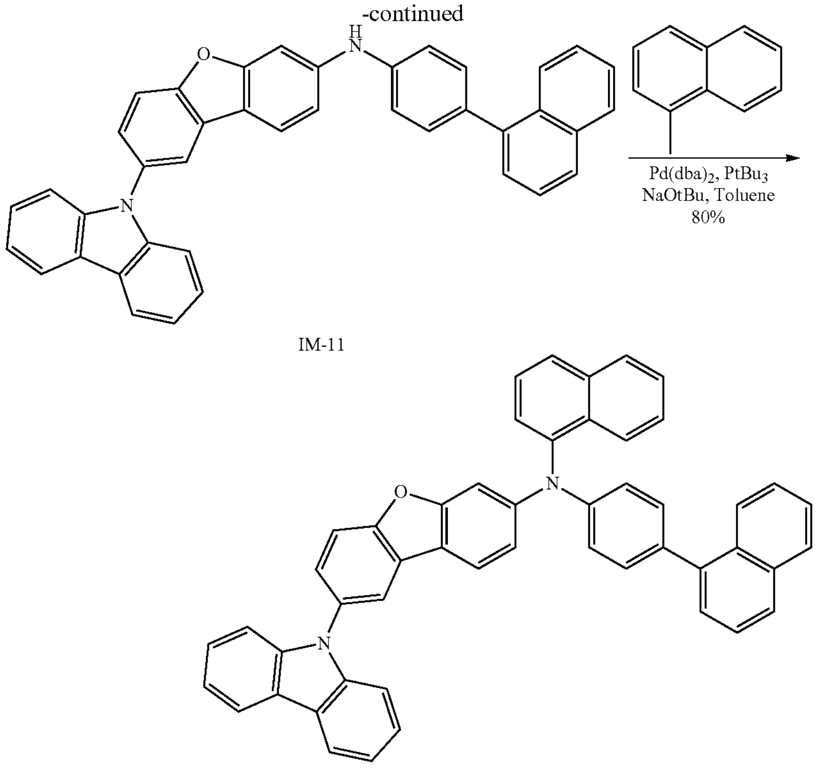

IM-11

B8

Synthesis of Intermediate Compound IM-8

Under Ar atmosphere, to a 500 mL, three-neck flask, 25.00 g (120.5 mmol) of 2-bromo-5-chlorophenol, 31.63 g (1.5 equiv, 180.8 mmol) of 1-bromo-4-fluorobenzene, 196.32 g (5.0 equiv, 602.6 mmol) of $Cs_2CO_3$ and 241 mL (0.5 M) of DMSO were added in order, followed by heating to about 140° C. and stirring. After cooling to room temperature, water was added to the reaction solution, and extraction with toluene was performed. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Intermediate Compound IM-8 (28.34 g, yield 78%). By FAB-MS measurement, a molecular ion peak of m/z=301 was observed, and Intermediate Compound IM-8 was identified.

Synthesis of Intermediate Compound IM-9

Under Ar atmosphere, to a 1000 mL, three-neck flask, 25.00 g (82.9 mmol) of Intermediate Compound IM-8, 1.12 g (0.06 equiv, 5.0 mmol) of $Pd(OAc)_2$, 2.61 g (0.12 equiv, 9.9 mmol) of $PPh_3$, 22.92 g (2.0 equiv, 165.8 mmol) of potassium carbonate ($K_2CO_3$) and 415 mL (0.2 M) of DMA were added in order, followed by heating to about 120° C. and stirring. After cooling to room temperature, water was added to the reaction solution, and extraction with toluene was performed. Toluene was added to an aqueous layer, and an organic layer was extracted further. Organic layers were collected, washed with a saline solution and dried with $MgSO_4$. The reaction solution was distilled off, and the crude product thus obtained was separated by silica gel column chromatography (using a mixture solvent of hexane and toluene as a developing layer) to obtain Intermediate Compound IM-9 (14.45 g, yield 79%). By FAB-MS measurement, a molecular ion peak of m/z=220 was observed, and Intermediate Compound IM-9 was identified.

Synthesis of Intermediate Compound IM-10

Under Ar atmosphere, to a 300 mL, three-neck flask, 10.00 g (45.3 mmol) of Intermediate Compound IM-9, 11.37 g (1.5 equiv, 68.0 mmol) of 9H-carbazole, 73.84 g (5.0 equiv, 226.6 mmol) of $Cs_2CO_3$ and 90 mL (0.5 M) of DMA were added in order, followed by heating to about 140° C. and stirring. After cooling to room temperature, water was added to the reaction solution, and extraction with toluene was performed. Then, toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Intermediate Compound IM-10 (12.84 g, yield 77%). By FAB-MS measurement, a molecular ion peak of m/z=367 was observed, and Intermediate Compound IM-10 was identified.

Synthesis of Intermediate Compound IM-11

Under Ar atmosphere, to a 300 mL, three-neck flask, 10.00 g (27.2 mmol) of Intermediate Compound IM-10, 0.47 g (0.03 equiv, 0.8 mmol) of $Pd(dba)_2$, 2.61 g (1.0 equiv, 27.2 mmol) of NaOtBu, 136 mL (0.2 M) of toluene, 6.56 g (1.1 equiv, 29.9 mmol) of 4-(naphthalene-1-yl)aniline and 0.55 g (0.1 equiv, 2.7 mmol) of $PtBu_3$ were added in order, followed by heating, refluxing and stirring. After cooling to room temperature, water was added to the reaction solution, and an organic layer was separately taken. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Intermediate Compound IM-11 (11.08 g, yield 74%). By FAB-MS measurement, a molecular ion peak of m/z=550 was observed, and Intermediate Compound IM-11 was identified.

Synthesis of Compound B8

Under Ar atmosphere, to a 300 mL, three-neck flask, 10.00 g (18.2 mmol) of Intermediate Compound IM-11, 0.31 g (0.03 equiv, 0.5 mmol) of $Pd(dba)_2$, 5.24 g (2.0 equiv, 54.5 mmol) of NaOtBu, 91 mL (0.2 M) of toluene, 5.08 g (1.1 equiv, 20.0 mmol) of 1-iodonaphthalene and 0.37 g (0.1 equiv, 1.8 mmol) of $PtBu_3$ were added in order, followed by heating, refluxing and stirring. After cooling to room temperature, water was added to the reaction solution, and an organic layer was separately taken. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Compound B8 (9.83 g, yield 80%) of a solid. By FAB-MS measurement, a molecular ion peak of m/z=676 was observed, and Compound B8 was identified.

(8) Synthesis of Compound B23

Amine Compound B23 may be synthesized, for example, by the steps of Reaction 8 below.

Reaction 8

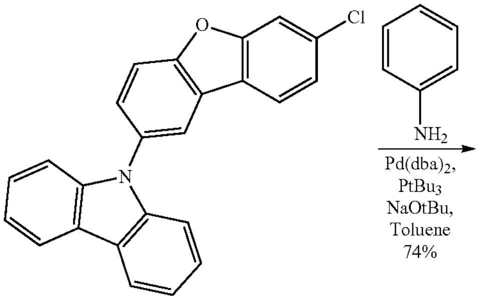

IM-10

-continued

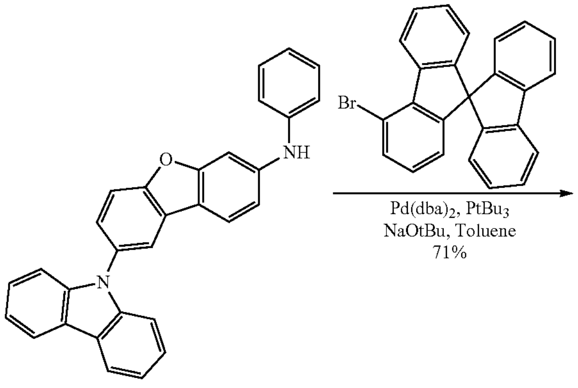

IM-12

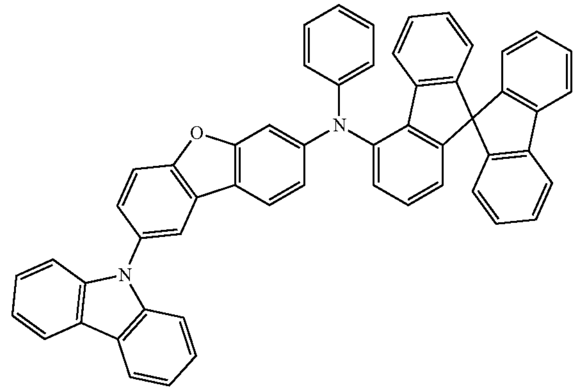

B23

<Synthesis of Intermediate Compound IM-12

Under Ar atmosphere, to a 300 mL, three-neck flask, 10.00 g (27.2 mmol) of Intermediate Compound IM-10, 0.47 g (0.03 equiv, 0.8 mmol) of $Pd(dba)_2$, 2.61 g (1.0 equiv, 27.2 mmol) of NaOtBu, 136 mL (0.2 M) of toluene, 2.79 g (1.1 equiv, 29.9 mmol) of aniline and 0.55 g (0.1 equiv, 2.7 mmol) of $PtBu_3$ were added in order, followed by heating, refluxing and stirring. After cooling to room temperature, water was added to the reaction solution, and an organic layer was separately taken. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Intermediate Compound IM-12 (8.54 g, yield 74%). By FAB-MS measurement, a molecular ion peak of m/z=424 was observed, and Intermediate Compound IM-12 was identified.

Synthesis of Compound B23

Under Ar atmosphere, to a 300 mL, three-neck flask, 8.00 g (18.8 mmol) of Intermediate Compound IM-12, 0.33 g (0.03 equiv, 0.6 mmol) of $Pd(dba)_2$, 5.43 g (2.0 equiv, 56.5 mmol) of NaOtBu, 94 mL (0.2 M) of toluene, 8.19 g (1.1 equiv, 20.7 mmol) of 4-bromo-9,9'-spirobi[fluorene] and 0.38 g (0.1 equiv, 1.9 mmol) of $PtBu_3$ were added in order, followed by heating, refluxing and stirring. After cooling to room temperature, water was added to the reaction solution, and an organic layer was separately taken. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Compound B23 (9.89 g, yield 71%) of a solid. By FAB-MS measurement, a molecular ion peak of m/z=738 was observed, and Compound B23 was identified.

(9) Synthesis of Compound B32

Amine Compound B32 may be synthesized, for example, by the step of Reaction 9 below.

Synthesis of Compound B32

Under Ar atmosphere, to a 300 mL, three-neck flask, 10.00 g (18.2 mmol) of Intermediate Compound IM-11, 0.31 g (0.03 equiv, 0.5 mmol) of $Pd(dba)_2$, 5.24 g (2.0 equiv, 54.5 mmol) of NaOtBu, 91 mL (0.2 M) of toluene, 5.26 g (1.1 equiv, 20.0 mmol) of 4-bromodibenzothiophene and 0.37 g (0.1 equiv, 1.8 mmol) of $PtBu_3$ were added in order, followed by heating, refluxing and stirring. After cooling to room temperature, water was added to the reaction solution, and an organic layer was separately taken. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Compound B32 (9.45 g, yield 77%) of a solid. By FAB-MS measurement, a molecular ion peak of m/z=732 was observed, and Compound B32 was identified.

Reaction 9

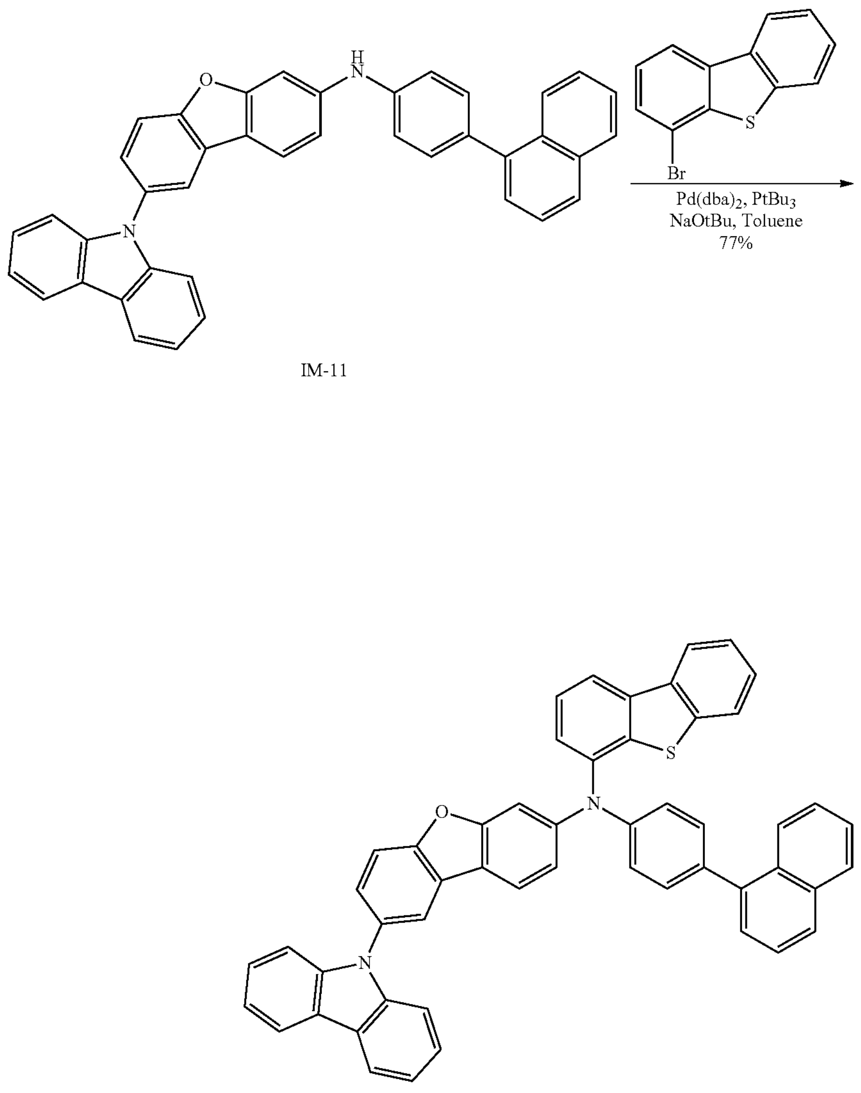

IM-11

B32

(10) Synthesis of Compound B47

Amine Compound B47 may be synthesized, for example, by the step of Reaction 10 below.

Reaction 10

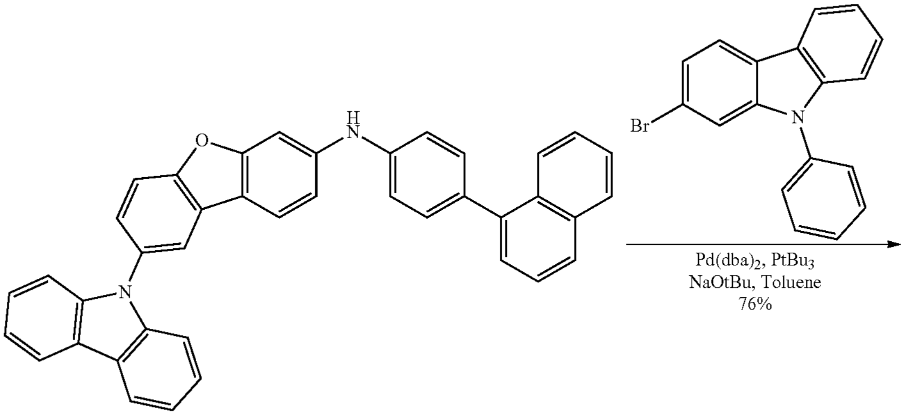

IM-11

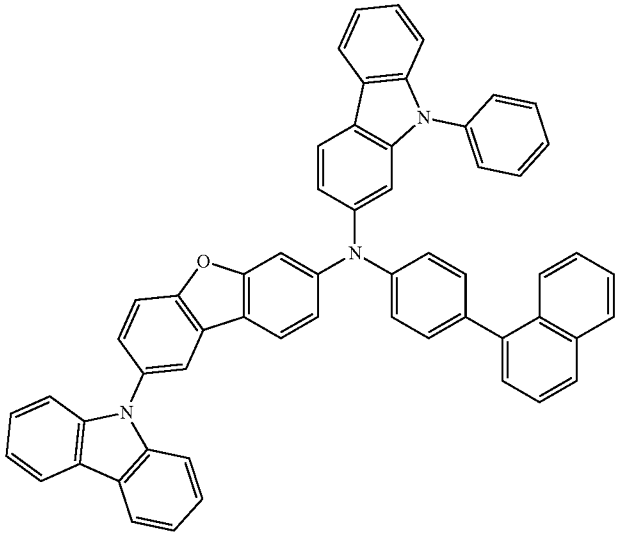

B47

Synthesis of Compound B47

Under Ar atmosphere, to a 300 mL, three-neck flask, 10.00 g (18.2 mmol) of Intermediate Compound IM-11, 0.31 g (0.03 equiv, 0.5 mmol) of $Pd(dba)_2$, 5.24 g (2.0 equiv, 54.5 mmol) of NaOtBu, 91 mL (0.2 M) of toluene, 6.44 g (1.1 equiv, 20.0 mmol) of 2-bromo-9-phenyl-9H-carbazole and 0.37 g (0.1 equiv, 1.8 mmol) of $PtBu_3$ were added in order, followed by heating, refluxing and stirring. After cooling to room temperature, water was added to the reaction solution, and an organic layer was separately taken. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Compound B47 (10.93 g, yield 76%) of a solid. By FAB-MS measurement, a molecular ion peak of m/z=791 was observed, and Compound B47 was identified.

(11) Synthesis of Compound B55

Amine Compound B55 may be synthesized, for example, by the steps of Reaction 11 below.

Reaction 11

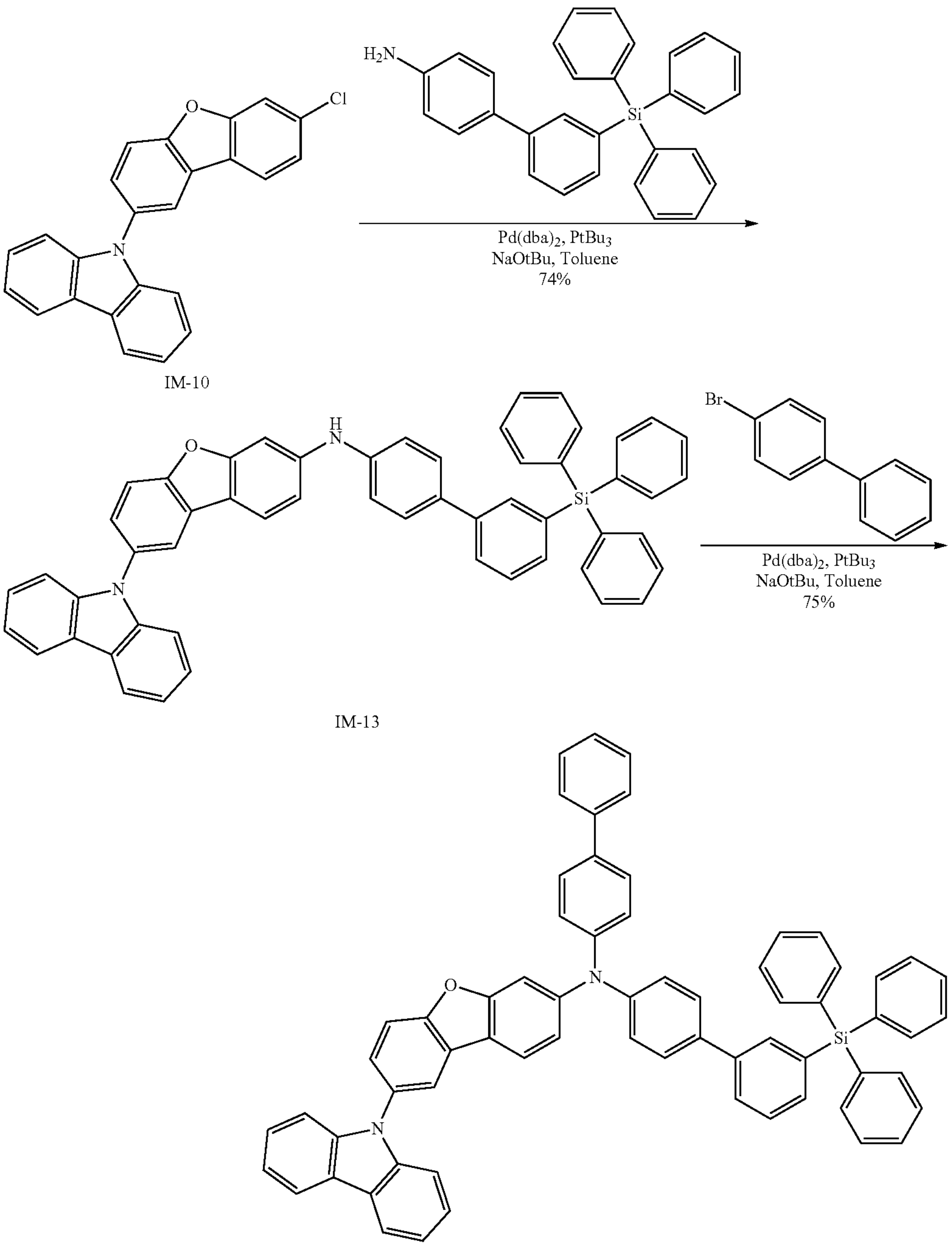

IM-10

IM-13

B55

Synthesis of Intermediate Compound IM-13

Under Ar atmosphere, to a 300 mL, three-neck flask, 10.00 g (27.2 mmol) of Intermediate Compound IM-10, 0.47 g (0.03 equiv, 0.8 mmol) of $Pd(dba)_2$, 2.61 g (1.0 equiv, 27.2 mmol) of NaOtBu, 136 mL (0.2 M) of toluene, 13.27 g (1.1 equiv, 29.9 mmol) of 3'-(triphenylsilyl)-(1,1'-biphenyl)-4-amine and 0.55 g (0.1 equiv, 2.7 mmol) of $PtBu_3$ were added in order, followed by heating, refluxing and stirring. After cooling to room temperature, water was added to the reaction solution, and an organic layer was separately taken. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Intermediate Compound IM-13 (14.65 g, yield 71%). By FAB-MS measurement, a molecular ion peak of m/z=759 was observed, and Intermediate Compound IM-13 was identified.

Synthesis of Compound B55

Under Ar atmosphere, to a 300 mL, three-neck flask, 10.00 g (13.2 mmol) of Intermediate Compound IM-13, 0.23 g (0.03 equiv, 0.4 mmol) of $Pd(dba)_2$, 3.80 g (2.0 equiv, 39.5 mmol) of NaOtBu, 66 mL (0.2 M) of toluene, 3.38 g (1.1 equiv, 14.5 mmol) of 4-bromobiphenyl and 0.27 g (0.1 equiv, 1.3 mmol) of $PtBu_3$ were added in order, followed by heating, refluxing and stirring. After cooling to room temperature, water was added to the reaction solution, and an organic layer was separately taken. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Compound B55 (9.00 g, yield 75%) of a solid. By FAB-MS measurement, a molecular ion peak of m/z=911 was observed, and Compound B55 was identified.

(12) Synthesis of Compound C5

Amine Compound C5 may be synthesized, for example, by the steps of Reaction 12 below.

Reaction 12

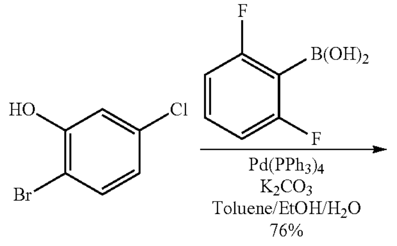

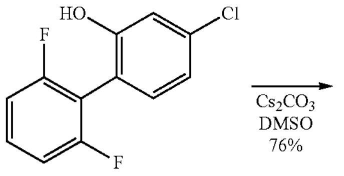

IM-14

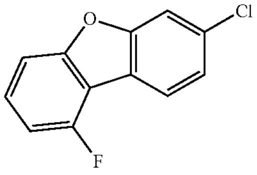

IM-15

-continued

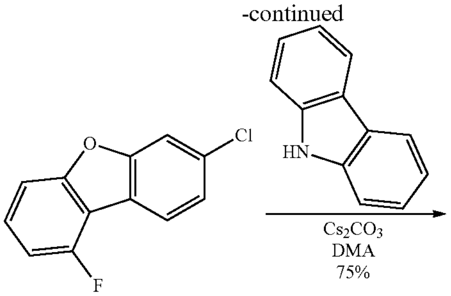

IM-15

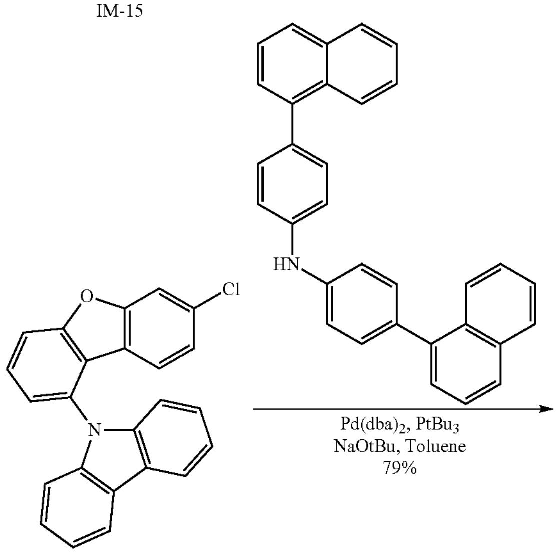

IM-16

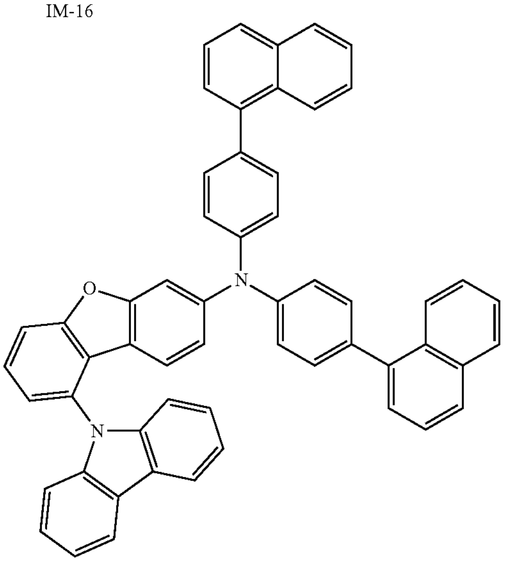

C5

Synthesis of Intermediate Compound IM-14

Under Ar atmosphere, to a 2000 mL, three-neck flask, 25.00 g (120.5 mmol) of 2-bromo-5-chlorophenol, 19.03 g (1.0 equiv, 120.5 mmol) of 2,6-difluorophenylboronic acid, 49.97 g (3.0 equiv, 361.5 mmol) of $K_2CO_3$, 6.96 g (0.05 eq, 6.0 mmol) of tetrakis(triphenylphosphine)palladium(0) (Pd $(PPh_3)_4$), and 844 mL of a mixture solution of toluene/ethanol (EtOH)/$H_2O$ (a volume ratio of 4/2/1) were added in order, followed by heating to about 80° C. and stirring. After cooling to room temperature, the reaction solution was extracted with toluene. An aqueous layer was removed, and an organic layer was washed with a saturated saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Intermediate Compound IM-14 (22.04 g, yield 76%). By FAB-MS measurement, a molecular ion peak of m/z=240 was observed, and Intermediate Compound IM-14 was identified.

Synthesis of Intermediate Compound IM-15

Under Ar atmosphere, to a 500 mL, three-neck flask, 20.00 g (83.1 mmol) of Intermediate Compound IM-14, 135.40 g (5.0 equiv, 415.6 mmol) of $Cs_2CO_3$ and 166 mL (0.5 M) of DMSO were added in order, followed by heating to about 140° C. and stirring. After cooling to room temperature, water was added to the reaction solution, and extraction with toluene was performed. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Intermediate Compound IM-15 (13.94 g, yield 76%). By FAB-MS measurement, a molecular ion peak of m/z=220 was observed, and Intermediate Compound IM-15 was identified.

Synthesis of Intermediate Compound IM-16

Under Ar atmosphere, to a 300 mL, three-neck flask, 10.00 g (45.3 mmol) of Intermediate Compound IM-15, 11.37 g (1.5 equiv, 68.0 mmol) of 9H-carbazole, 73.84 g (5.0 equiv, 226.6 mmol) of $Cs_2CO_3$ and 90 mL (0.5 M) of DMA were added in order, followed by heating to about 140° C. and stirring. After cooling to room temperature, water was added to the reaction solution, and extraction with toluene was performed. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Intermediate Compound IM-16 (12.50 g, yield 75%). By FAB-MS measurement, a molecular ion peak of m/z=367 was observed, and Intermediate Compound IM-16 was identified.

Synthesis of Compound C5

Under Ar atmosphere, to a 300 mL, three-neck flask, 10.00 g (27.2 mmol) of Intermediate Compound IM-16, 0.47 g (0.03 equiv, 0.8 mmol) of $Pd(dba)_2$, 5.23 g (2.0 equiv, 54.4 mmol) of NaOtBu, 136 mL (0.2 M) of toluene, 12.61 g (1.1 equiv, 29.9 mmol) of bis[4-(naphthalen-1-yl)phenyl]amine and 0.55 g (0.1 equiv, 2.7 mmol) of $PtBu_3$ were added in order, followed by heating, refluxing and stirring. After cooling to room temperature, water was added to the reaction solution, and an organic layer was separately taken. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Compound C5 (16.17 g, yield 79%) of a solid. By FAB-MS measurement, a molecular ion peak of m/z=752 was observed, and Compound C5 was identified.

(13) Synthesis of Compound C26

Amine Compound C26 may be synthesized, for example, by the steps of Reaction 13 below.

Reaction 13

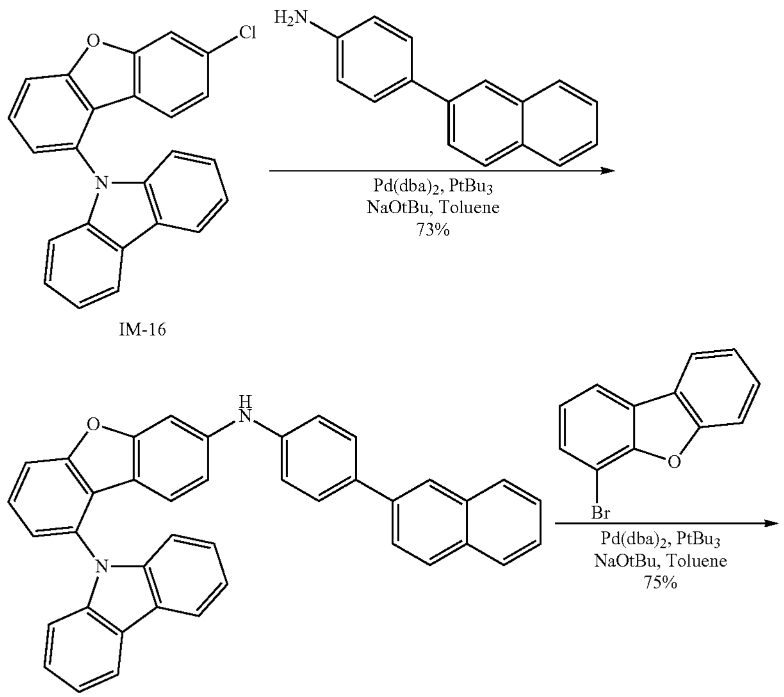

IM-16

IM-17

-continued

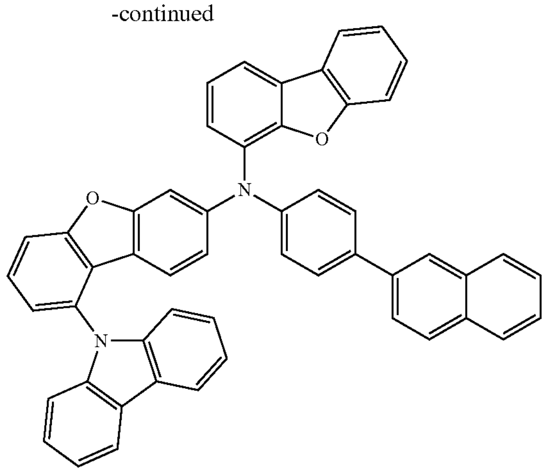

C26

Synthesis of Intermediate Compound IM-17

Under Ar atmosphere, to a 300 mL, three-neck flask, 10.00 g (27.2 mmol) of Intermediate Compound IM-16, 0.47 g (0.03 equiv, 0.8 mmol) of $Pd(dba)_2$, 2.61 g (1.0 equiv, 27.2 mmol) of NaOtBu, 136 mL (0.2 M) of toluene, 6.56 g (1.1 equiv, 29.9 mmol) of 4-(naphthalene-2-yl)aniline and 0.55 g (0.1 equiv, 2.7 mmol) of $PtBu_3$ were added in order, followed by heating, refluxing and stirring. After cooling to room temperature, water was added to the reaction solution, and an organic layer was separately taken. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Intermediate Compound IM-17 (10.93 g, yield 73%). By FAB-MS measurement, a molecular ion peak of m/z=550 was observed, and Intermediate Compound IM-17 was identified.

Synthesis of Compound C26

Under Ar atmosphere, to a 300 mL, three-neck flask, 10.00 g (18.2 mmol) of Intermediate Compound IM-17, 0.31 g (0.03 equiv, 0.5 mmol) of $Pd(dba)_2$, 5.24 g (2.0 equiv, 54.5 mmol) of NaOtBu, 91 mL (0.2 M) of toluene, 4.94 g (1.1 equiv, 20.0 mmol) of 4-bromodibenzofuran and 0.37 g (0.1 equiv, 1.8 mmol) of $PtBu_3$ were added in order, followed by heating, refluxing and stirring. After cooling to room temperature, water was added to the reaction solution, and an organic layer was separately taken. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Compound C26 (9.77 g, yield 75%) of a solid. By FAB-MS measurement, a molecular ion peak of m/z=716 was observed, and Compound C26 was identified.

(14) Synthesis of Compound C41

Amine Compound C41 may be synthesized, for example, by the steps of Reaction 14 below.

Reaction 14

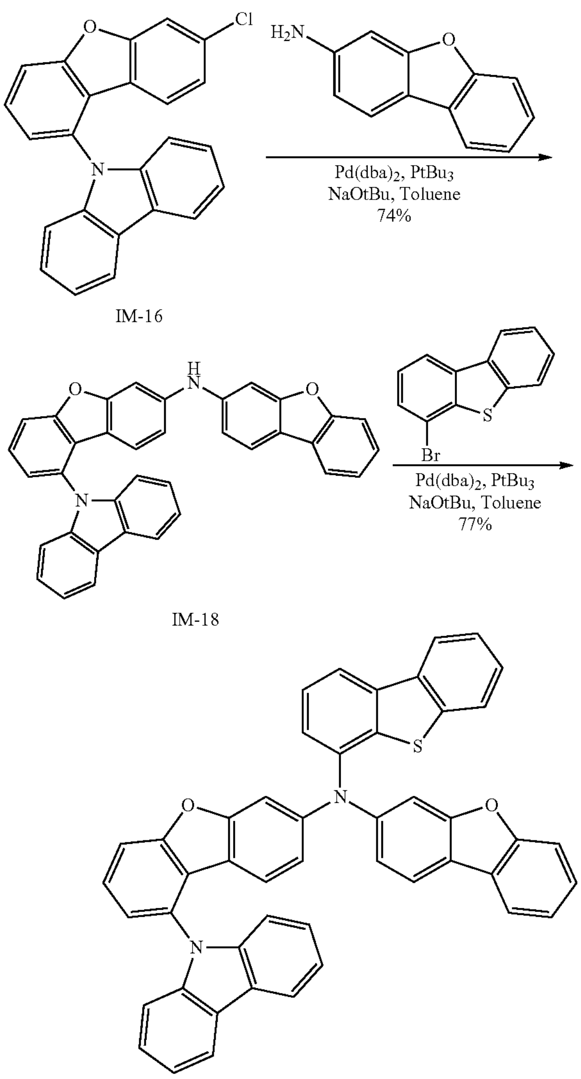

IM-16

IM-18

C41

Synthesis of Intermediate Compound IM-18

Under Ar atmosphere, to a 300 mL, three-neck flask, 10.00 g (27.2 mmol) of Intermediate Compound IM-16, 0.47 g (0.03 equiv, 0.8 mmol) of $Pd(dba)_2$, 2.61 g (1.0 equiv, 27.2 mmol) of NaOtBu, 136 mL (0.2 M) of toluene, 5.48 g (1.1 equiv, 29.9 mmol) of 3-aminodibenzofuran and 0.55 g (0.1 equiv, 2.7 mmol) of $PtBu_3$ were added in order, followed by heating, refluxing and stirring. After cooling to room temperature, water was added to the reaction solution, and an organic layer was separately taken. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Intermediate Compound IM-18 (10.35 g, yield 74%). By FAB-MS measurement, a molecular ion peak of m/z=514 was observed, and Intermediate Compound IM-18 was identified.

Synthesis of Compound C41

Under Ar atmosphere, to a 300 mL, three-neck flask, 10.00 g (19.4 mmol) of Intermediate Compound IM-18, 0.34 g (0.03 equiv, 0.6 mmol) of $Pd(dba)_2$, 5.60 g (2.0 equiv, 58.3 mmol) of NaOtBu, 97 mL (0.2 M) of toluene, 5.63 g (1.1 equiv, 21.4 mmol) of 4-bromodibenzothiophene and 0.39 g (0.1 equiv, 1.9 mmol) of $PtBu_3$ were added in order, followed by heating, refluxing and stirring. After cooling to room temperature, water was added to the reaction solution, and an organic layer was separately taken. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Compound C41 (10.43 g, yield 77%) of a solid. By FAB-MS measurement, a molecular ion peak of m/z=696 was observed, and Compound C41 was identified.

(15) Synthesis of Compound C48

Amine Compound C48 may be synthesized, for example, by the steps of Reaction 15 below.

Reaction 15

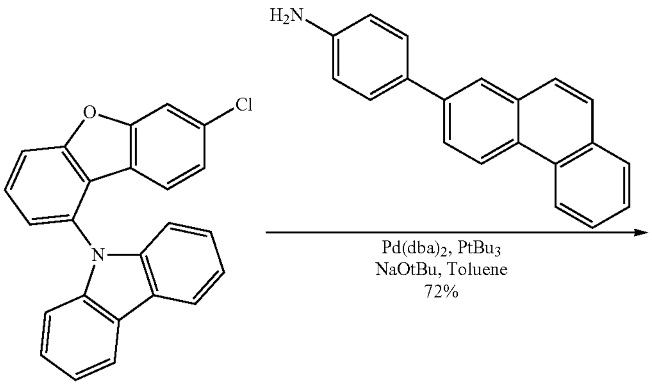

IM-16

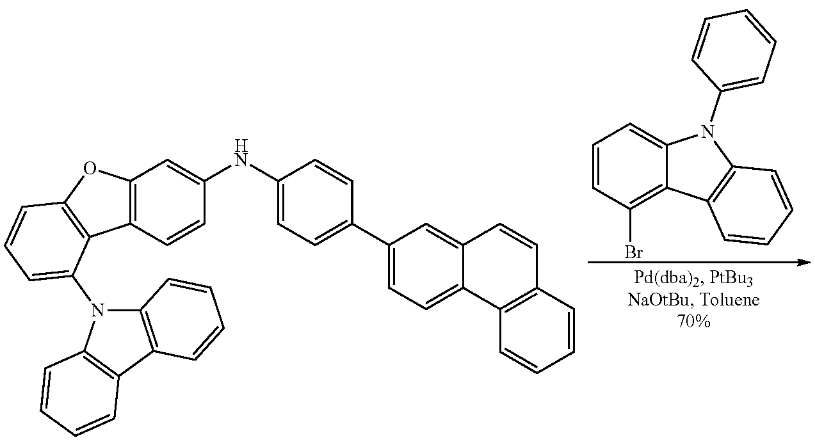

IM-19

-continued

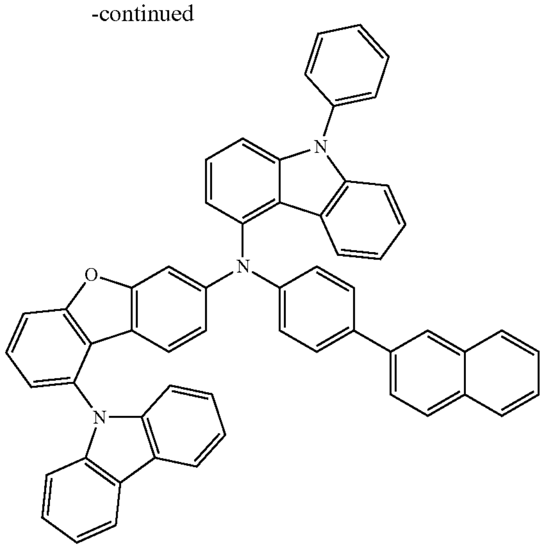

C48

Synthesis of Intermediate Compound IM-19

Under Ar atmosphere, to a 300 mL, three-neck flask, 10.00 g (27.2 mmol) of Intermediate Compound IM-16, 0.47 g (0.03 equiv, 0.8 mmol) of $Pd(dba)_2$, 2.61 g (1.0 equiv, 27.2 mmol) of NaOtBu, 136 mL (0.2 M) of toluene, 8.05 g (1.1 equiv, 29.9 mmol) of 4-(phenanthren-2-yl)aniline and 0.55 g (0.1 equiv, 2.7 mmol) of $PtBu_3$ were added in order, followed by heating, refluxing and stirring. After cooling to room temperature, water was added to the reaction solution, and an organic layer was separately taken. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Intermediate Compound IM-19 (11.76 g, yield 72%). By FAB-MS measurement, a molecular ion peak of m/z=600 was observed, and Intermediate Compound IM-19 was identified.

Synthesis of Compound C48

Under Ar atmosphere, to a 300 mL, three-neck flask, 10.00 g (16.6 mmol) of Intermediate Compound IM-19, 0.29 g (0.03 equiv, 0.5 mmol) of $Pd(dba)_2$, 4.80 g (2.0 equiv, 49.9 mmol) of NaOtBu, 83 mL (0.2 M) of toluene, 6.49 g (1.1 equiv, 18.3 mmol) of 4-bromo-9-phenyl-9H-carbazole and 0.34 g (0.1 equiv, 1.7 mmol) of $PtBu_3$ were added in order, followed by heating, refluxing and stirring. After cooling to room temperature, water was added to the reaction solution, and an organic layer was separately taken. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Compound C48 (9.81 g, yield 70%) of a solid. By FAB-MS measurement, a molecular ion peak of m/z=842 was observed, and Compound C48 was identified.

(16) Synthesis of Compound C53

Amine Compound C53 may be synthesized, for example, by the steps of Reaction 16 below.

Reaction 16

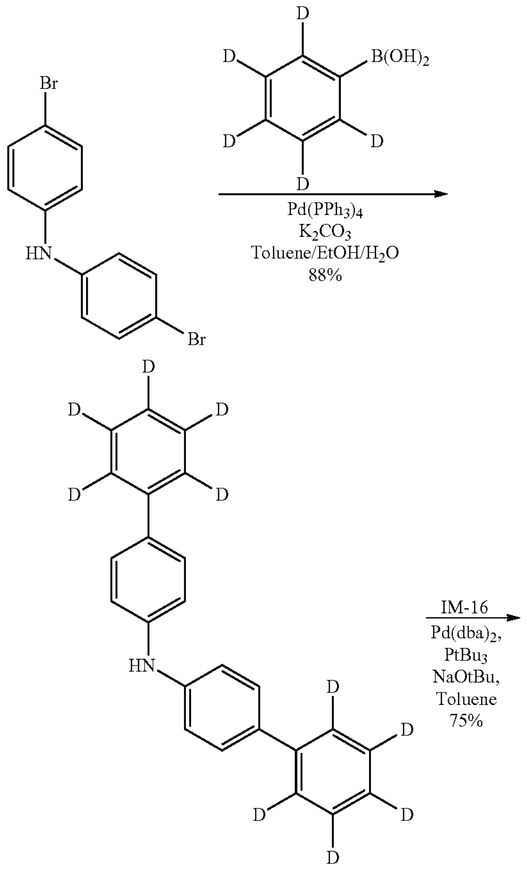

IM-20

-continued

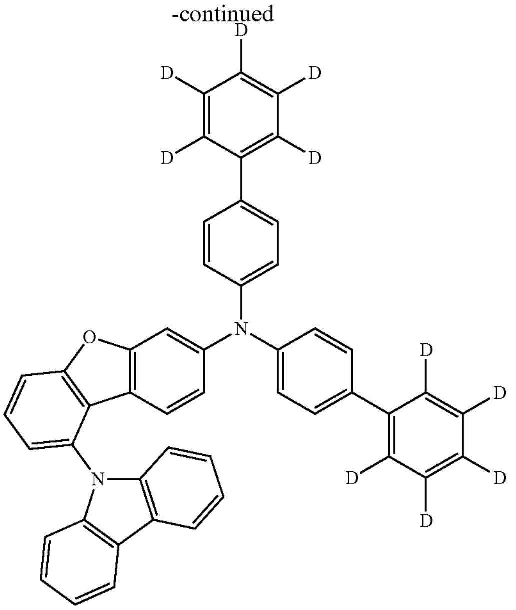

C53

Synthesis of Intermediate Compound IM-20

Under Ar atmosphere, to a 1000 mL, three-neck flask, 20.00 g (61.2 mmol) of bis(4-bromophenyl)aniline, 17.05 g (2.2 equiv, 120.5 mmol) of (phenyl-d5)boronic acid, 50.72 g (6.0 equiv, 367.0 mmol) of $K_2CO_3$, 7.07 g (0.1 eq, 6.1 mmol) of $Pd(PPh_3)_4$, and 428 mL of a mixture solution of toluene/EtOH/$H_2O$ (volume ratio of 4/2/1) were added in order, followed by heating to about 80° C. and stirring. After cooling to room temperature, the reaction solution was extracted with toluene. An aqueous layer was removed, and an organic layer was washed with a saturated saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Intermediate Compound IM-20 (13.79 g, yield 68%). By FAB-MS measurement, a molecular ion peak of m/z=331 was observed, and Intermediate Compound IM-20 was identified.

Synthesis of Compound C53

Under Ar atmosphere, to a 300 mL, three-neck flask, 10.00 g (27.2 mmol) of Intermediate Compound IM-16, 0.47 g (0.03 equiv, 0.8 mmol) of $Pd(dba)_2$, 5.23 g (2.0 equiv, 54.4 mmol) of NaOtBu, 136 mL (0.2 M) of toluene, 9.91 g (1.1 equiv, 29.9 mmol) of Intermediate Compound IM-20 and 0.55 g (0.1 equiv, 2.7 mmol) of $PtBu_3$ were added in order, followed by heating, refluxing and stirring. After cooling to room temperature, water was added to the reaction solution, and an organic layer was separately taken. Toluene was added to an aqueous layer, and an organic layer was extracted further. Organic layers were collected, washed with a saline solution and dried with $MgSO_4$. The compound $MgSO_4$ was filtered, an organic layer was concentrated, and the crude product thus obtained was separated by silica gel column chromatography (using a mixture solvent of hexane and toluene as a developing layer) to obtain Compound C53 (13.52 g, yield 75%) of a solid. By FAB-MS measurement, a molecular ion peak of m/z=662 was observed, and Compound C53 was identified.

2. Manufacture and Evaluation of Light Emitting Device I

1) Manufacture of Light Emitting Device I

Light emitting devices of embodiments, including the amine compounds of embodiments in hole transport layers were manufactured by a method below. By using the amine compounds of Compound A2, Compound A18, Compound A29, Compound A33, Compound A39, Compound A46, Compound B8, Compound B23, Compound B32, Compound B47, Compound B55, Compound C5, Compound C26, Compound C41, Compound C48, and Compound C53 as materials for hole transport layers, light emitting devices of Example 1-1 to Example 1-16 were manufactured. In Comparative Example 1-1 to Comparative Example 1-11, organic light emitting devices were manufactured using Comparative Compounds R1 to R11 below as the materials of hole transport layers.

The compounds used in the hole transport layers in Example 1-1 to Example 1-16, and Comparative Example 1-1 to Comparative Example 1-11 are shown below.

Example Compounds Used for Manufacturing Light Emitting Devices

A2

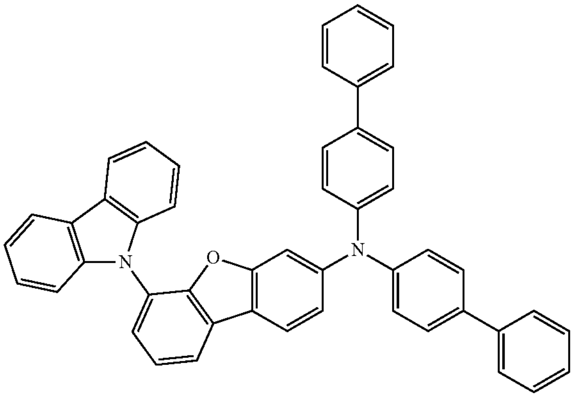

A18

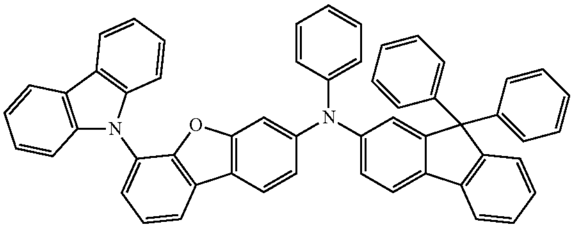

-continued
A29
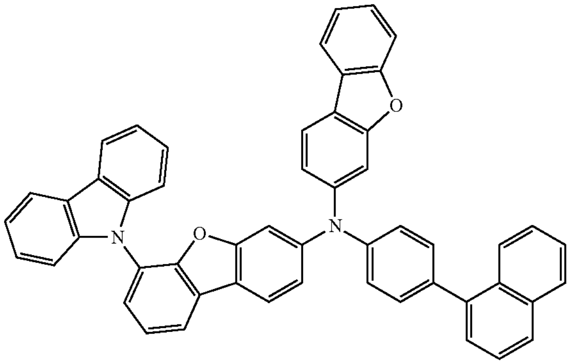
A33
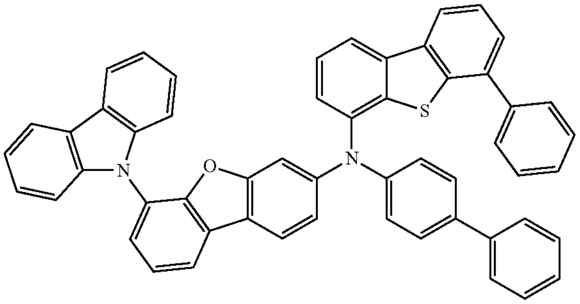
A39
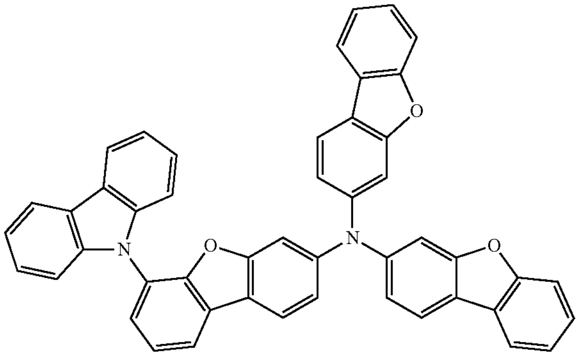
A46
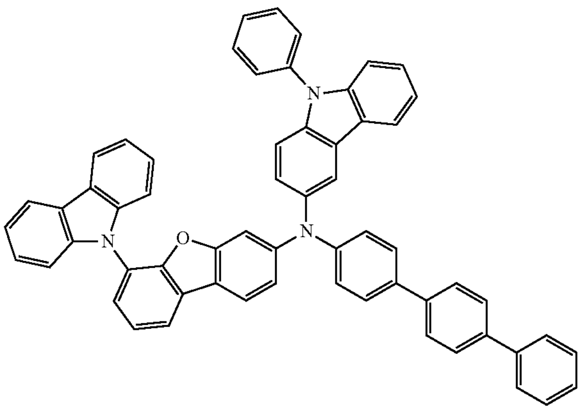
-continued
B8
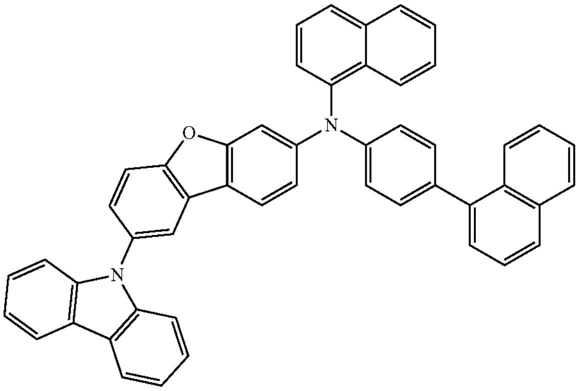
B23
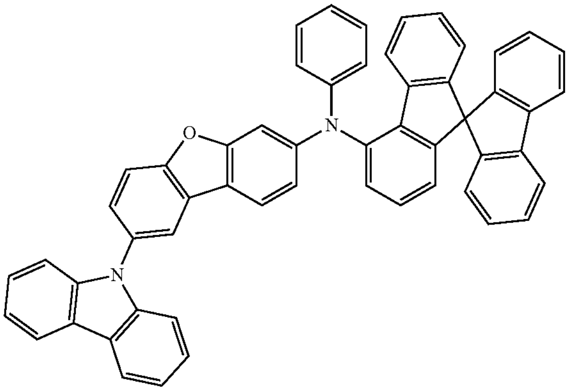
B32
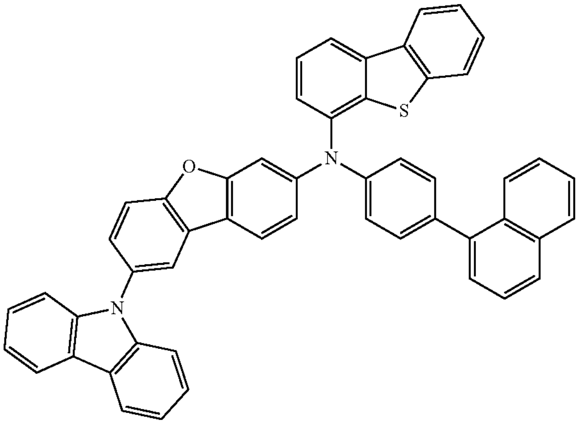

-continued
B47
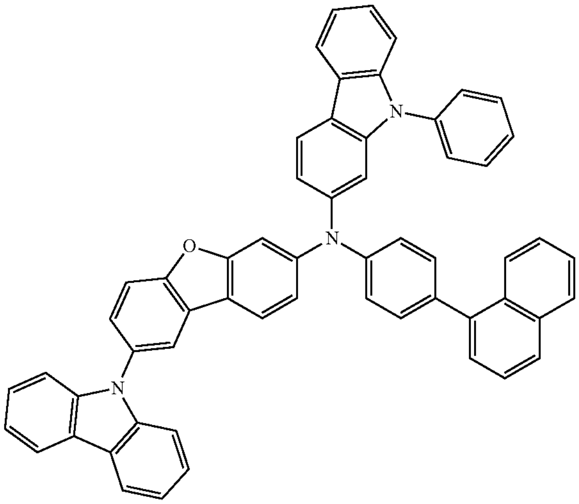
B55
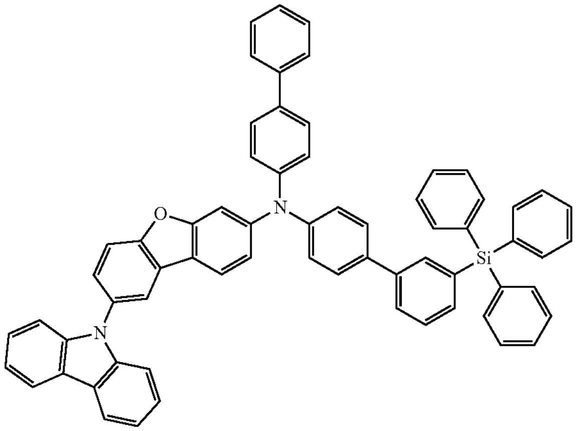
C5
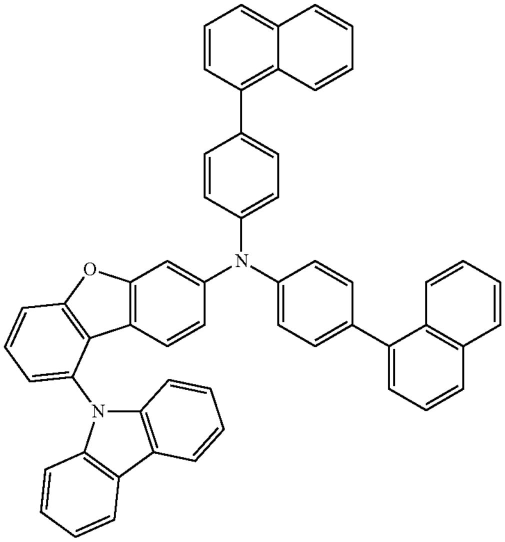
-continued
C26
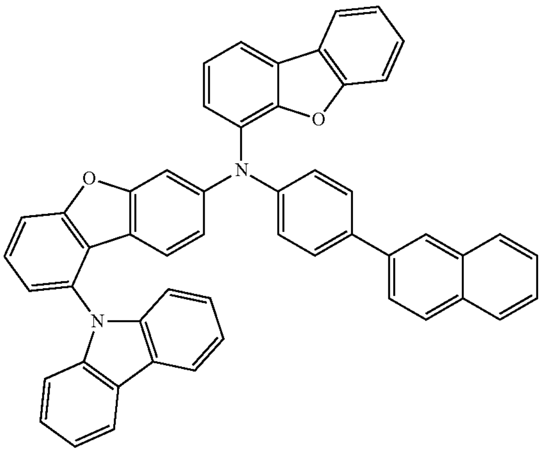
C41
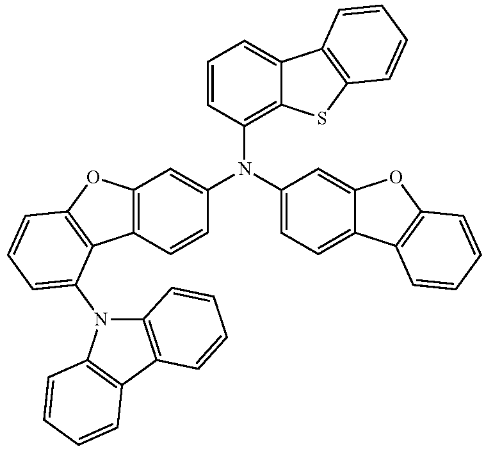
C48
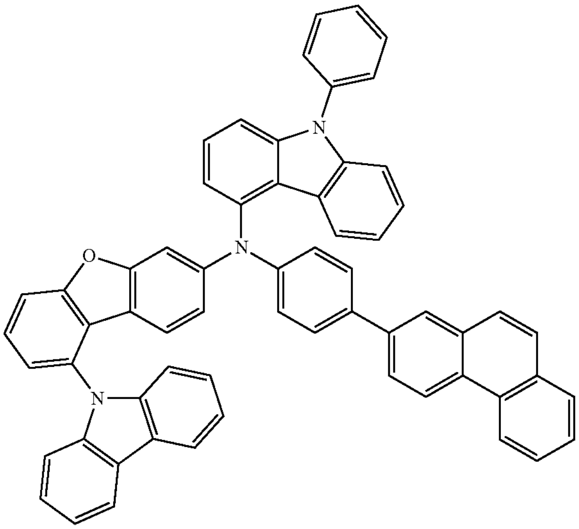

-continued
C53
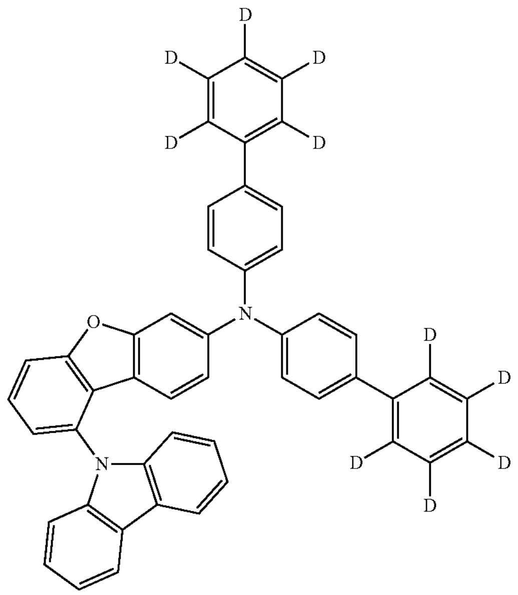
Comparative Compounds Used for Manufacturing Light Emitting Devices
R1
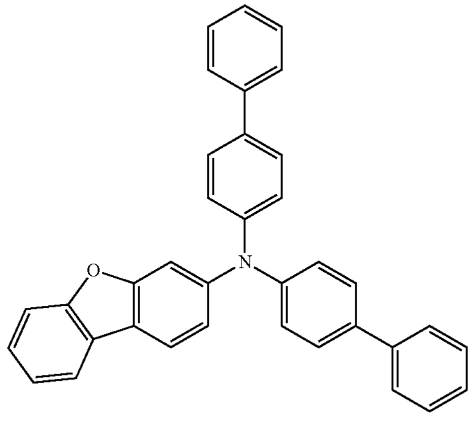
R2
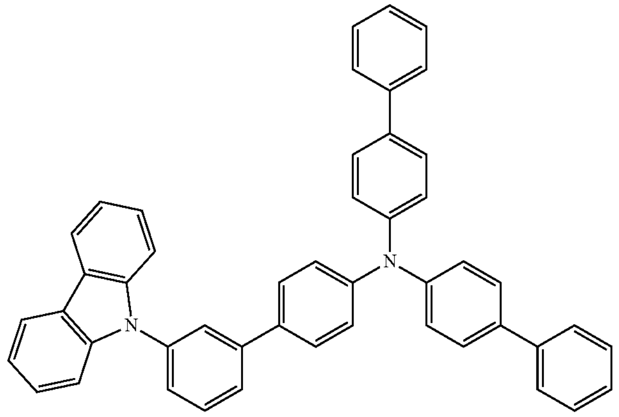

-continued
R3
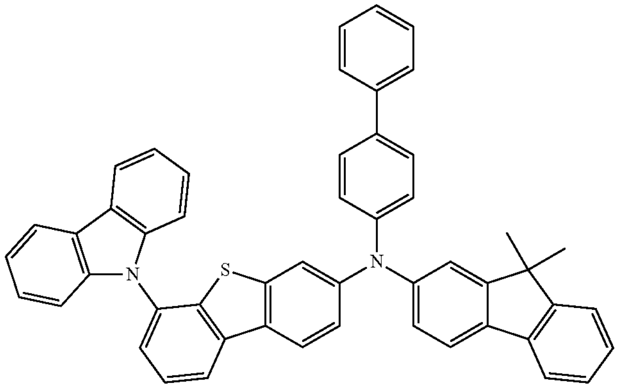
R4
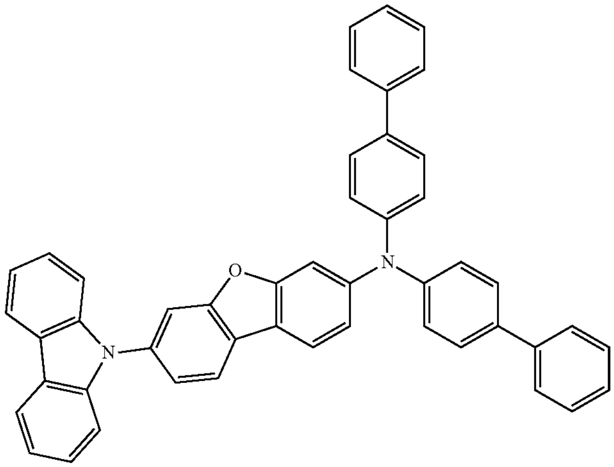
R5
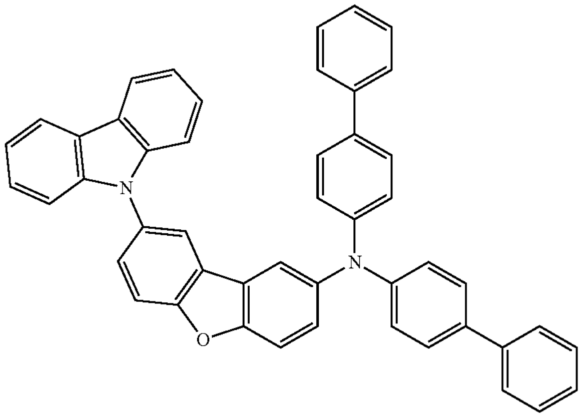

-continued
R6
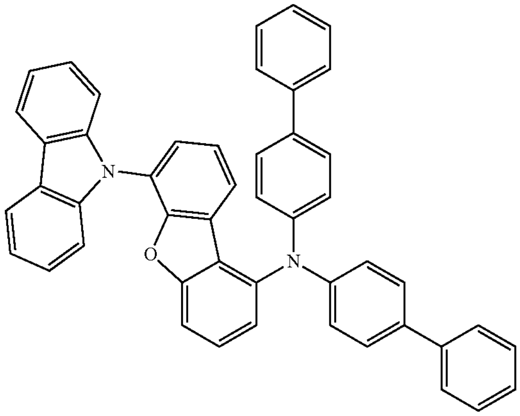
R7
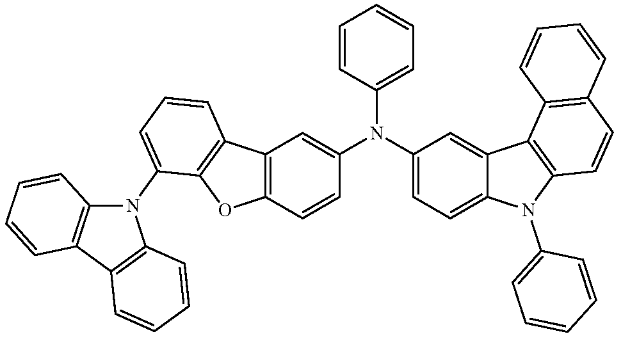
R8
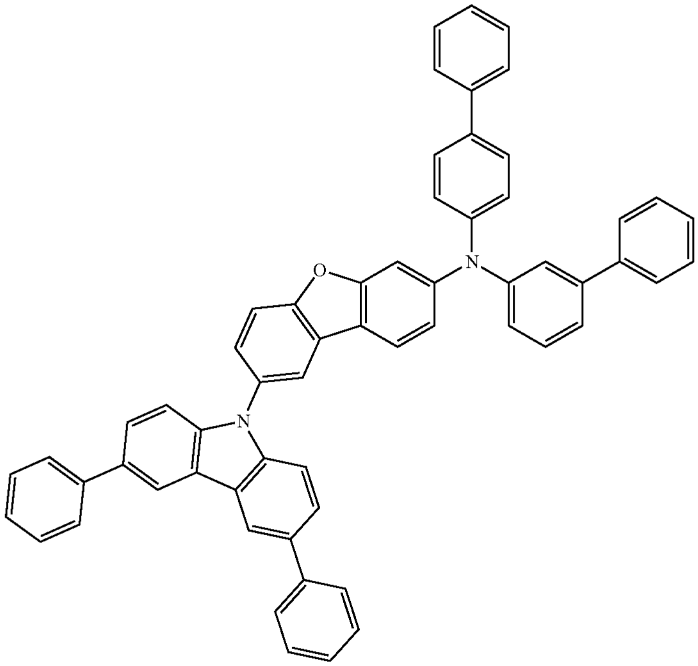

-continued
R9
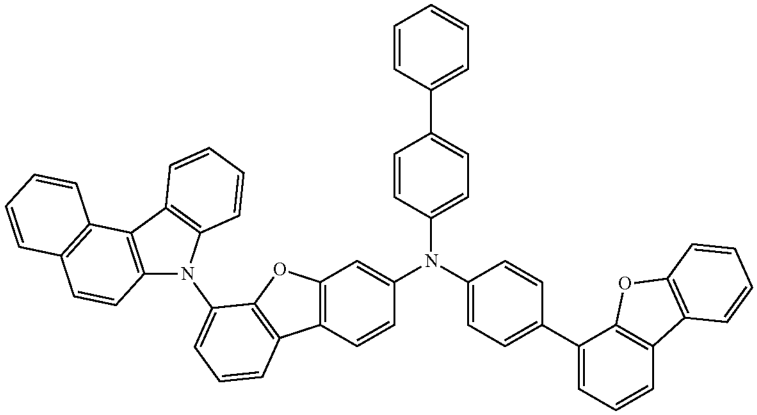
R10
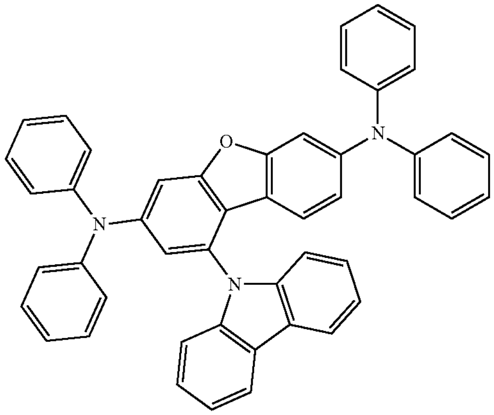

-continued

R11

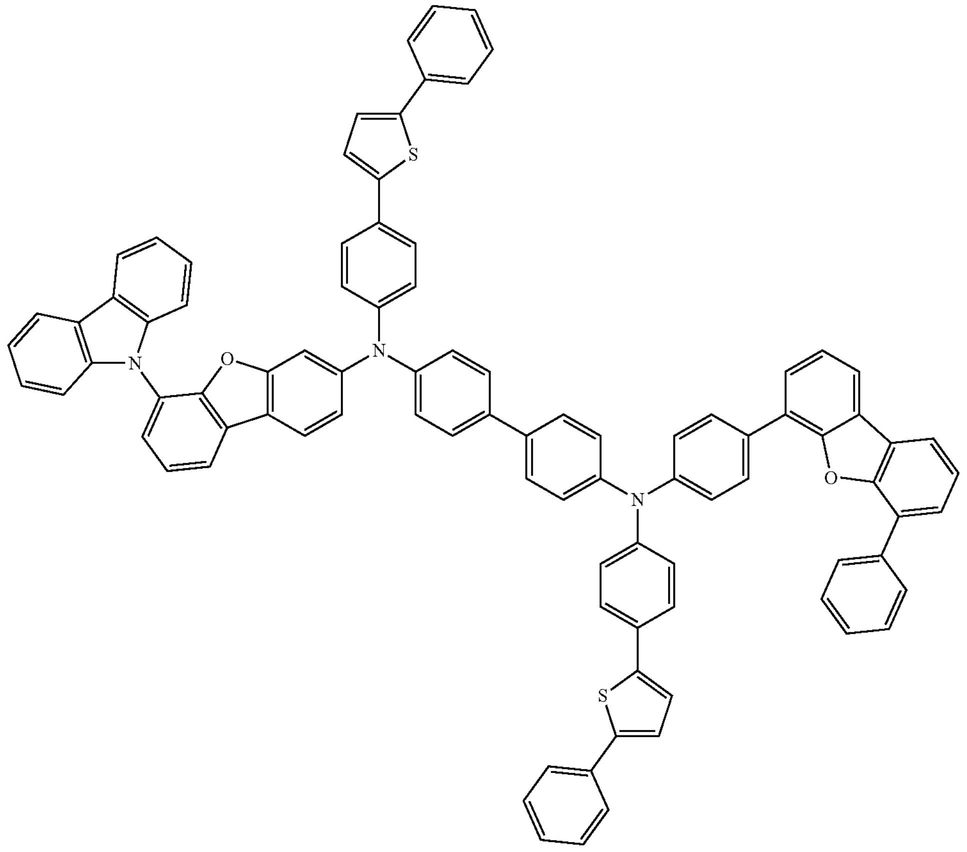

On a glass substrate, ITO of a thickness of about 1500 Å was patterned and then, washed with ultrapure water and treated with UV ozone for about 10 minutes. Then, 2-TNATA was deposited to a thickness of about 600 Å to form a hole injection layer. Then, the Example Compound or the Comparative Compound was deposited to a thickness of about 300 Å to form a hole transport layer.

After that, ADN doped with 3% (weight ratio) TBP was applied to form an emission layer with a thickness of about 250 Å. Then, $Alq_3$ was deposited to a thickness of about 250 Å to form an electron transport layer, and lithium fluoride (LiF) was deposited to a thickness of about 10 Å to form an electron injection layer.

Then, aluminum (Al) was provided to a thickness of about 1000 Å to form a second electrode. In the Examples, the hole injection layer, the hole transport layer, the emission layer, the electron transport layer, the electron injection layer and the second electrode were formed using a vacuum deposition apparatus.

2) Evaluation of Properties of Light Emitting Device I

In Table 1, the evaluation results of the light emitting devices according to Example 1-1 to Example 1-16, and Comparative Example 1-1 to Comparative Example 1-11 are shown. In Table 1, the emission efficiency and lifespan of the light emitting devices manufactured are compared and shown. In Table 1, the emission efficiency and lifespan are relative values and compared values with 100% of the emission efficiency and lifespan of the light emitting device of Comparative Example 1-2. The emission efficiency is a compared value by measuring an efficiency value at a current density of about 10 milliamp per centimeter squared ($mA/cm^2$), and the lifespan ($LT^{50}$) is a compared value by measuring luminance half-life at about 1.0 $mA/cm^2$.

The current density, voltage, and emission efficiency of the light emitting devices of the Examples and Comparative Examples were measured using a meter sold under the trade designation 2400 series Source Meter of Keithley Instrument Co. by Tektronix, Inc., of Beaverton, Oregon, a CS-200 luminance and a color meter sold under the trade designation CS-200 by Konica Minolta Co., of Tokyo, Japan and a PC program sold under the trade designation LabVIEW 8.2 for measurement of NI, Inc., formerly National Instruments Corp., of Austin, Texas in a dark room.

TABLE 1

| Device manufacturing example | Hole transport layer material | Efficiency | Life ($LT^{50}$) |
|---|---|---|---|
| Example 1-1 | Example Compound A2 | 137% | 155% |
| Example 1-2 | Example Compound A18 | 135% | 149% |
| Example 1-3 | Example Compound A29 | 135% | 153% |
| Example 1-4 | Example Compound A33 | 140% | 145% |
| Example 1-5 | Example Compound A39 | 135% | 158% |
| Example 1-6 | Example Compound A46 | 142% | 147% |
| Example 1-7 | Example Compound B8 | 135% | 158% |
| Example 1-8 | Example Compound B23 | 138% | 150% |
| Example 1-9 | Example Compound B32 | 136% | 156% |
| Example 1-10 | Example Compound B47 | 132% | 160% |
| Example 1-11 | Example Compound B55 | 134% | 162% |
| Example 1-12 | Example Compound C5 | 140% | 138% |
| Example 1-13 | Example Compound C26 | 138% | 145% |
| Example 1-14 | Example Compound C41 | 139% | 143% |
| Example 1-15 | Example Compound C48 | 137% | 140% |
| Example 1-16 | Example Compound C53 | 135% | 144% |

TABLE 1-continued

| Device manufacturing example | Hole transport layer material | Efficiency | Life ($LT^{50}$) |
| --- | --- | --- | --- |
| Comparative Example 1-1 | Comparative Compound R1 | 85% | 80% |
| Comparative Example 1-2 | Comparative Compound R2 | 100% | 100% |
| Comparative Example 1-3 | Comparative Compound R3 | 103% | 110% |
| Comparative Example 1-4 | Comparative Compound R4 | 98% | 95% |
| Comparative Example 1-5 | Comparative Compound R5 | 96% | 90% |
| Comparative Example 1-6 | Comparative Compound R6 | 101% | 65% |
| Comparative Example 1-7 | Comparative Compound R7 | 99% | 88% |
| Comparative Example 1-8 | Comparative Compound R8 | 94% | 93% |
| Comparative Example 1-9 | Comparative Compound R9 | 95% | 99% |
| Comparative Example 1-10 | Comparative Compound R10 | 90% | 75% |
| Comparative Example 1-11 | Comparative Compound R11 | 75% | 60% |

The results summarized in Table 1 show that the light emitting devices of Example 1-1 to Example 1-16 had significantly and unexpectedly improved characteristics in terms of emission efficiency and lifespan than the light emitting devices of Comparative Example 1-1 to Comparative Example 1-11. The light emitting devices of Example 1-1 to Example 1-16 include Compound A2, Compound A18, Compound A29, Compound A33, Compound A39, Compound A46, Compound B8, Compound B23, Compound B32, Compound B47, Compound B55, Compound C5, Compound C26, Compound C41, Compound C48, and Compound C53, respectively, which are amine compounds of embodiments. The Example Compounds correspond to dibenzofuran in which an amine group and a carbazole group are bonded to both benzene rings, respectively.

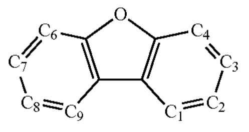

Dibenzofuran

In the Example Compounds, an amine group is bonded to the carbon at position 3 ($C_3$) of the dibenzofuran, and the highest occupied molecular orbital (HOMO) is increased, and the unstable state of radicals, radical cations, or the like may be stabilized. In the Example Compounds, a carbazole group is bonded to the carbon at position 6 ($C_6$), carbon at position 8 ($C_8$), or carbon at position 9 ($C_9$) of the dibenzofuran, and hole transport properties may be improved, and tolerance to electrons and excitons may be increased. Excitons may be produced by the combination of holes and electrons in an emission layer. In addition, in the Example Compounds, the carbazole group and the amine group are bonded to carbon atoms at asymmetric positions in the dibenzofuran, and the molecular structure may show three-dimensional properties. Although not wanting to bound by theory, due to the Example Compounds having a three-dimensional molecular structure, layer properties may be improved. The Example Compounds having such molecular properties may contribute to the achievement of the high efficiency and long lifespan of the light emitting devices.

The light emitting device of Comparative Example 1-1 includes Comparative Compound R1, and Comparative Compound R1 includes a dibenzofuran and an amine group bonded to the dibenzofuran but does not include a carbazole group. Accordingly, the light emitting device of Comparative Example 1-1 showed inferior hole transport properties, tolerance to electrons, and tolerance to excitons when compared to the light emitting devices of the Examples, and reduced results of efficiency and life were shown.

The light emitting device of Comparative Example 1-2 includes Comparative Compound R2, and Comparative Compound R2 includes an amine group and a carbazole group, bonded to biphenylene. Comparative Compound R2 not including dibenzofuran showed degraded hole transport properties, and the stabilization of radicals or radical cations was not obtained. Accordingly, when compared to the light emitting devices of the Examples, manufactured using the Example Compounds including an amine group and a carbazole group, bonded to dibenzofuran, the light emitting device of Comparative Example 1-2 showed inferior results of efficiency and lifespan.

The light emitting device of Comparative Example 1-3 includes Comparative Compound R3, and Comparative Compound R3 includes an amine group and a carbazole group, bonded to dibenzothiophene. Comparative Compound R3 showed inferior hole transport properties when compared to the Example Compounds including dibenzofuran, and hole injection from a hole transport region to an emission layer was delayed. Due to the delay of the hole injection, the light emitting device of Comparative Example 1-3 showed inferior emission efficiency when compared to the light emitting devices of the Examples.

The light emitting devices of Comparative Example 1-4 and Comparative Example 1-5 include Comparative Compound R4 and Comparative Compound R5, respectively, and Comparative Compound R4 and Comparative Compound R5 include an amine group and a carbazole group, bonded to dibenzofuran, but the amine group and the carbazole group are bonded to carbon atoms at symmetric positions. Comparative Compound R4 and Comparative Compound R5, in which the amine group and the carbazole group are bonded at symmetric carbon atoms showed increased planarity of a whole molecule, and intermolecular stacking was increased. Accordingly, although not wanting to be bound by theory, the temperature increase of a deposition process and the deterioration of layer-forming properties occurred, and the efficiency and lifespan of the light emitting devices of Comparative Example 1-4 and Comparative Example 1-5 were degraded.

The light emitting devices of Comparative Example 1-6 and Comparative Example 1-7 include Comparative Compound R6 and Comparative Compound R7, respectively, and Comparative Compound R6 and Comparative Compound R7 include an amine group and a carbazole group, bonded to dibenzofuran. In Comparative Compound R6 and Comparative Compound R7, the amine group is bonded to the carbon at position 1 ($C_1$) of the dibenzofuran and is different from the amine group bonded to the carbon at position 3 ($C_3$) of the dibenzofuran in the Example Compounds. In Comparative Compound R6 and Comparative Compound R7, which include the amine group bonded to carbon at a position other than the carbon at position 3 ($C_3$) of the dibenzofuran, the increase of a $\pi$ conjugation system might be unfavorable, and the expansion of the highest occupied molecular orbital function might be difficult. Accordingly, although not wanting to be bound theory, radicals or radical cations were present in an unstable state, and the lifespan of the emitting devices of Comparative Example 1-6 and Comparative Example 1-7 was short.

The light emitting devices of Comparative Example 1-8 and Comparative Example 1-9 include Comparative Compound R8 and Comparative Compound R9, respectively, and Comparative Compound R8 and Comparative Compound R9 include an amine group and a carbazole group, bonded to dibenzofuran. In Comparative Compound R8, aromatic ring groups are bonded to both benzene rings of the carbazole group. In Comparative Compound R9, an aromatic ring group is fused to the carbazole group in the carbazole group, and the carbazole group bonded to the dibenzofuran is benzocarbazole. Due to the bonded or fused structure of the aromatic ring group to the benzene ring of the carbazole in Comparative Compound R8 and Comparative Compound R9, although not wanting to be bound theory, the temperature increase of a deposition process and the deterioration of layer-forming properties occurred, and the efficiency and lifespan of the light emitting devices of Comparative Example 1-8 and Comparative Example 1-9 were degraded.

The light emitting devices of Comparative Example 1-10 and Comparative Example 1-11 include Comparative Compound R10 and Comparative Compound R11, respectively, and Comparative Compound R10 and Comparative Compound R11 include an amine group and a carbazole group, bonded to dibenzofuran, but have structures including two tertiary amines. Comparative Compound R10 and Comparative Compound R11 are different from the amine compounds of the Examples which include only one tertiary amine. Because Comparative Compound R10 and Comparative Compound R11 include two tertiary amines, hole transport properties increased excessively, and carrier balance was collapsed. Accordingly, although not wanting to be bound theory, the efficiency and lifespan of the light emitting devices of Comparative Example 1-10 and Comparative Example 1-11 were degraded.

In addition, unlike the amine compound, not including a thiophene group, Comparative Compound R11 includes a thiophene group. Accordingly, stability is low in high-temperature conditions and the energization driving conditions of a light emitting device, and the efficiency and lifespan of the light emitting device of Comparative Example 1-11 were greatly degraded.

3. Manufacture and Evaluation of Light Emitting Device II

1) Manufacture of Light Emitting Device II

Embodiments of light emitting devices, including embodiments of the amine compounds of the invention in electron blocking layers were manufactured by the method described below. By using the amine compounds of Compound A2, Compound A18, Compound A29, Compound A33, Compound A39, Compound A46, Compound B8, Compound B23, Compound B32, Compound B47, Compound B55, Compound C5, Compound C26, Compound C41, Compound C48, and Compound C53 as materials for electron blocking layers, light emitting devices of Example 2-1 to Example 2-16 were manufactured. In Comparative Example 2-1 to Comparative Example 2-11, organic light emitting devices were manufactured using Comparative Compounds R1 to R11 as the materials of electron blocking layers.

Unlike the light emitting devices of Comparative Example 1-1 to Comparative Example 1-11 and the light emitting devices of Example 1-1 to Example 1-16, the light emitting devices of Comparative Example 2-1 to Comparative Example 2-11 and the light emitting devices of Example 2-1 to Example 2-16 included the amine compounds of embodiments in electron blocking layers.

On a glass substrate, ITO of a thickness of about 1500 angstrom (Å) was patterned and then, washed with ultrapure water and treated with ultraviolet (UV) ozone for about 10 minutes. Then, 2-TNATA was deposited to a thickness of about 600 Å to form a hole injection layer. Then, Compound H-1-1 was deposited to a thickness of about 200 Å to form a hole transport layer, and the Example Compound or Comparative Compound was deposited to a thickness of about 100 Å to form an electron blocking layer.

After that, ADN doped with 3% (weight ratio) TBP was applied to form an emission layer with a thickness of about 250 Å. Then, $Alq_3$ was deposited to a thickness of about 250 Å to form an electron transport layer, and LiF was deposited to a thickness of about 10 Å to form an electron injection layer.

Then, Al was provided to a thickness of about 1000 Å to form a second electrode. In the Examples, the hole injection layer, the hole transport layer, the emission layer, the electron transport layer, the electron injection layer and the second electrode were formed using a vacuum deposition apparatus.

H-1-1

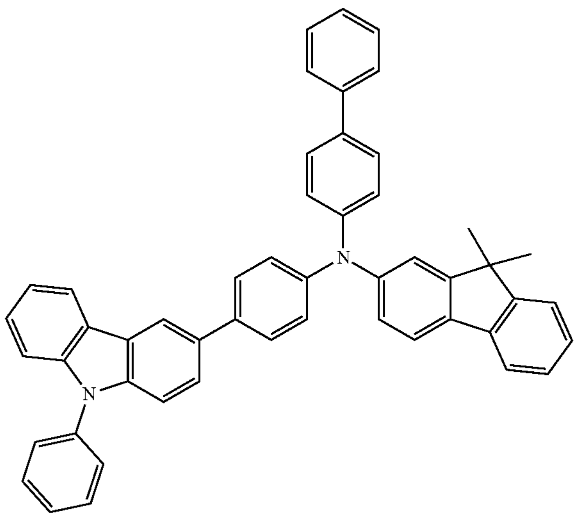

2) Evaluation of Properties of Light Emitting Device II

In Table 2, the emission efficiency and lifespan of the light emitting devices according to Example 2-1 to Example 2-16, and Comparative Example 2-1 to Comparative Example 2-11 are compared and shown. In Table 2, the emission efficiency and lifespan are relative values and compared values with 100% of the emission efficiency and lifespan of the light emitting device of Comparative Example 2-2. In the evaluation results of properties on the Examples and Comparative Examples, shown in Table 2, the emission efficiency shows efficiency at a current density of about 10 $mA/cm^2$, and the lifespan ($LT^{50}$) shows luminance half-life at about 1.0 $mA/cm^2$. By the same method as for the light emitting devices of Comparative Examples 1-1 to 1-11 and Examples 1-1 to 1-16, the emission efficiency and lifespan of the light emitting devices of Example 2-1 to Example 2-16 and Comparative Example 2-1 to Comparative Example 2-11 were evaluated.

TABLE 2

| Device manufacturing example | Electron blocking layer material | Efficiency | Life ($LT^{50}$) |
|---|---|---|---|
| Example 2-1 | Example Compound A2 | 140% | 160% |
| Example 2-2 | Example Compound A18 | 139% | 152% |
| Example 2-3 | Example Compound A29 | 135% | 155% |
| Example 2-4 | Example Compound A33 | 142% | 149% |
| Example 2-5 | Example Compound A39 | 138% | 162% |
| Example 2-6 | Example Compound A46 | 146% | 155% |
| Example 2-7 | Example Compound B8 | 130% | 161% |
| Example 2-8 | Example Compound B23 | 142% | 160% |
| Example 2-9 | Example Compound B32 | 139% | 159% |
| Example 2-10 | Example Compound B47 | 135% | 165% |
| Example 2-11 | Example Compound B55 | 137% | 159% |
| Example 2-12 | Example Compound C5 | 144% | 165% |
| Example 2-13 | Example Compound C26 | 140% | 155% |
| Example 2-14 | Example Compound C41 | 145% | 151% |
| Example 2-15 | Example Compound C48 | 135% | 148% |
| Example 2-16 | Example Compound C53 | 132% | 153% |
| Comparative Example 2-1 | Comparative Compound R1 | 87% | 91% |
| Comparative Example 2-2 | Comparative Compound R2 | 100% | 100% |
| Comparative Example 2-3 | Comparative Compound R3 | 105% | 109% |
| Comparative Example 2-4 | Comparative Compound R4 | 101% | 99% |
| Comparative Example 2-5 | Comparative Compound R5 | 99% | 89% |
| Comparative Example 2-6 | Comparative Compound R6 | 106% | 62% |
| Comparative Example 2-7 | Comparative Compound R7 | 104% | 87% |
| Comparative Example 2-8 | Comparative Compound R8 | 98% | 97% |
| Comparative Example 2-9 | Comparative Compound R9 | 90% | 96% |
| Comparative Example 2-10 | Comparative Compound R10 | 88% | 77% |
| Comparative Example 2-11 | Comparative Compound R11 | 72% | 58% |

The results summarized in Table 2 show that the light emitting devices of Example 2-1 to Example 2-16 exhibited significantly and unexpectedly improved characteristics in terms of emission efficiency and lifespan than the light emitting devices of Comparative Example 2-1 to Comparative Example 2-11. Different from the light emitting devices of Example 1-1 to Example 1-16, the light emitting devices of Example 2-1 to Example 2-16 used the Example Compounds when forming the electron blocking layers of the light emitting devices. Accordingly, although not wanting to be bound theory, a light emitting device including an embodiment of the amine compound in at least one of a hole transport layer or an electron blocking layer showed high efficiency and long-lifespan.

The light emitting devices of Example 2-1 to Example 2-16 include Compound A2, Compound A18, Compound A29, Compound A33, Compound A39, Compound A46, Compound B8, Compound B23, Compound B32, Compound B47, Compound B55, Compound C5, Compound C26, Compound C41, Compound C48, and Compound C53, respectively, which are the amine compounds of embodiments. In the Example Compounds, an amine group and a carbazole group are bonded to both benzene rings of dibenzofuran, respectively. As described above, in the Example Compounds, the amine group is bonded to the carbon at position 3 of the dibenzofuran, and the carbazole group is bonded to carbon at an asymmetric position to the carbon at position 3. In the Example Compounds, the carbazole group is bonded to the carbon at position 6, carbon at position 8, or carbon at position 9 of the dibenzofuran.

The light emitting devices of Comparative Example 2-1 to Comparative Example 2-11 include Comparative Compounds R1 to R11, respectively. Different from the light emitting devices of Comparative Example 1-1 to Comparative Example 1-11, Comparative Example 2-1 to Comparative Example 2-11 used the Comparative Compounds in electron blocking layers in the light emitting devices. With respect to the light emitting devices of Comparative Example 2-1 to Comparative Example 2-11, the same explanation of the light emitting devices of Comparative Example 1-1 to Comparative Example 1-11 of Table 1 could be applied.

The light emitting device of Comparative Example 2-1 includes Comparative Compound R1, and Comparative Compound R1 does not include a carbazole group. Accordingly, the light emitting device of Comparative Example 2-1 showed inferior results of efficiency and lifespan when compared to the light emitting devices of the Examples.

The light emitting device of Comparative Example 2-2 includes Comparative Compound R2, and Comparative Compound R2 does not include dibenzofuran but include biphenyelene. The light emitting device of Comparative Example 2-3 includes Comparative Compound R3, and Comparative Compound R3 does not include dibenzofuran but include dibenzothiophene. Accordingly, when compared to the light emitting devices of the Examples, manufactured using the Example Compounds including the dibenzofuran, the light emitting devices of Comparative Example 2-2 and Comparative Example 2-3 showed inferior results of efficiency and lifespan.

The light emitting devices of Comparative Example 2-4 and Comparative Example 2-5 include Comparative Compound R4 and Comparative Compound R5, respectively, and Comparative Compound R4 and Comparative Compound R5 include an amine group and a carbazole group, bonded at symmetric positions. Accordingly, although not wanting to be bound theory, the temperature increase of a deposition process and the deterioration of layer-forming properties occurred, and the efficiency and lifespan of the light emitting devices of Comparative Example 2-4 and Comparative Example 2-5 were degraded.

The light emitting devices of Comparative Example 2-6 and Comparative Example 2-7 include Comparative Compound R6 and Comparative Compound R7, respectively, and in Comparative Compound R6 and Comparative Compound R7, an amine group is bonded to the carbon at position 1 ($C_1$) of dibenzofuran. Accordingly, although not wanting to be bound theory, radicals or radical cations were present in an unstable state, and the lifespan of the emitting devices of Comparative Example 2-6 and Comparative Example 2-7 was short.

The light emitting devices of Comparative example 2-8 and Comparative Example 2-9 include Comparative Compound R8 and Comparative Compound R9, respectively. In Comparative Compound R8, phenyl groups are bonded to both benzene rings of a carbazole group, respectively, and in Comparative Compound R9, a phenyl group is fused to a carbazole group. Accordingly, although not wanting to be bound theory, the temperature increase of a deposition process and the deterioration of layer-forming properties occurred, and the efficiency and lifespan of the light emitting devices of Comparative Example 2-8 and Comparative Example 2-9 were degraded.

The light emitting devices of Comparative Example 2-10 and Comparative Example 2-11 include Comparative Compound R10 and Comparative Compound R11, respectively, and Comparative Compound R10 and Comparative Compound R11 have structures including two tertiary amines. In addition, Comparative Compound R11 includes a thiophene group. Accordingly, although not wanting to be bound theory, the efficiency and lifespan of the light emitting devices of Comparative Example 2-10 and Comparative Example 2-11 were degraded.

An organic light emitting device made according to the principles and one or more embodiments of the invention may include a first electrode, a second electrode disposed on the first electrode, and at least one functional layer, including at least one of an electron transport region, an emission layer, and a hole transport region, disposed between the first electrode and the second electrode. The at least one functional layer includes an embodiment of and amine compound made according to the principles of the invention, and the amine compound has a structure in which an amine group and a carbazole group are bonded to both benzene rings of dibenzofuran, respectively. The amine group is bonded to the carbon at position 3 of the dibenzofuran, and the carbazole group is bonded to the carbon at an asymmetric position to the carbon at position 3. The molecular structure of the amine compound including the amine group and the carbazole group, bonded to carbon atoms at asymmetric positions in the dibenzofuran may show three-dimensional properties. Accordingly, layer properties of the amine compound may be improved, and excellent tolerance to electrons and tolerance to excitons may be shown. The light emitting device including the amine compound may show high efficiency and long-lifespan.

The amine compound may include an amine group and a carbazole group, bonded to carbon atoms at asymmetric positions. The amine compound may not include a thiophene group as a substituent, and may not include a tertiary amine in addition to an amine group bonded to dibenzofuran. The amine compound showing asymmetricity shows three-dimensional molecular properties, and may be used as a material for a hole transport region of a light emitting device to contribute to the increase of the emission efficiency and lifespan of the light emitting device. Light emitting devices that include an embodiment of the amine compound in a hole transport region may show high efficiency and long-lifespan. Embodiments of amine compounds made according to the principles of the invention may improve the emission efficiency and lifespan of a light emitting device.

Although certain embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A light emitting device, comprising:

a first electrode;

a second electrode disposed on the first electrode; and at least one functional layer disposed between the first electrode and the second electrode and comprising an amine compound of Formula 1:

Formula 1

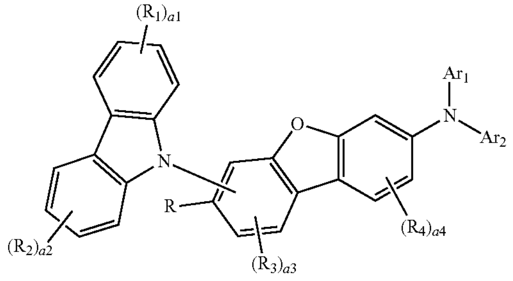

in Formula 1,

R is a hydrogen atom or a deuterium atom, a1 and a2 are each, independently from one another, an integer of 0 to 4, $R_1$ and $R_2$ are each, independently from one another, a hydrogen atom, a deuterium atom, a halogen atom, or a substituted or unsubstituted alkyl group of 1 to 20 carbon atoms, a3 is an integer of 0 to 2, a4 is an integer of 0 to 3, $R_3$ and $R_4$ are each, independently from one another, a hydrogen atom, a deuterium atom, a halogen atom, a substituted or unsubstituted alkyl group of 1 to 20 carbon atoms, or a substituted or unsubstituted aryl group of 6 to 40 ring-forming carbon atoms, $Ar_1$ and $Ar_2$ are each, independently from one another, a substituted or unsubstituted aryl group of 6 to 40 ring-forming carbon atoms, or a substituted or unsubstituted heteroaryl group of 2 to 40 ring-forming carbon atoms, with the proviso that $R_1$ to $R_4$, $Ar_1$ and $Ar_2$ do not comprise an amine group as a substituent, with the proviso that the amine compound does not comprise a substituted or unsubstituted thiophenyl group, and with the proviso that the thiophenyl group is not fused to another ring.

2. The light emitting device of claim 1, wherein Formula 1 is of Formula 2-1:

Formula 2-1

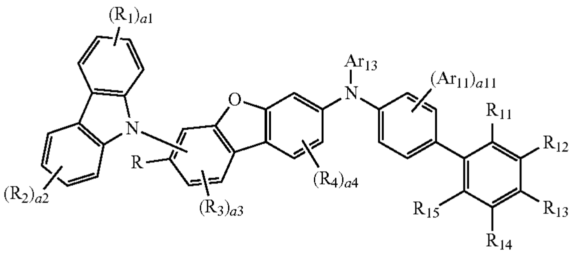

in Formula 2-1, a11 is an integer of 0 to 4, $Ar_{11}$ is a hydrogen atom, a deuterium atom, or a substituted or unsubstituted aryl group of 6 to 40 ring-forming carbon atoms, $R_{11}$ to $R_{15}$ are each, independently from one another, a hydrogen atom, a deuterium atom, a halogen atom, a substituted or unsubstituted silyl group, a substituted or unsubstituted alkenyl group of 2 to 10 carbon atoms, a substituted or unsubstituted aryl group of 6 to 40 ring-forming carbon atoms, or a substituted or unsubstituted heteroaryl group of 2 to 40 ring-forming carbon atoms, or combined with an adjacent group to form a ring, $Ar_{13}$ is a substituted or unsubstituted aryl group of 6 to 40 ring-forming carbon atoms, or a substituted or unsubstituted heteroaryl group of 2 to 40 ring-forming carbon atoms, and a1 to a4, R, and $R_1$ to $R_4$ have, independently from one another, the same meaning as defined in Formula 1.

3. The light emitting device of claim 1, wherein Formula 1 is of Formula 2-2:

Formula 2-2

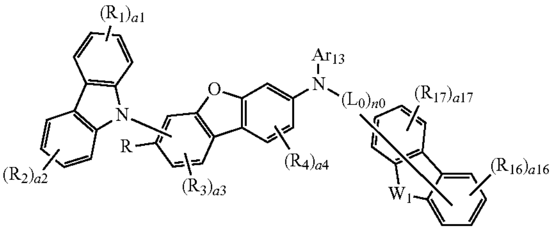

in Formula 2-2, n0 is an integer of 0 to 3, $L_0$ is a direct linkage, a substituted or unsubstituted aryl group of 6 to 40 ring-forming carbon atoms, or a substituted or unsubstituted heteroaryl group of 2 to 40 ring-forming carbon atoms, $W_1$ is $CR_{18}R_{19}$, $NR_{20}$, O, or S, a16 and a17 are each, independently from one another, an integer of 0 to 4, $R_{16}$ to $R_{20}$ are each, independently from one another, a hydrogen atom, a deuterium atom, a substituted or unsubstituted alkenyl group of 2 to 10 carbon atoms, a substituted or unsubstituted aryl group of 6 to 40 ring-forming carbon atoms, or a substituted or unsubstituted heteroaryl group of 2 to 40 ring-forming carbon atoms, or combined with an adjacent group to form a ring, $Ar_{13}$ is a substituted or unsubstituted aryl group of 6 to 40 ring-forming carbon atoms, or a substituted or unsubstituted heteroaryl group of 2 to 40 ring-forming carbon atoms, and a1 to a4, R, and $R_1$ to $R_4$ have, independently from one another, the same meaning as defined in Formula 1.

4. The light emitting device of claim 1, wherein $Ar_1$ and $Ar_2$ are each, independently from one another, a substituted or unsubstituted phenyl group, a substituted or unsubstituted naphthyl group, a substituted or unsubstituted phenanthryl group, a substituted or unsubstituted triphenylenyl group, a substituted or unsubstituted fluorenyl group, a substituted or unsubstituted dibenzofuran group, a substituted or unsubstituted dibenzothiophene group, a substituted carbazole group, an unsubstituted naphthobenzofuran group, or an unsubstituted benzonaphthothiophene group.

5. The light emitting device of claim 1, wherein $Ar_1$ and $Ar_2$ are each, independently from one another, one of A-1 to A-7:

A-1

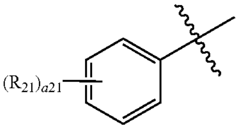

A-2

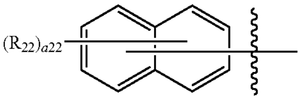

A-3

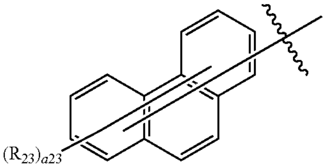

A-4

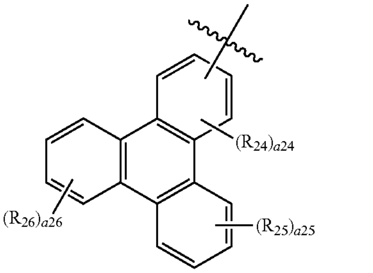

A-5

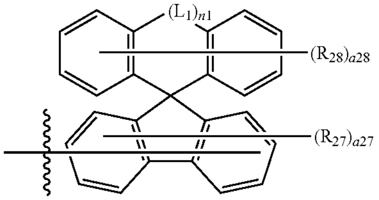

A-6

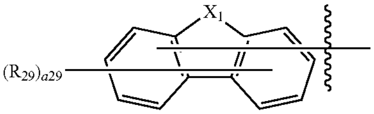

A-7

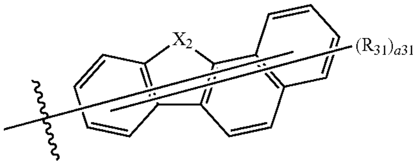

a21 is an integer of 0 to 5, in A-2, a22 is an integer of 0 to 7, and $R_{22}$ is a hydrogen atom, a deuterium atom, or a substituted or unsubstituted aryl group of 6 to 40 ring-forming carbon atoms, in A-3, a23 is an integer of 0 to 9, in A-4, a24 is an integer of 0 to 3, and a25 and a26 are each, independently from one another, an integer of 0 to 4, in A-5, n1 is 0 or 1, $L_1$ is a direct linkage, a27 is an integer of 0 to 7, and a28 is an integer of 0 to 10, in A-6, $X_1$ is $NR_{30}$, O, or S, and a29 is an integer of 0 to 7, in A-7, $X_2$ is O, or S, and a31 is an integer of 0 to 9, and in A-1, and A-3 to A-7, $R_{21}$, and $R_{23}$ to $R_{31}$ are each, independently from one another, a hydrogen atom, a deuterium atom, a substituted or unsubstituted aryl group of 6 to 40 ring-forming carbon atoms, or a substituted or unsubstituted heteroaryl group of 2 to 40 ring-forming carbon atoms.

6. The light emitting device of claim 1, wherein at least one of $Ar_1$ and $Ar_2$ is a substituted or unsubstituted phenyl group.

7. The light emitting device of claim 1, wherein $R_1$ and $R_2$ are each, independently from one another, a deuterium atom, a fluorine atom, a methyl group, or a t-butyl group.

8. The light emitting device of claim 1, wherein at least one of $R_1$ to $R_4$ is a deuterium atom, or at least one of $R_1$ to $R_4$, $Ar_1$ and $Ar_2$ comprises a deuterium atom as a substituent.

9. The light emitting device of claim 1, wherein the at least one functional layer comprises an emission layer, a hole transport region disposed between the first electrode and the emission layer, and an electron transport region disposed between the emission layer and the second electrode, and the hole transport region comprises the amine compound.

10. The light emitting device of claim 9, wherein the hole transport region comprises a hole injection layer disposed on the first electrode, a hole transport layer disposed on the hole injection layer, and an electron blocking layer disposed on the hole transport layer, and at least one of the hole injection layer, the hole transport layer, and the electron blocking layer comprises the amine compound.

11. The light emitting device of claim 10, wherein the electron blocking layer comprises the amine compound, and the hole transport layer comprises a compound of Formula H-1:

Formula H-1

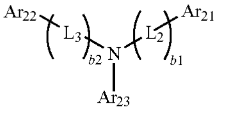

in Formula H-1, b1 and b2 are each, independently from one another, an integer of 0 to 10, $L_2$ and $L_3$ are each, independently from one another, a direct linkage, a substituted or unsubstituted arylene group of 6 to 30 ring-forming carbon atoms, or a substituted or unsubstituted heteroarylene group of 2 to 30 ring-forming carbon atoms, and $Ar_{21}$ to $Ar_{23}$ are each, independently from one another, a substituted or unsubstituted aryl group of 6 to 30 ring-forming carbon atoms, or a substituted or unsubstituted heteroaryl group of 2 to 30 ring-forming carbon atoms.

12. The light emitting device of claim 1, wherein the amine compound comprises one compound of Compound Group 1:

Compound 1

A1

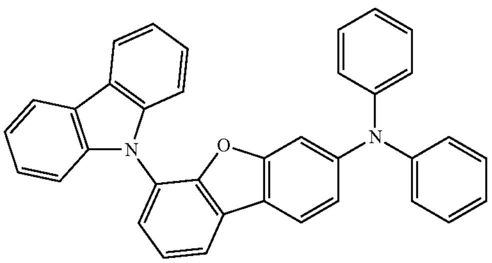

A2

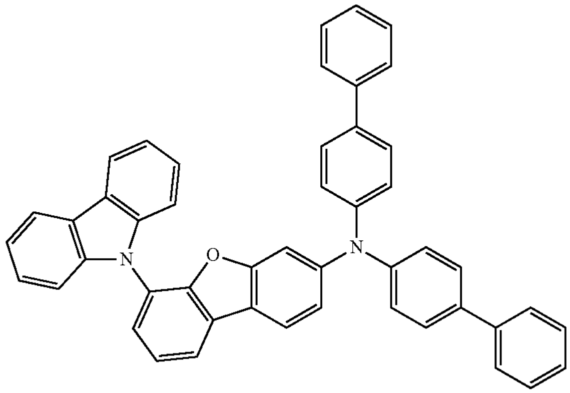

A3

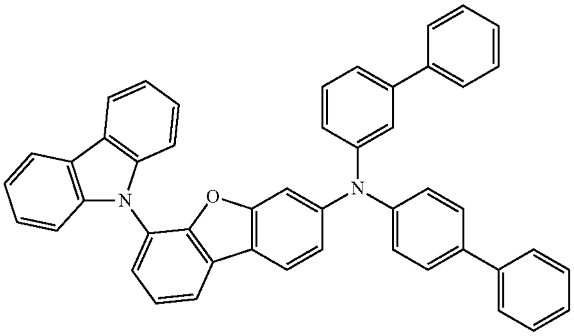

A4

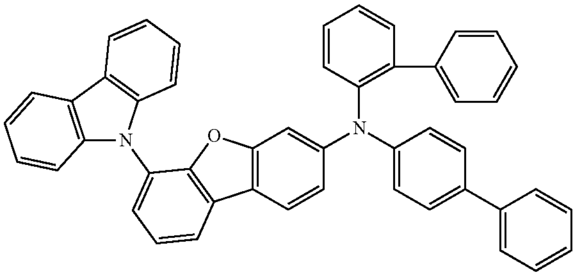

-continued
A5
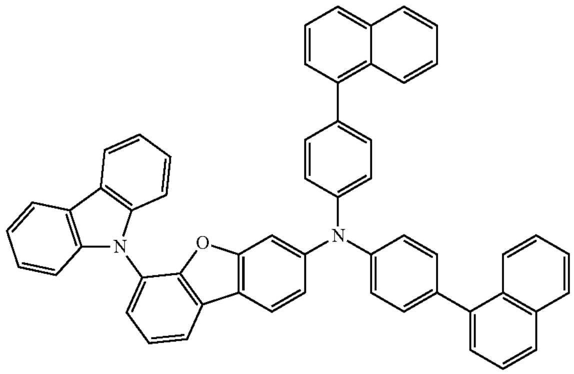
A6
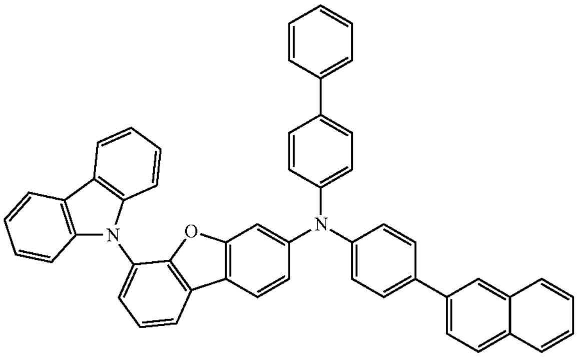
A7
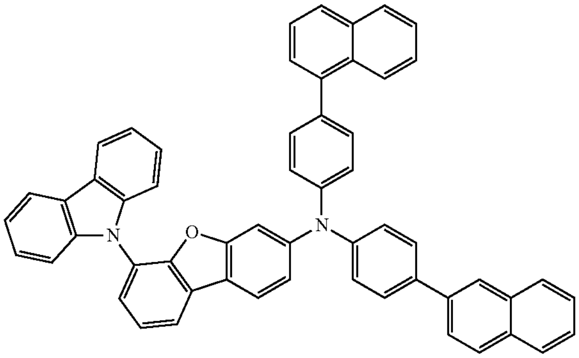
A8
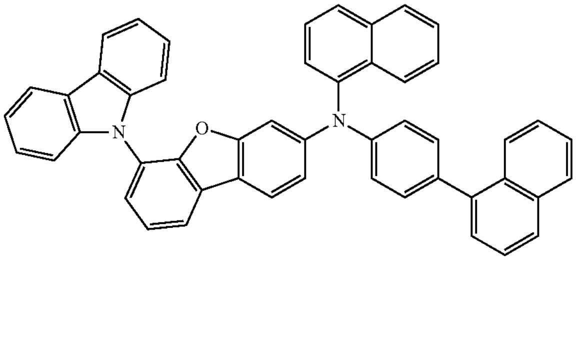
-continued
A9
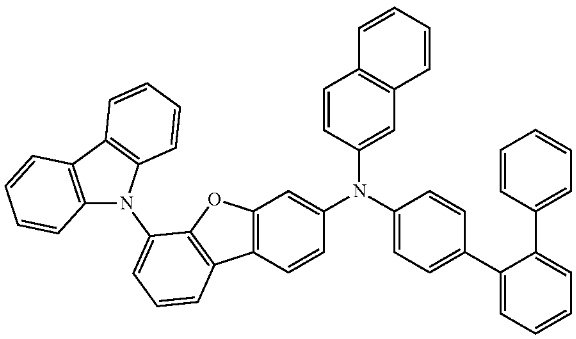
A10
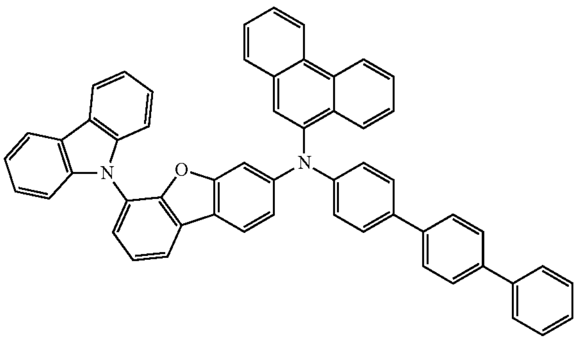
A11
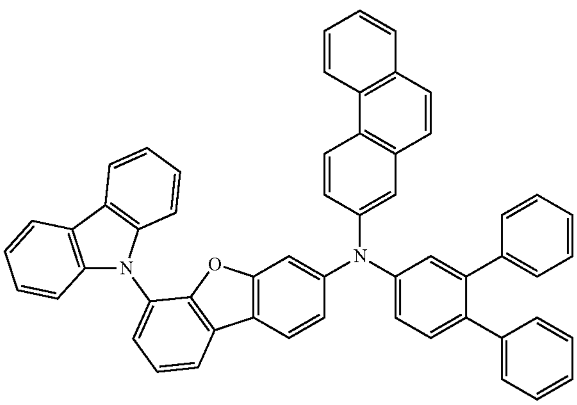
A12
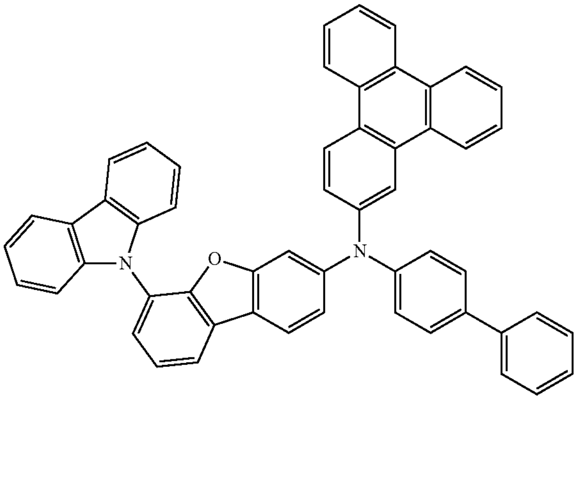

-continued
A13
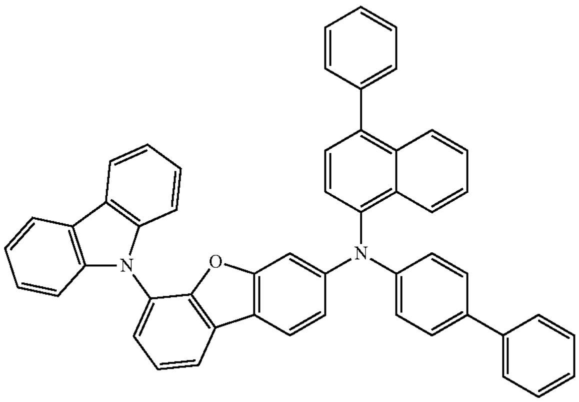
A14
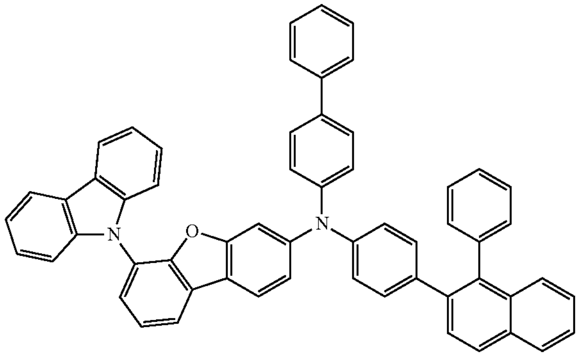
A15
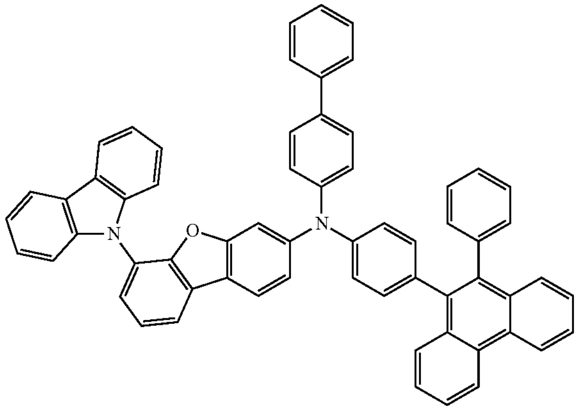
-continued
A16
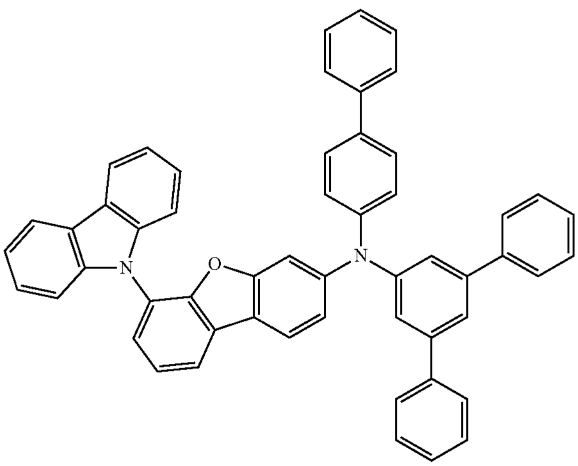
A17
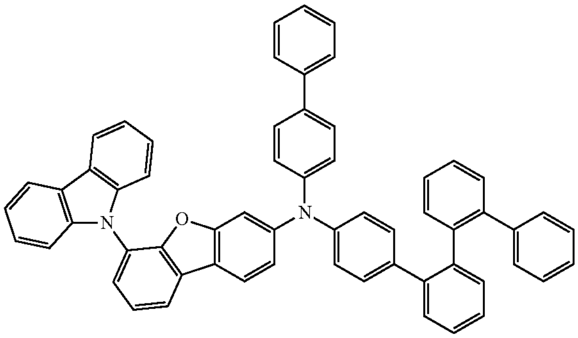
A18
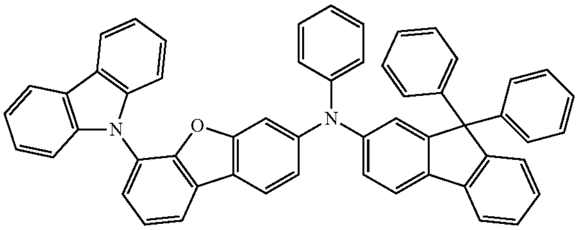
A19
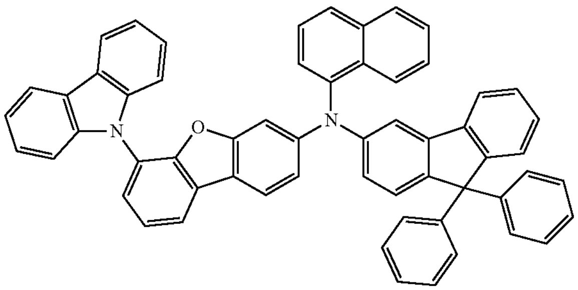

A20
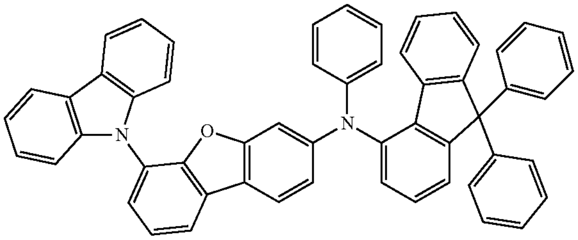
A21
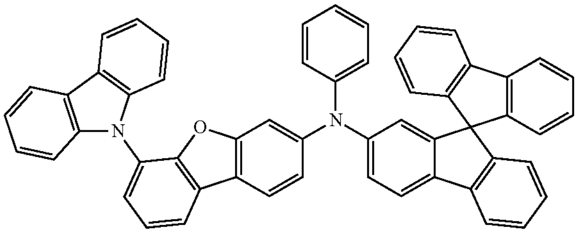
A22
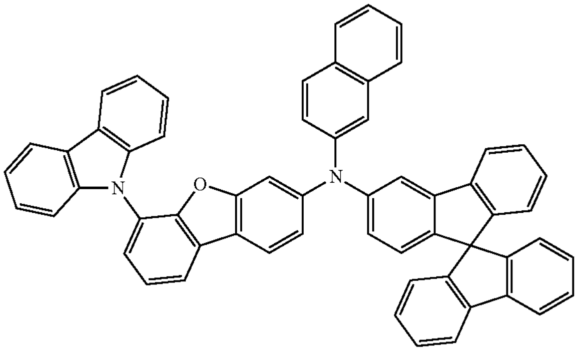
A23
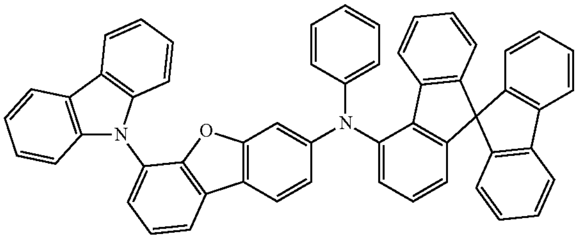
A24
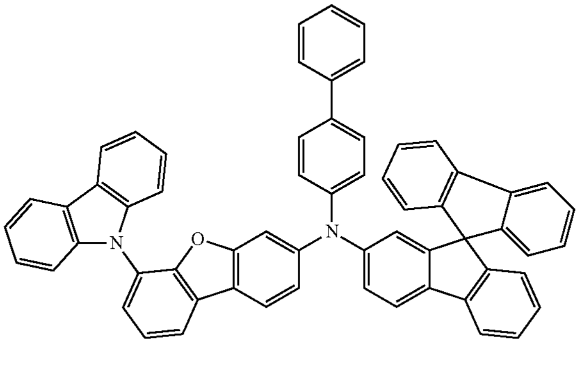
A25
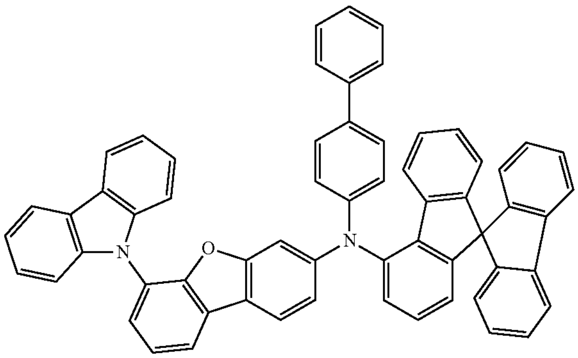
A26
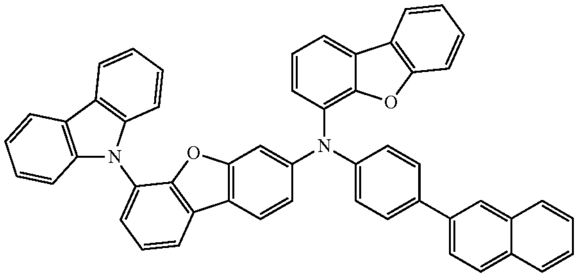
A27
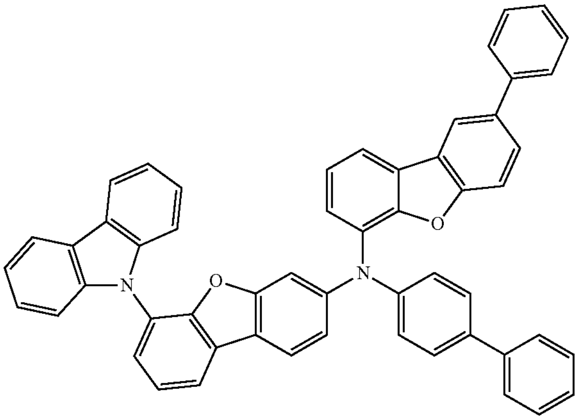
A28
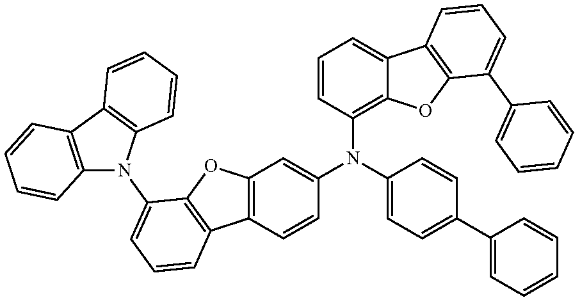

-continued
A29
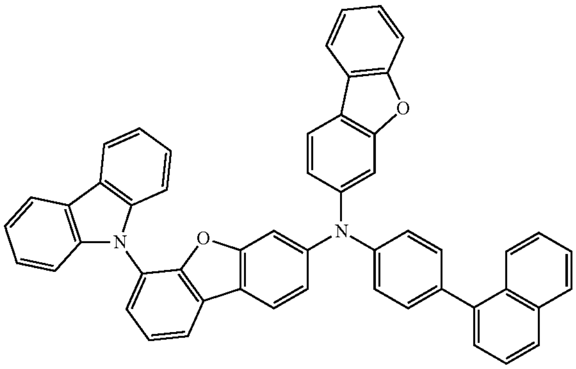
A30
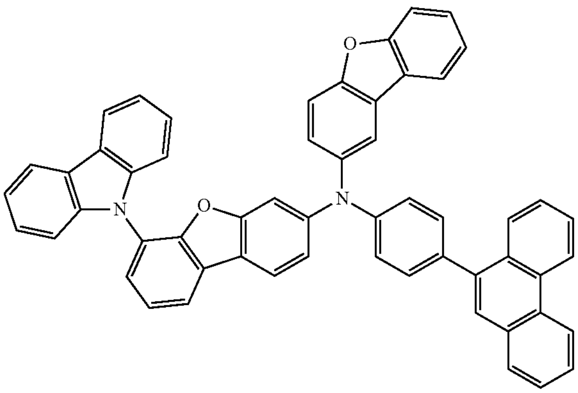
A31
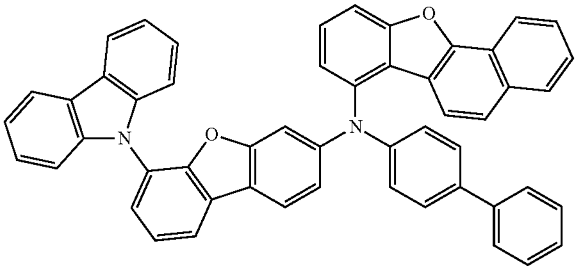
A32
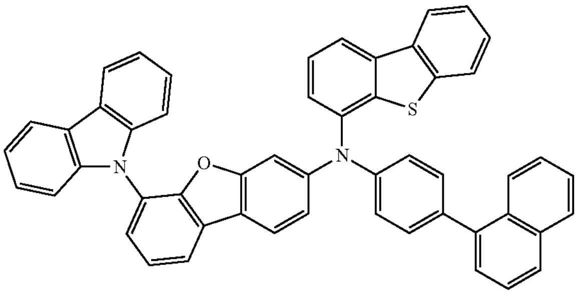
-continued
A33
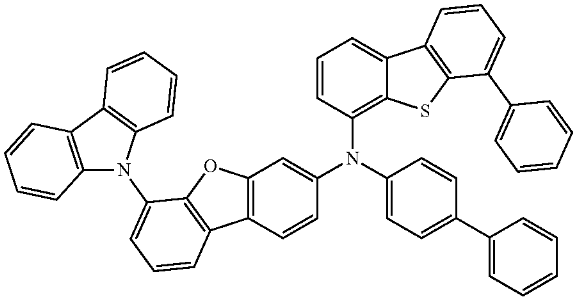
A34
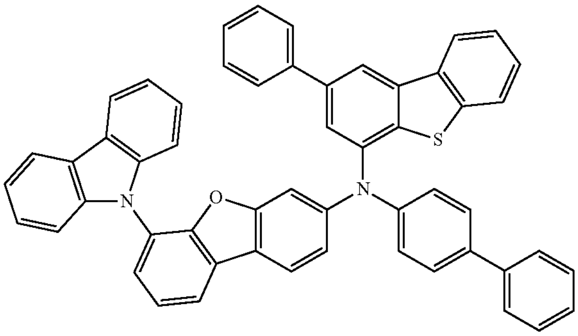
A35
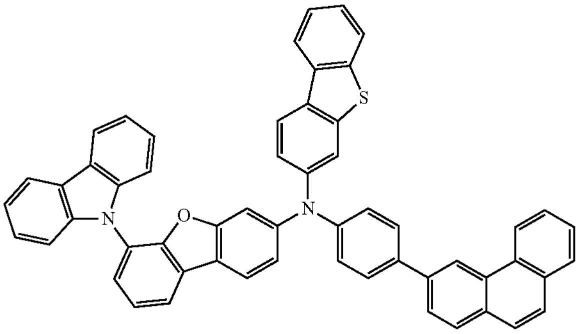
A36
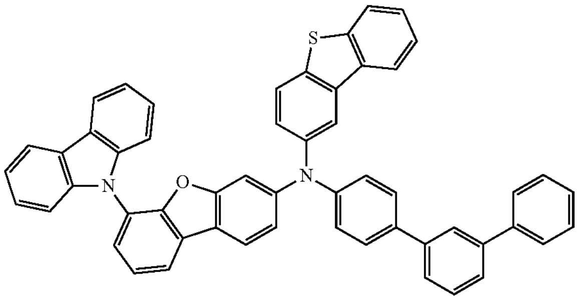

A37
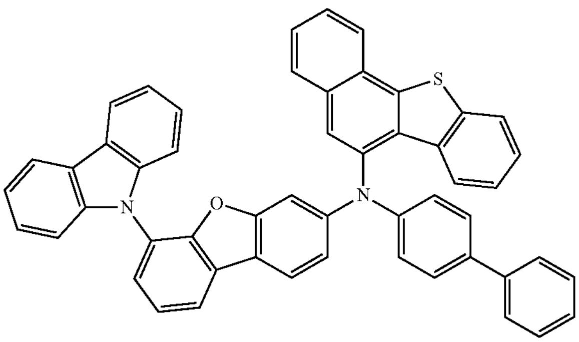
A38
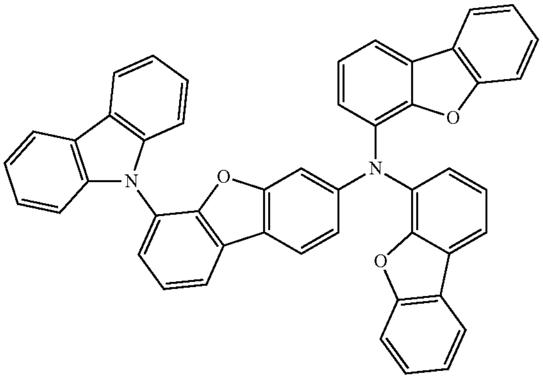
A39
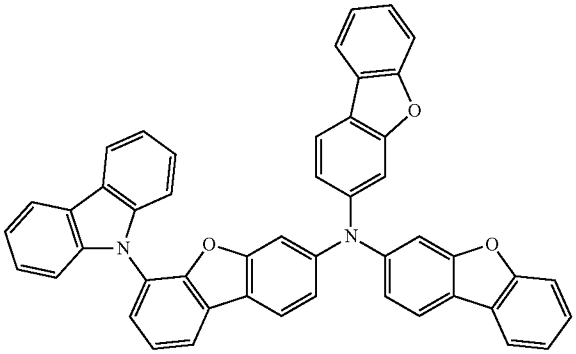
A40
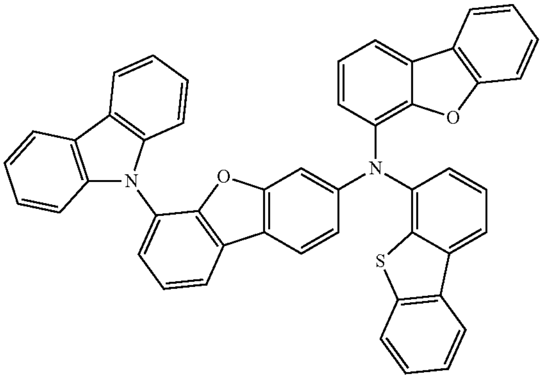
A41
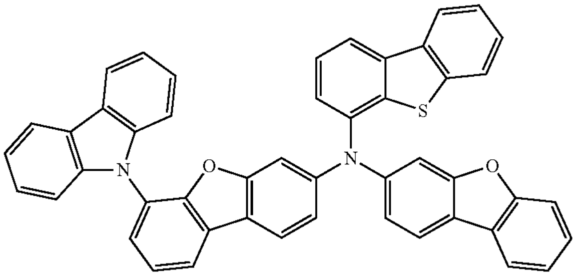
A42
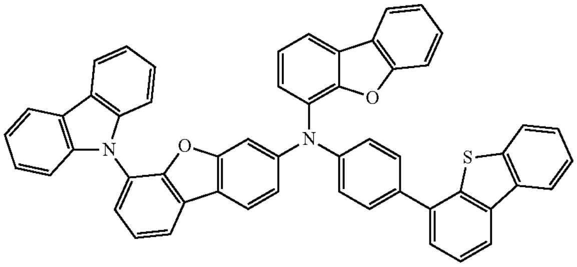
A43
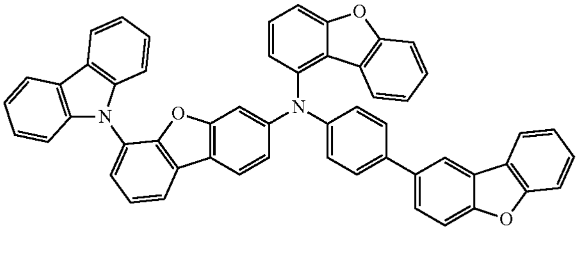
A44
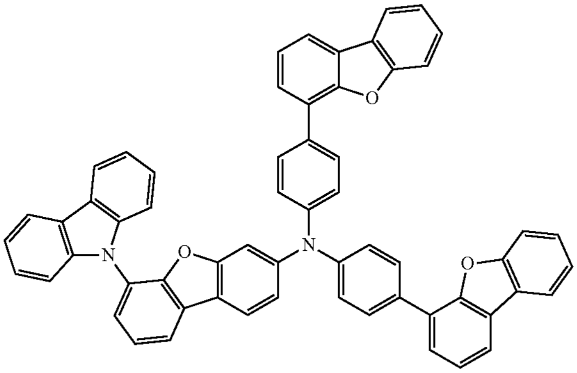

-continued
A45
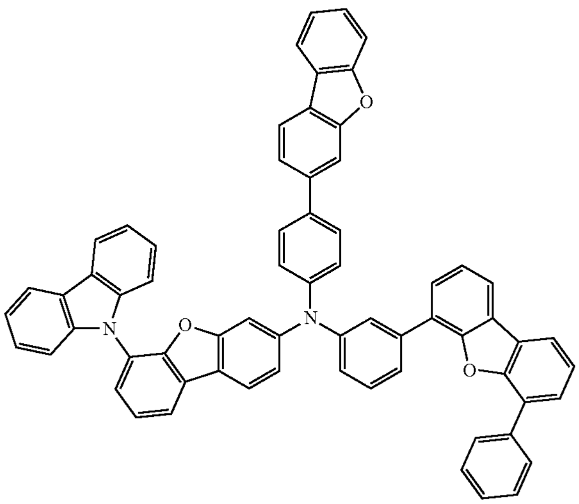
A46
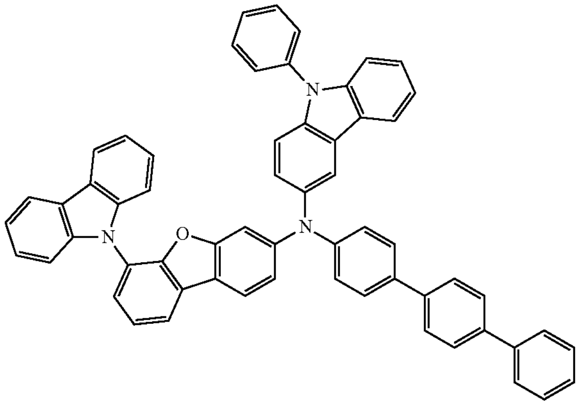
A47
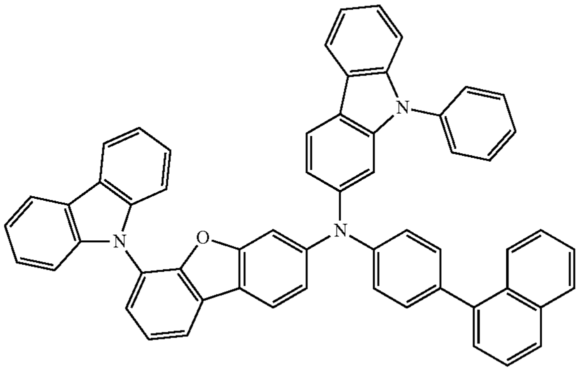
-continued
A48
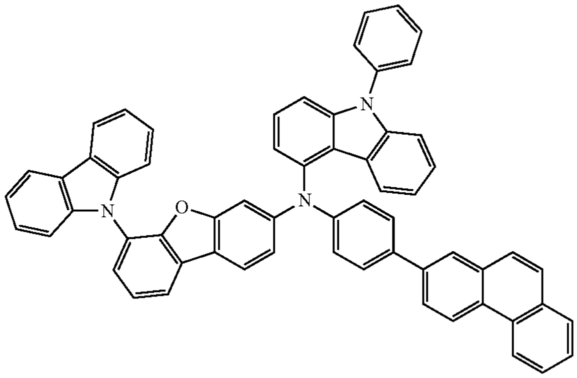
A49
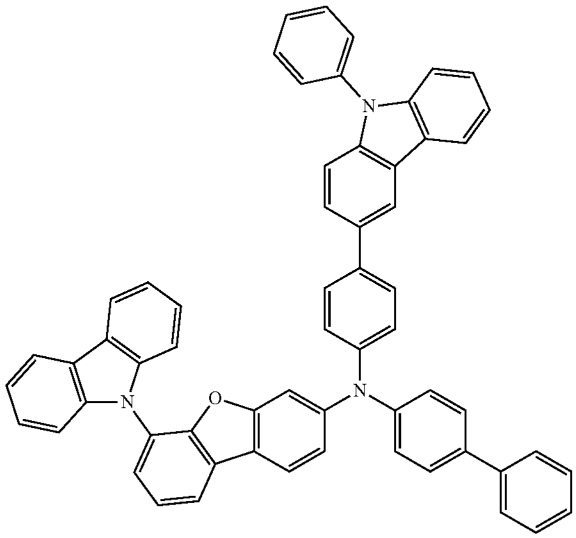
A50
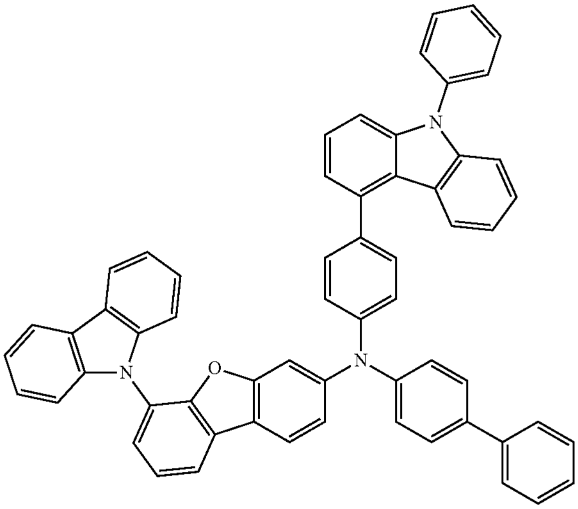

-continued
A51
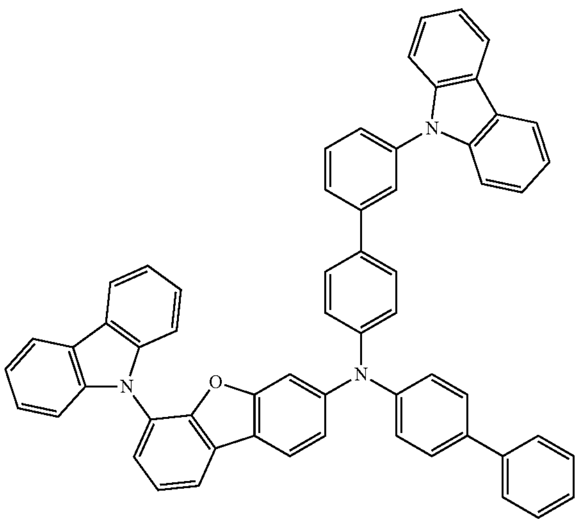
A52
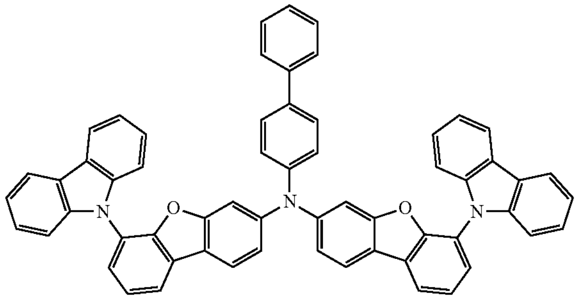
A53
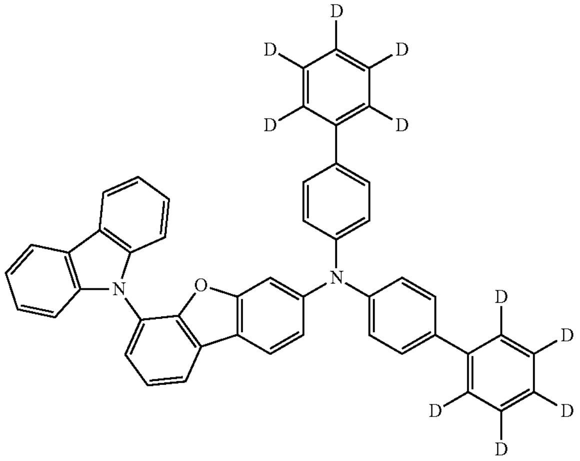
-continued
A54
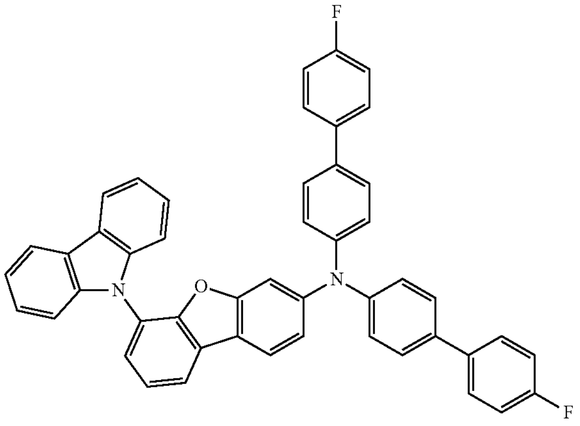
A55
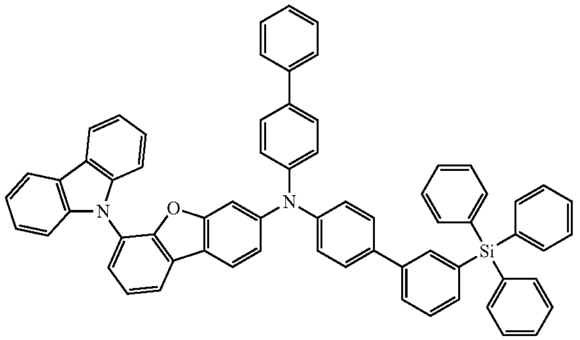
A56
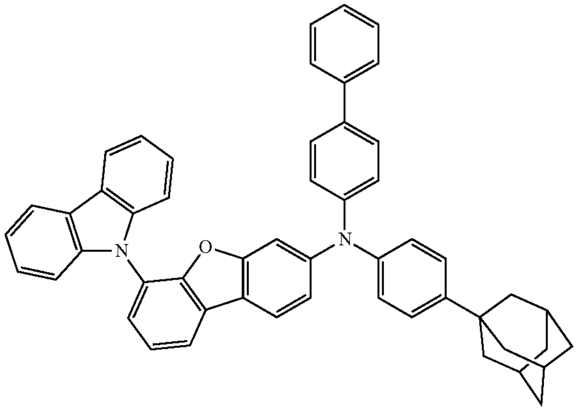
A57
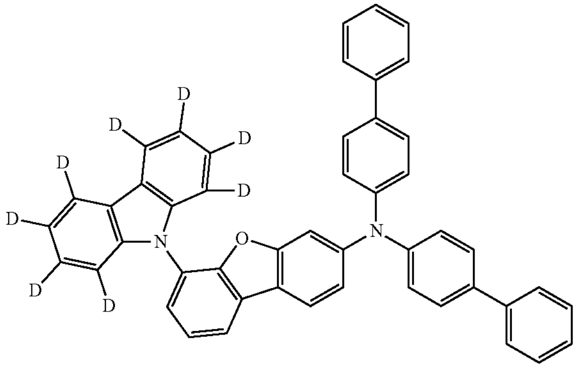

-continued
A58
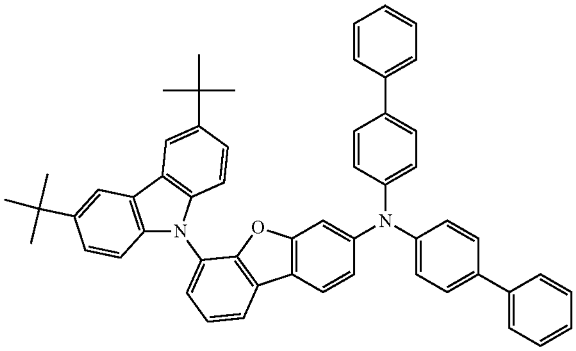
A59
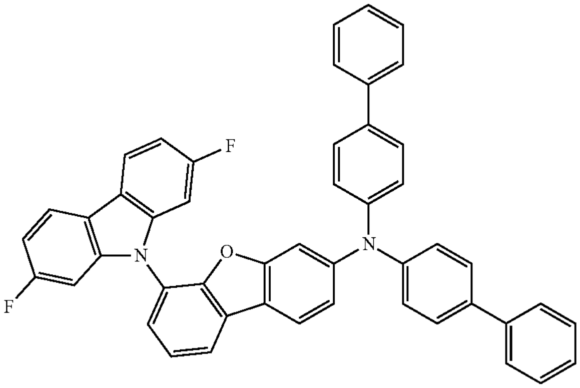
A60
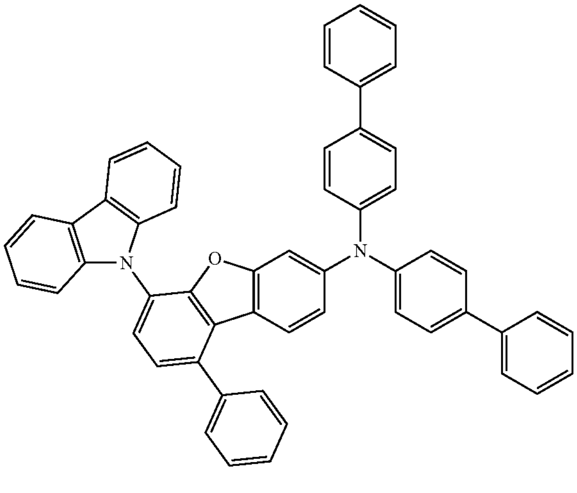
-continued
A61
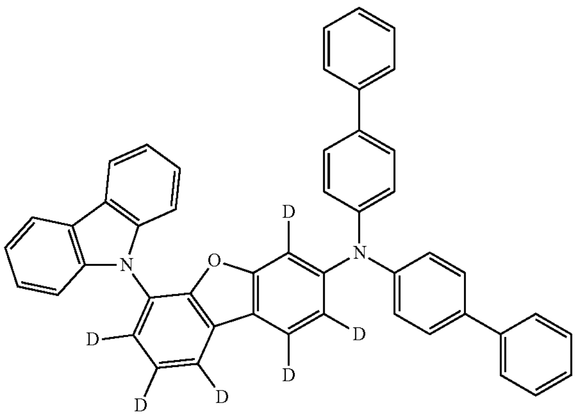
A62
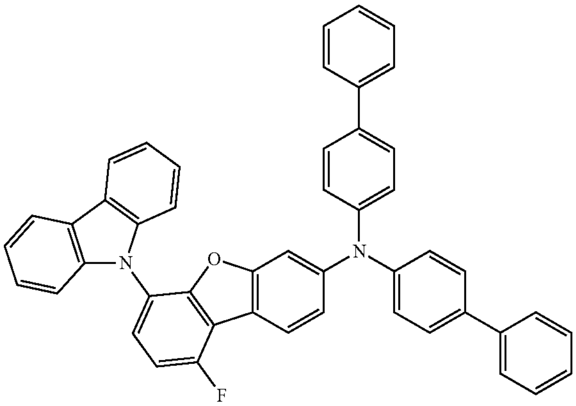
A63
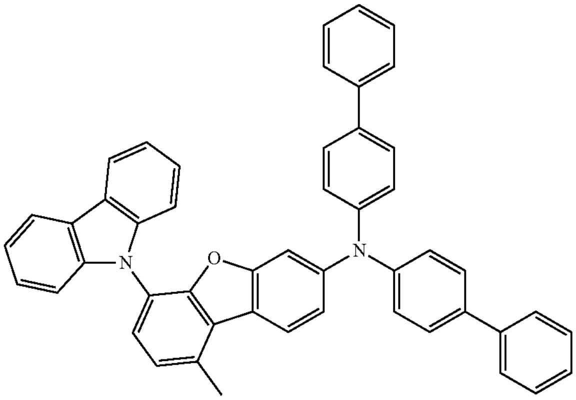

A64
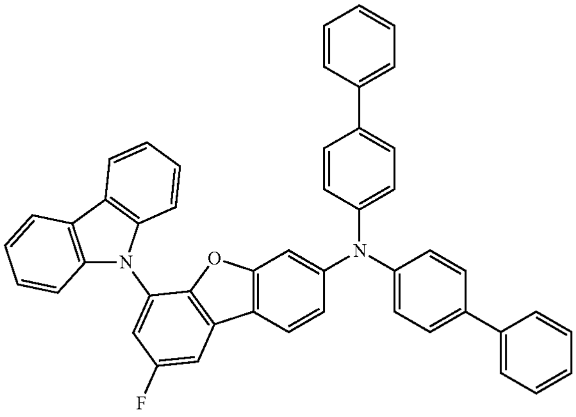
A65
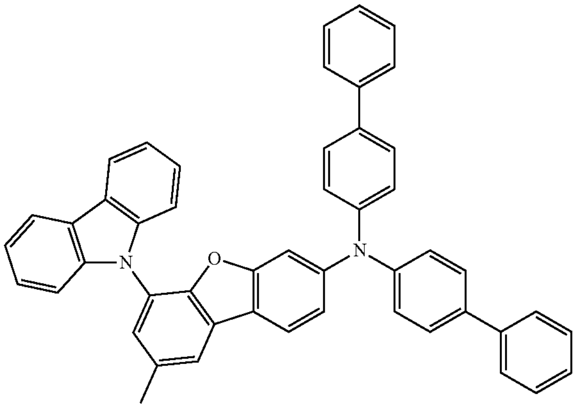
B1
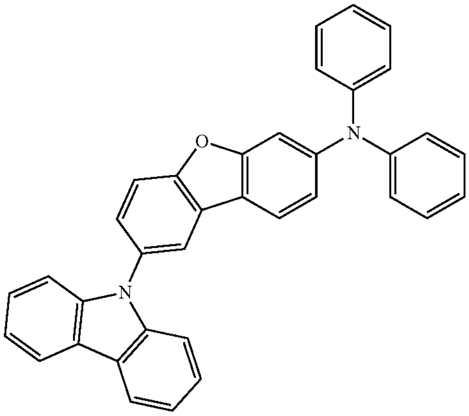
B2
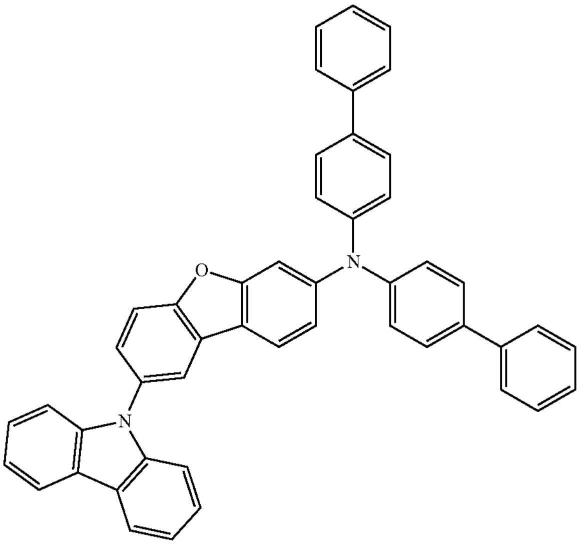
B3
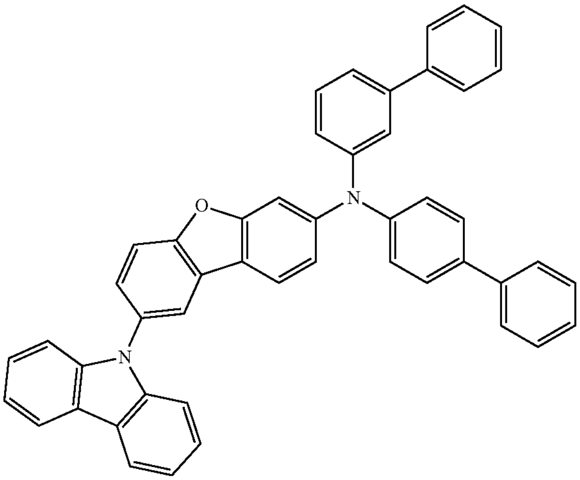
B4
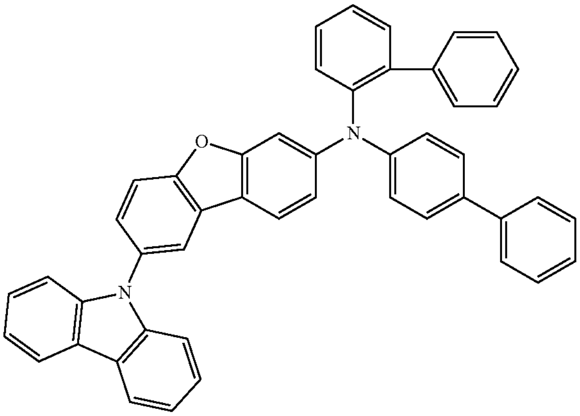

-continued
B5
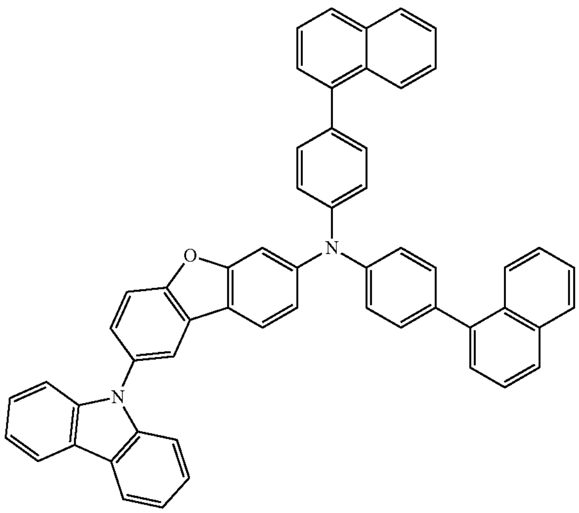
B6
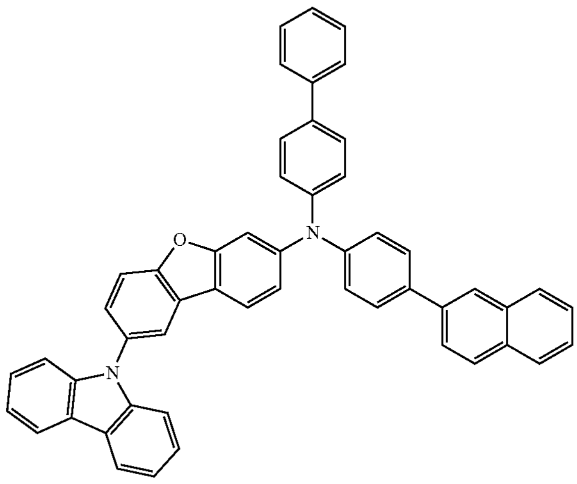
B7
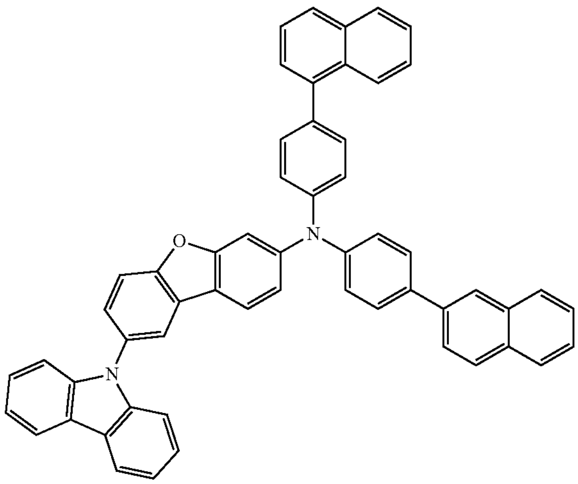
-continued
B8
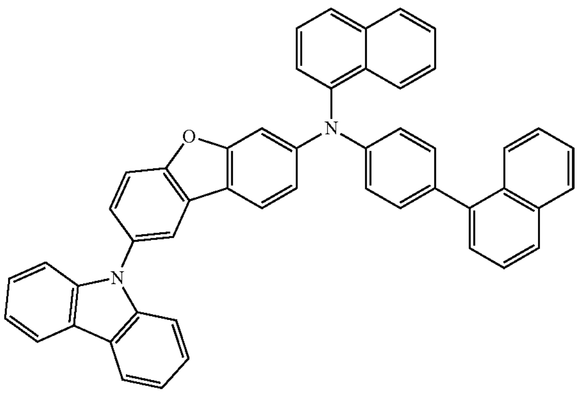
B9
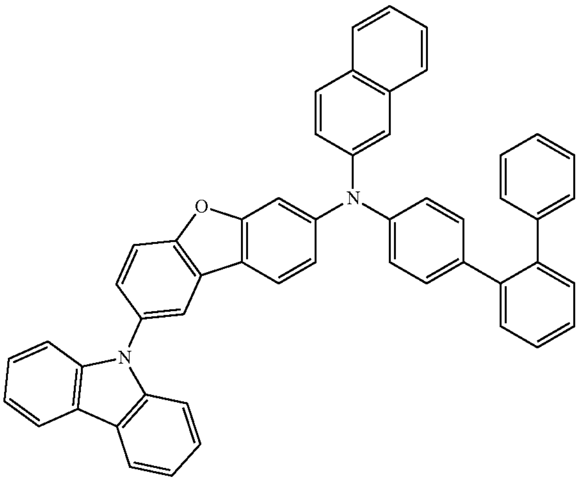
B10
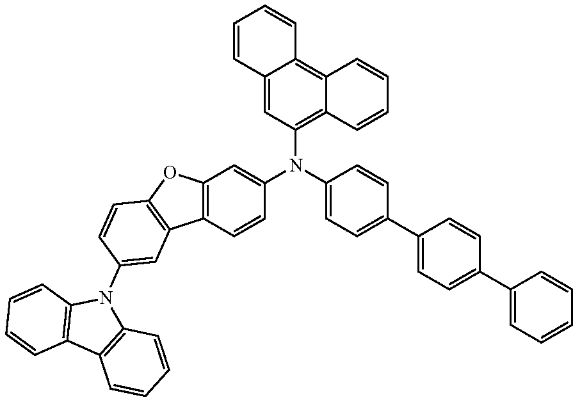

-continued
B11
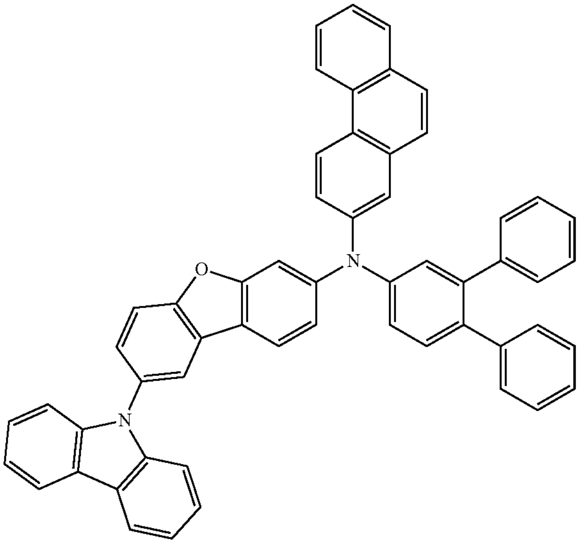
B12
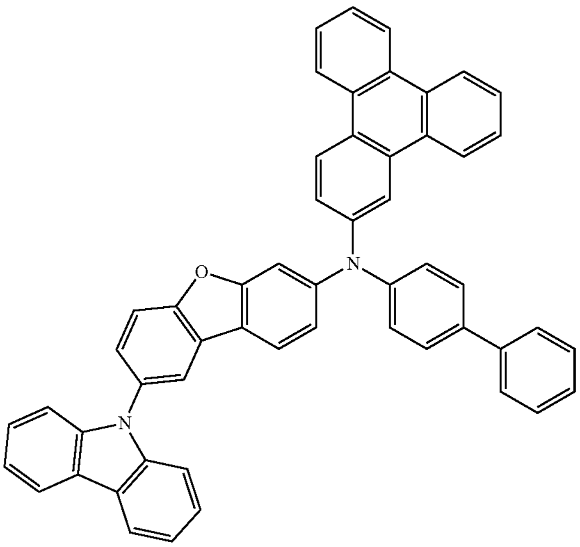
-continued
B13
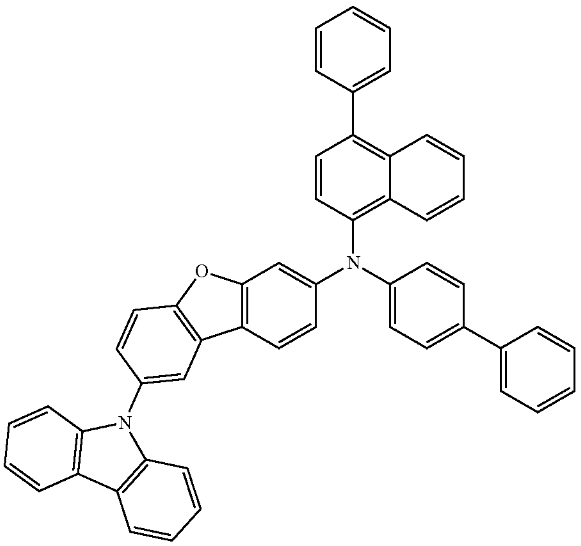
B14
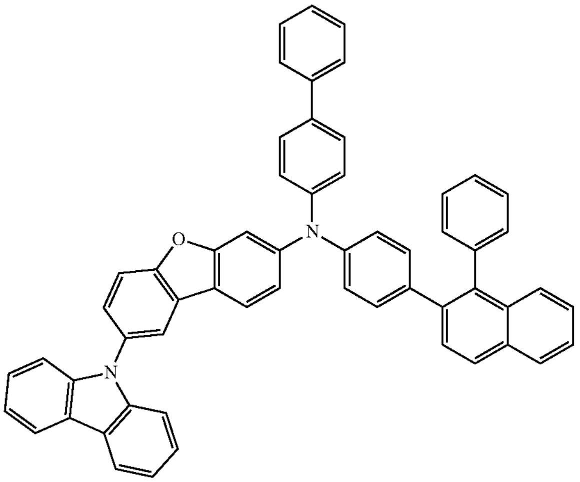
B15
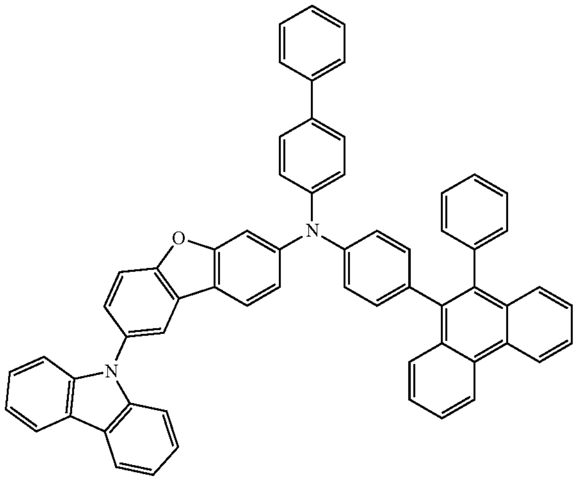

-continued
B16
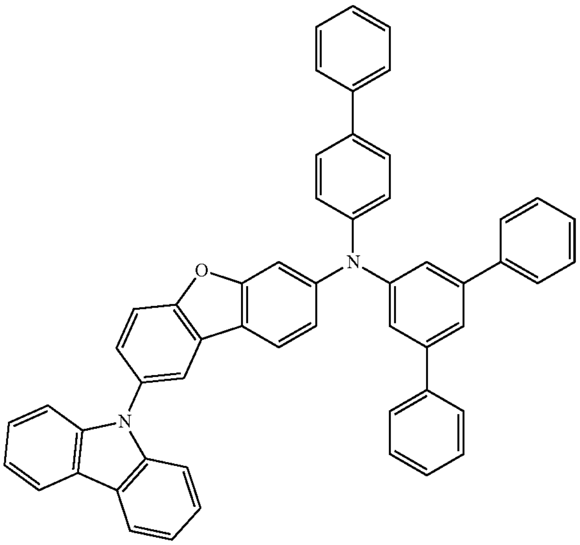
B17
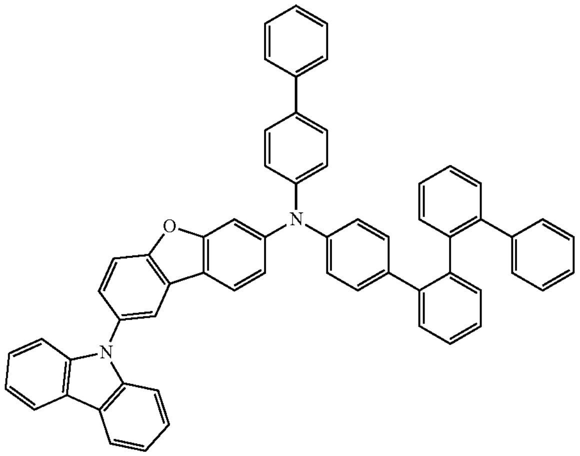
B18
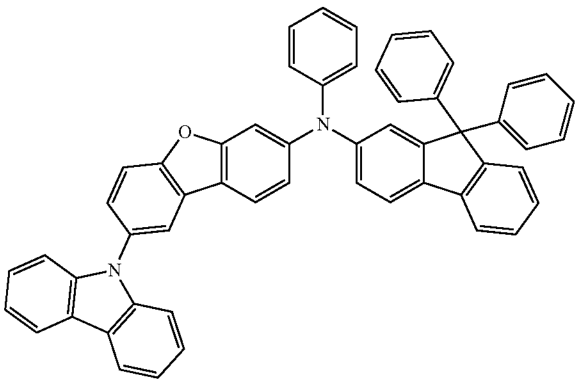
-continued
B19
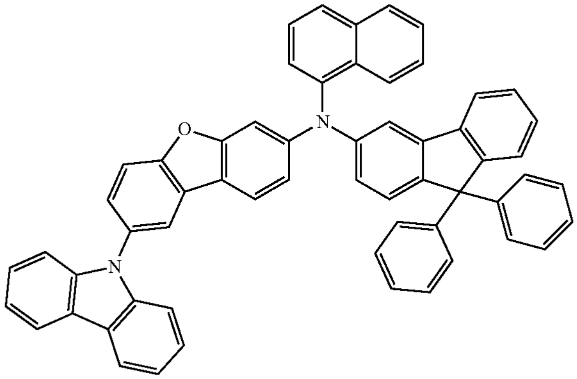
B20
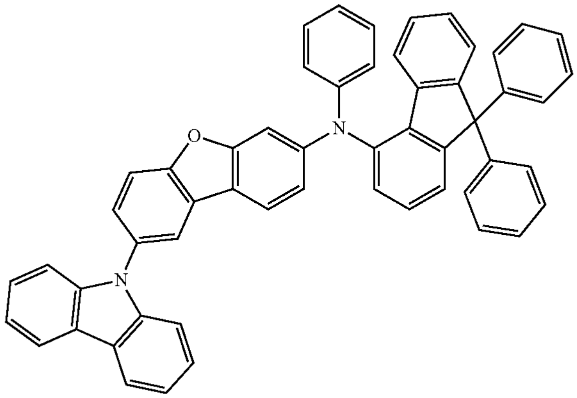
B21
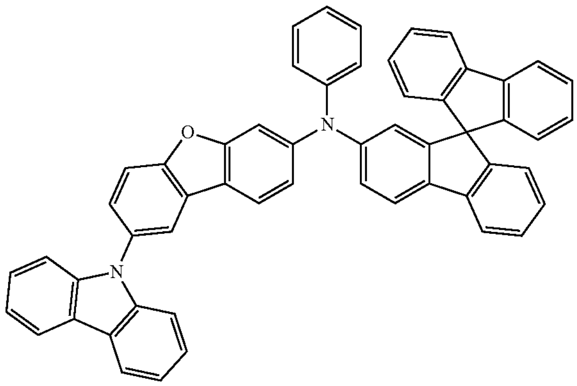

-continued
B22
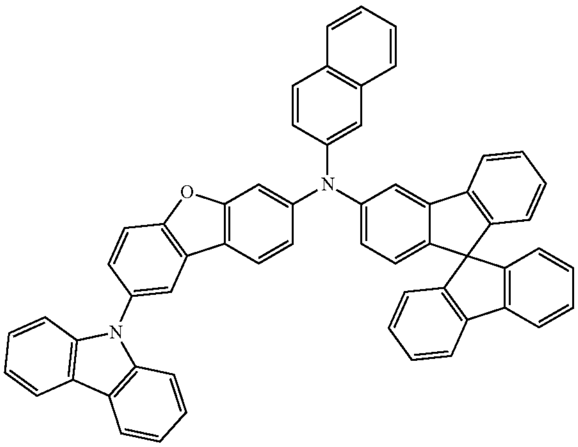
B23
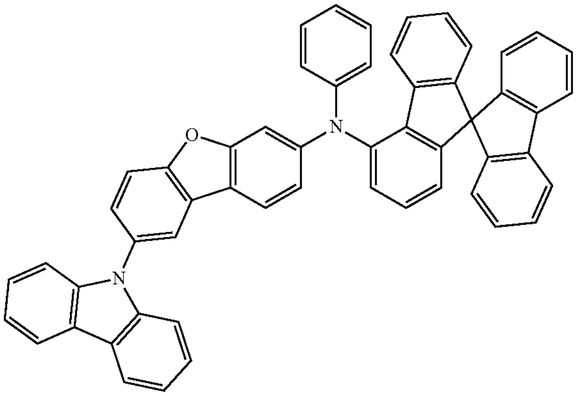
B24
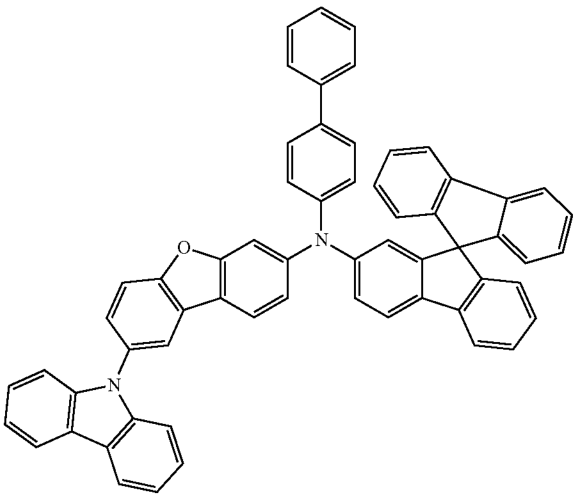
-continued
B25
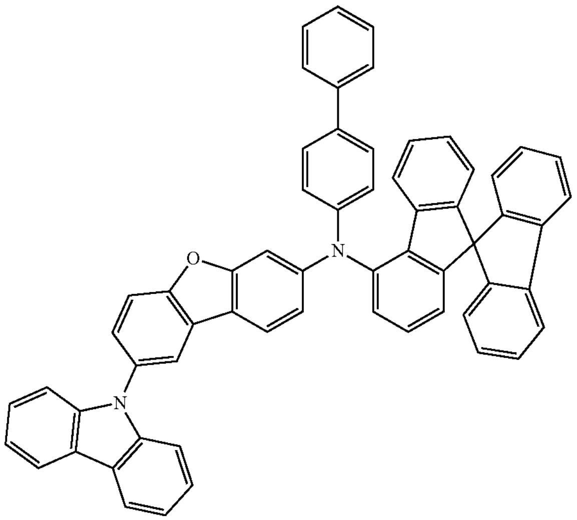
B26
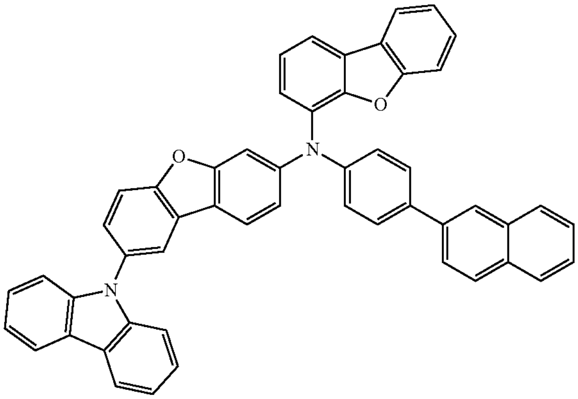
B27
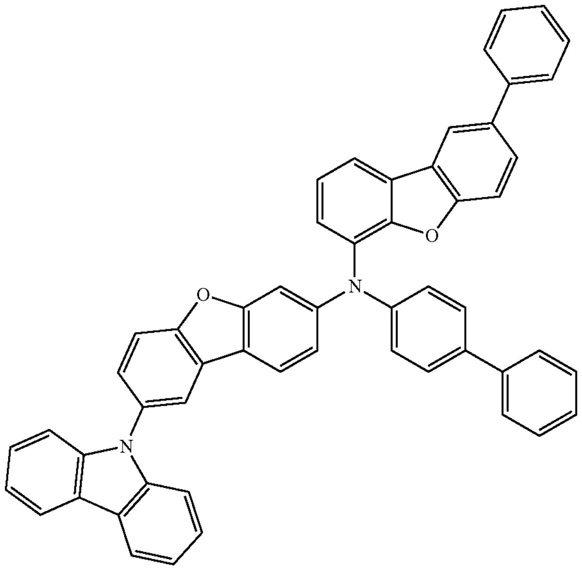

-continued
B28
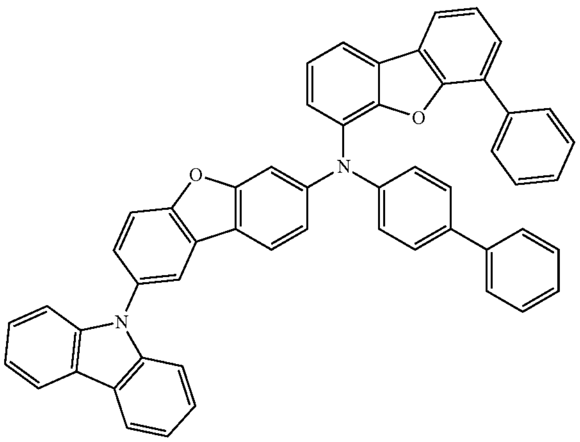
B29
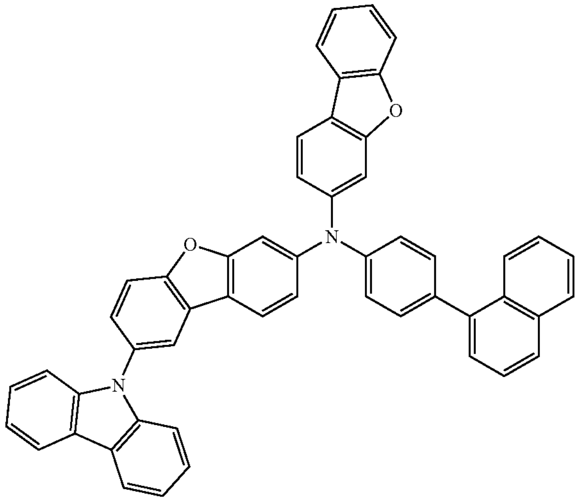
B30
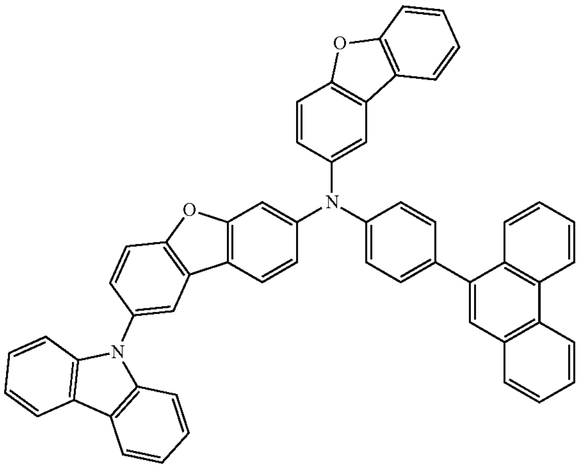
-continued
B31
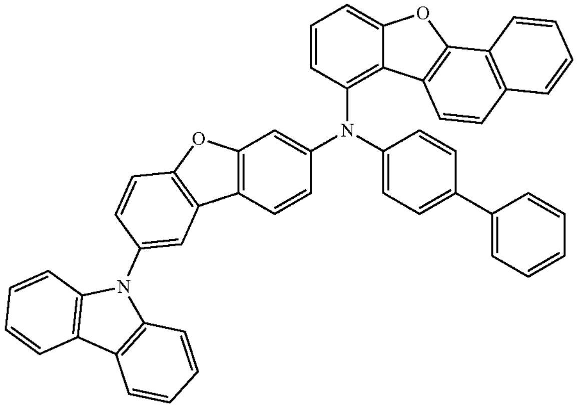
B32
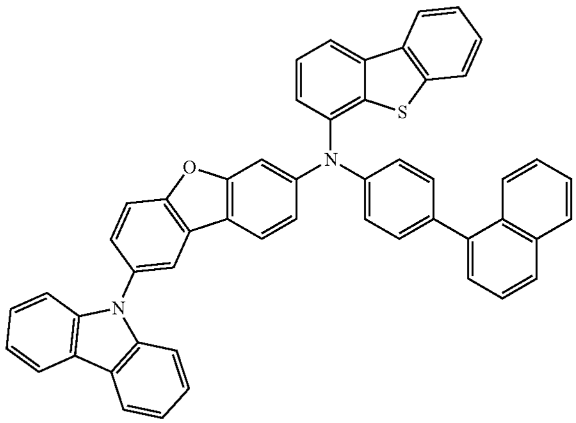
B33
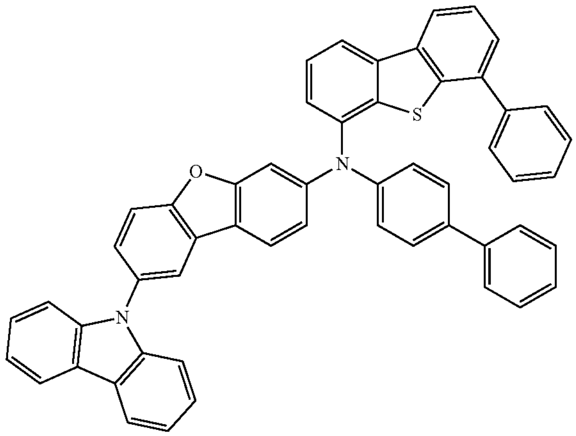

-continued
B34
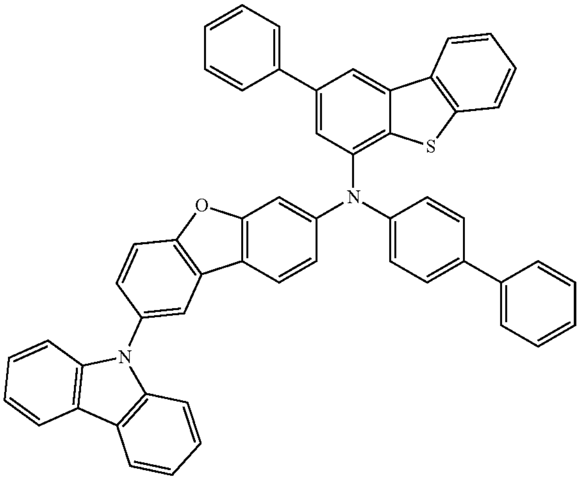
B35
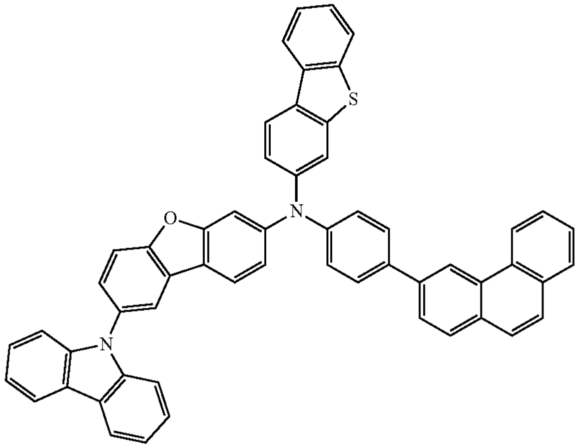
B36
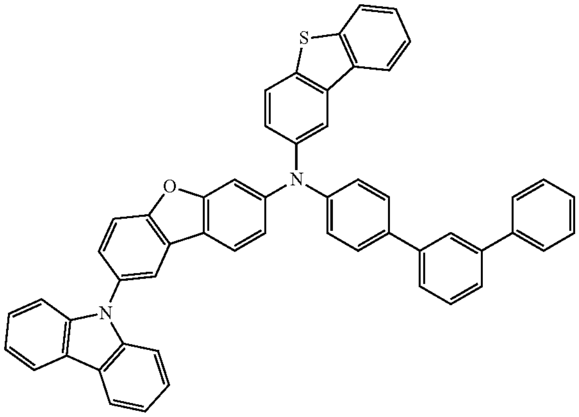
-continued
B37
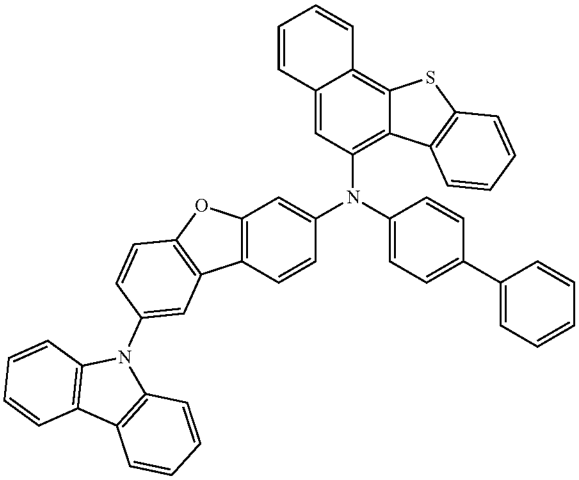
B38
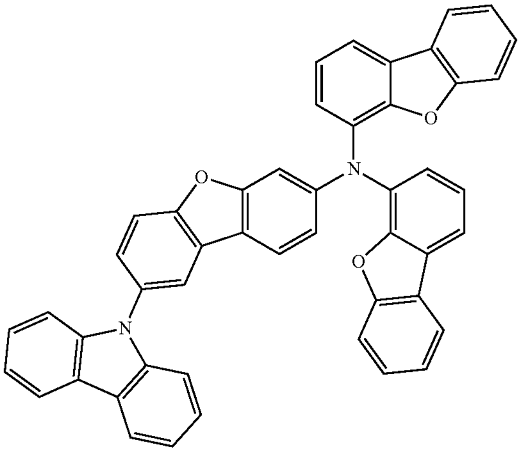
B39
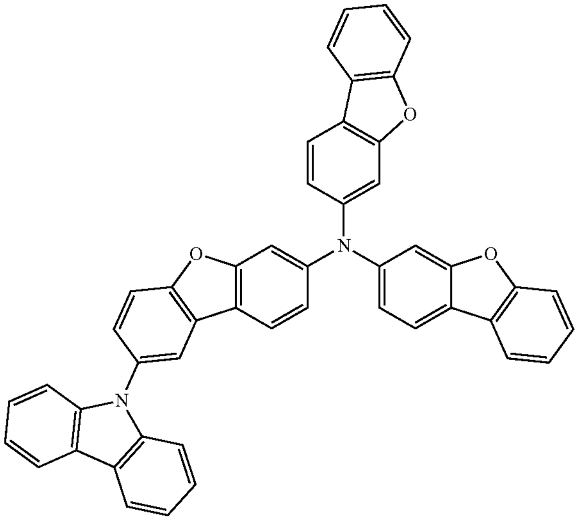

-continued
B40
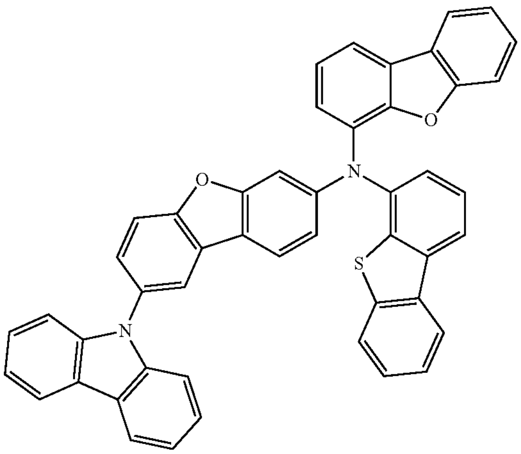
B41
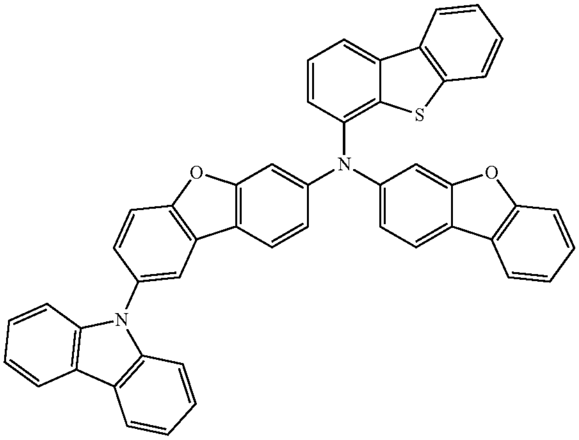
B42
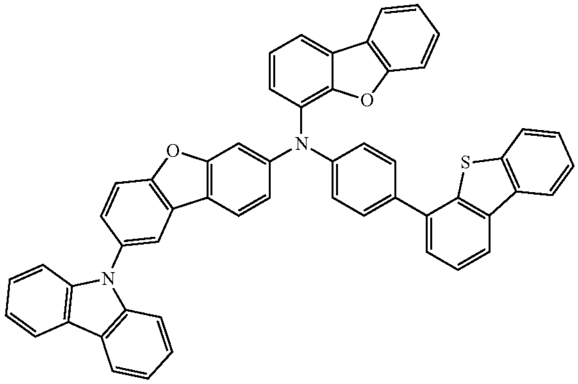
-continued
B43
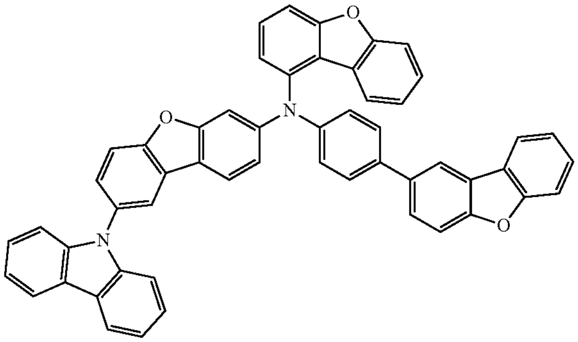
B44
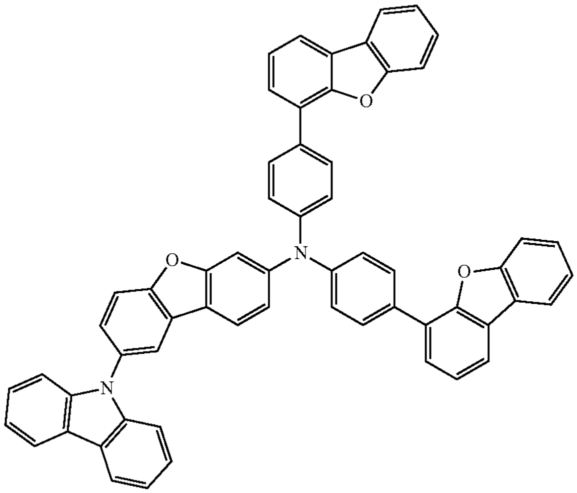
B45
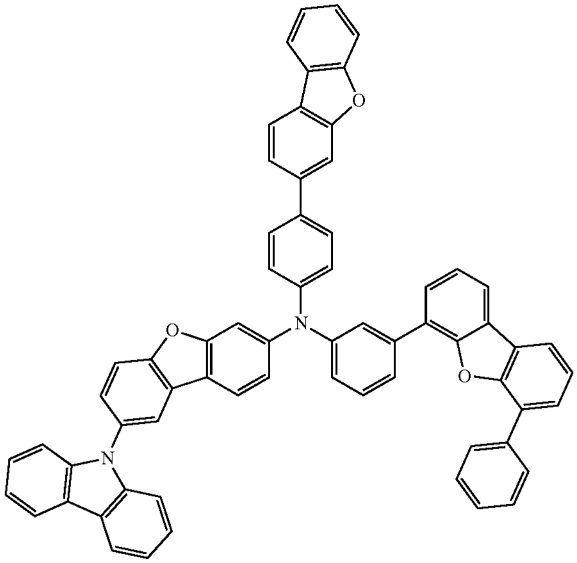

-continued
B46
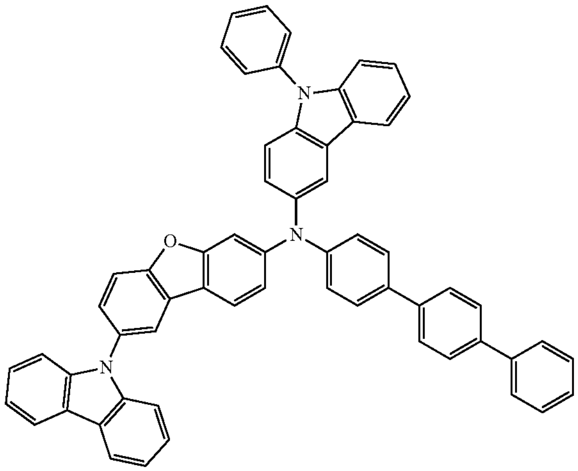
B47
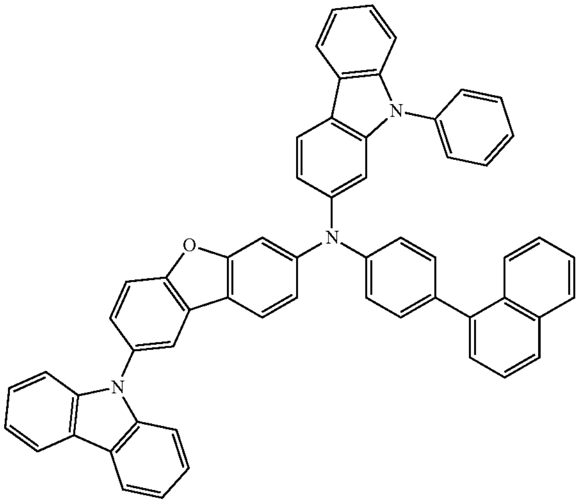
B48
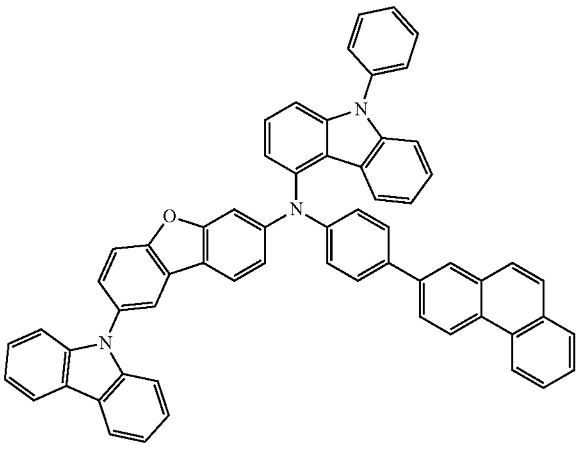
B49
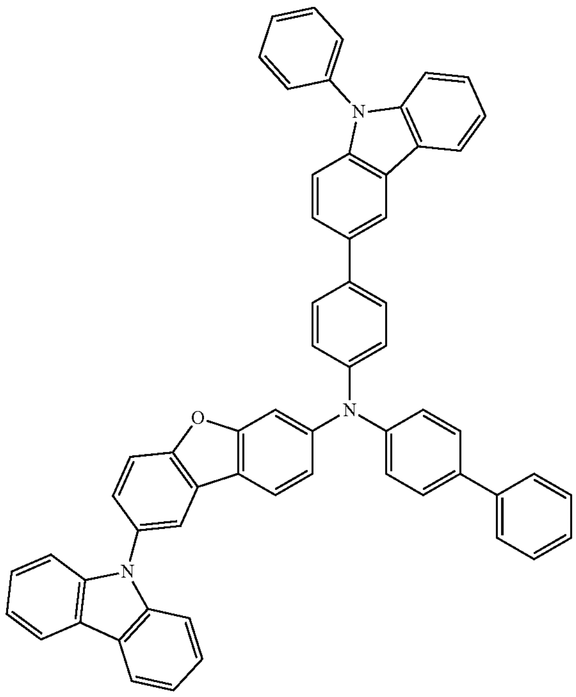
B50
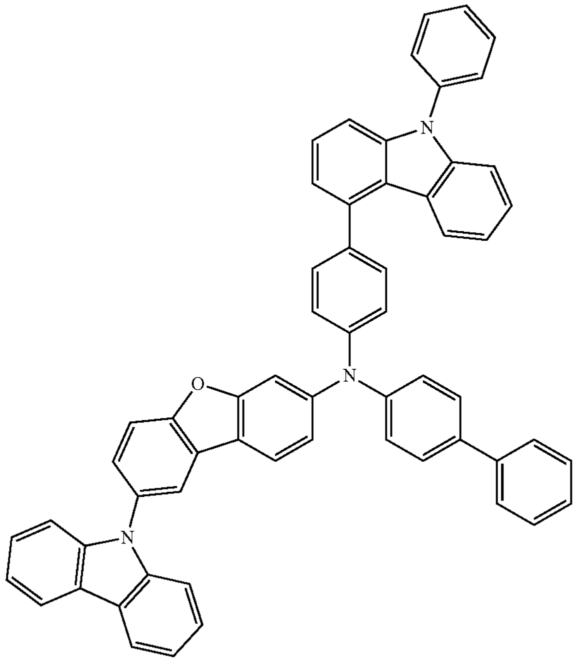

-continued
B51
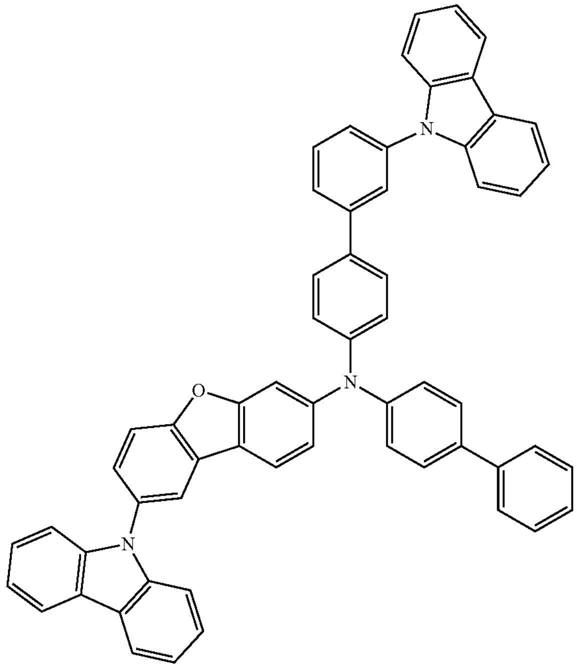
B52
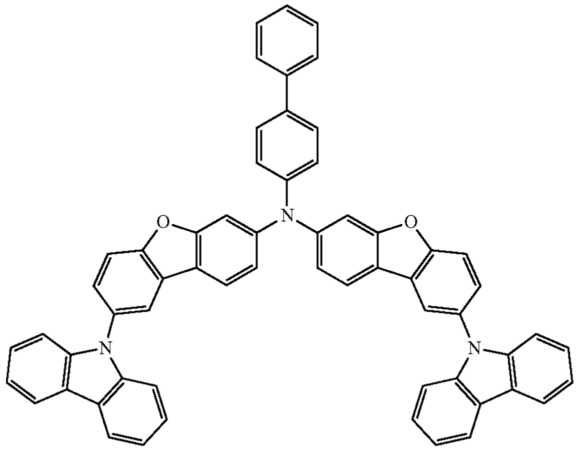
-continued
B53
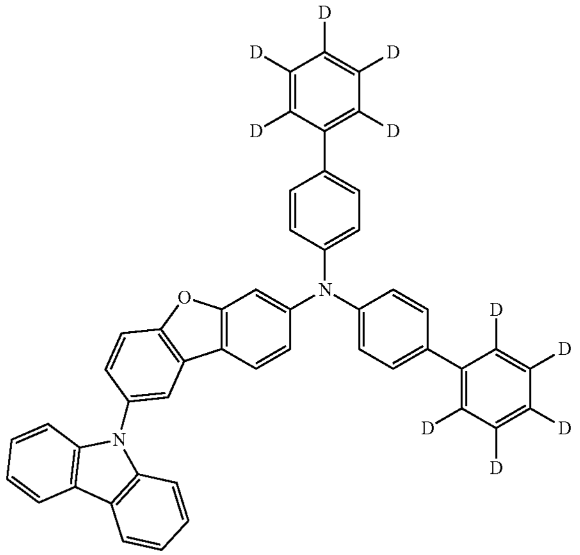
B54
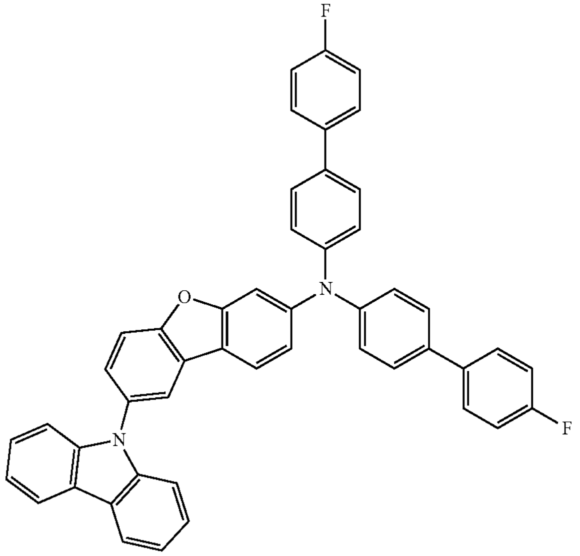
B55
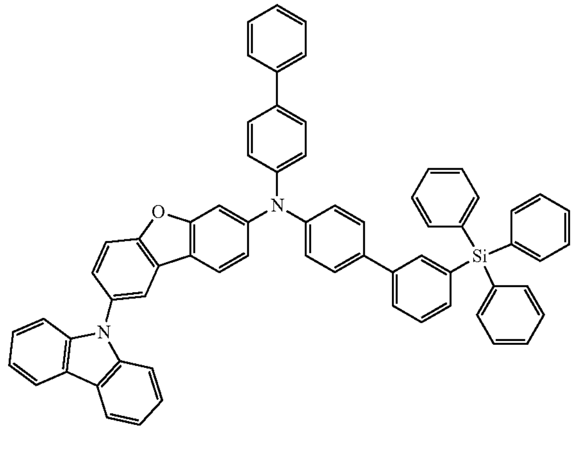

-continued
B56
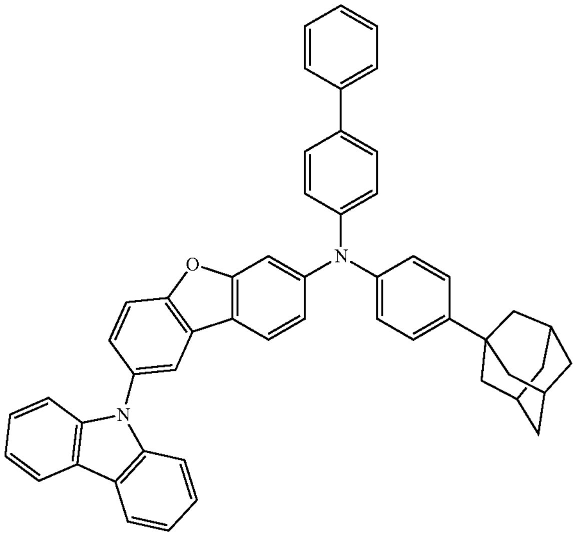
B57
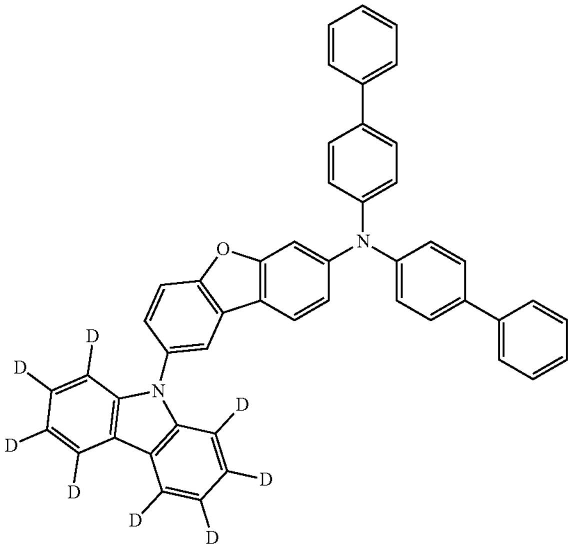
-continued
B58
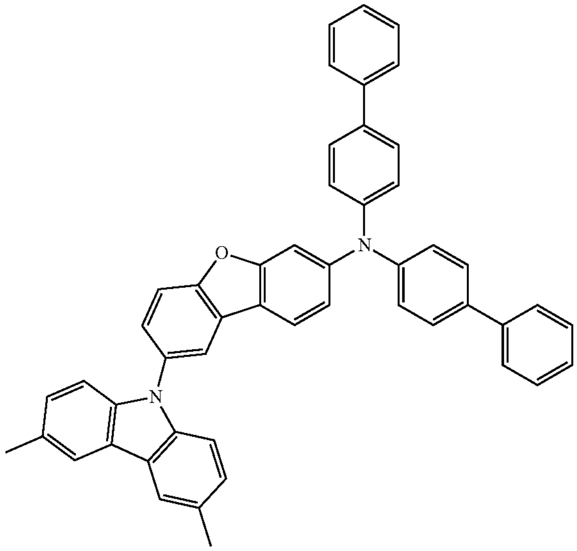
B59
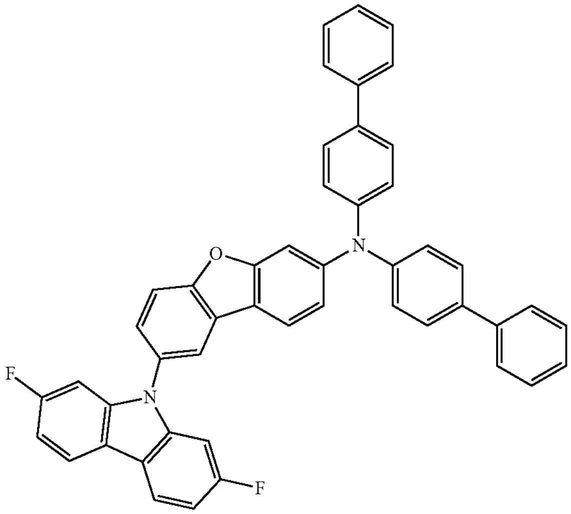

-continued
B60
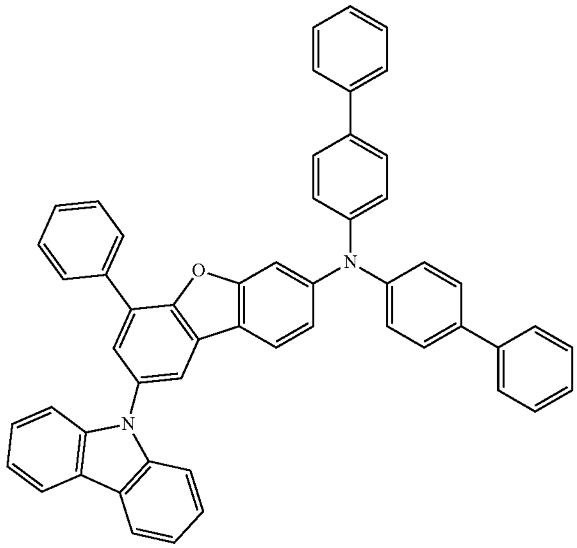
B61
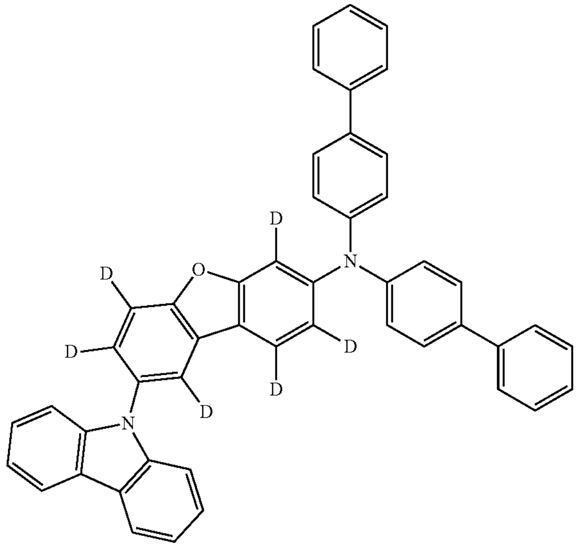
-continued
B62
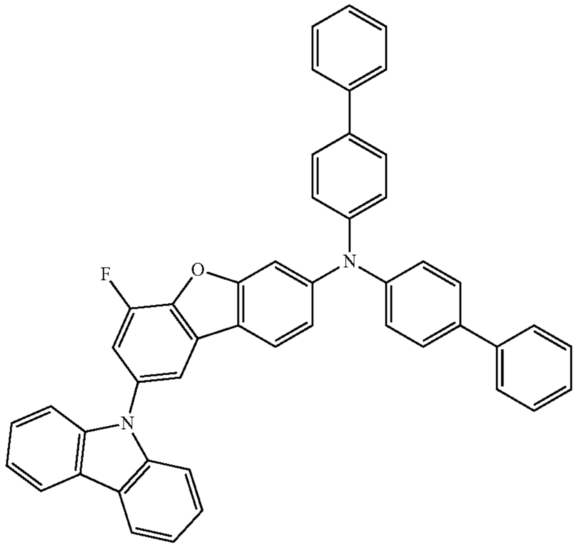
B63
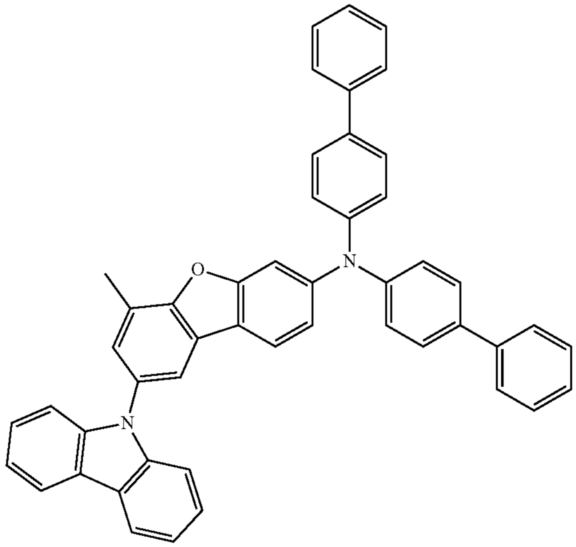
C1
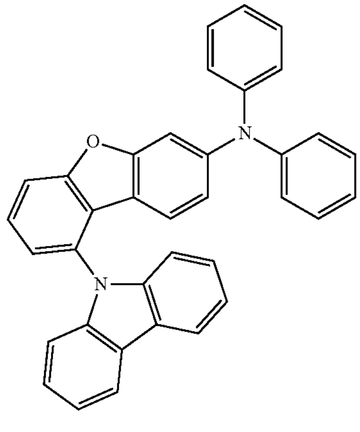

-continued
C2
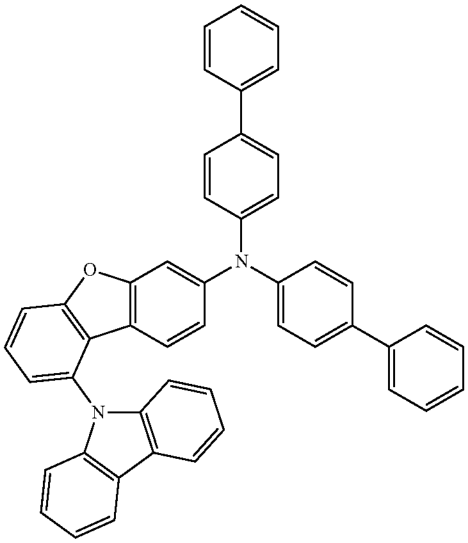
C3
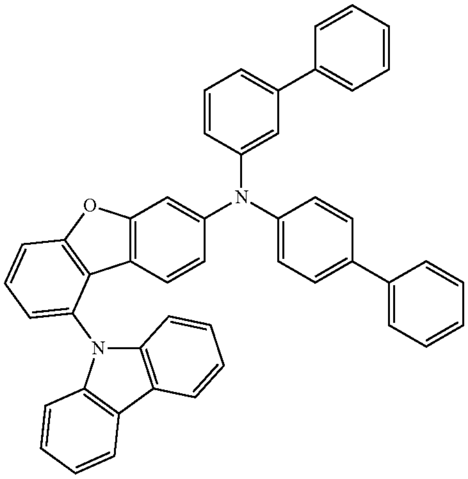
C4
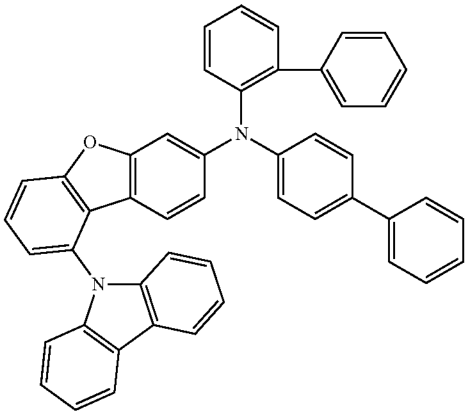
-continued
C5
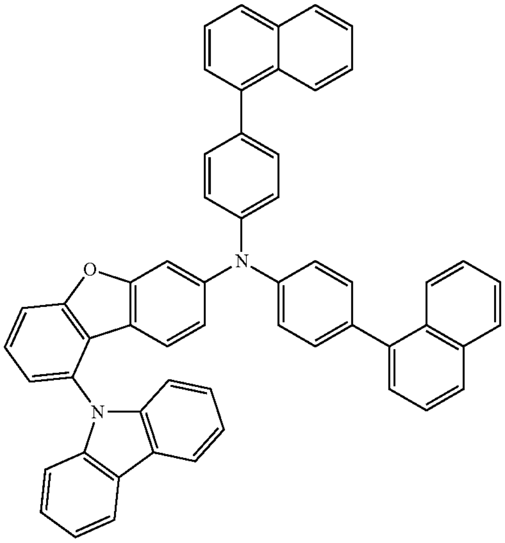
C6
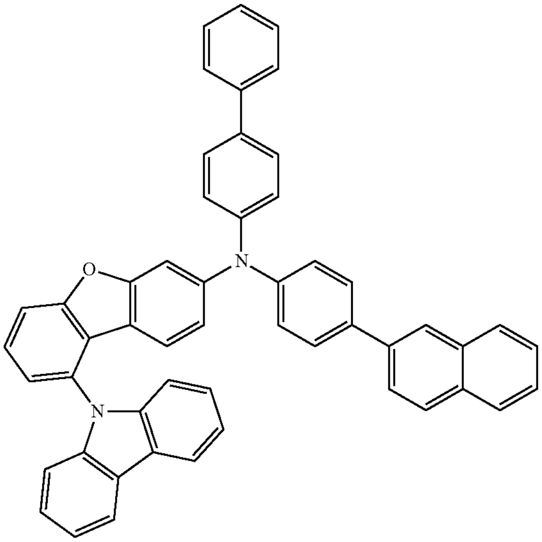

-continued
C7
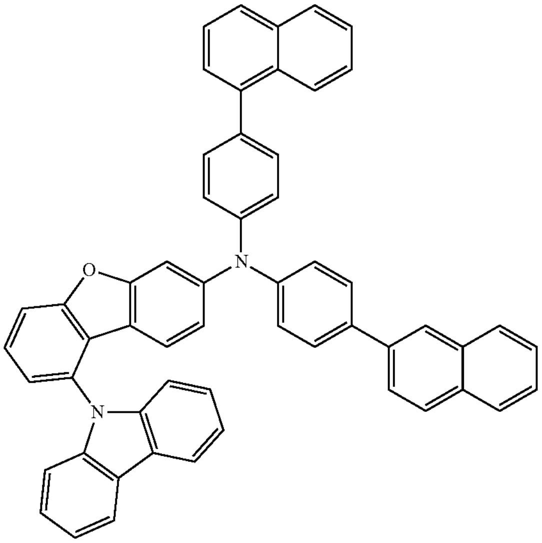
C8
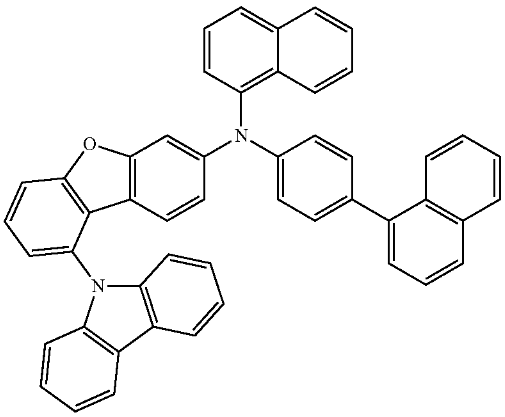
C9
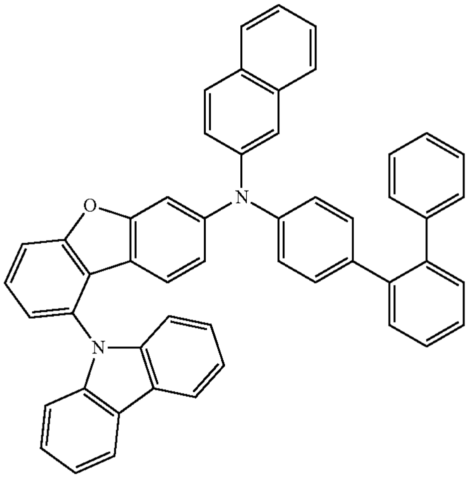
-continued
C10
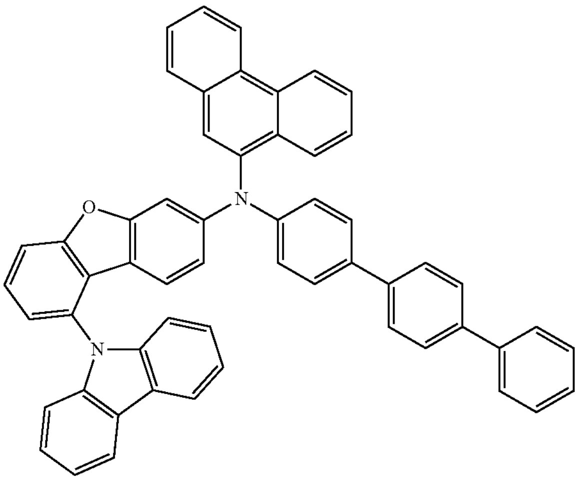
C11
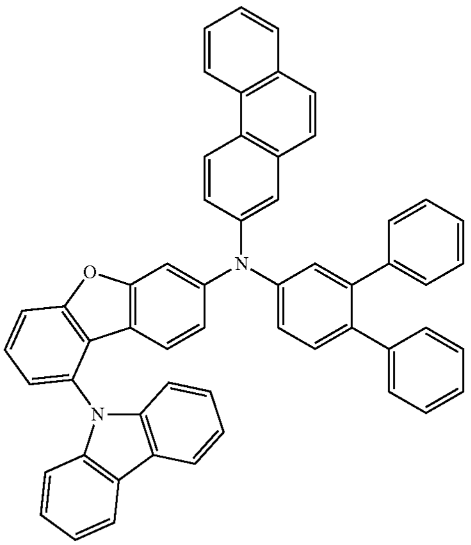
C12
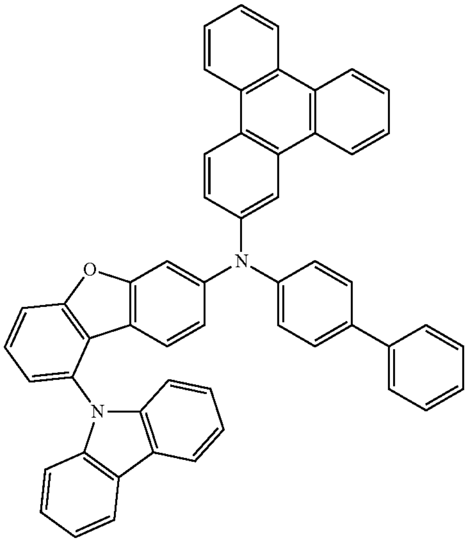

-continued
C13
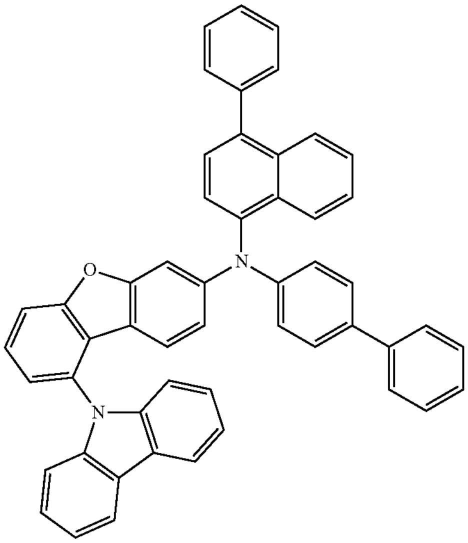
C14
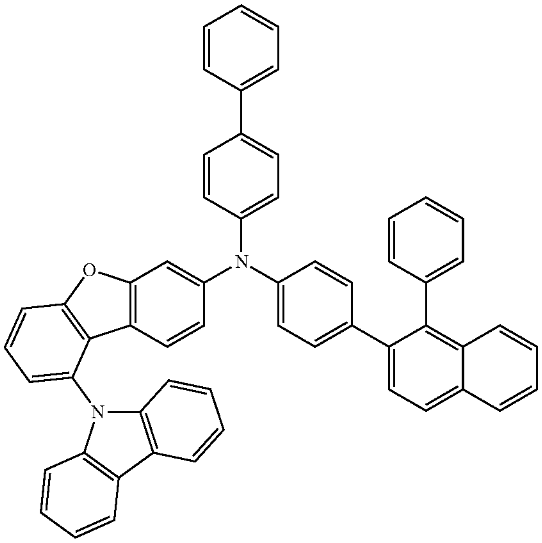
C15
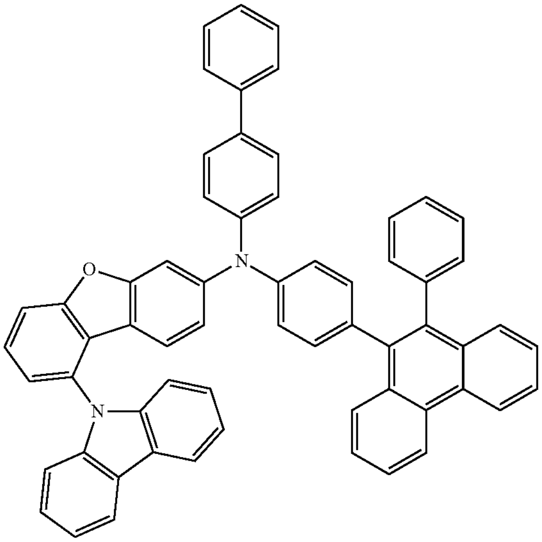
-continued
C16
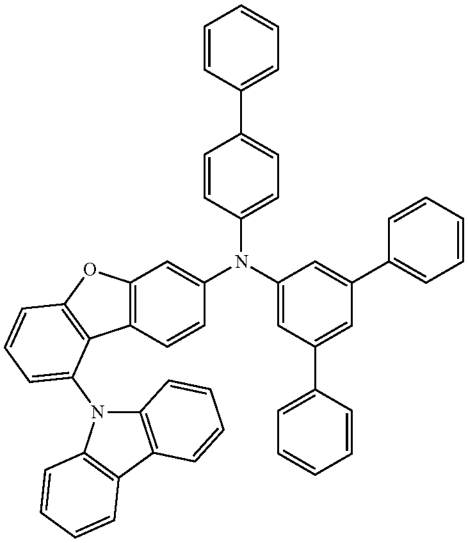
C17
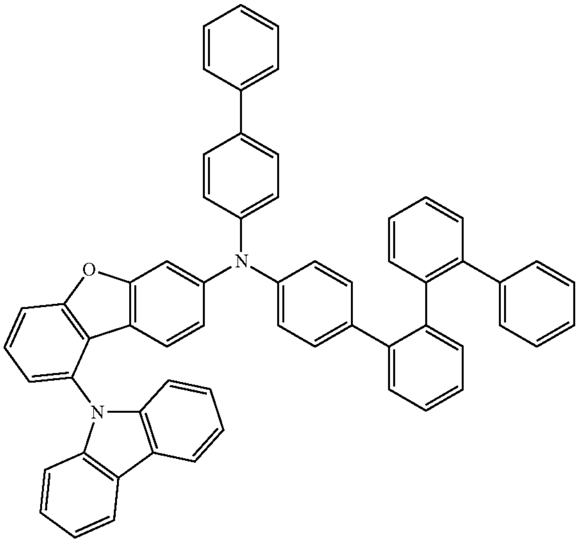
C18
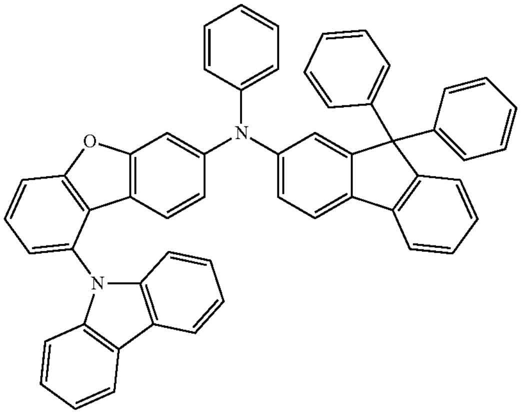

-continued
C19
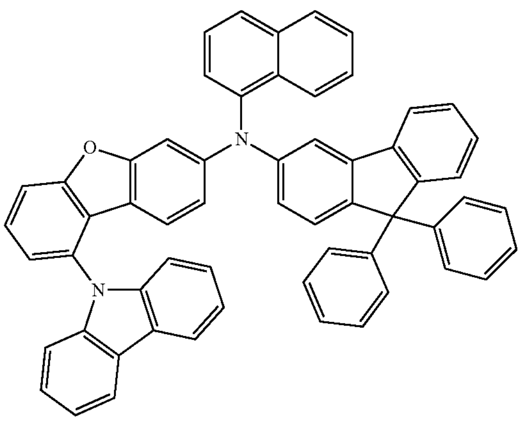
C20
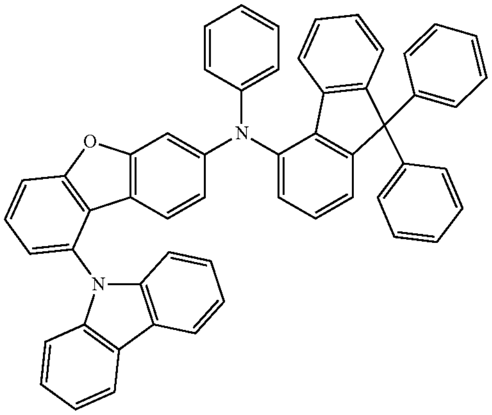
C21
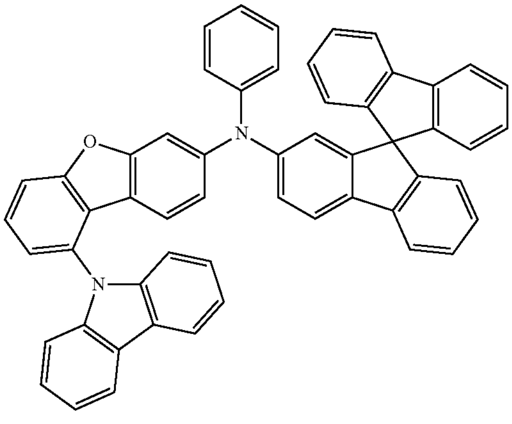
-continued
C22
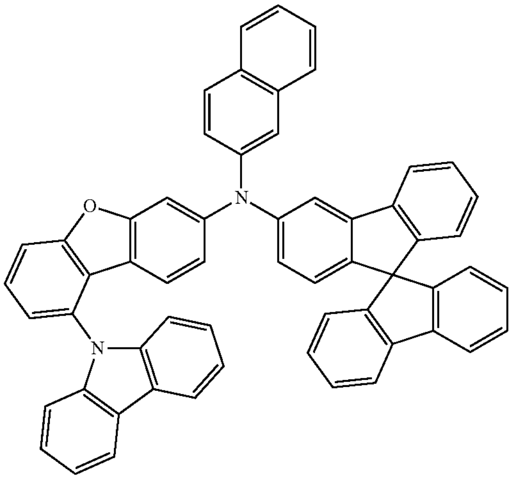
C23
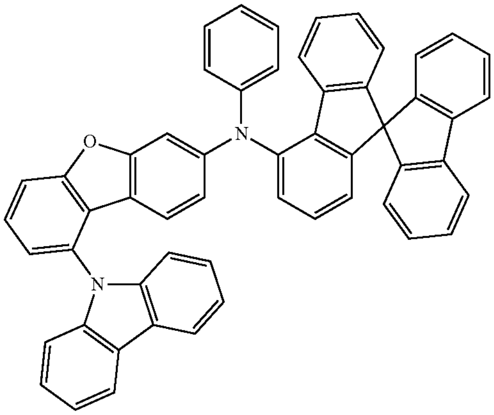
C24
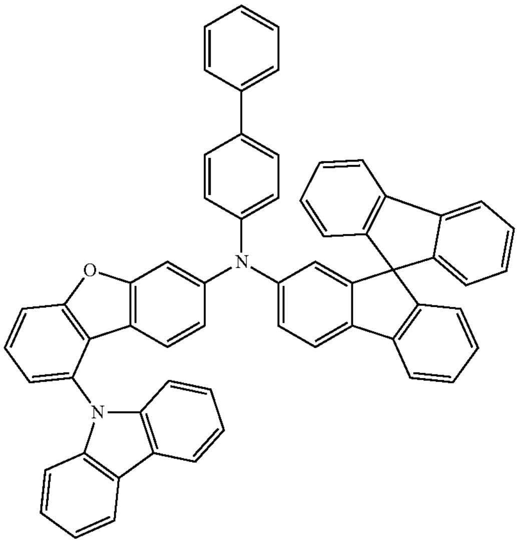

-continued
C25
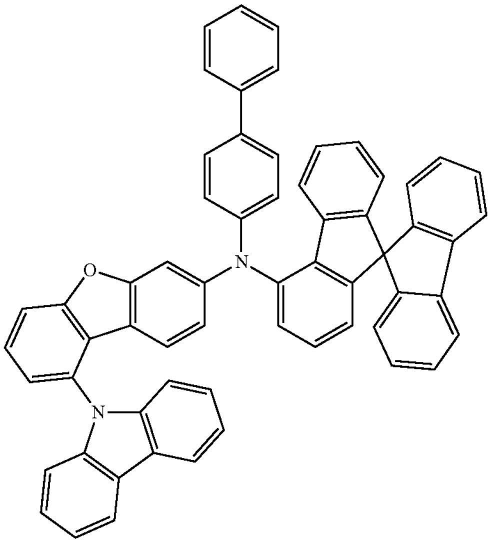
C26
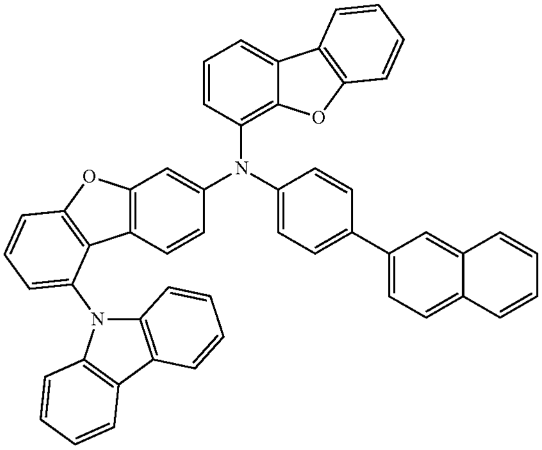
C27
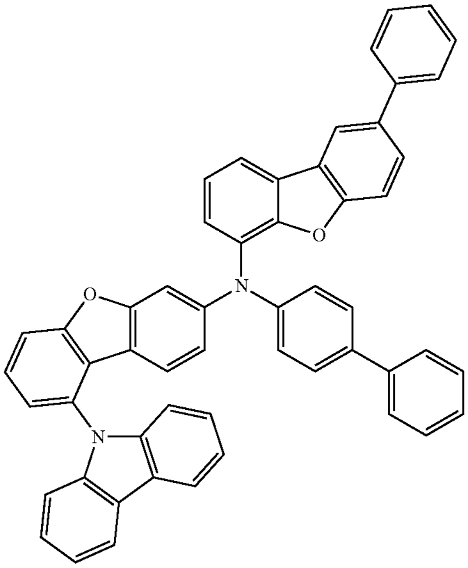
-continued
C28
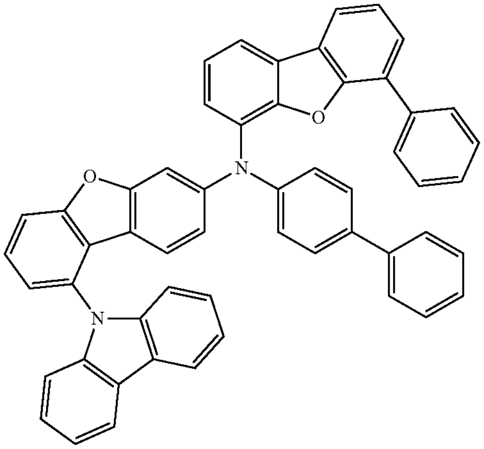
C29
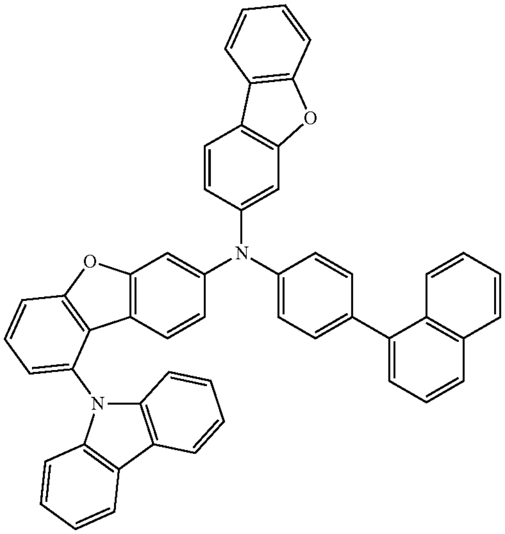
C30
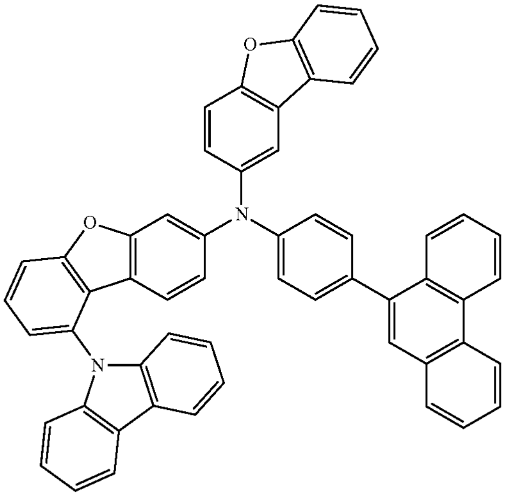

-continued
C31
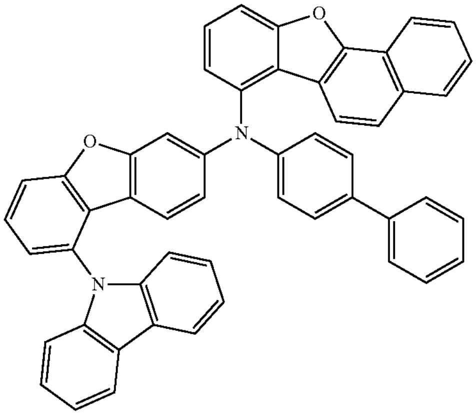
C32
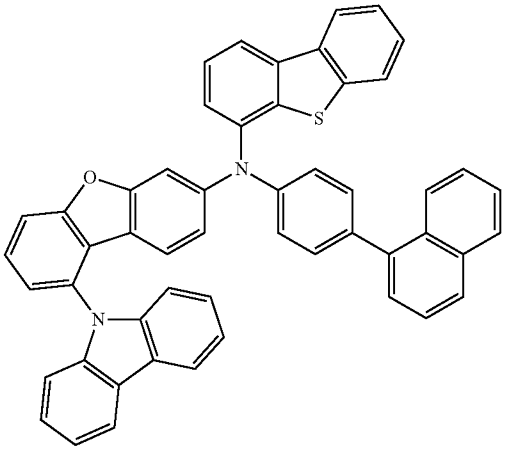
C33
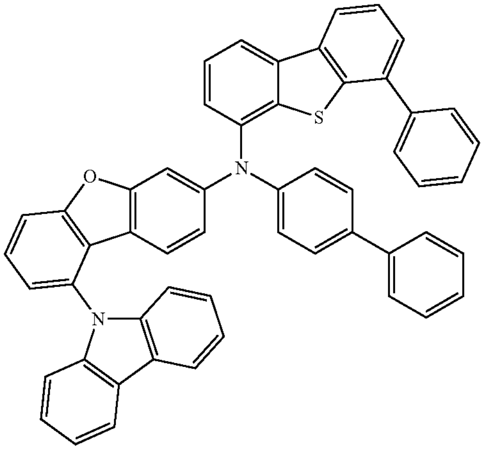
-continued
C34
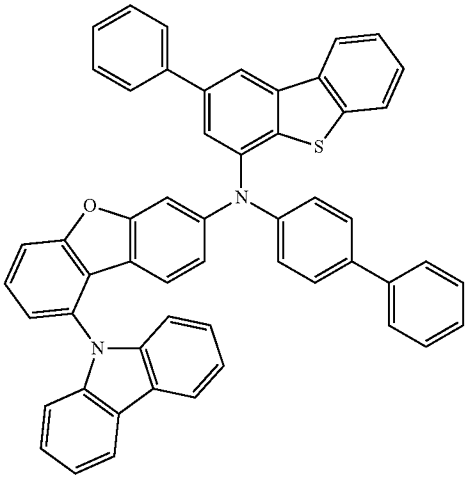
C35
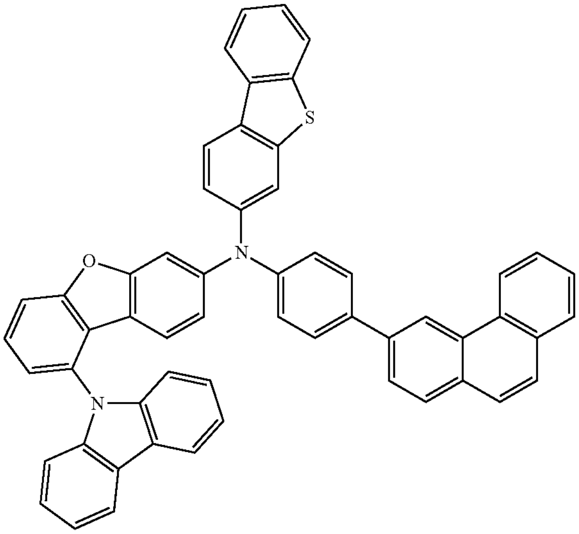
C36
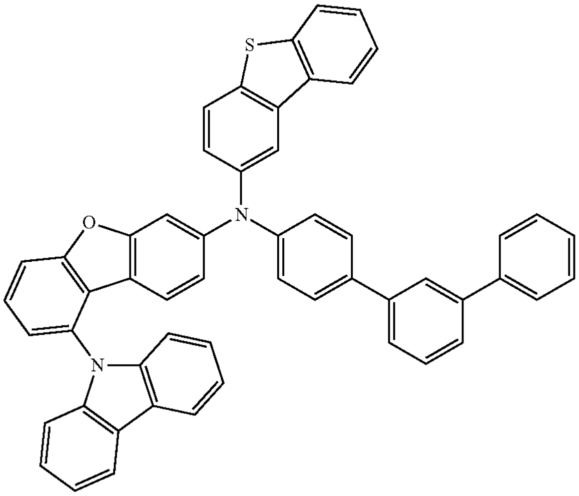

-continued
C37
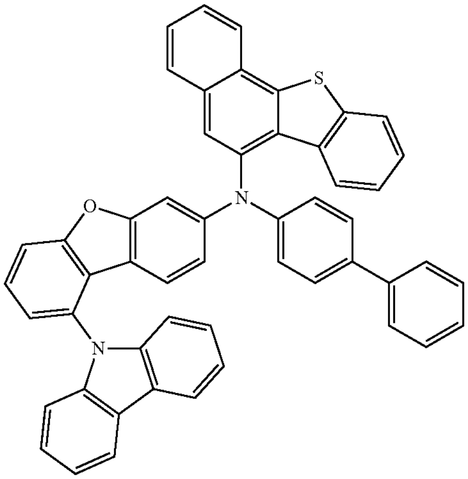
C38
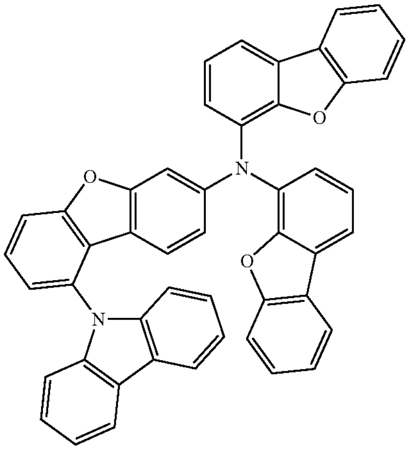
C39
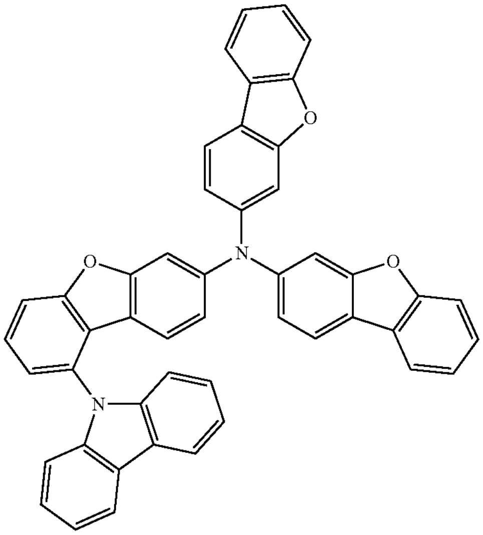
-continued
C40
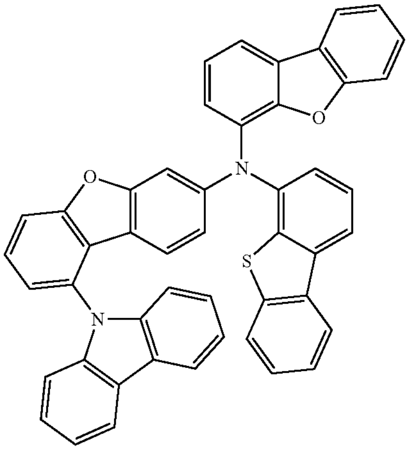
C41
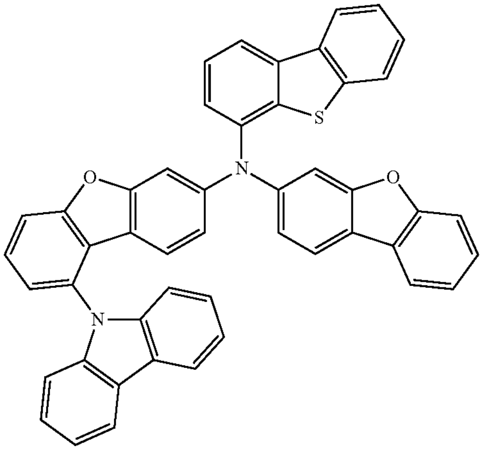
C42
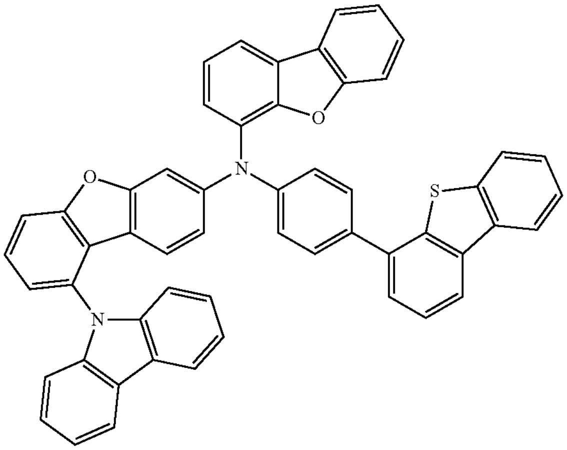

-continued
C43
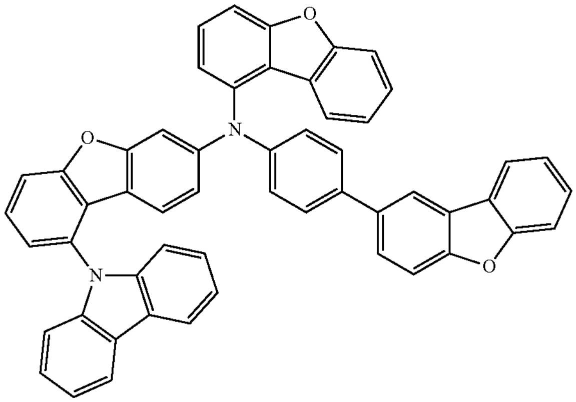
C44
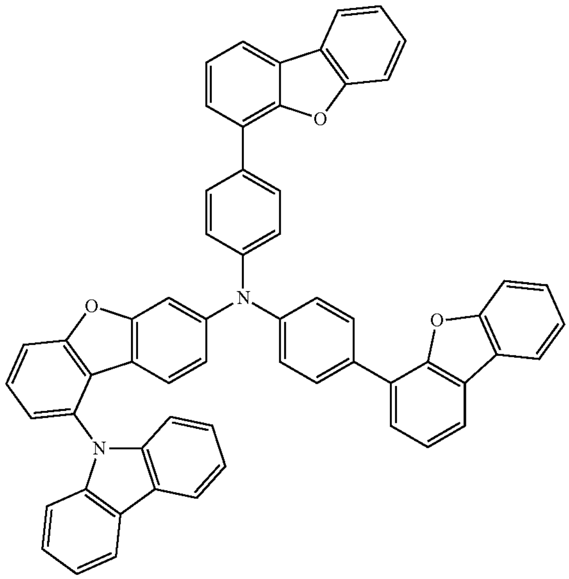
-continued
C45
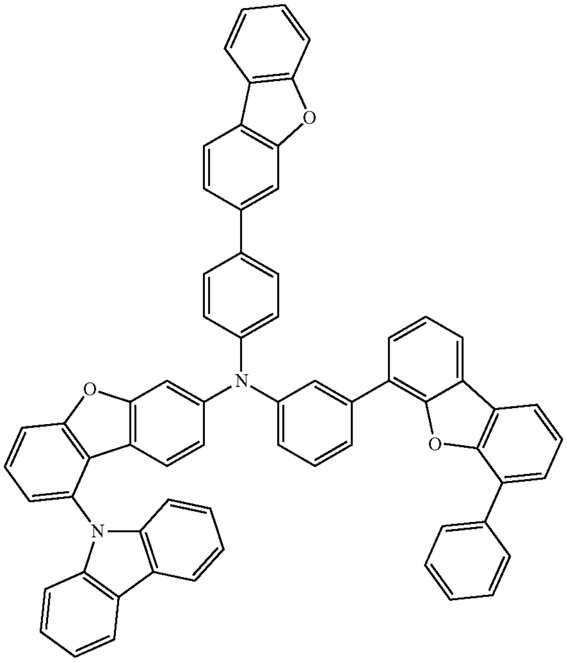
C46
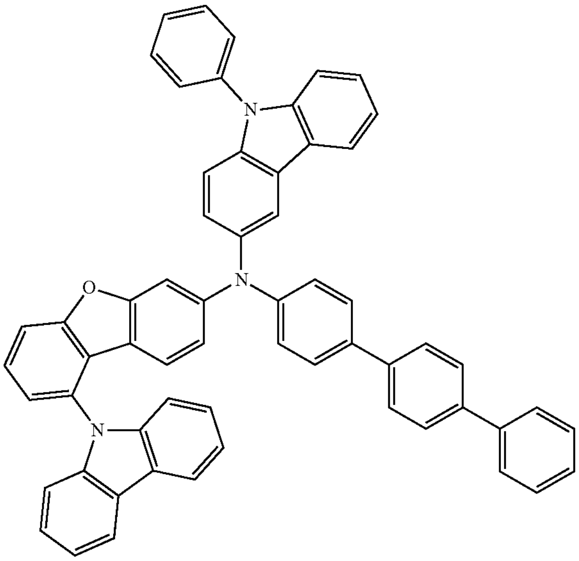

-continued
C47
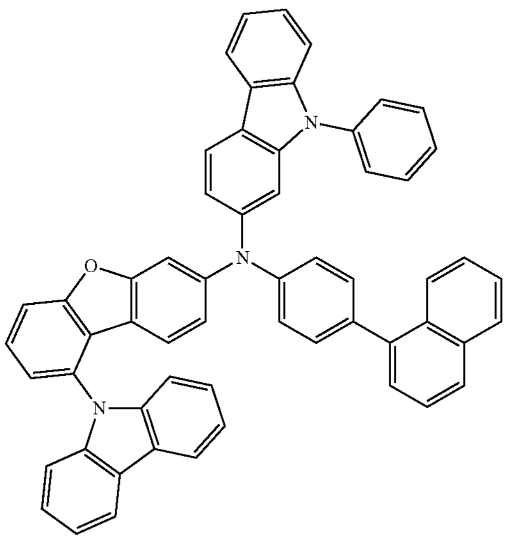
C48
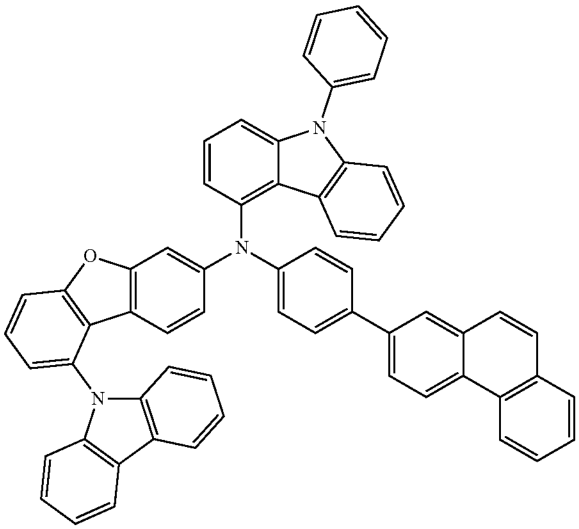
-continued
C49
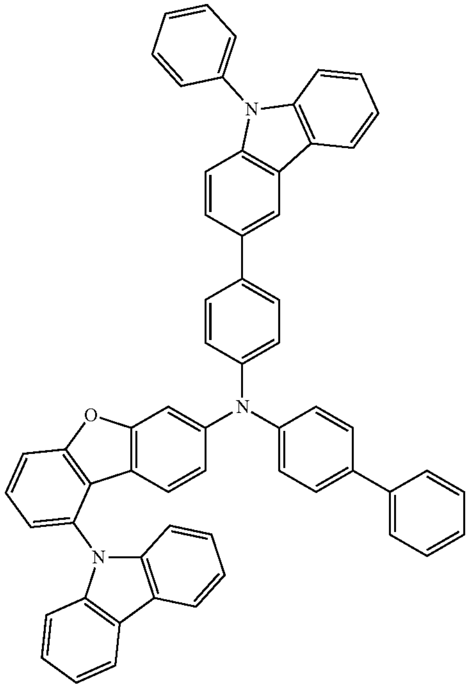
C50
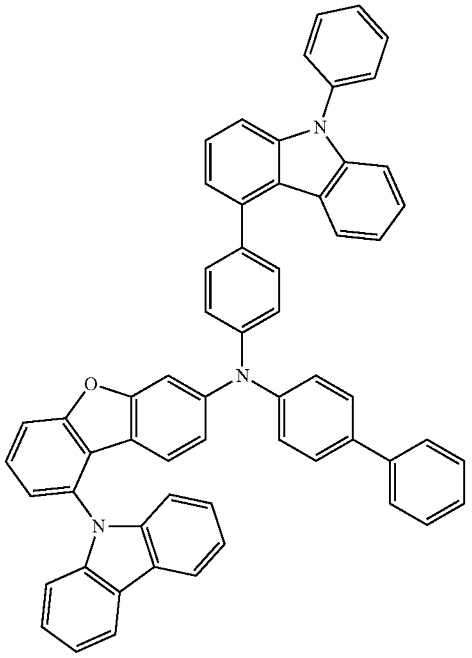

-continued
C51
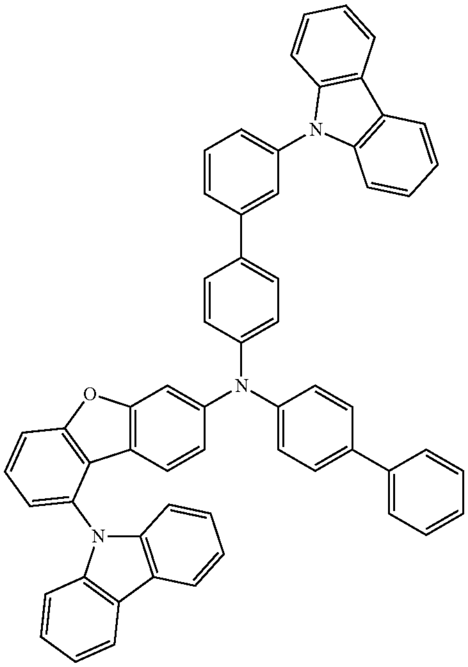
C52
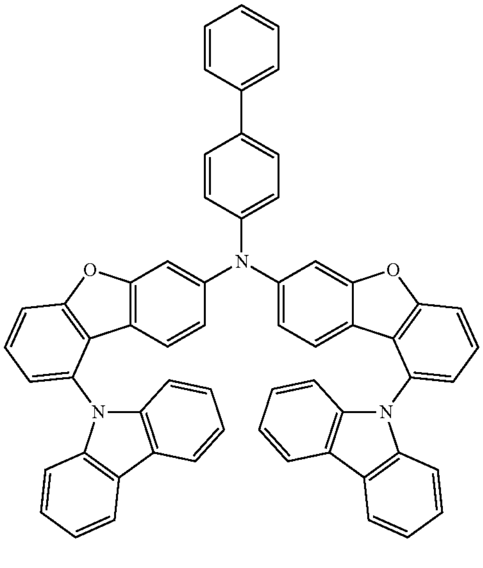
-continued
C53
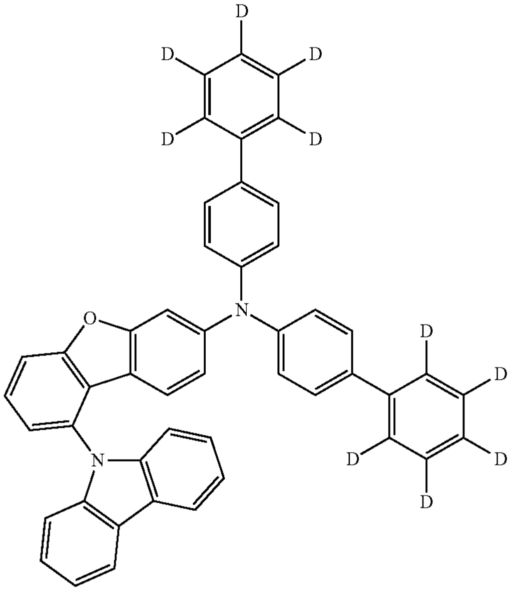
C54
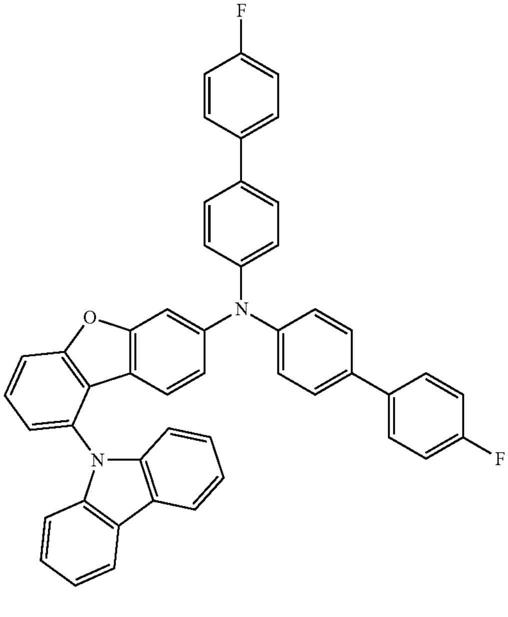

-continued
C55
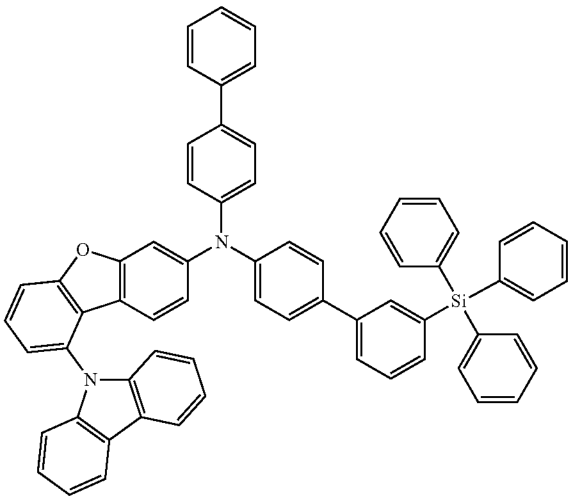
C56
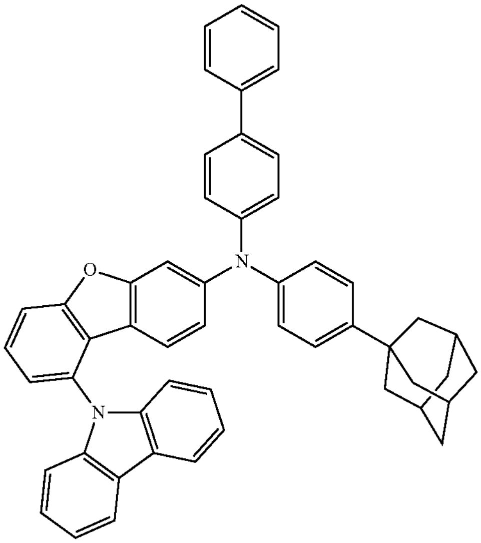
C57
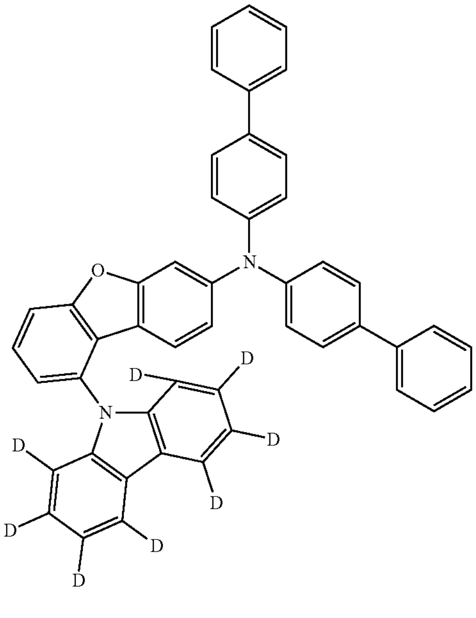
-continued
C58
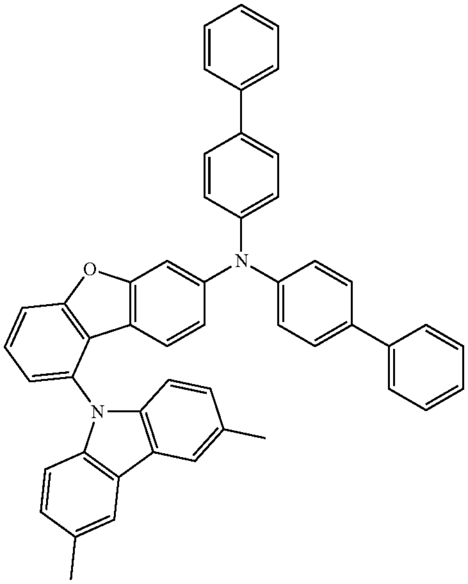
C59
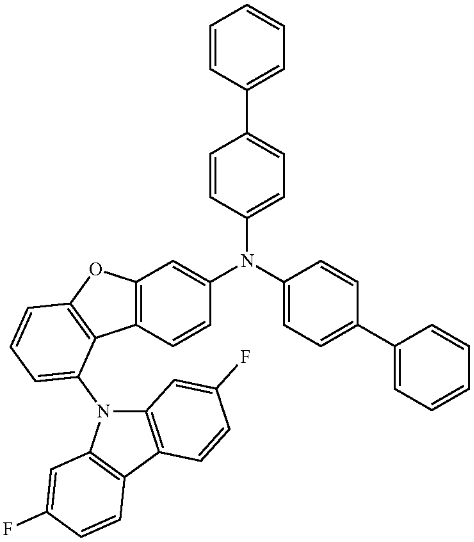

-continued

C60

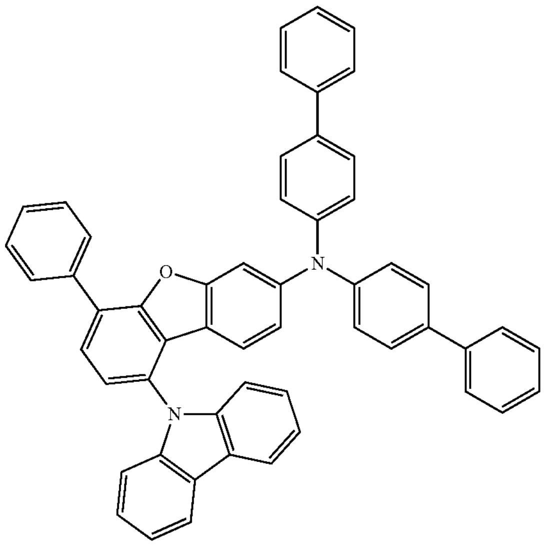

C61

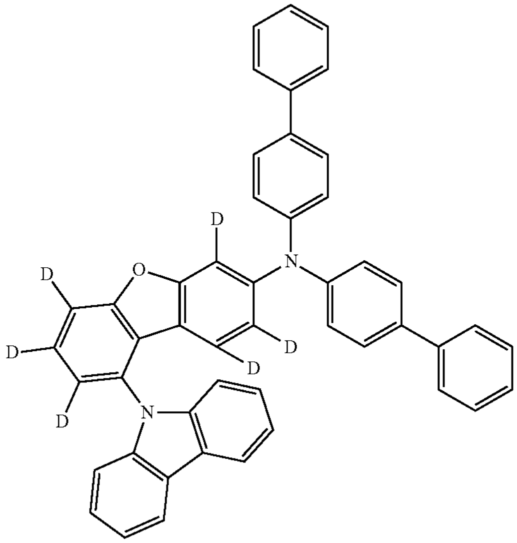

C62

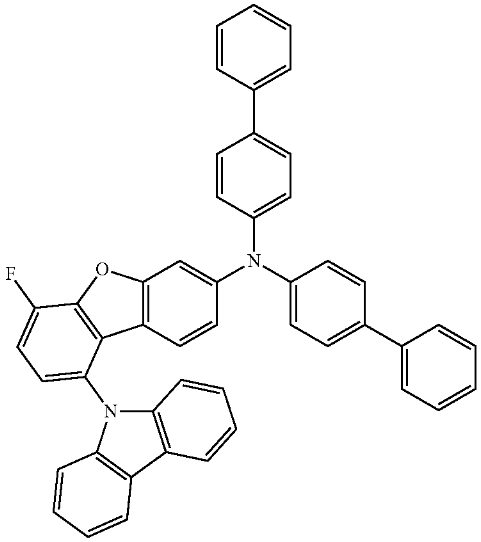

-continued

C63

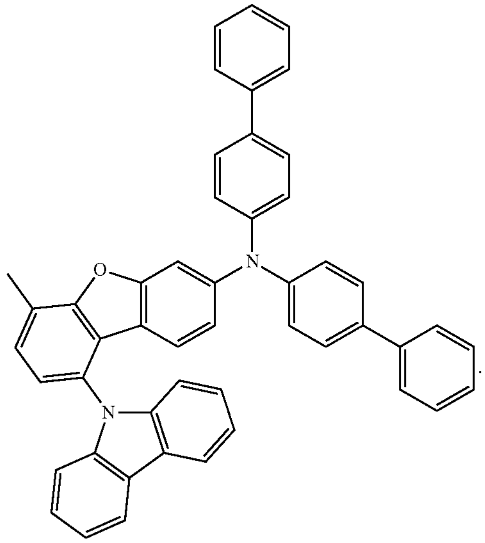

13. An amine compound of Formula 1:

Formula 1

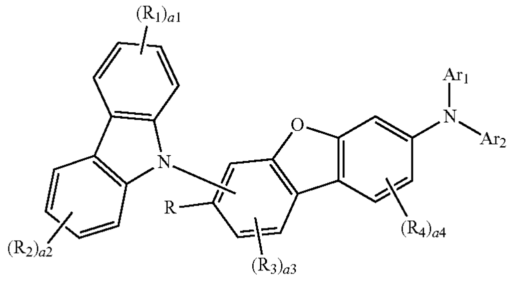

in Formula 1,

R is a hydrogen atom or a deuterium atom, a1 and a2 are each, independently from one another, an integer of 0 to 4, $R_1$ and $R_2$ are each, independently from one another, a hydrogen atom, a deuterium atom, a halogen atom, or a substituted or unsubstituted alkyl group of 1 to 20 carbon atoms, a3 is an integer of 0 to 2, a4 is an integer of 0 to 3, $R_3$ and $R_4$ are each, independently from one another, a hydrogen atom, a deuterium atom, a halogen atom, a substituted or unsubstituted alkyl group of 1 to 20 carbon atoms, or a substituted or unsubstituted aryl group of 6 to 40 ring-forming carbon atoms, $Ar_1$ and $Ar_2$ are each, independently from one another, a substituted or unsubstituted aryl group of 6 to 40 ring-forming carbon atoms, or a substituted or unsubstituted heteroaryl group of 2 to 40 ring-forming carbon atoms, with the proviso that $R_1$ to $R_4$, $Ar_1$ and $Ar_2$ do not comprise an amine group as a substituent, with the proviso that the amine compound does not comprise a substituted or unsubstituted thiophenyl group, and with the proviso that the thiophenyl group is not fused to another ring.

14. The amine compound of claim 13, wherein Formula 1 is of Formula 2-1:

Formula 2-1

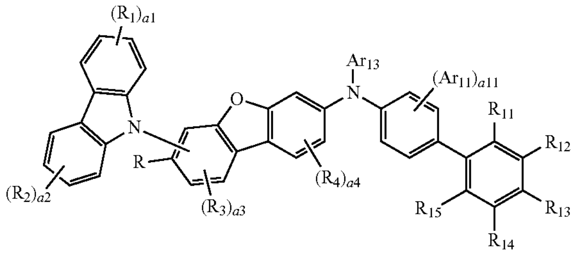

in Formula 2-1, a11 is an integer of 0 to 4, $Ar_{11}$ is a hydrogen atom, a deuterium atom, or a substituted or unsubstituted aryl group of 6 to 40 ring-forming carbon atoms, $R_{11}$ to $R_{15}$ are each, independently from one another, a hydrogen atom, a deuterium atom, a halogen atom, a substituted or unsubstituted silyl group, a substituted or unsubstituted alkenyl group of 2 to 10 carbon atoms, a substituted or unsubstituted aryl group of 6 to 40 ring-forming carbon atoms, or a substituted or unsubstituted heteroaryl group of 2 to 40 ring-forming carbon atoms, or combined with an adjacent group to form a ring, $Ar_3$ is a substituted or unsubstituted aryl group of 6 to 40 ring-forming carbon atoms, or a substituted or unsubstituted heteroaryl group of 2 to 40 ring-forming carbon atoms, and a1 to a4, R, and $R_1$ to $R_4$ have, independently from one another, the same meaning as defined in Formula 1.

15. The amine compound of claim 4, wherein Formula 1 is of Formula 2-2:

Formula 2-2

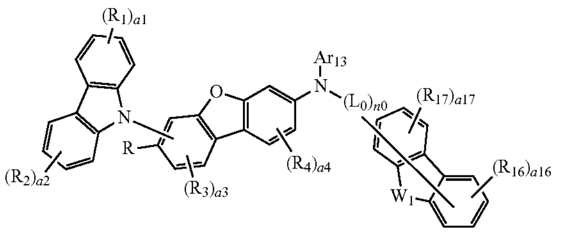

in Formula 2-2, n0 is an integer of 0 to 3, $L_0$ is a direct linkage, a substituted or unsubstituted aryl group of 6 to 40 ring-forming carbon atoms, or a substituted or unsubstituted heteroaryl group of 2 to 40 ring-forming carbon atoms, $W_1$ is $CR_{18}R_{19}$, $NR_{20}$, O, or S, a16 and a17 are each, independently from one another, an integer of 0 to 4, $R_{16}$ to $R_{20}$ are each, independently from one another, a hydrogen atom, a deuterium atom, a substituted or unsubstituted alkenyl group of 2 to 10 carbon atoms, a substituted or unsubstituted aryl group of 6 to 40 ring-forming carbon atoms, or a substituted or unsubstituted heteroaryl group of 2 to 40 ring-forming carbon atoms, or combined with an adjacent group to form a ring, $Ar_{13}$ is a substituted or unsubstituted aryl group of 6 to 40 ring-forming carbon atoms, or a substituted or unsubstituted heteroaryl group of 2 to 40 ring-forming carbon atoms, and a1 to A4, R, and $R_1$ to $R_4$ have, independently from one another, the same meaning as defined in Formula 1.

16. The amine compound of claim 13, wherein $Ar_1$ and $Ar_2$ are each, independently from one another, a substituted or unsubstituted phenyl group, a substituted or unsubstituted naphthyl group, a substituted or unsubstituted phenanthryl group, a substituted or unsubstituted triphenylenyl group, a substituted or unsubstituted fluorenyl group, a substituted or unsubstituted dibenzofuran group, a substituted or unsubstituted dibenzothiophene group, a substituted carbazole group, an unsubstituted naphthobenzofuran group, or an unsubstituted benzonaphthothiophene group.

17. The amine compound of claim 13, wherein $Ar_1$ and $Ar_2$ are each, independently from one another, one of A-1 to A-7:

A-1

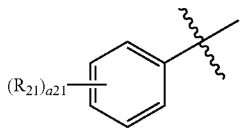

A-2

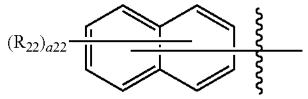

A-3

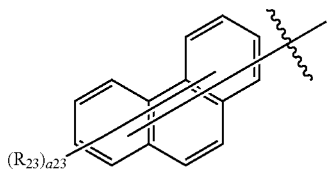

A-4

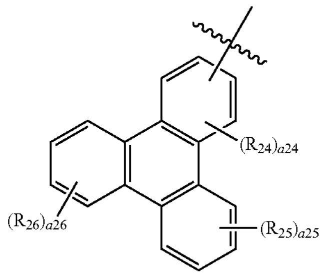

A-5

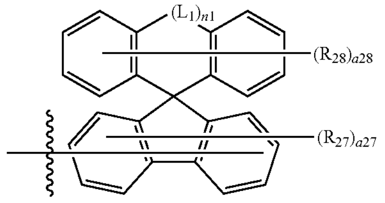

A-6

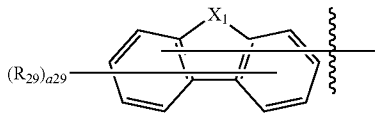

-continued

A-7

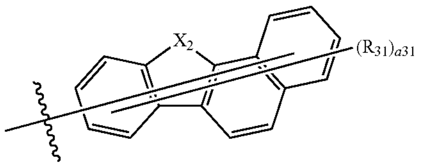

in A-1, a21 is an integer of 0 to 5, in A-2, a22 is an integer of 0 to 7, and $R_{22}$ is a hydrogen atom, a deuterium atom, or a substituted or unsubstituted aryl group of 6 to 40 ring-forming carbon atoms, in A-3, a23 is an integer of 0 to 9, in A-4, a24 is an integer of 0 to 3, and a25 and a26 are each, independently from one another, an integer of 0 to 4, in A-5, n1 is 0 or 1, $L_1$ is a direct linkage, a27 is an integer of 0 to 7, and a28 is an integer of 0 to 10, in A-6, $X_1$ is $NR_{30}$, O, or S, and a29 is an integer of 0 to 7, in A-7, $X_2$ is O, or S, and a31 is an integer of 0 to 9, and in A-1, and A-3 to A-7, $R_{21}$, and $R_{23}$ to $R_{31}$ are each, independently from one another, a hydrogen atom, a deuterium atom, a substituted or unsubstituted aryl group of 6 to 40 ring-forming carbon atoms, or a substituted or unsubstituted heteroaryl group of 2 to 40 ring-forming carbon atoms.

18. The amine compound of claim 13, wherein at least one of $Ar_1$ and $Ar_2$ is a substituted or unsubstituted phenyl group.

19. The amine compound of claim 13, wherein $R_1$ and $R_2$ are each, independently from one another, a deuterium atom, a fluorine atom, a methyl group, or a t-butyl group.

20. The amine compound of claim 13, wherein at least one of $R_1$ to $R_4$ is a deuterium atom, or at least one of $R_1$ to $R_4$, $Ar_1$ and $Ar_2$ comprises a deuterium atom as a substituent.

21. The amine compound of claim 13, wherein Formula 1 is one compound of Compound Group 1:

Compound Group 1

A1

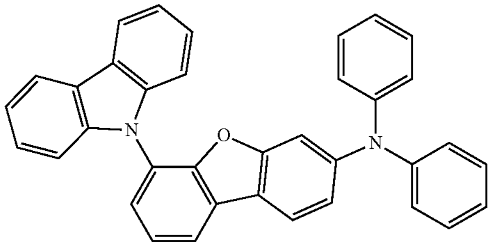

-continued

A2

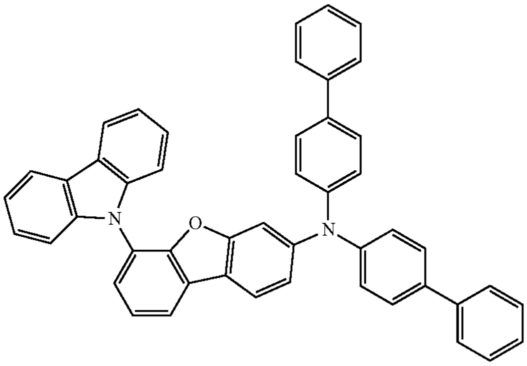

A3

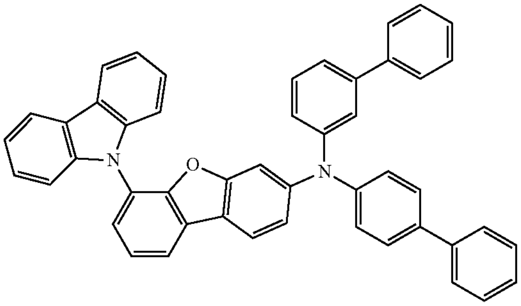

A4

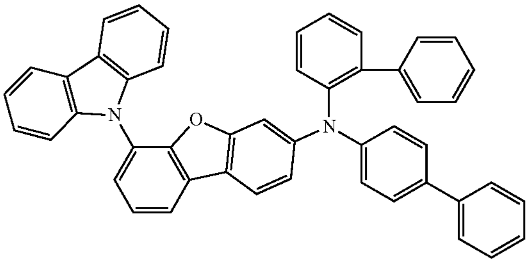

A5

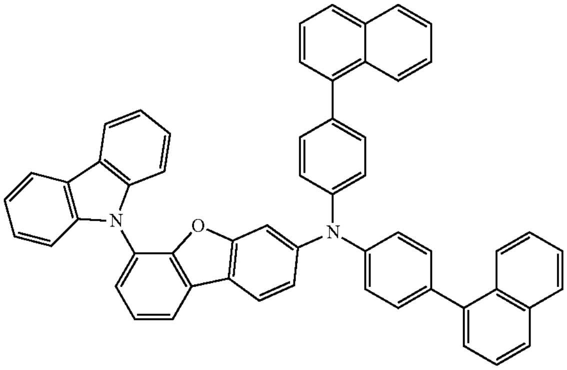

-continued
A6
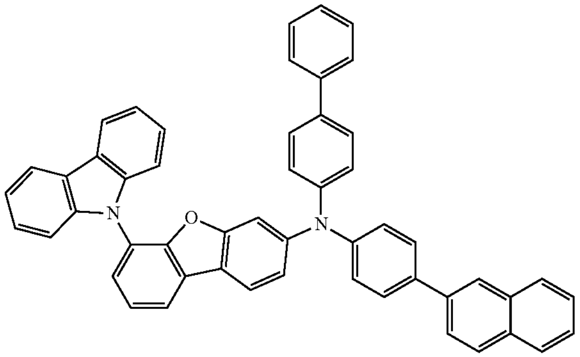
A7
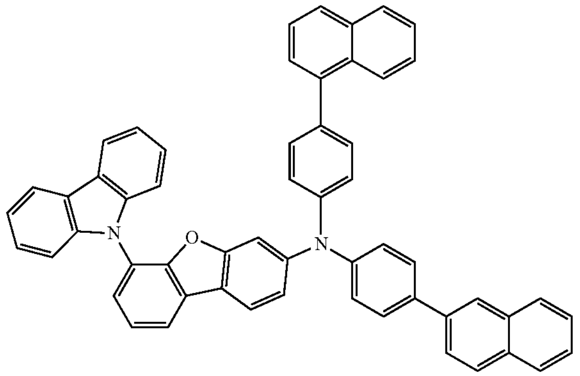
A8
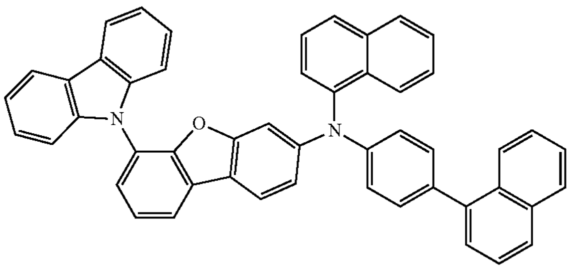
A9
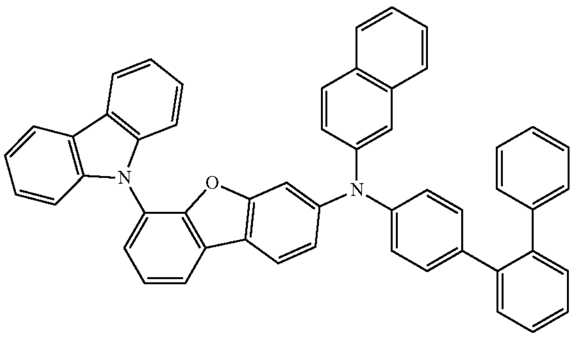
-continued
A10
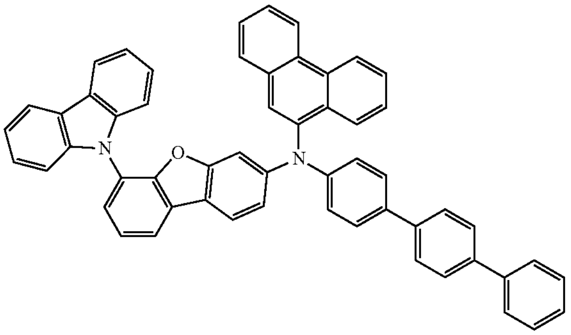
A11
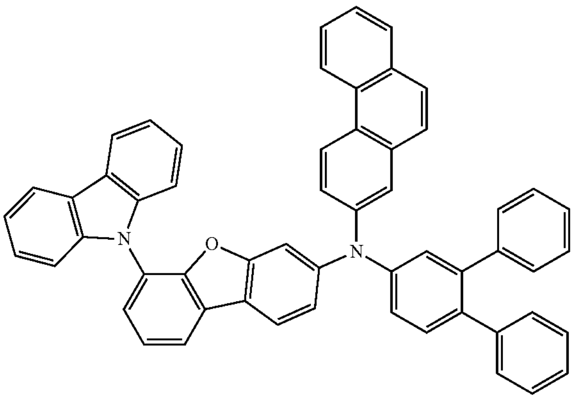
A12
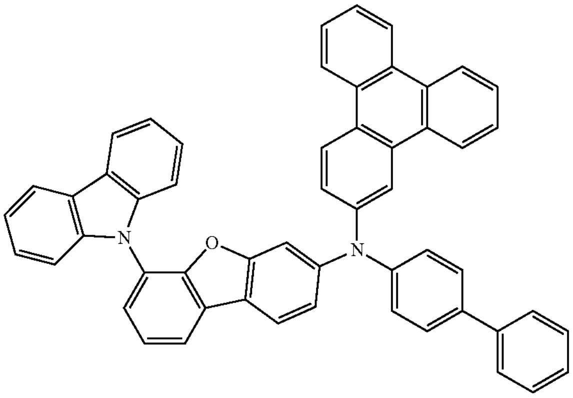
A13
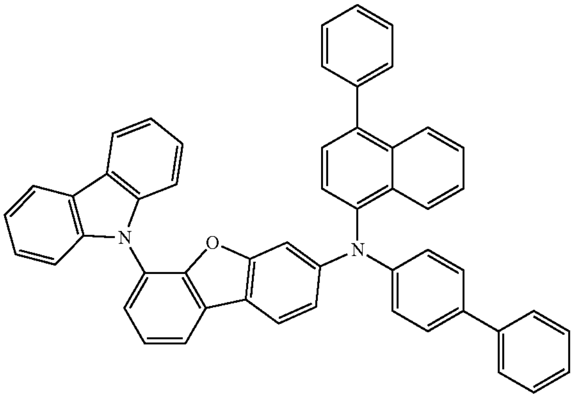

-continued
A14
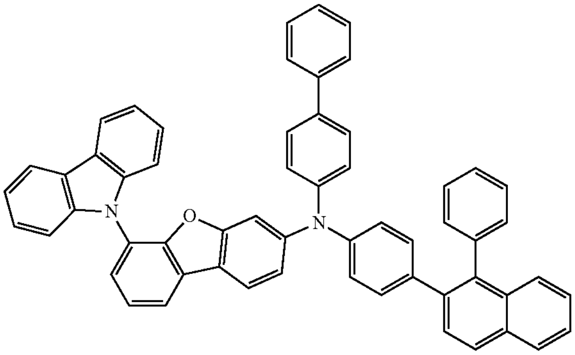
A15
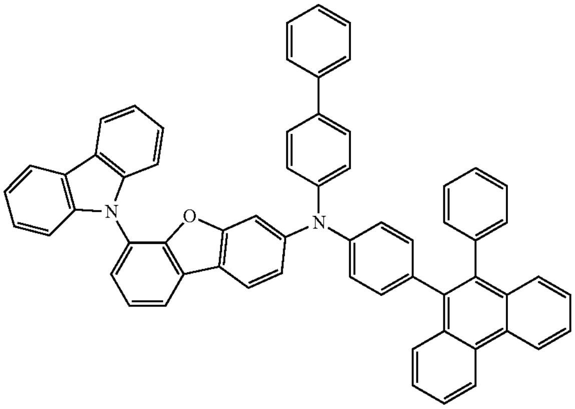
A16
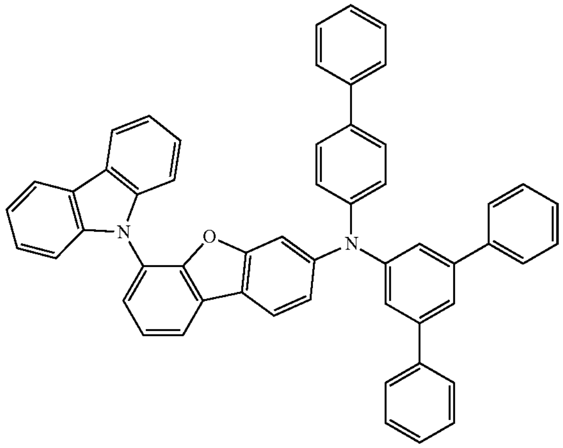
A17
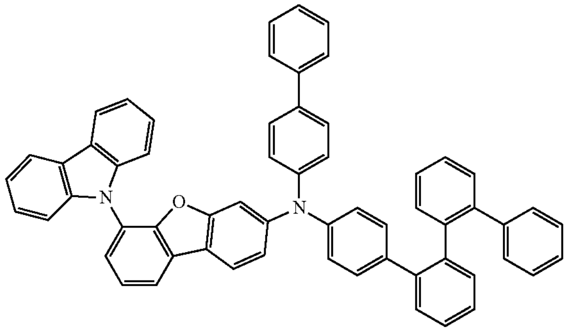
-continued
A18
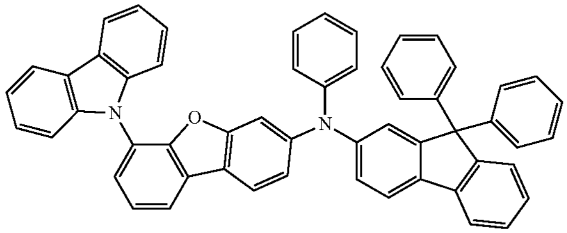
A19
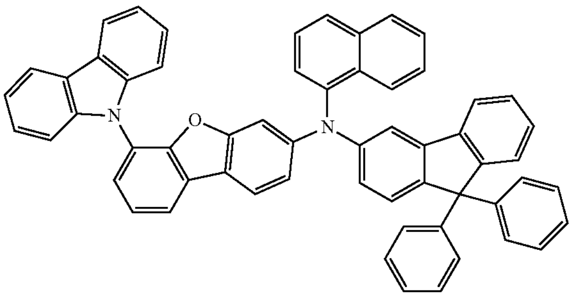
A20
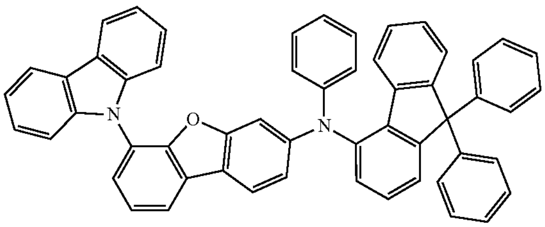
A21
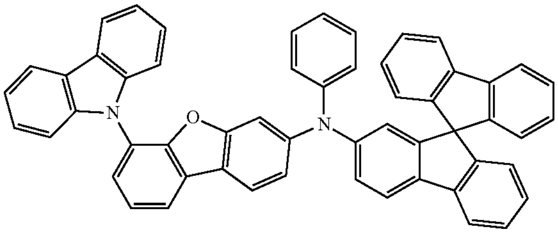
A22
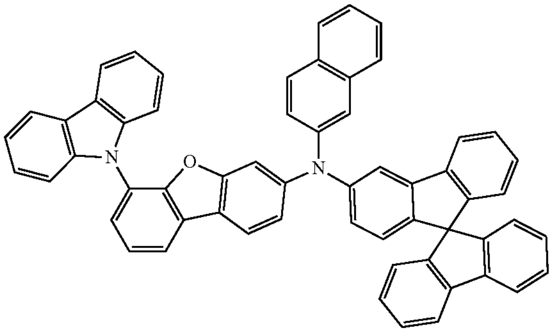

-continued
A23
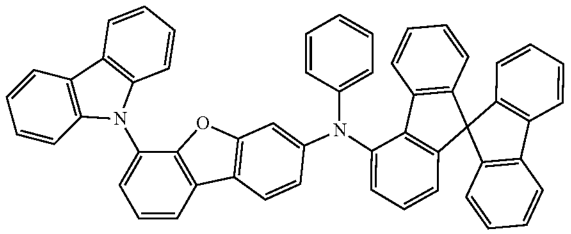
A24
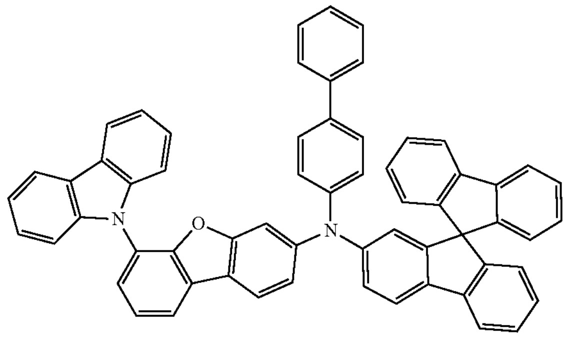
A25
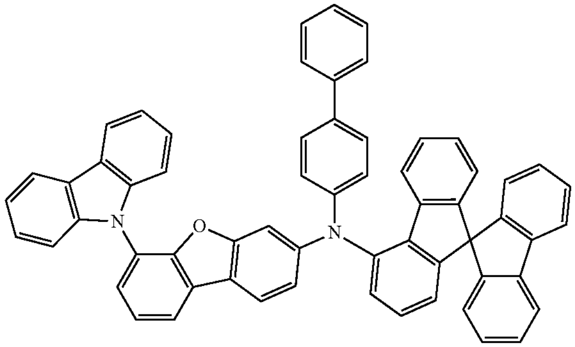
A26
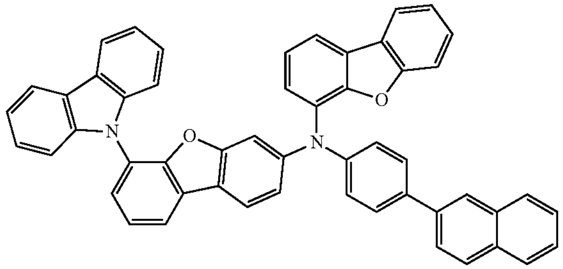
-continued
A27
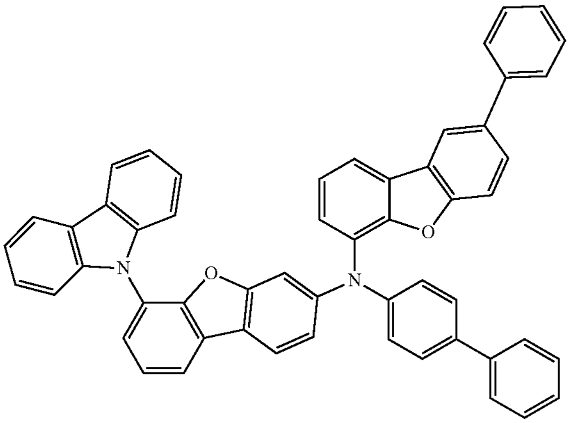
A28
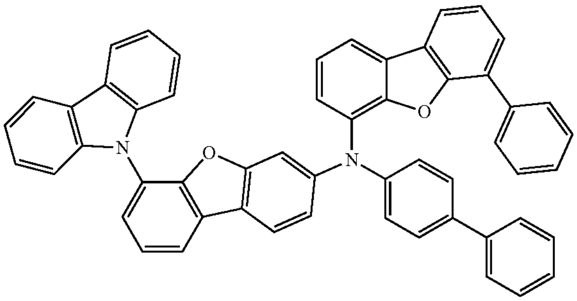
A29
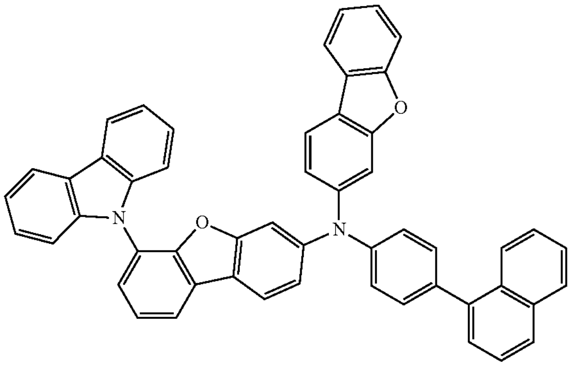
A30
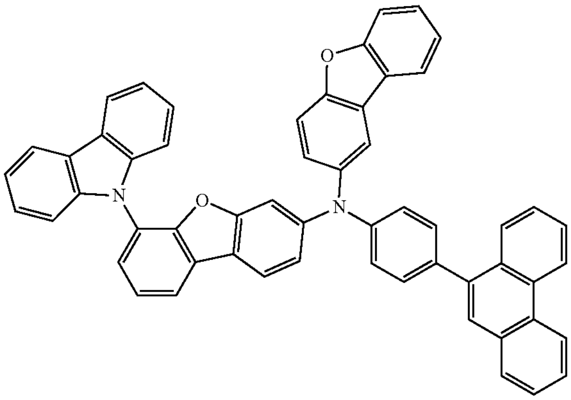

-continued
A31
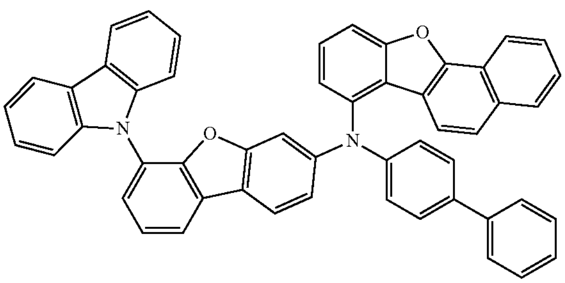
A32
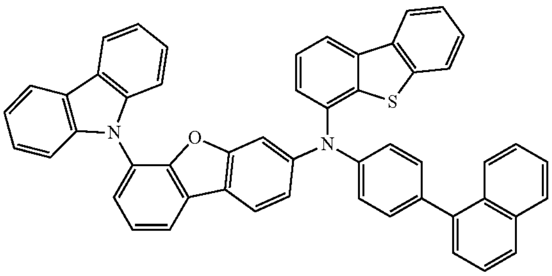
A33
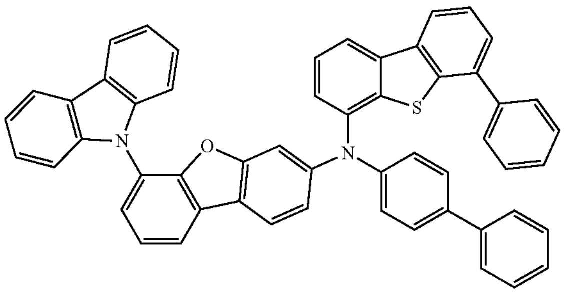
A34
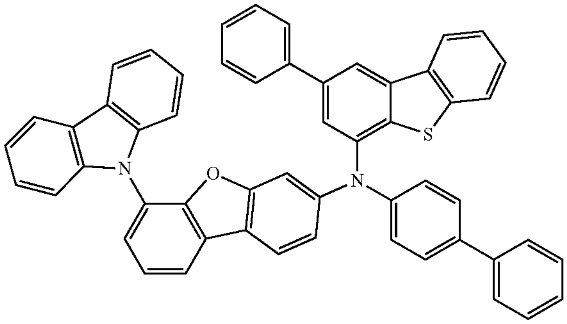
A35
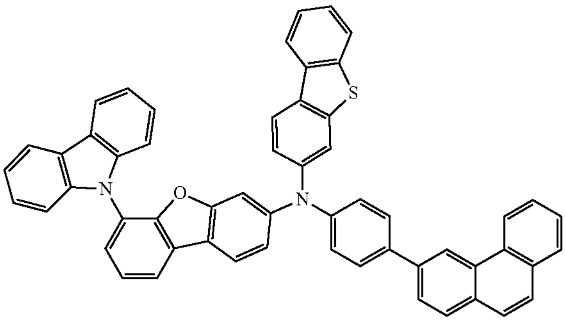
-continued
A36
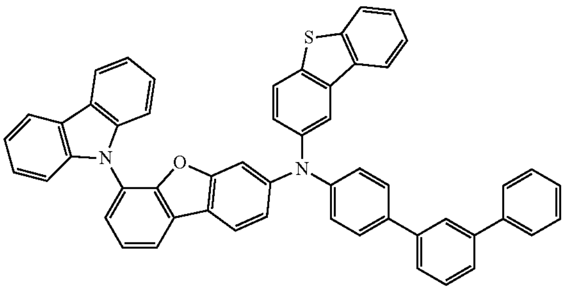
A37
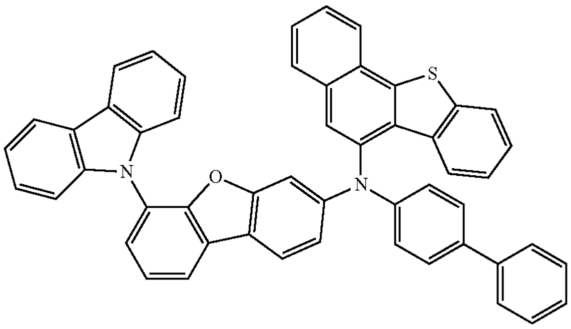
A38
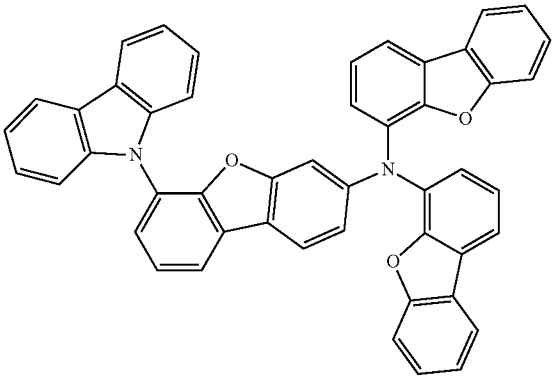
A39
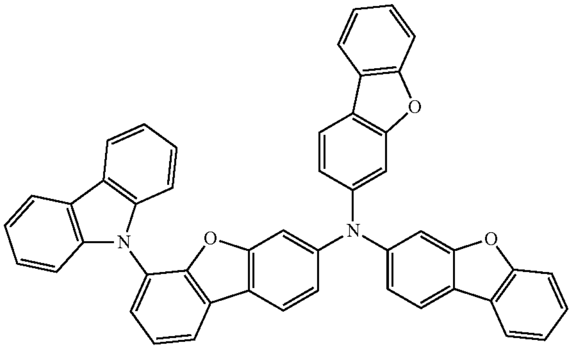

-continued
A40
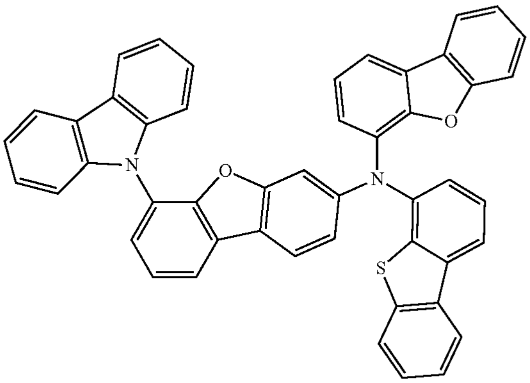
A41
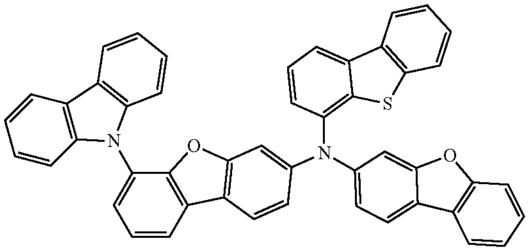
A42
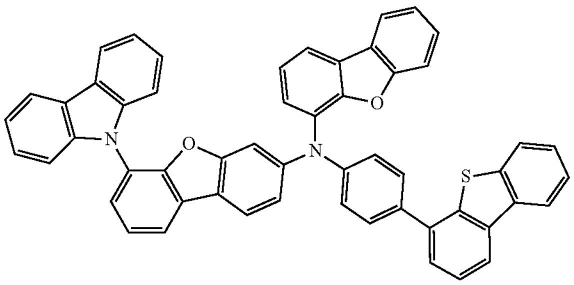
A43
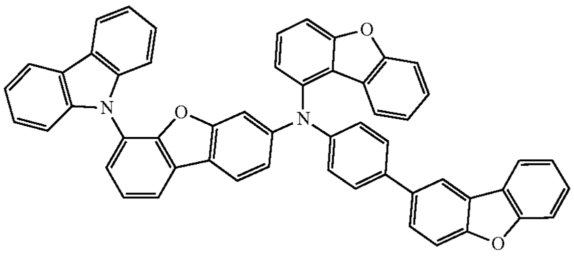
A44
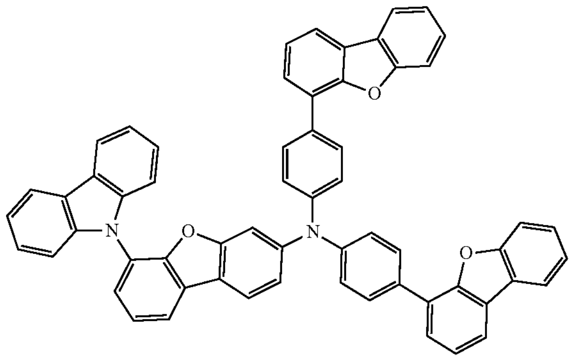
-continued
A45
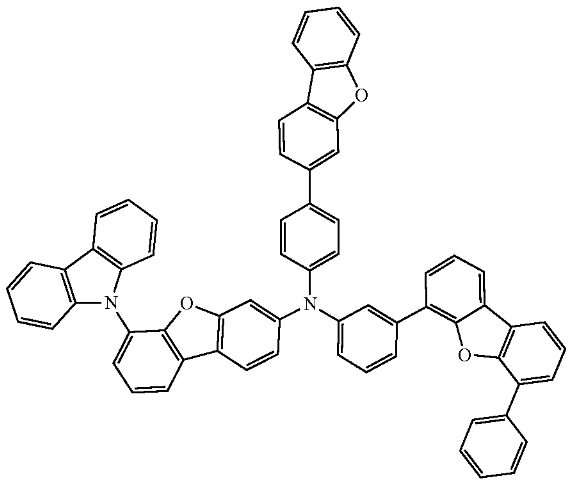
A46
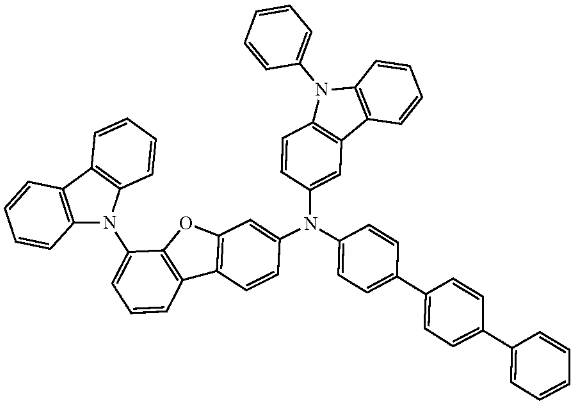
A47
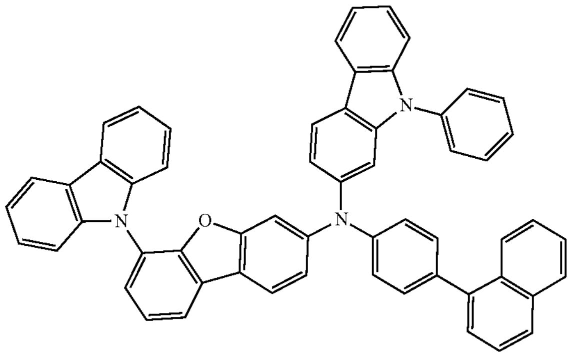

-continued
A48
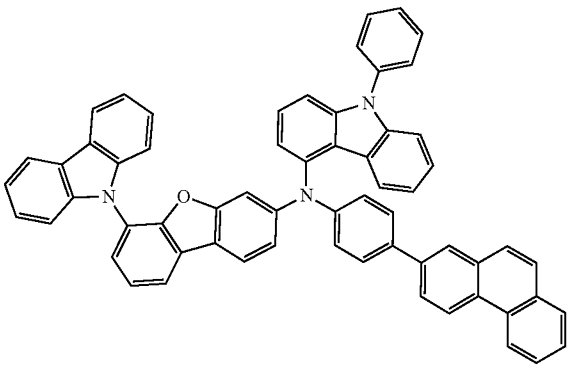
A49
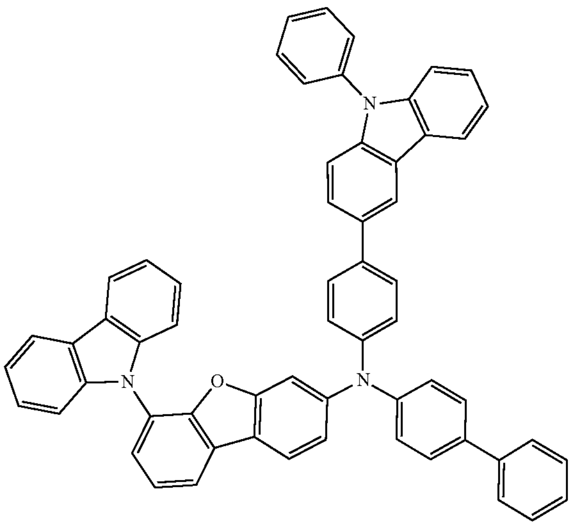
A50
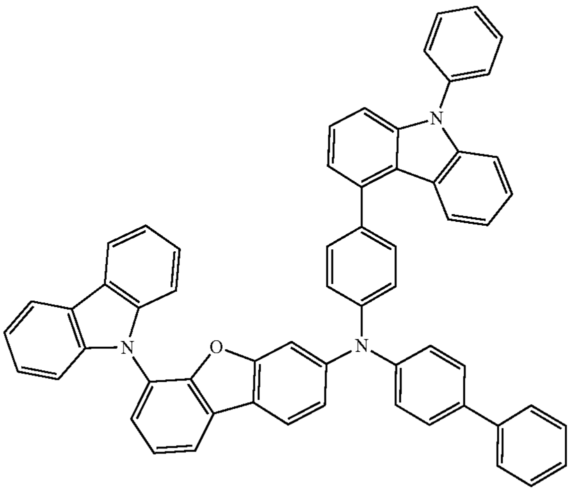
-continued
A51
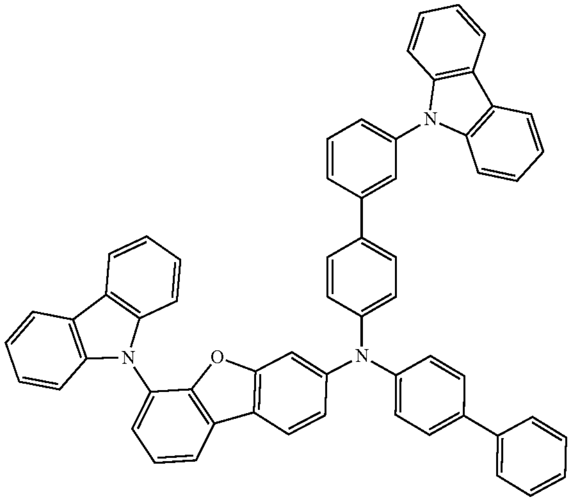
A52
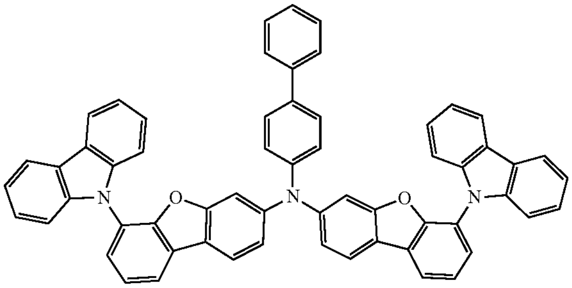
A53
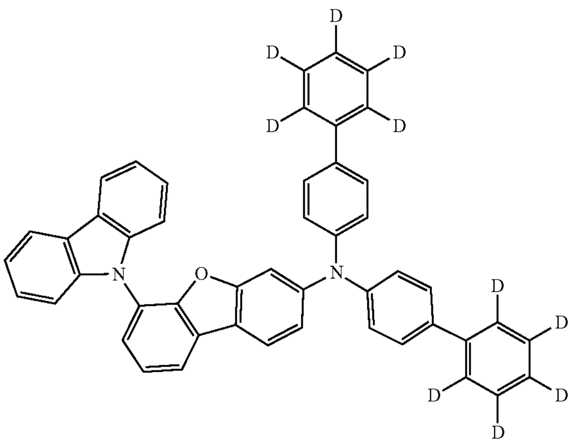

-continued
A54
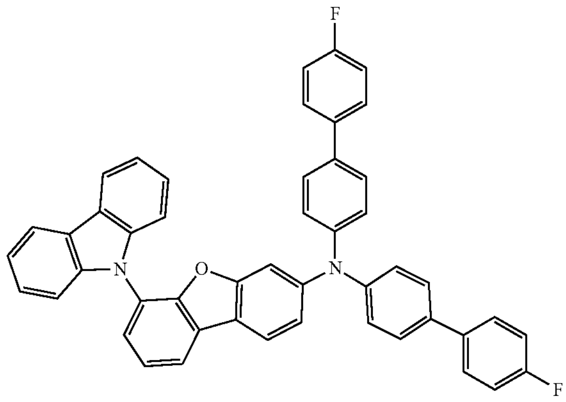
A55
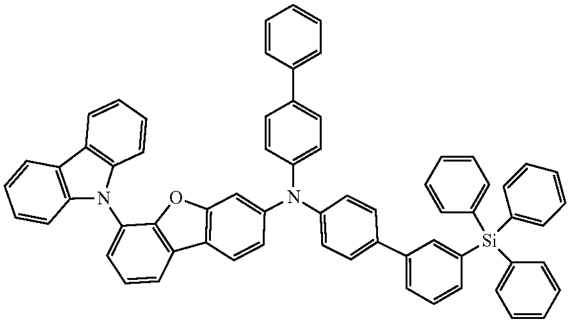
A56
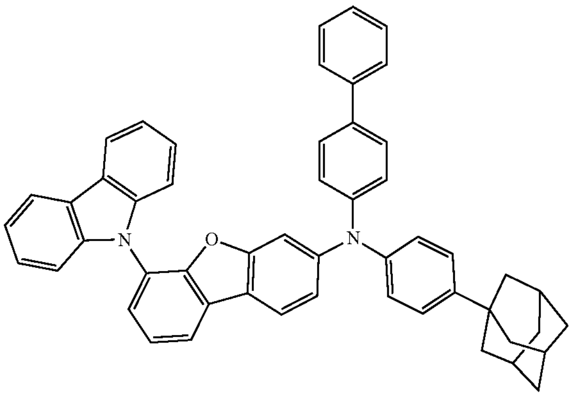
A57
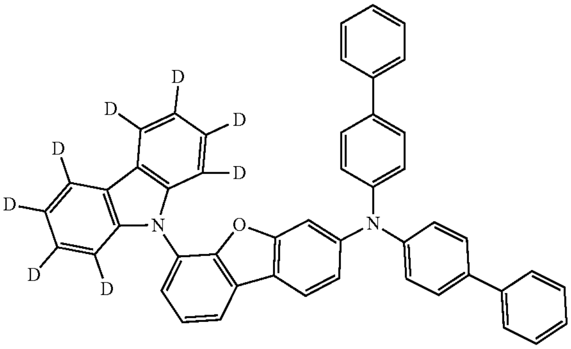
-continued
A58
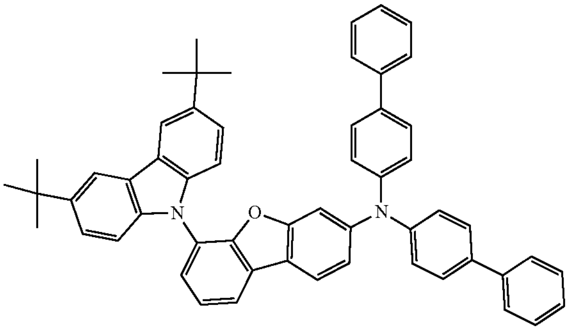
A59
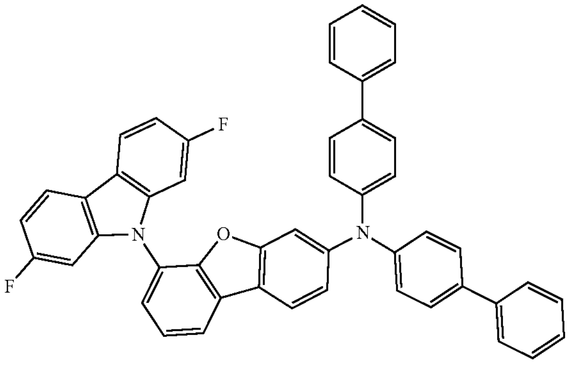
A60
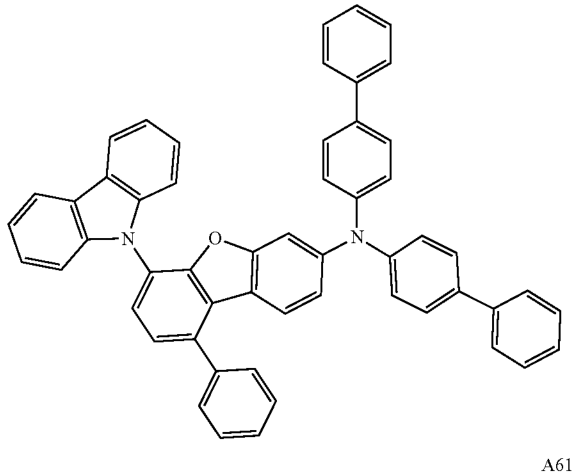
A61
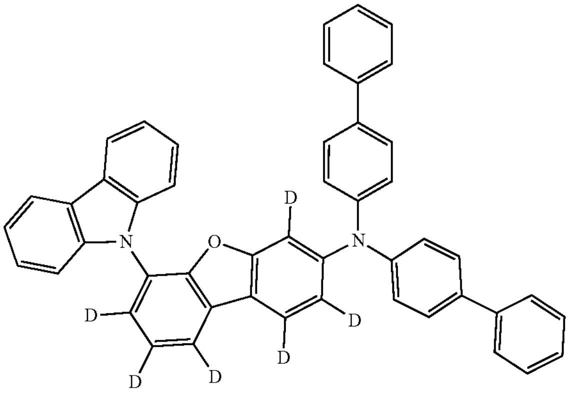

-continued
A62
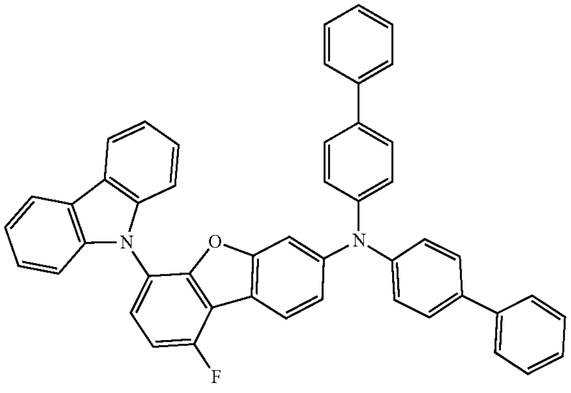
A63
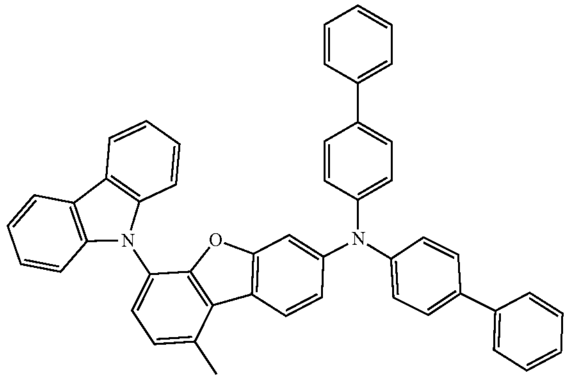
A64
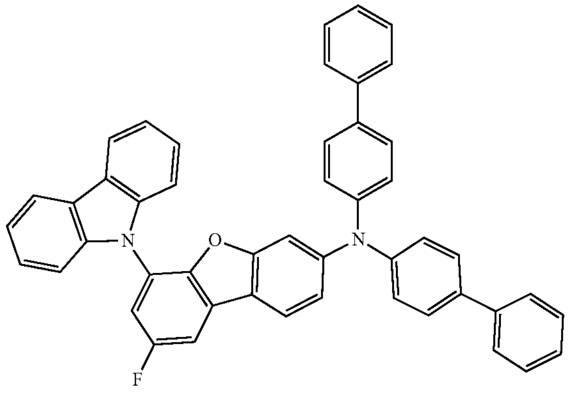
A65
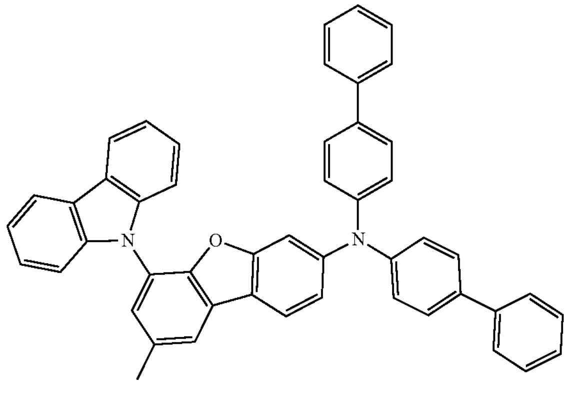
B1
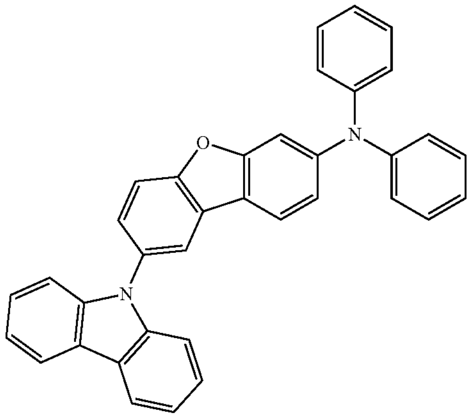
B2
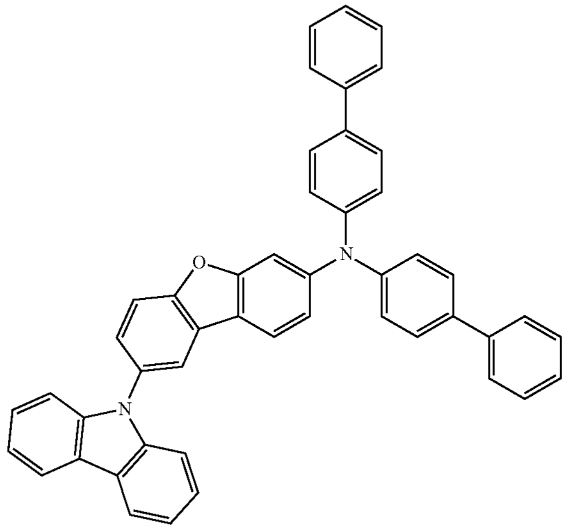
B3
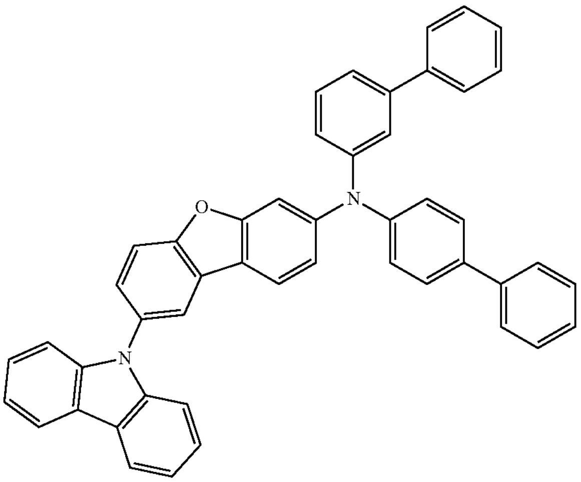

-continued
B4
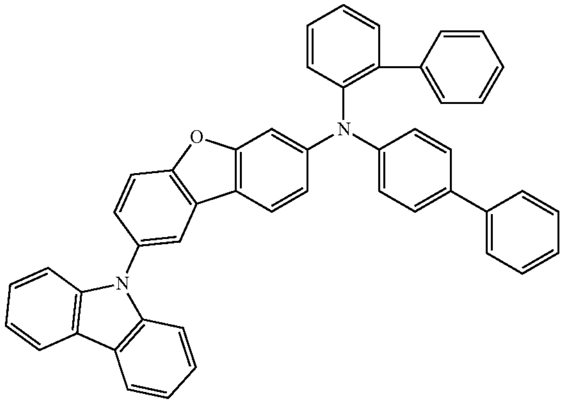
B5
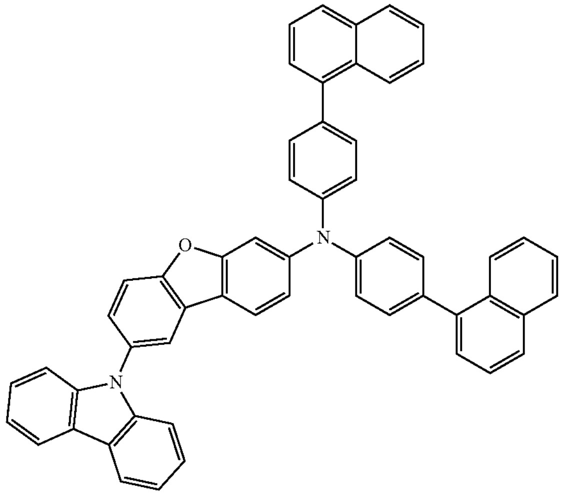
B6
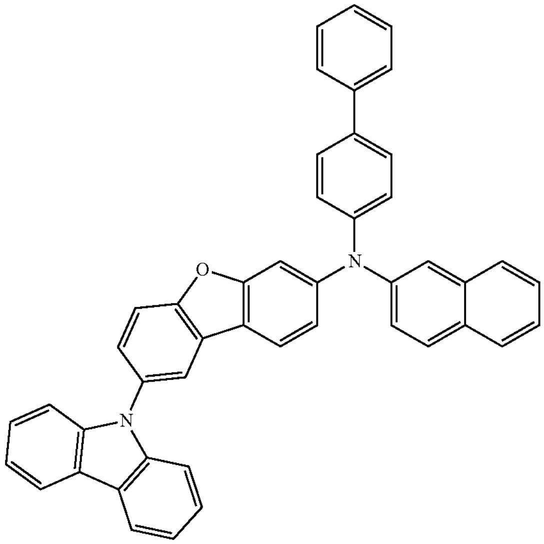
-continued
B7
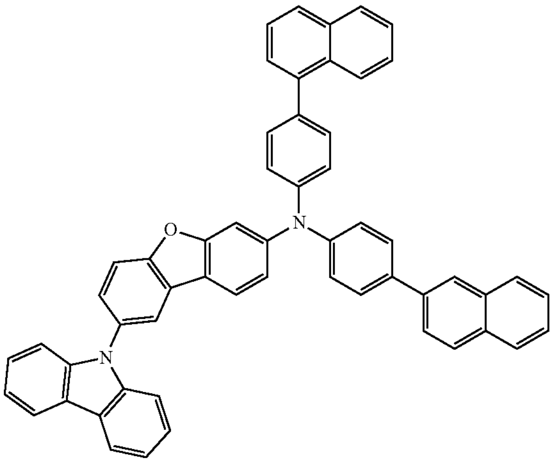
B8
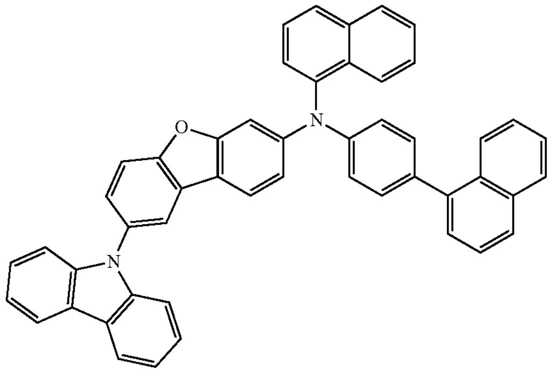
B9
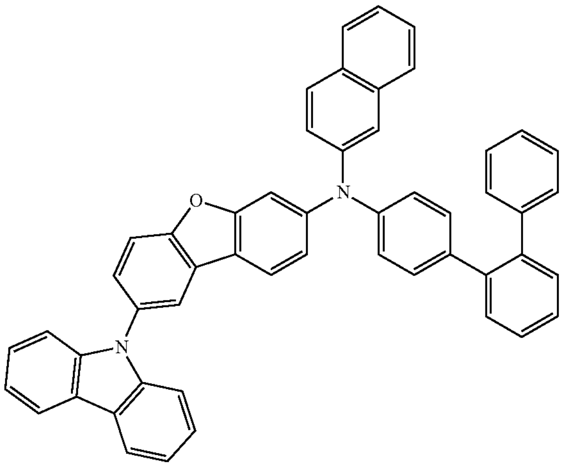

-continued
B10
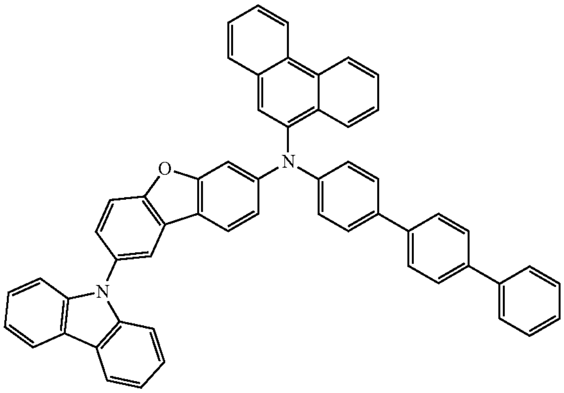
B11
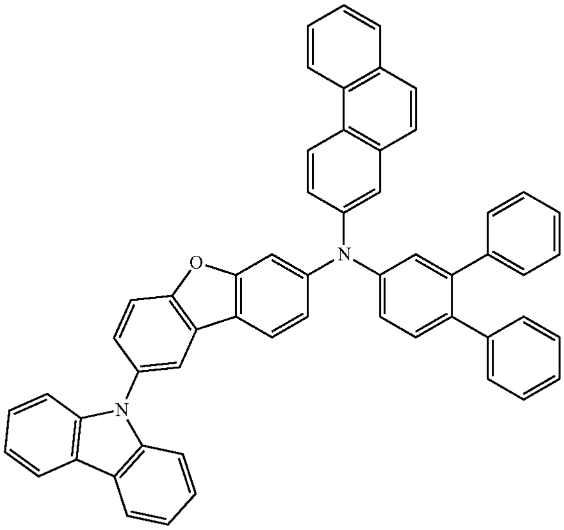
B12
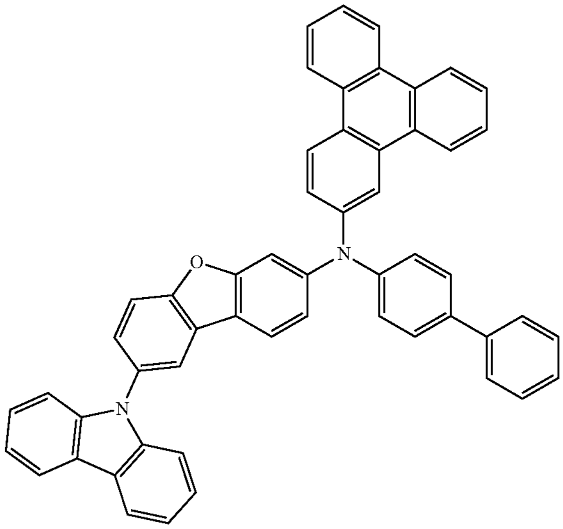
-continued
B13
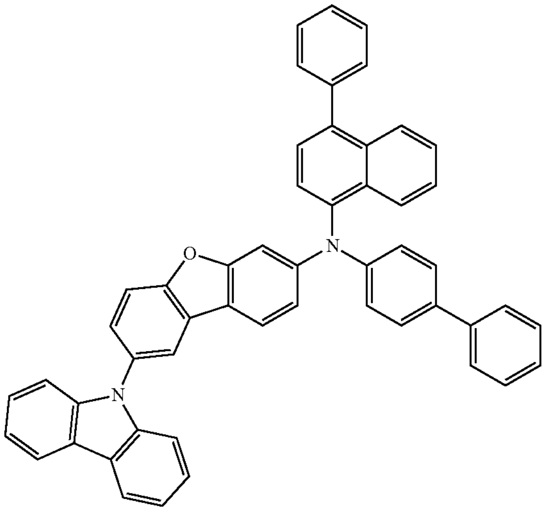
B14
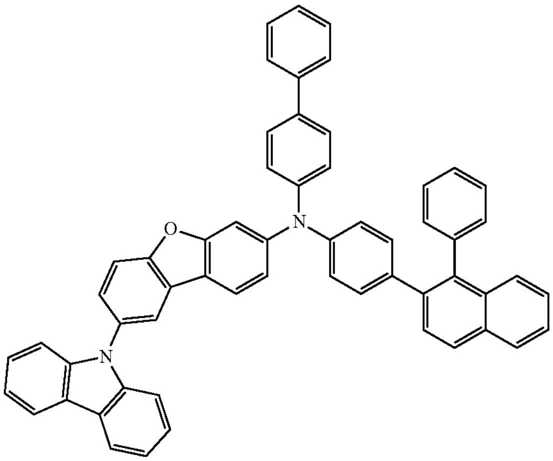
B15
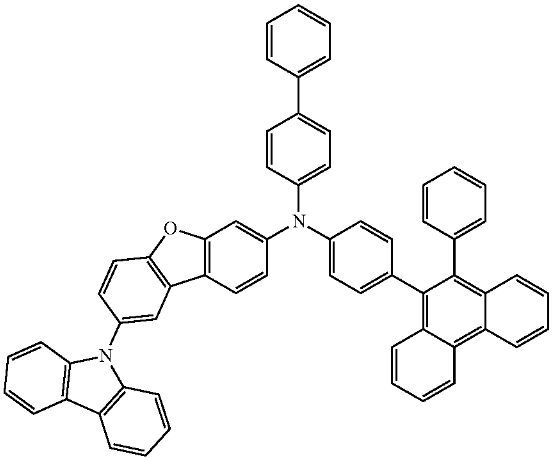

-continued
B16
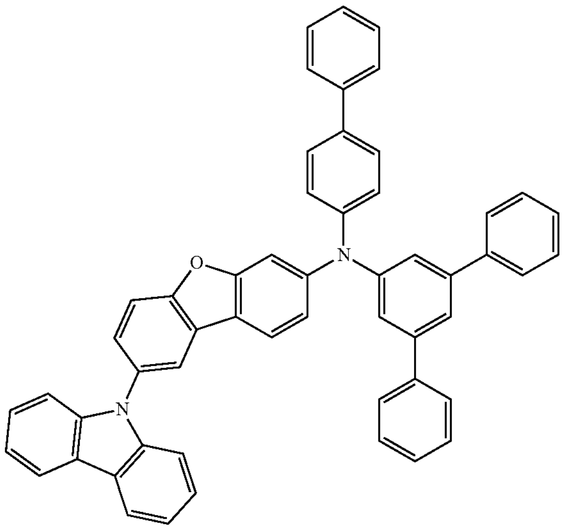
B17
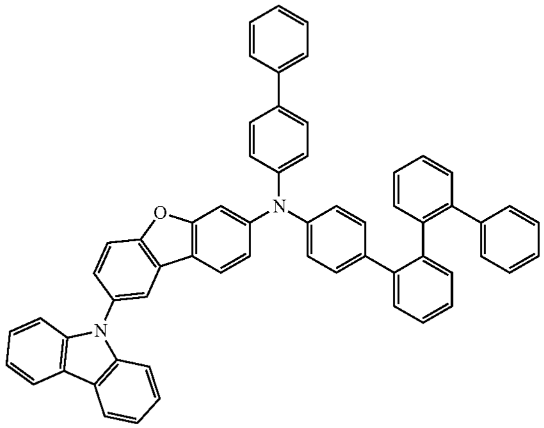
B18
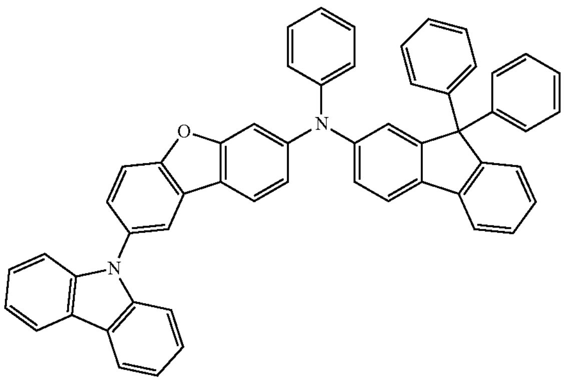
-continued
B19
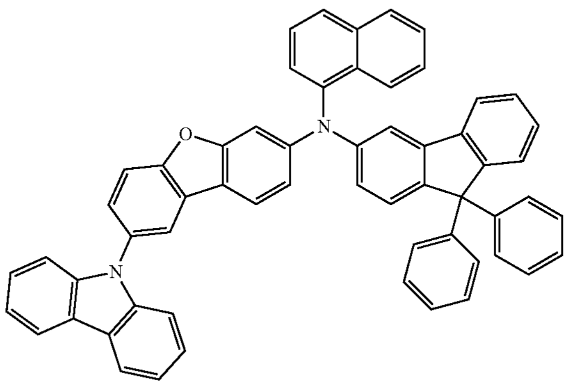
B20
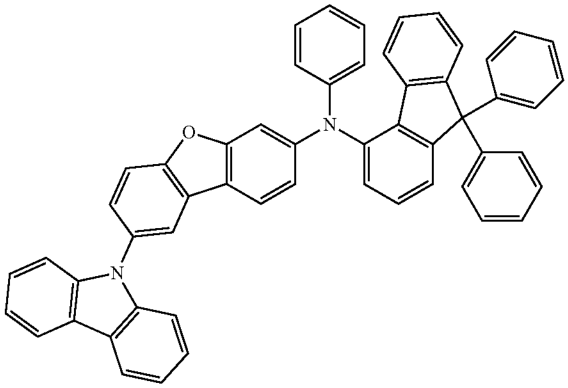
B21
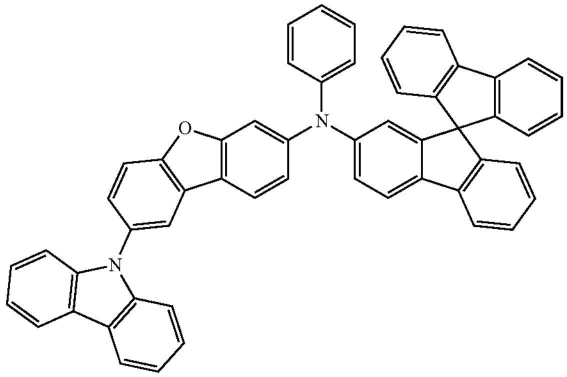

-continued
B22
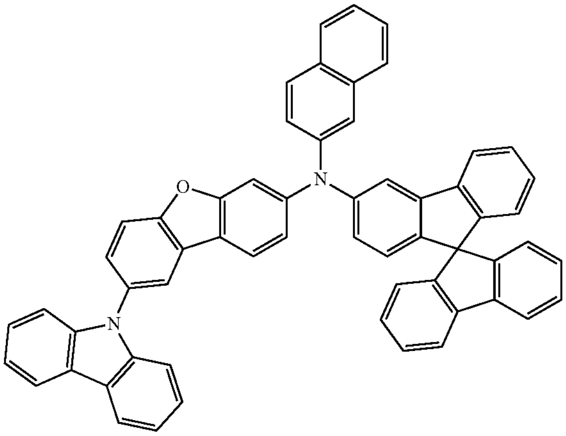
B23
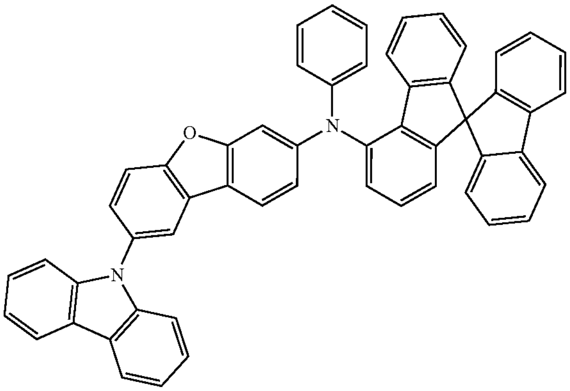
B24
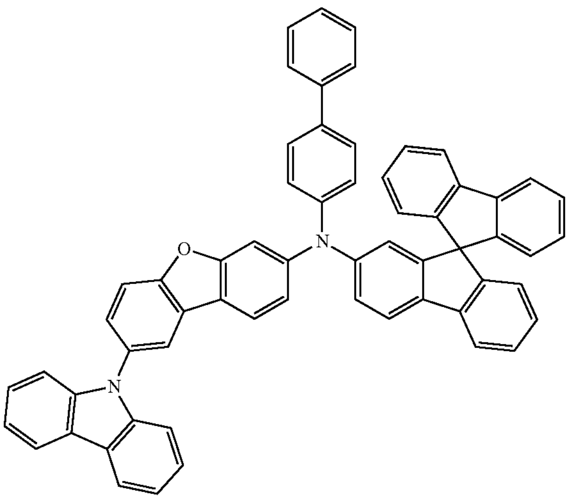
B25
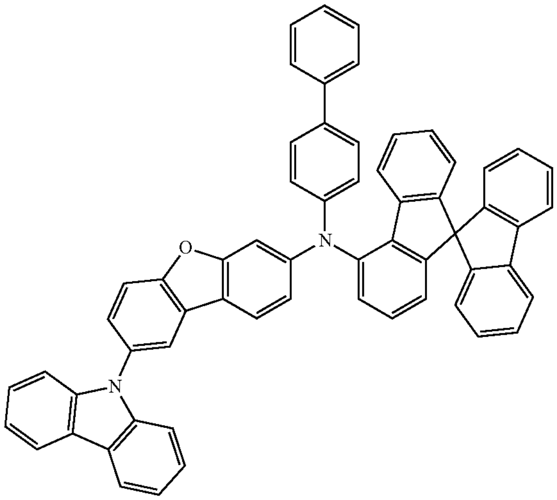
B26
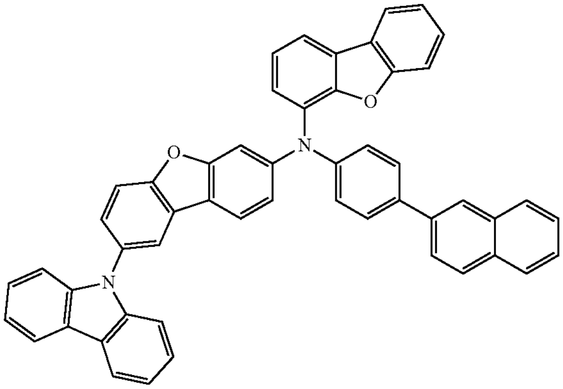
B27
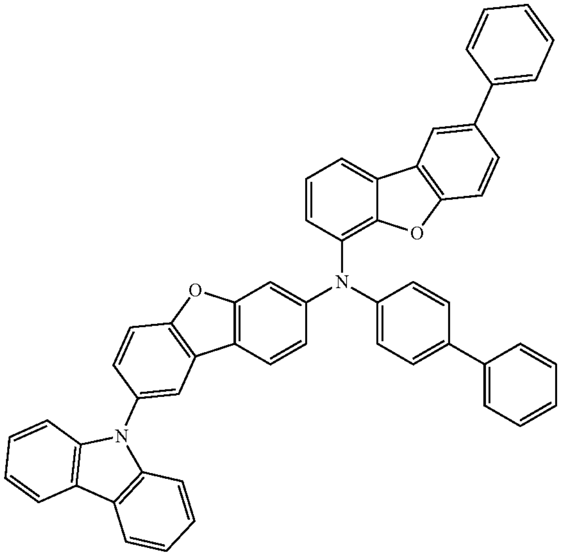

-continued
B28
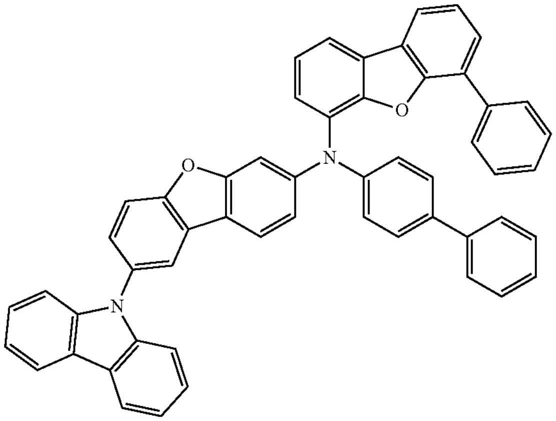
B29
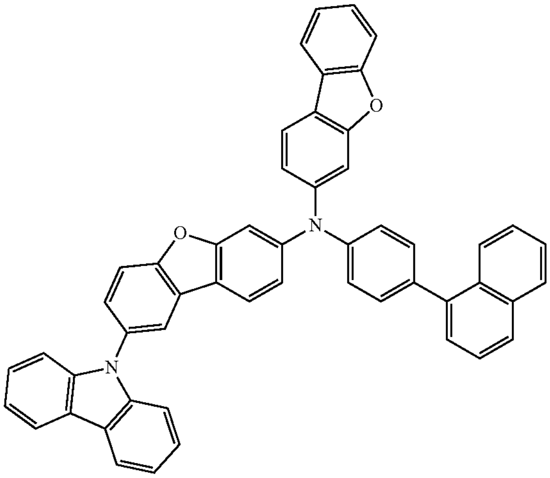
B30
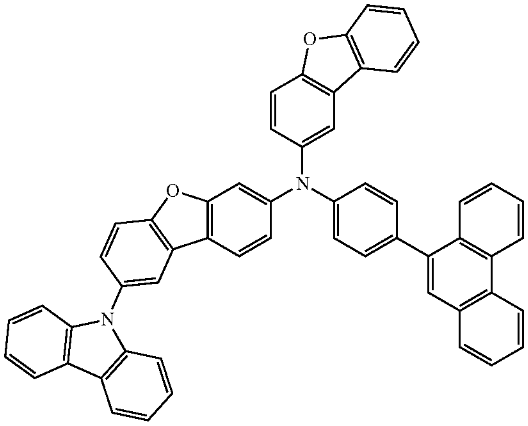
-continued
B31
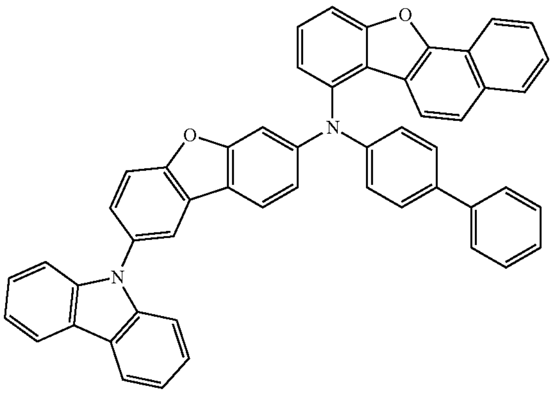
B32
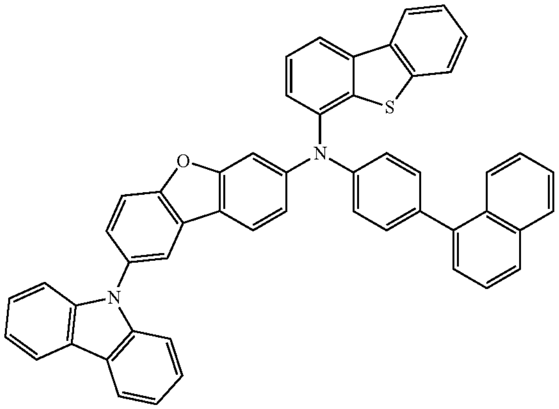
B33
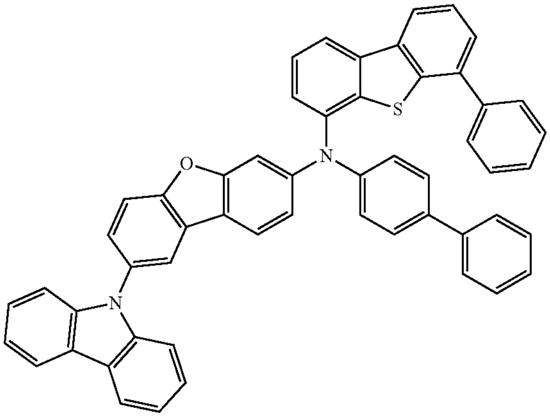

-continued
B34
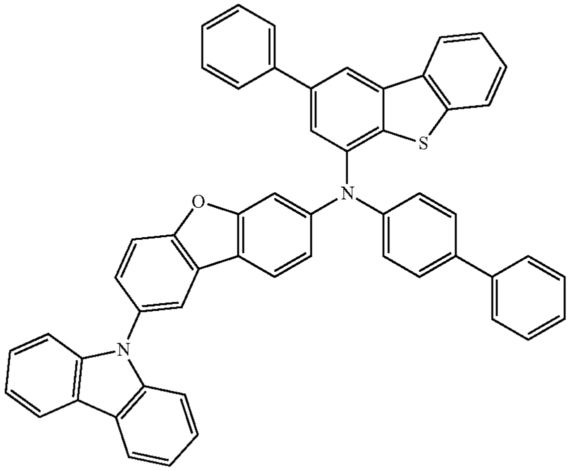
B35
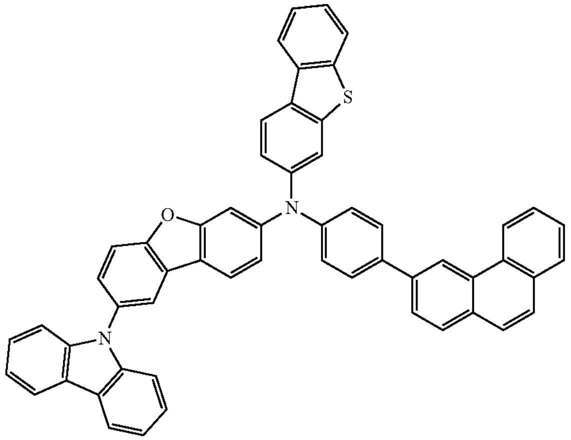
B36
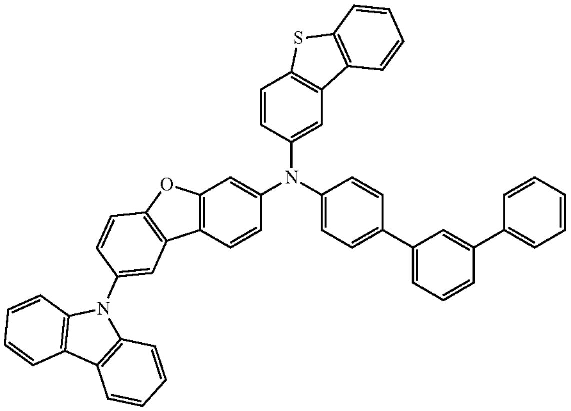
-continued
B37
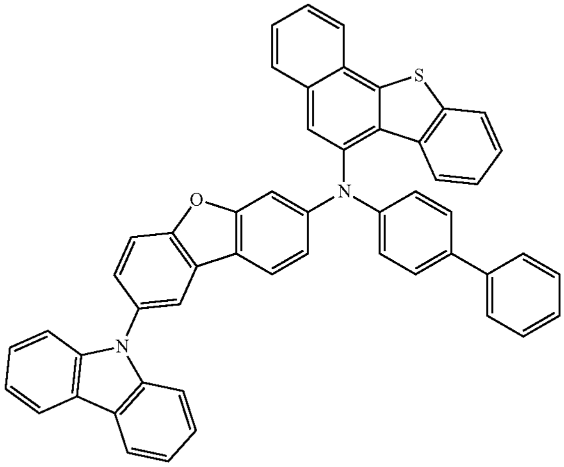
B38
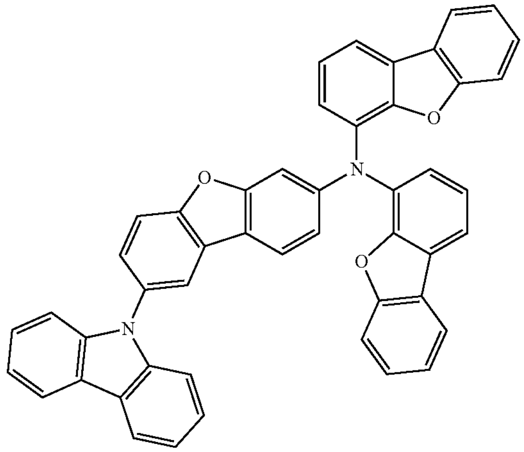
B39
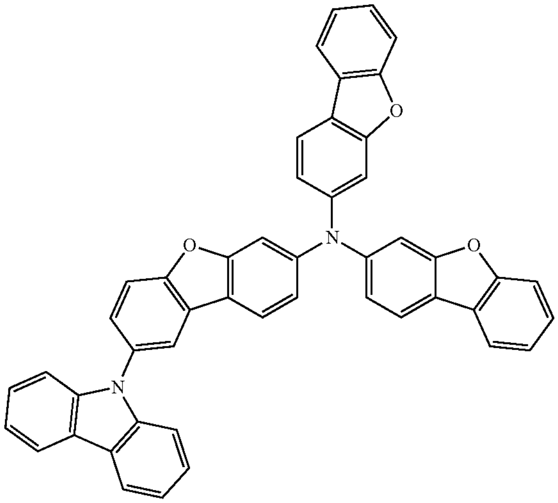

-continued
B40
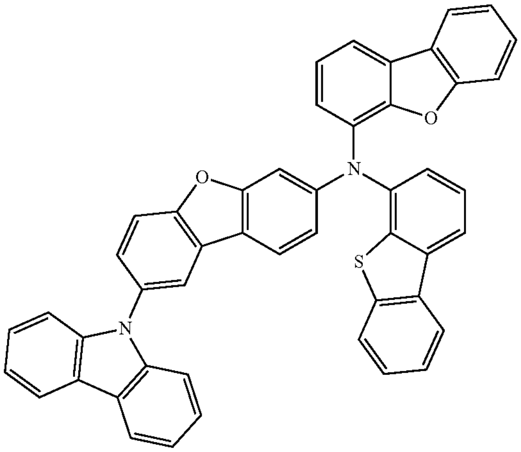
B41
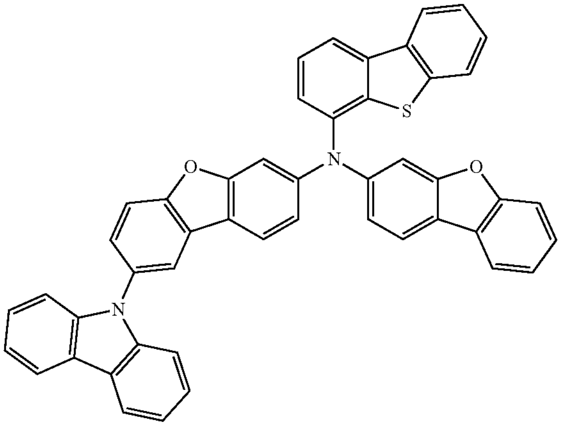
B42
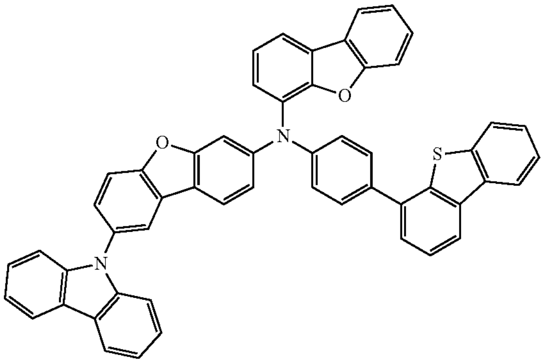
-continued
B43
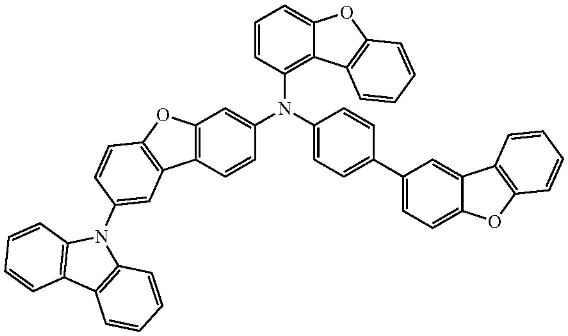
B44
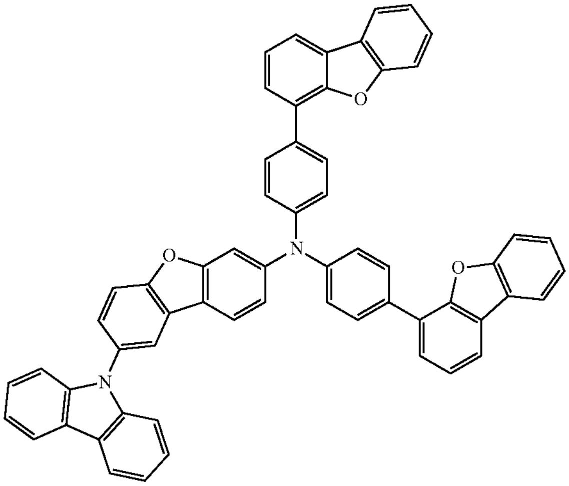
B45
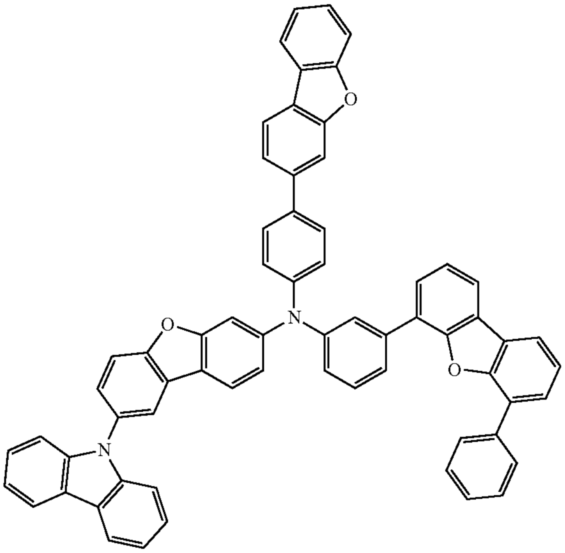

-continued
B46
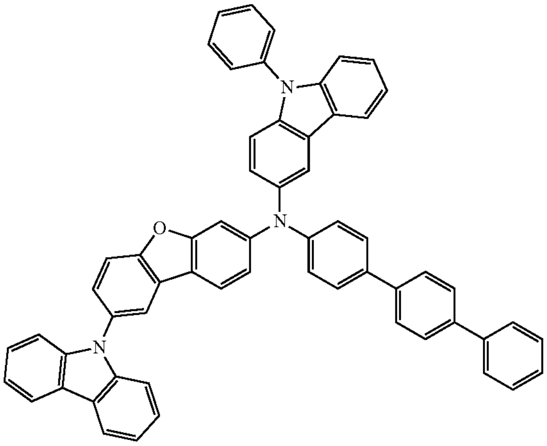
B47
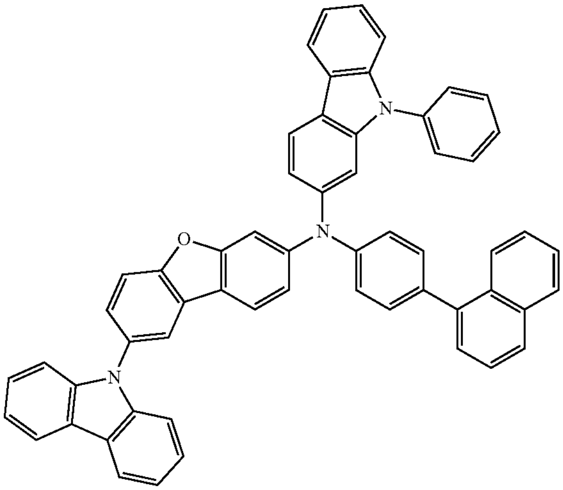
B48
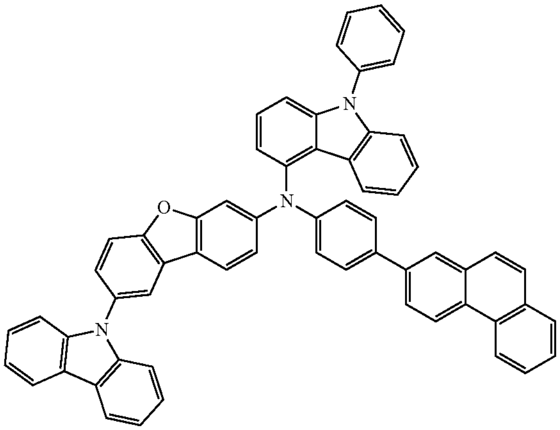
-continued
B49
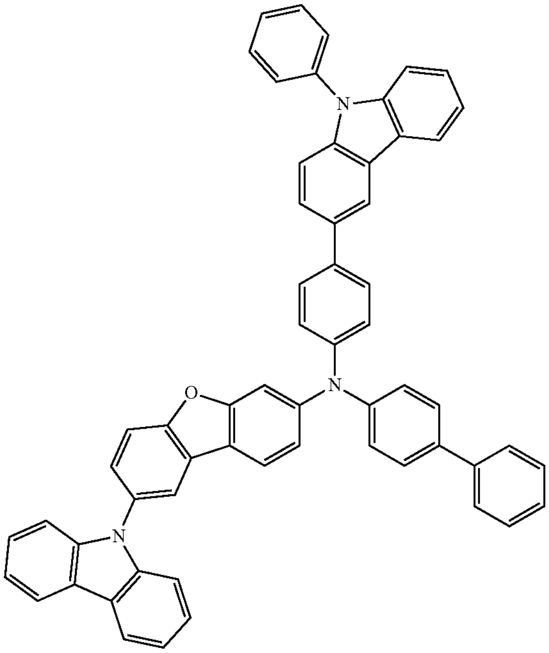
B50
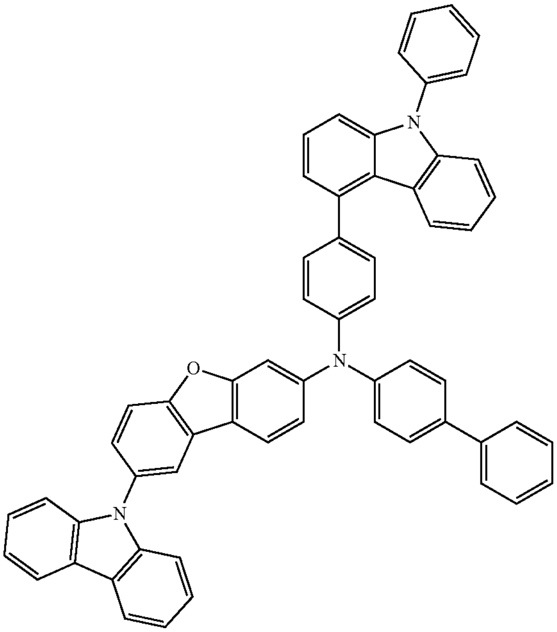

-continued
B51
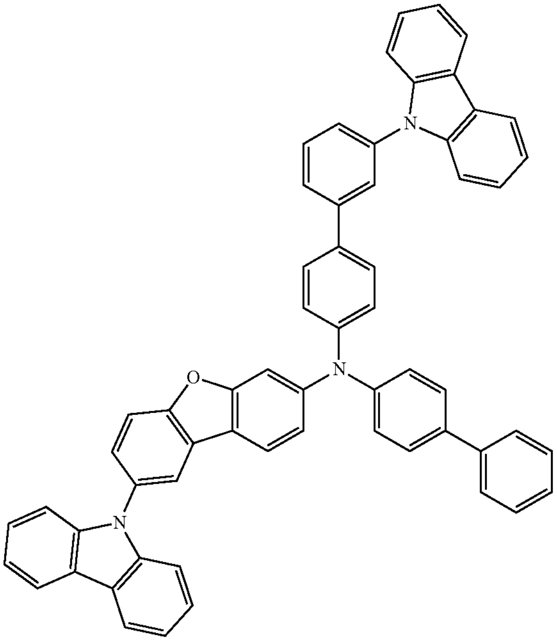
B52
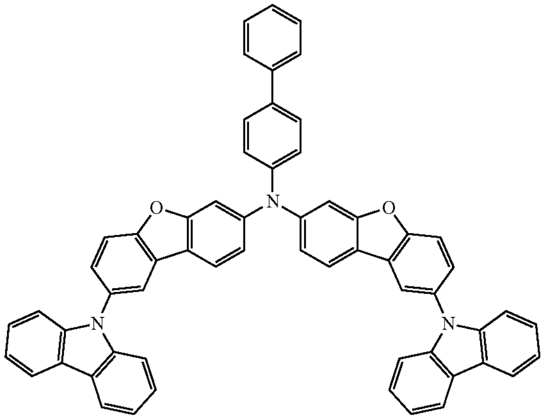
B53
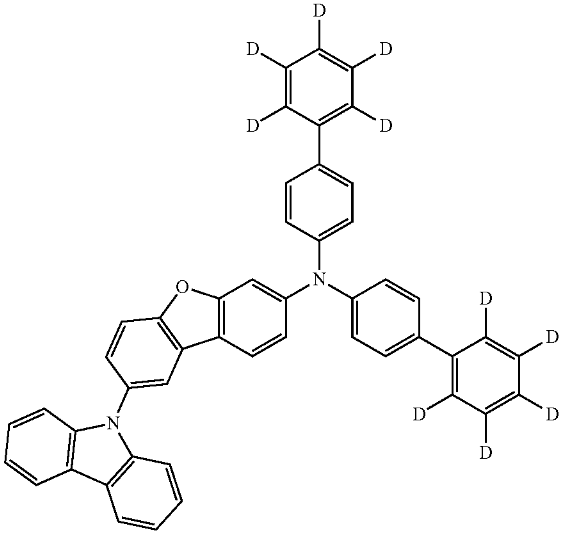
-continued
B54
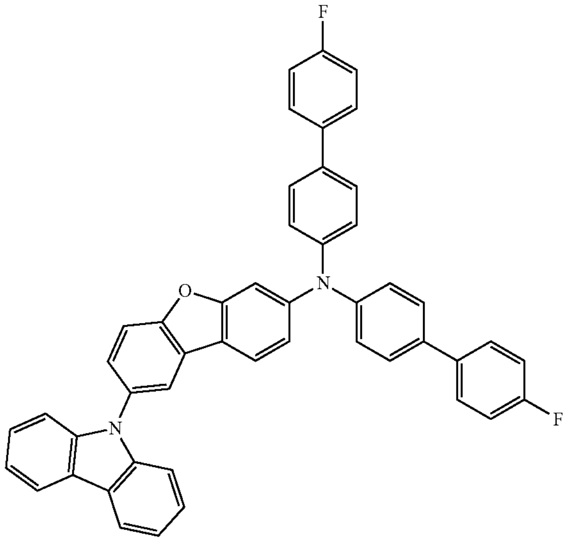
B55
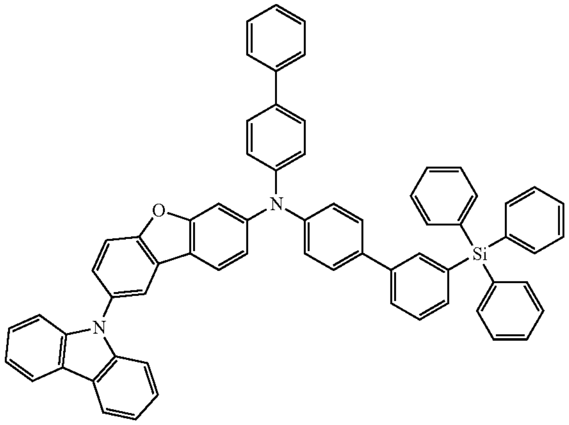
B56
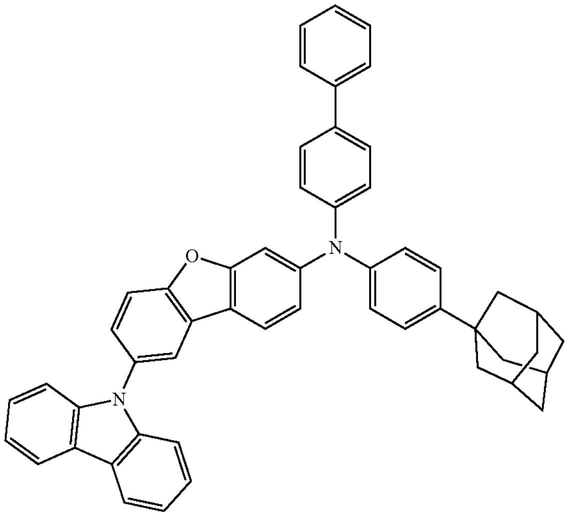

-continued
B57
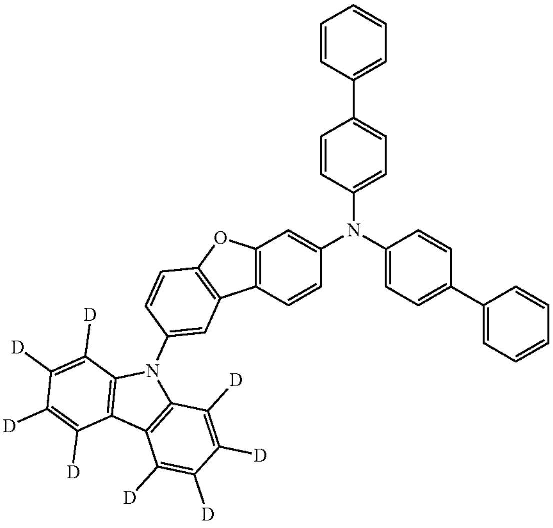
B58
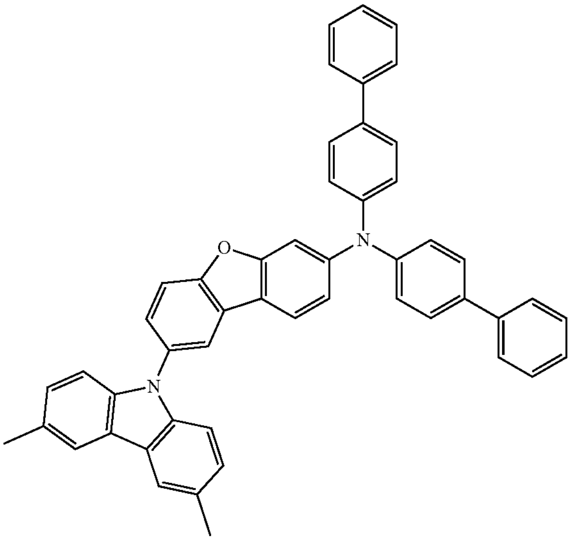
B59
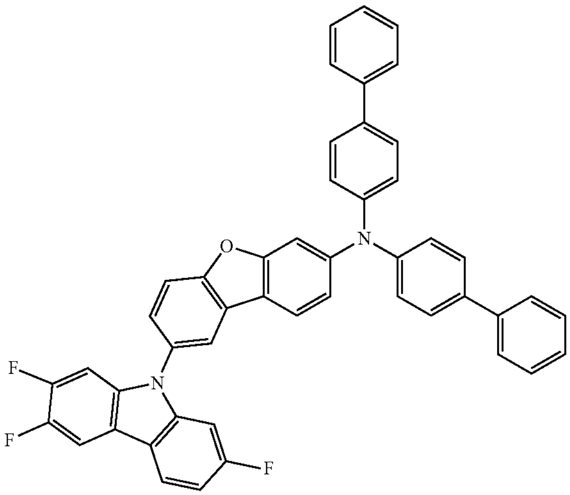
-continued
B60
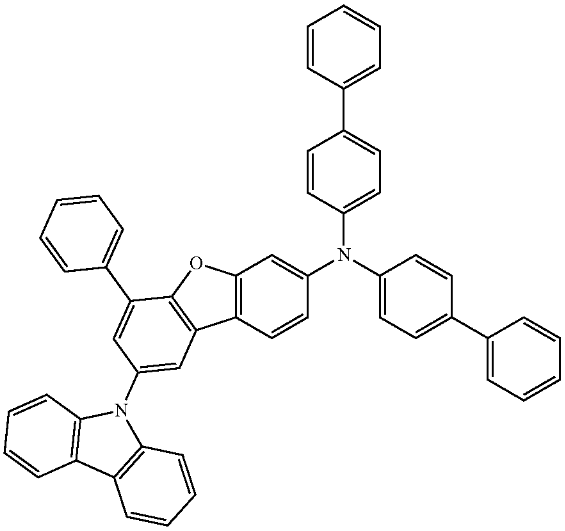
B61
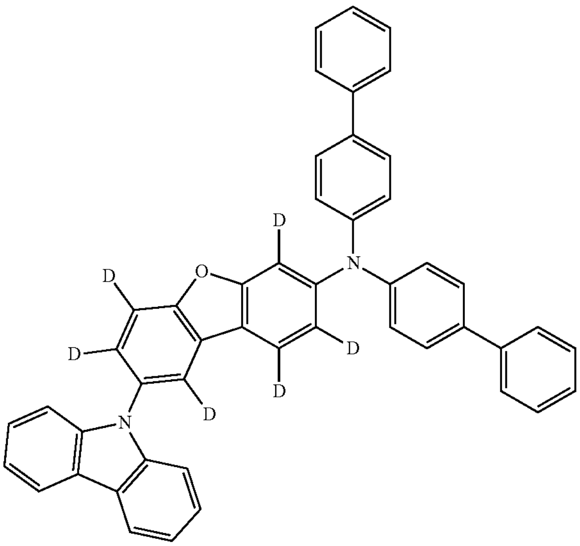

B62
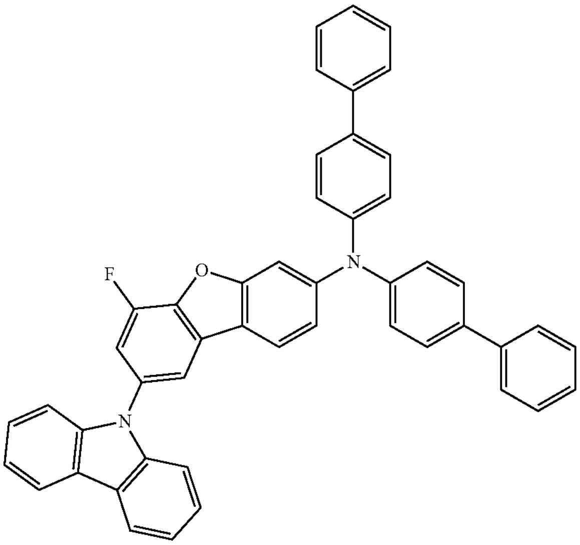
B63
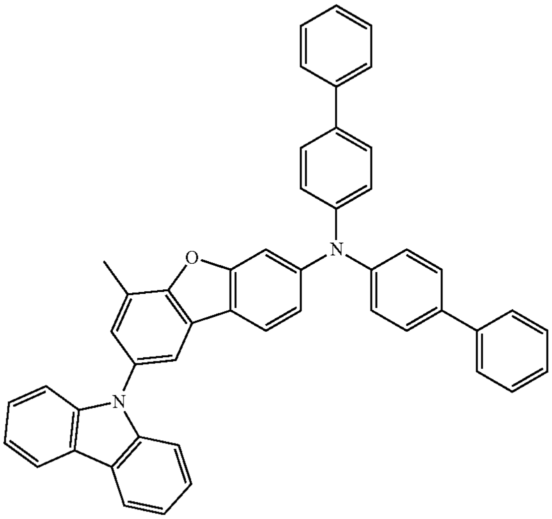
C1
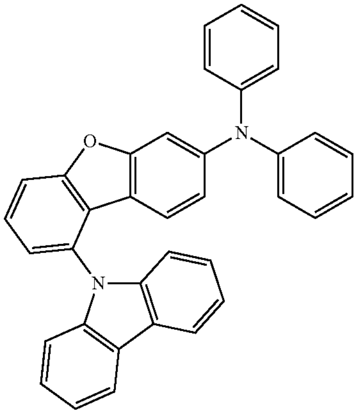
C2
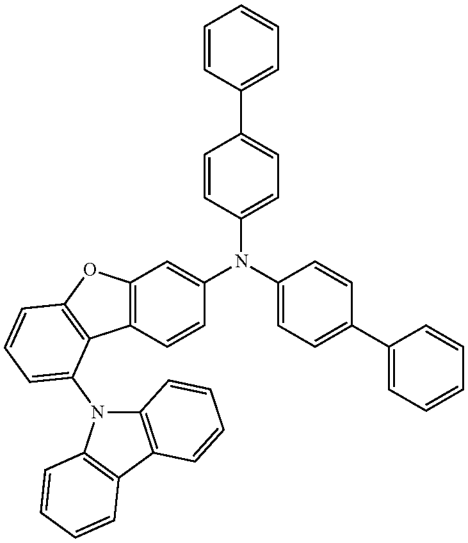
C3
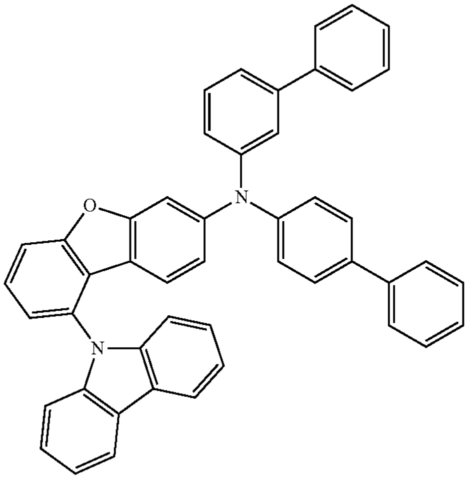
C4
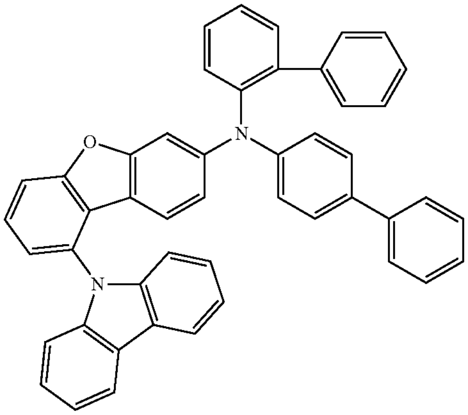

-continued
C5
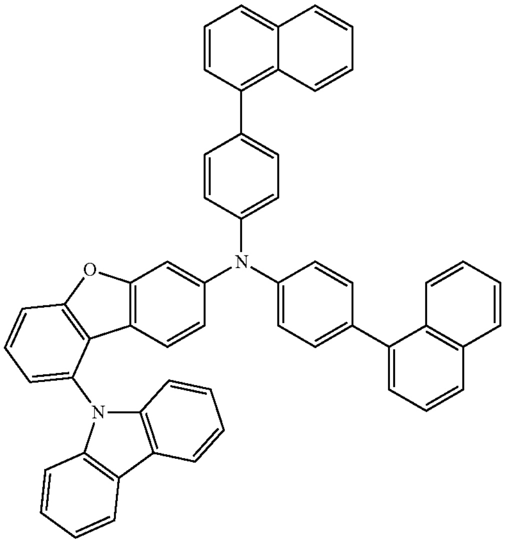
C6
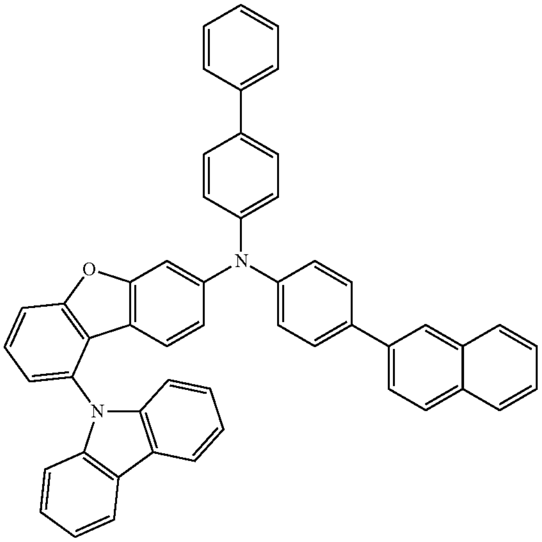
-continued
C7
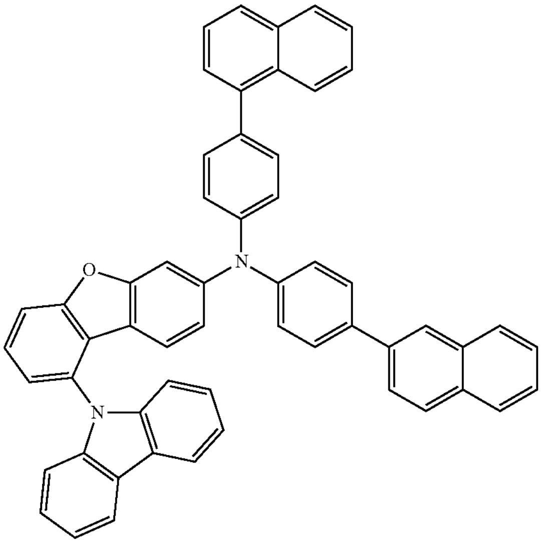
C8
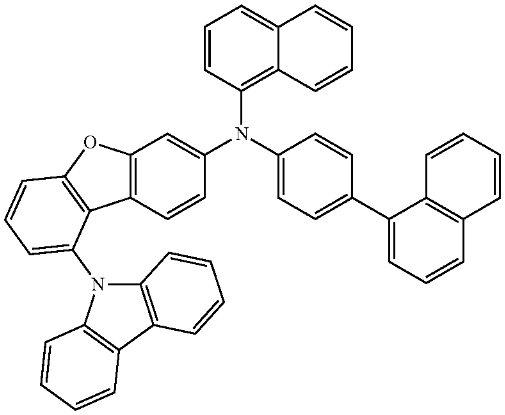
C9
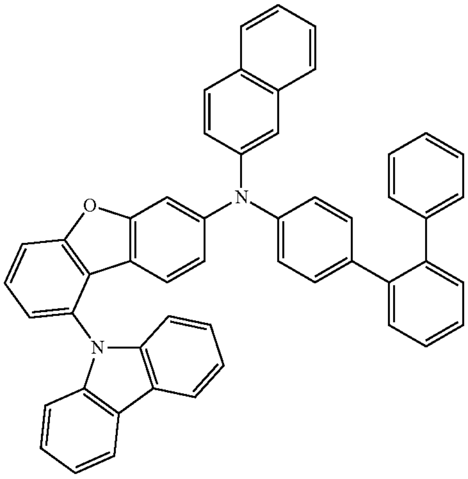

-continued
C10
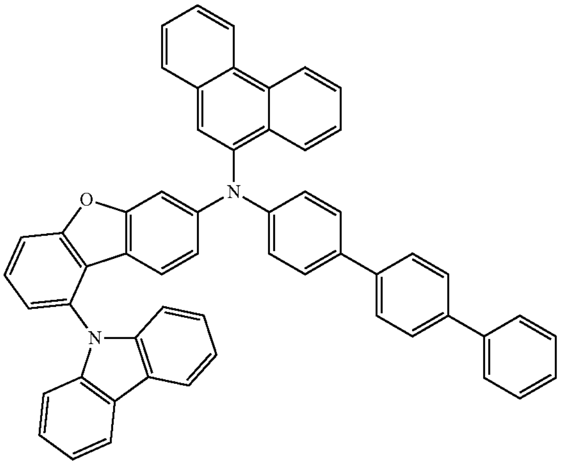
C11
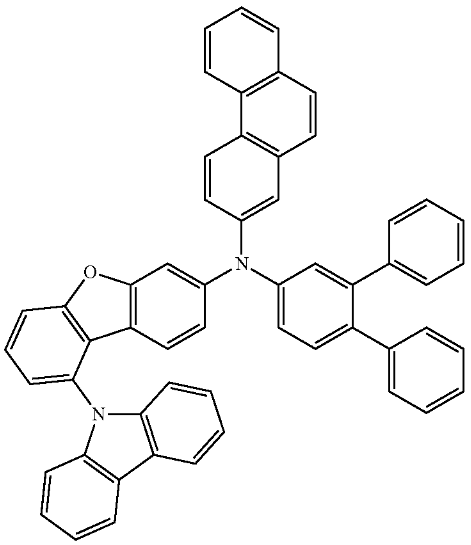
C12
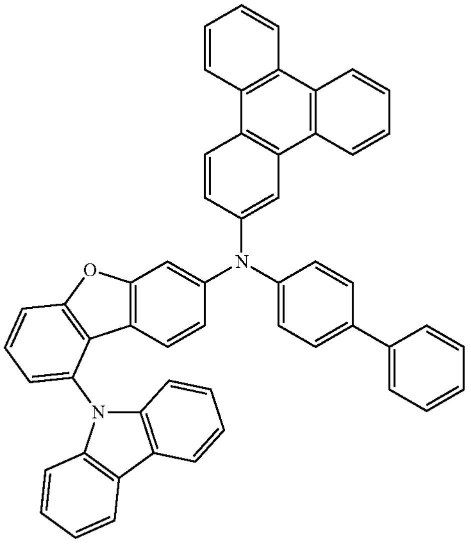
-continued
C13
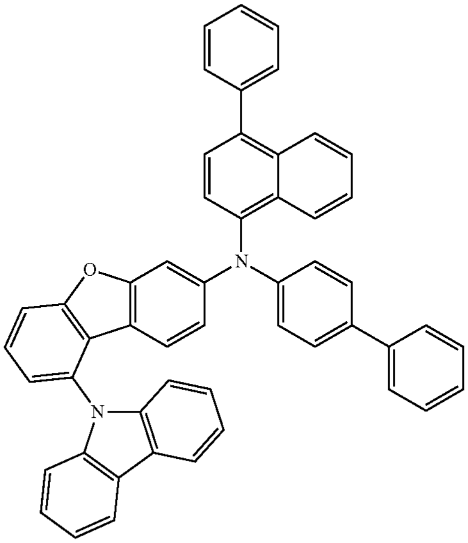
C14
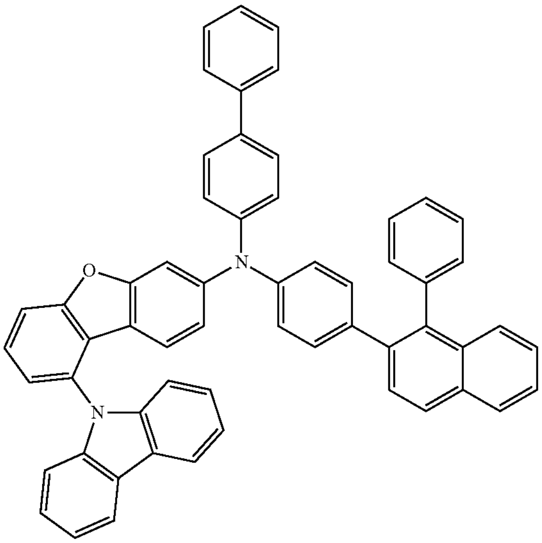
C15
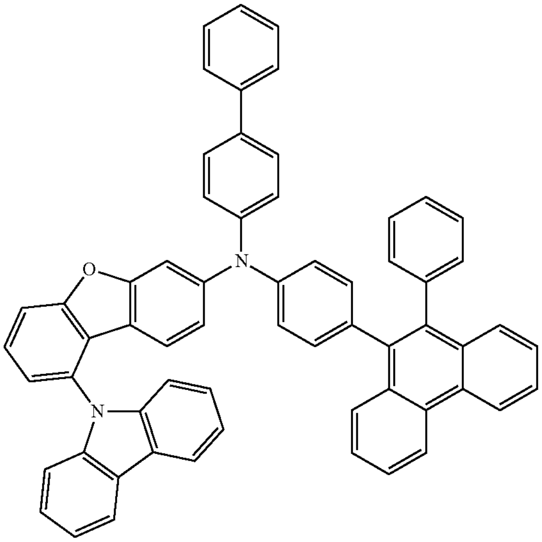

-continued
C16
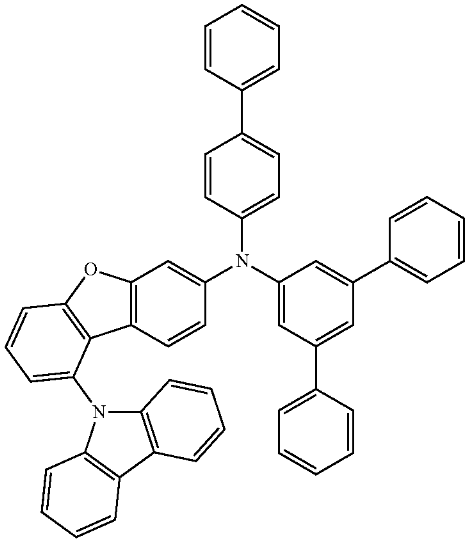
C17
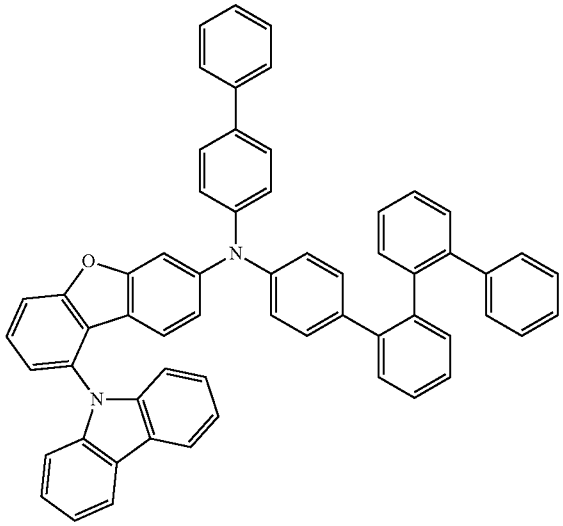
C18
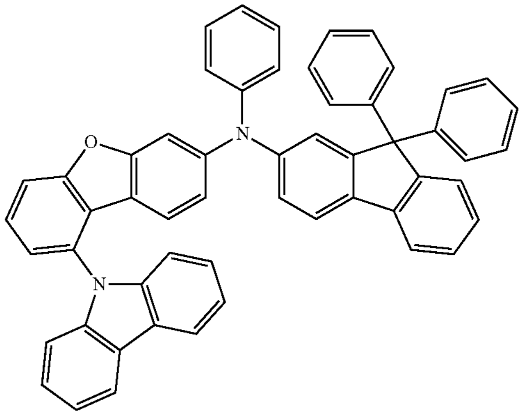
-continued
C19
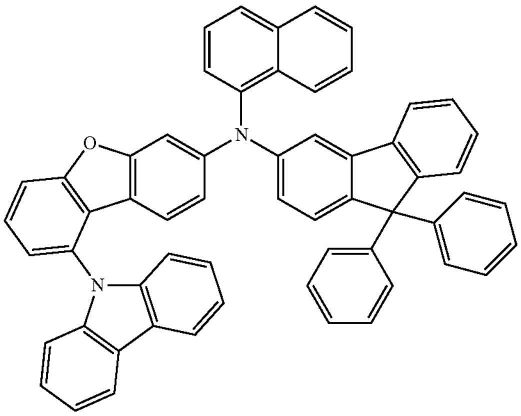
C20
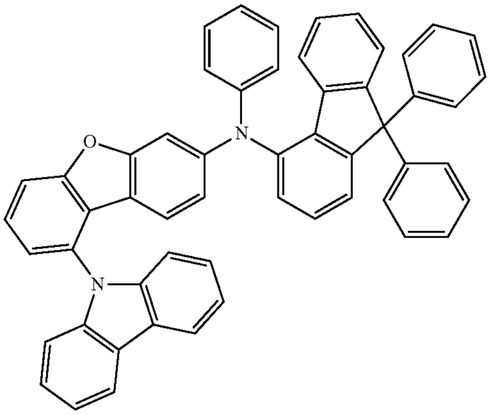
C21
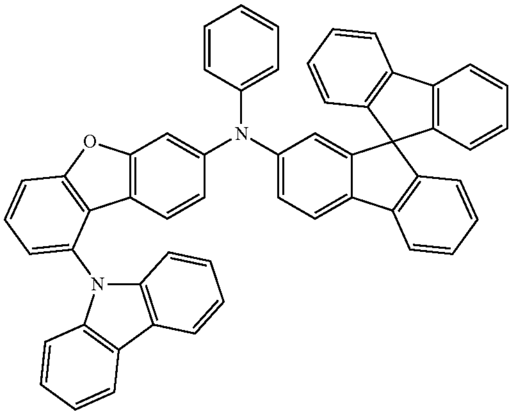

-continued
C23
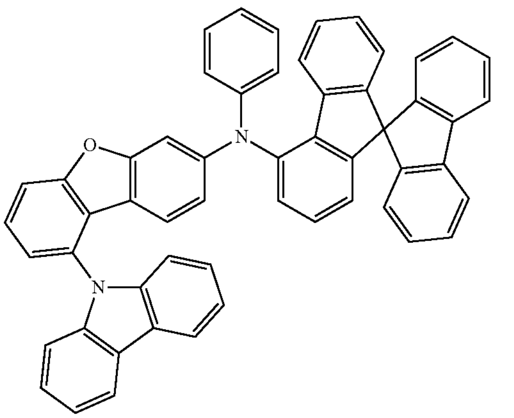
C24
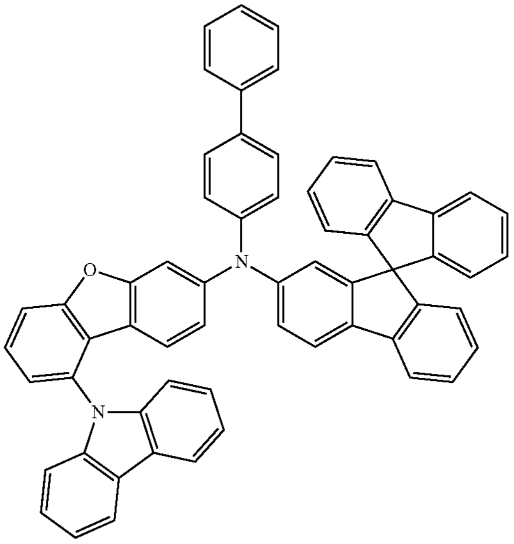
C25
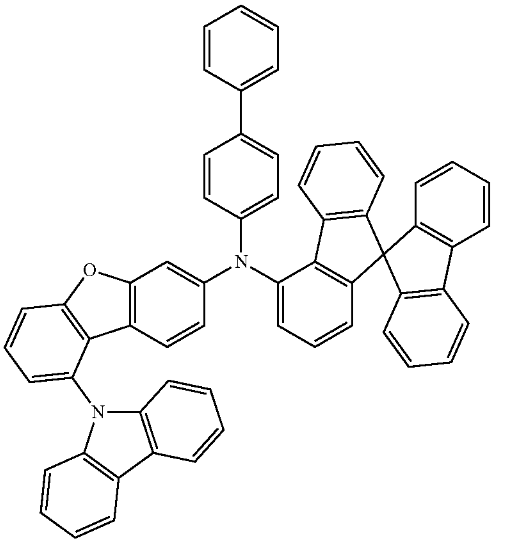
-continued
C26
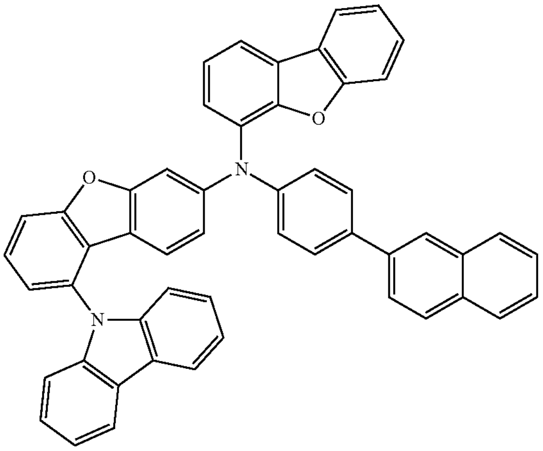
C27
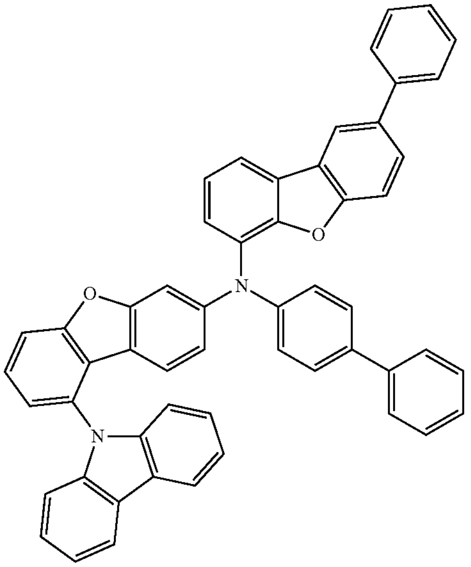
C28
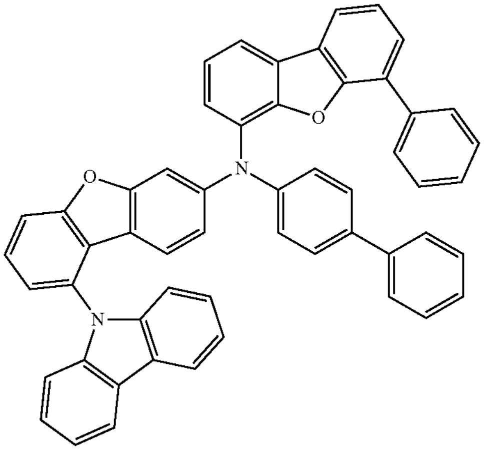

-continued
B29
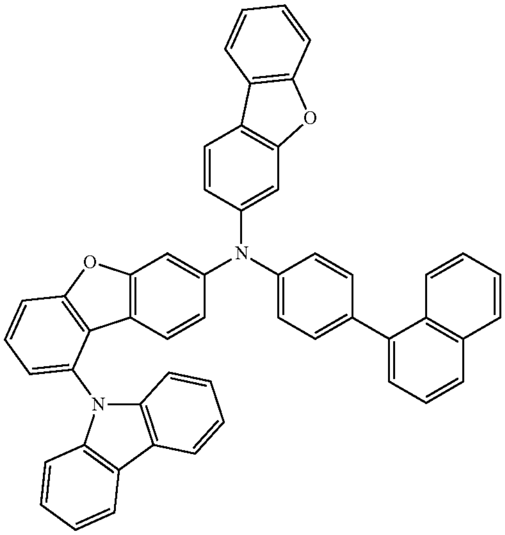
B30
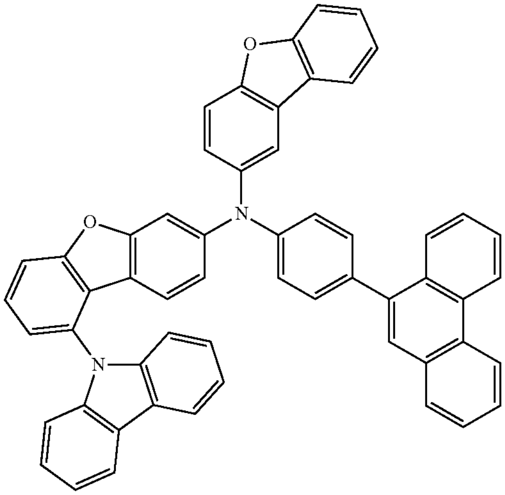
B31
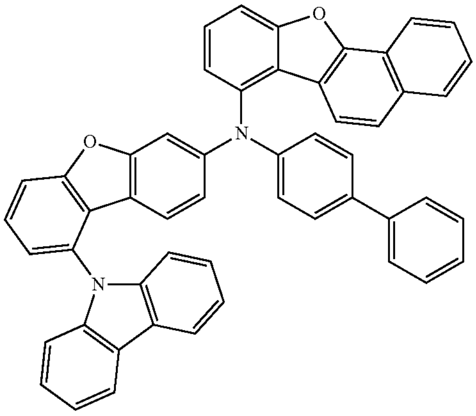
-continued
C32
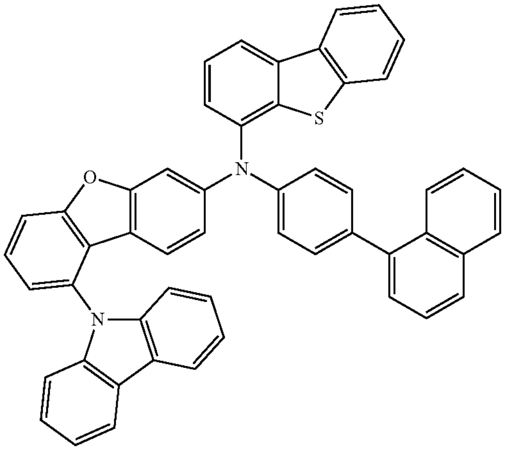
C33
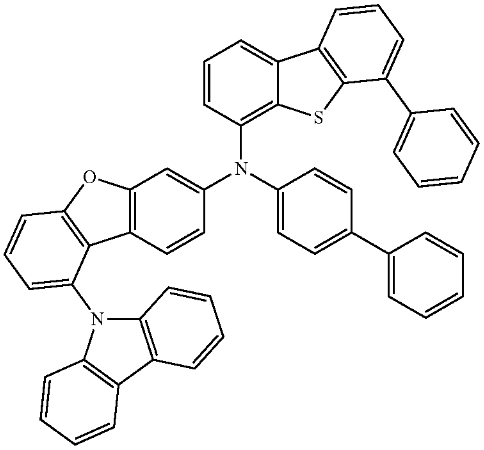
C34
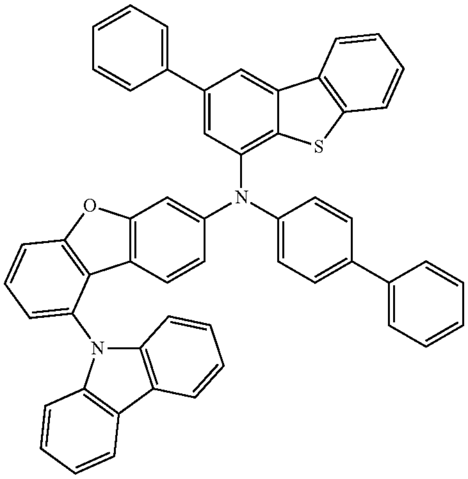

-continued
C35
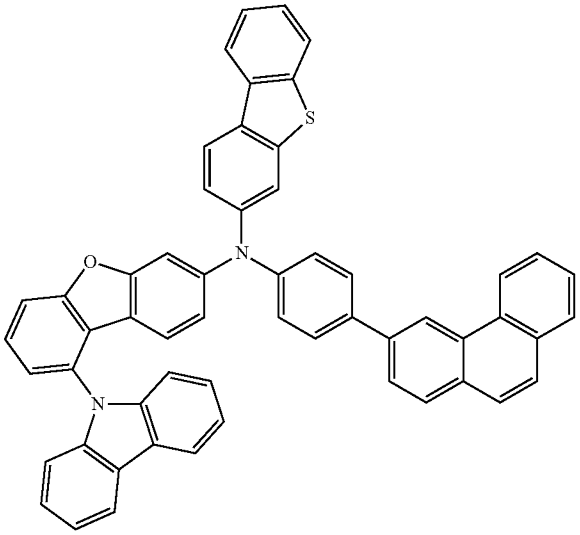
C36
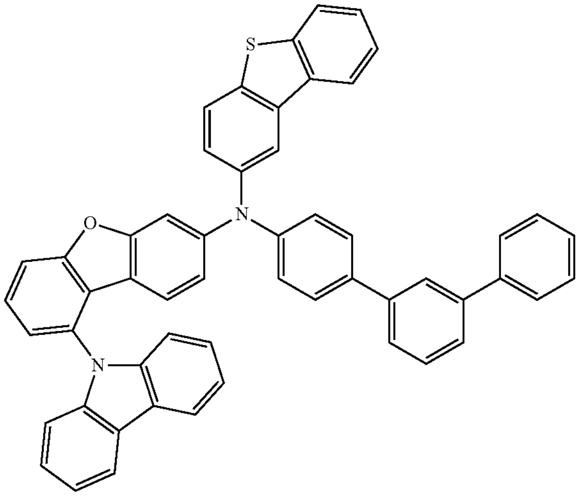
C37
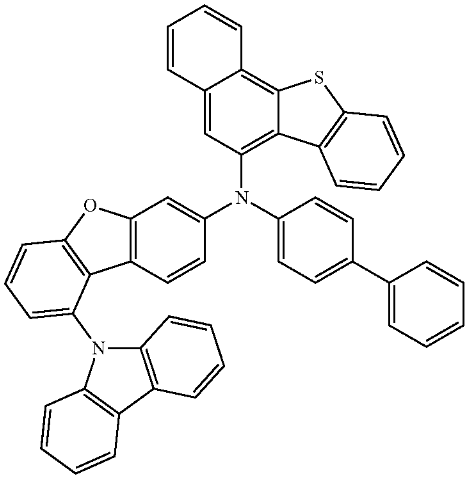
-continued
C38
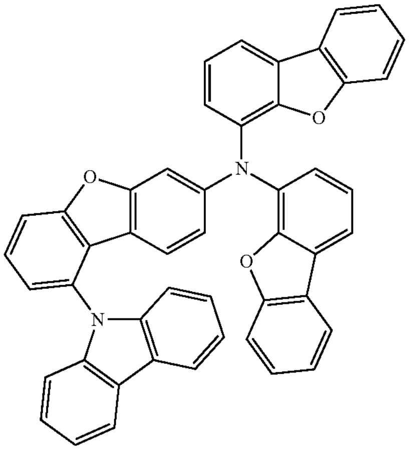
C39
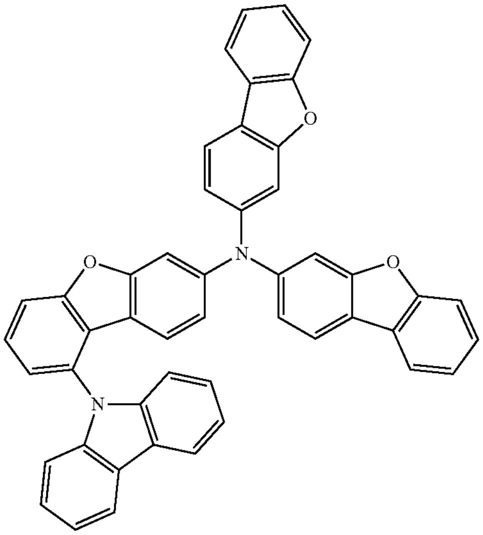
C40
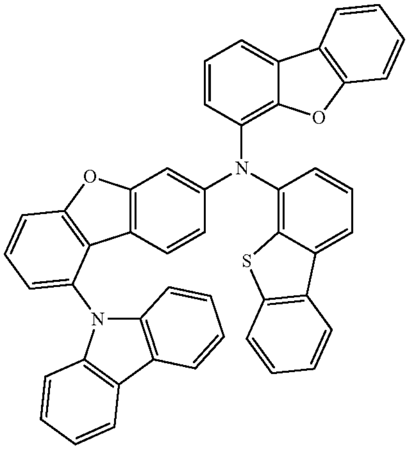

-continued
C41
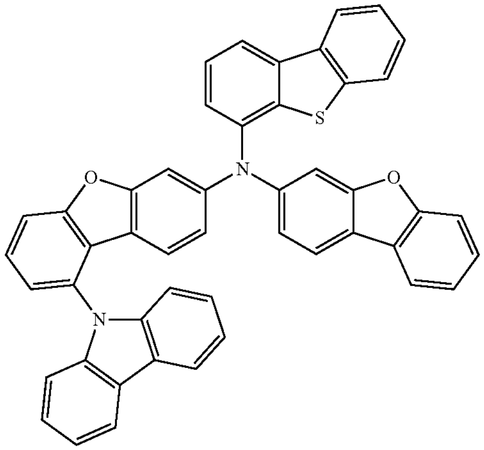
C42
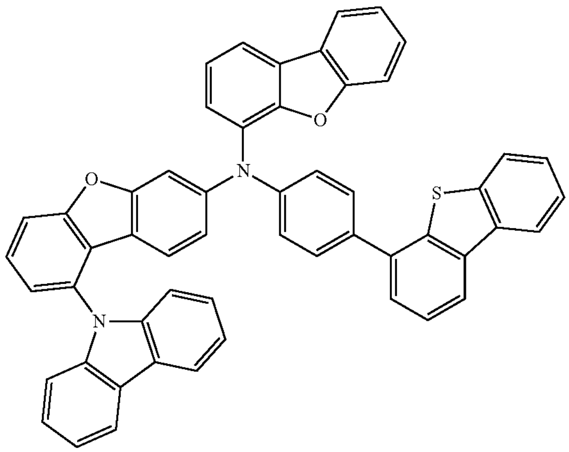
C43
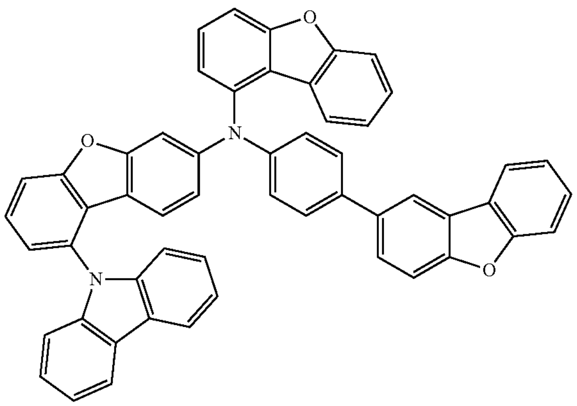
-continued
C44
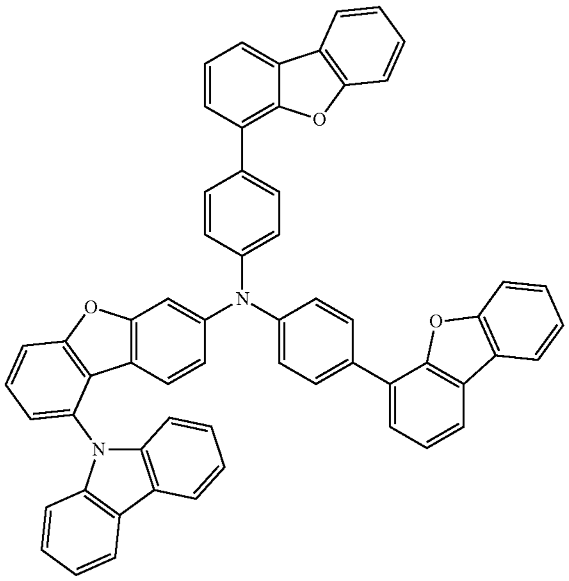
C45
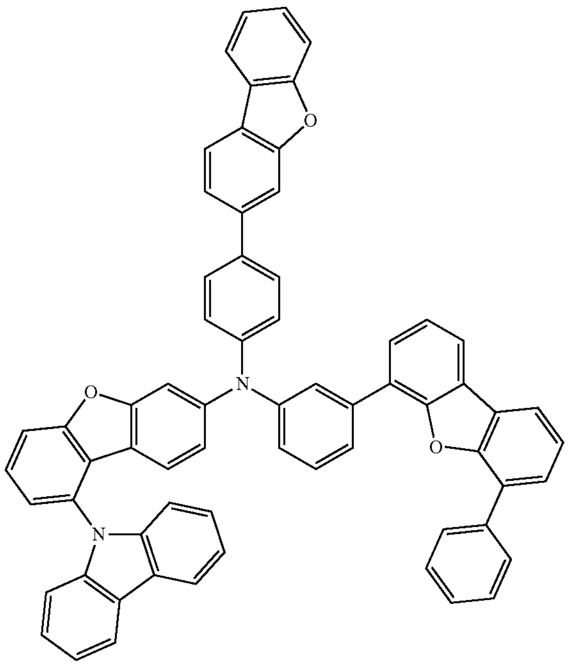

C46
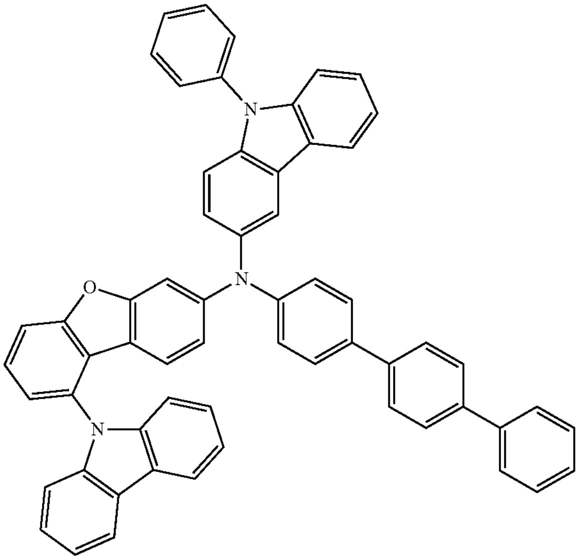
C47
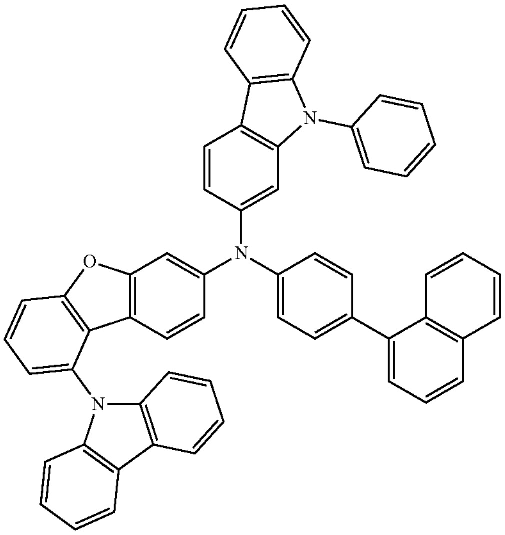
C48
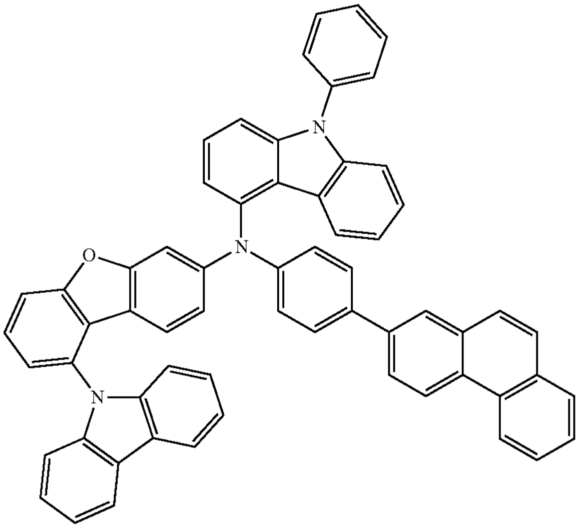
C49
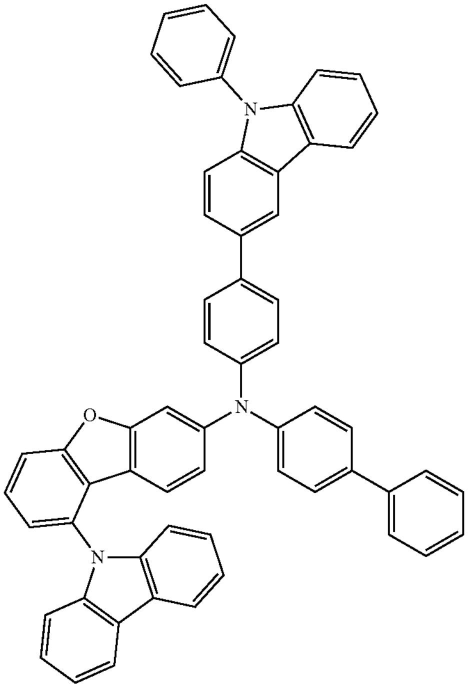

-continued
C50
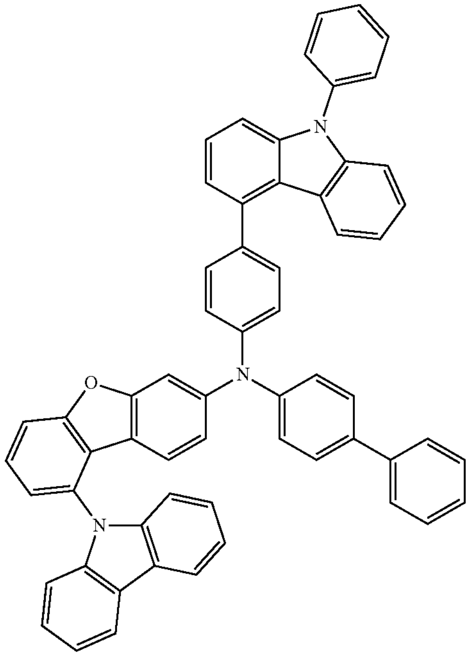
C51
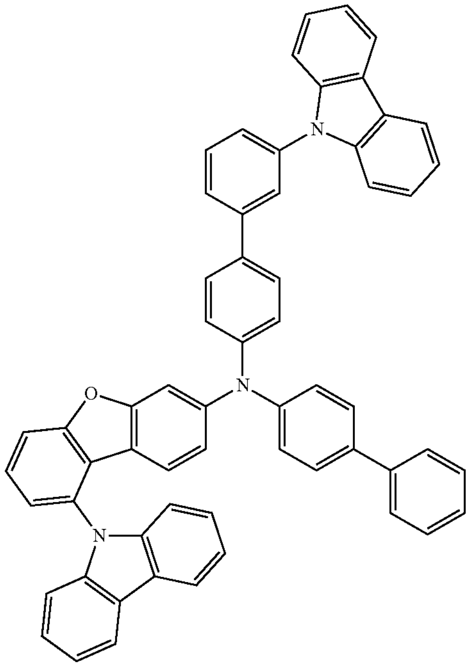
-continued
C52
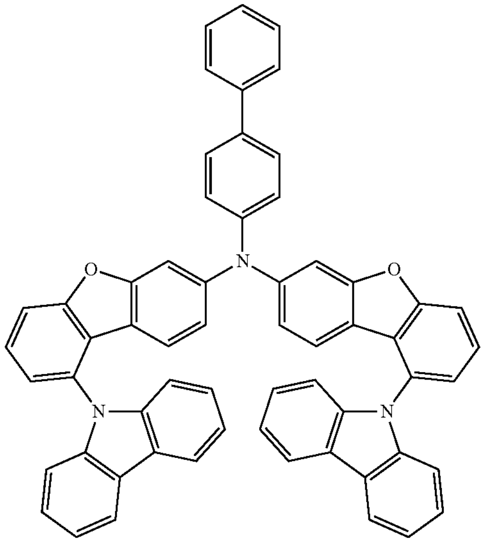
C53
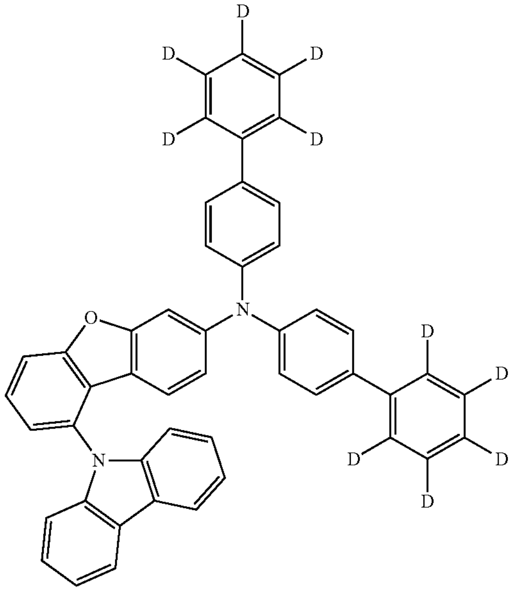

-continued
C54
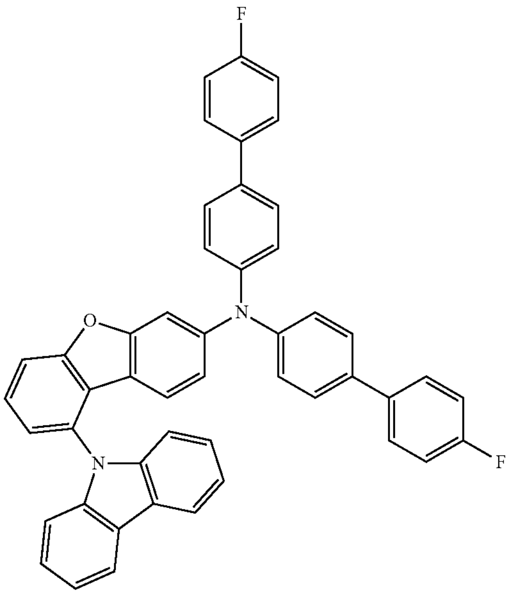
C55
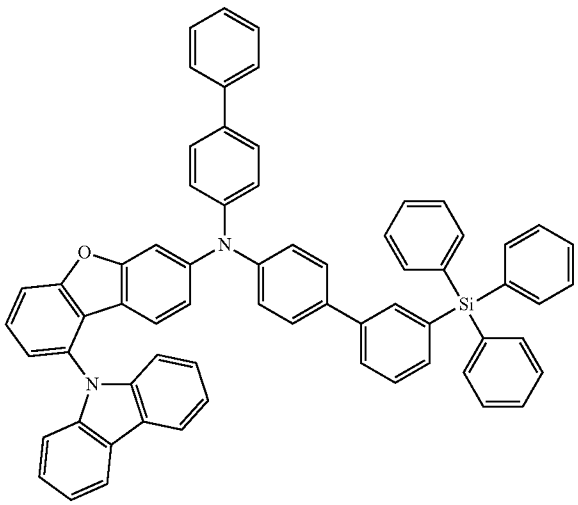
-continued
C56
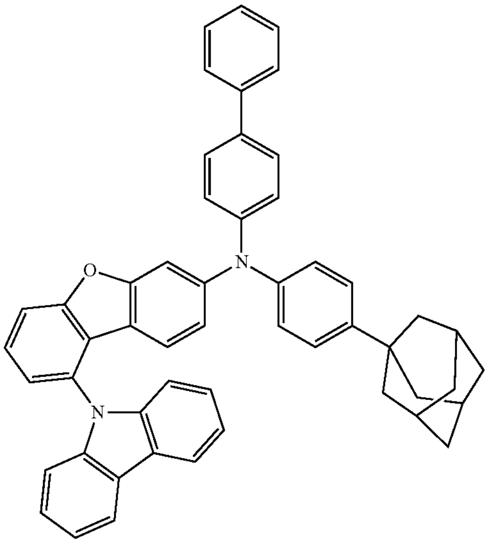
C57
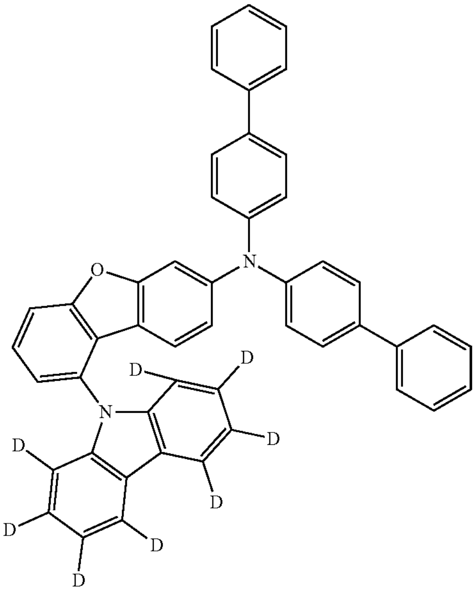

-continued
C58
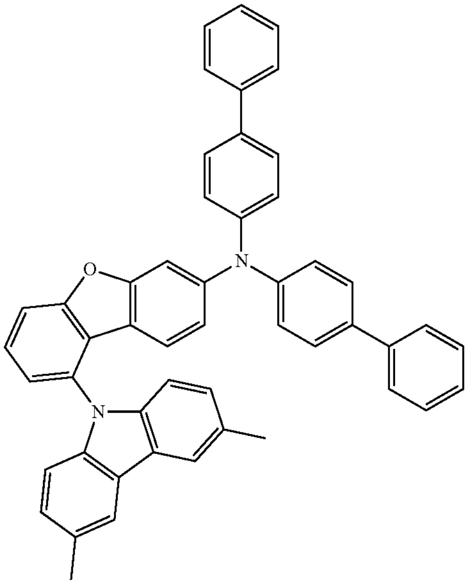
C59
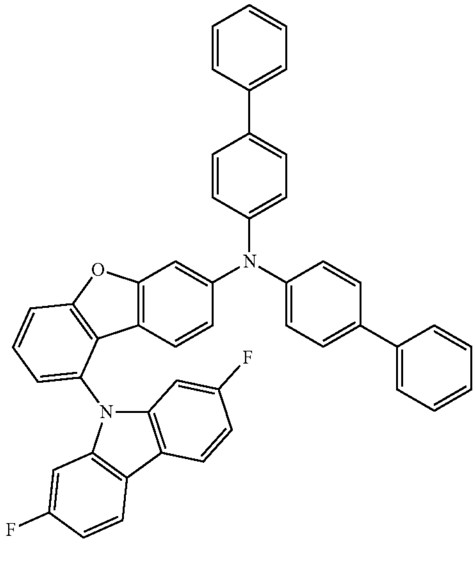
-continued
C60
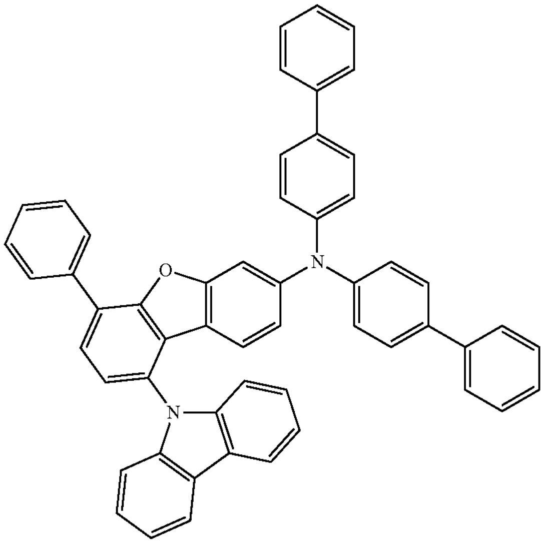
C61
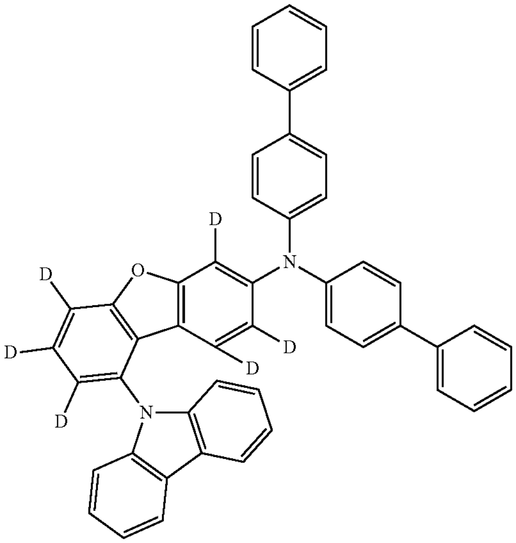
C62
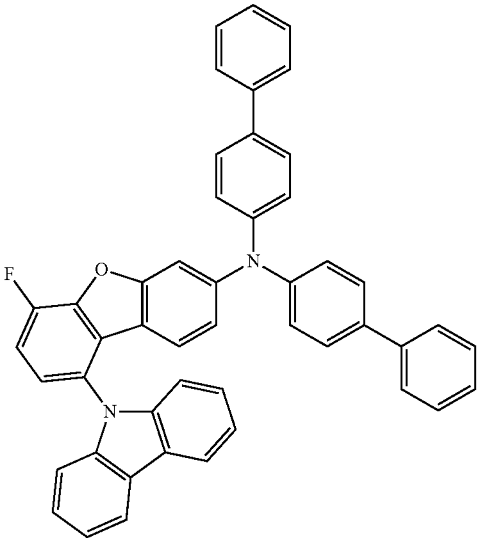

-continued
C63
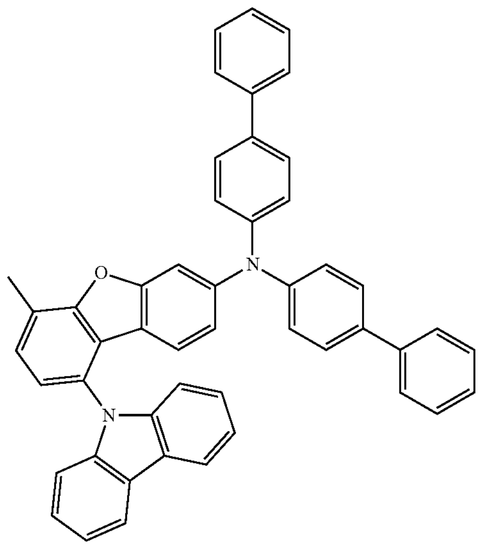
.
* * * * *